(12) United States Patent
Wraight et al.

(10) Patent No.: US 6,900,186 B1
(45) Date of Patent: May 31, 2005

(54) METHOD FOR THE PROPHYLAXIS AND/OR TREATMENT OF MEDICAL DISORDERS

(75) Inventors: Christopher John Wraight, Blackburn (AU); George Arthur Werther, Camberwell (AU); Stephanie Ruth Edmondson, Glen Waverley (AU)

(73) Assignee: Murdock Children's Research Institute, Victoria (AU)

( * ) Notice: Subject to any disclaimer, the term of this patent is extended or adjusted under 35 U.S.C. 154(b) by 0 days.

(21) Appl. No.: 09/598,274

(22) Filed: Jun. 21, 2000

Related U.S. Application Data

(60) Provisional application No. 60/140,345, filed on Jun. 21, 1999.

(51) Int. Cl.[7] .................. A61K 48/00; C07H 21/04; C12Q 1/68
(52) U.S. Cl. ..................... 514/44; 435/6; 536/24.5; 536/24.3
(58) Field of Search .................. 435/6, 91.1, 91.3, 435/325, 375; 536/23.1, 24.3, 24.33, 23.2, 24.5, 24.31; 514/44

(56) References Cited

U.S. PATENT DOCUMENTS

| | | | |
|---|---|---|---|
| 5,585,479 A | | 12/1996 | Hoke et al. |
| 5,643,788 A | * | 7/1997 | Baserga et al. |
| 5,681,940 A | * | 10/1997 | Wang et al. |
| 5,929,040 A | * | 7/1999 | Werther et al. |
| 6,071,891 A | * | 6/2000 | Low et al. |

FOREIGN PATENT DOCUMENTS

| | | | |
|---|---|---|---|
| JP | CN 1237582 A | * | 12/1999 |
| WO | WO9422486 | | 10/1994 |
| WO | WO9423034 | | 10/1994 |
| WO | 9601636 | | 1/1996 |
| WO | WO9610401 | | 4/1996 |
| WO | WO 96/10401 | * | 4/1996 |
| WO | WO 98/22579 | * | 5/1998 |
| WO | WO 99/60855 | * | 12/1999 |

OTHER PUBLICATIONS

Green et al, Antisense Oligonucleotides: An Evolving Technology for the Modulation of Gene Express In Human Disease, Jul. 2000, Antisense Therapy in Human Disease, vol. 191, pp. 93–105.*

Jen et al, Suppression of Gene Expression by Targeted Disruption of Messenger RNA: Available Options and Current Strategies, Stem Cells 2000, vol. 18, pp. 307–319.*

Sudhir Agrawal, Antisense Oligonucleotides: Towards Clinical Trials, Oct. 1996, TIBTECH, vol 14, pp. 376–387.*

Andrea D. Branch, A Good Antisense Molecule is Hard to Find, Feb. 1998, TIBS 23, pp. 45–50.*

Batch et al. (1994) Journal of Clinical Endocrinology and Metabolism 79:1444.

Cohick et al. (1993) Growth Regulation, 20–23.

Gewirtz et al. z91996) Proc. Natl. Acad. Sci. USA 93:3161.

Gouy (1987) in "Nucleic Acid and Protein Sequence Analysis: A Practical Approach" Bishop et al., eds. IRL Press, Oxford, 259–284.

Hodak et al. (1996) Journal of Investigative Dermatology 106:564.

Gura (1995) Science 270–575.

Long et al. (1995) Cancer Research 55:1006.

Resnicoff et al. (1994) Cancer Research 54:4848.

Rojanasukul (1996) Advanced Drug Delivery Reviews 18:115.

Shapiro et al. (1994) J. Clin. Invst. 94:1235.

Singh et al. (1994) Cancer Research 54:6563.

Stein et al. (1999) Nature Biotechnology 17:209.

Stull et al. (1995) Pharmaceutical Research 12:465.

Antisense '97 : A roundtable on the state of the industry, Nature Biotechnology 15:519.

U.S. Appl. No. 09/199,926, filed Nov. 25, 1998.

* cited by examiner

*Primary Examiner*—Karen Lacourciere
(74) *Attorney, Agent, or Firm*—Baker Botts LLP

(57) ABSTRACT

The present invention relates generally to a method for the prophylaxis and/or treatment of skin disorders, and in particular proliferative and/or inflamatory skin disorders, and to genetic molecules useful for same. The present invention is particularly directed to genetic molecules capable of modulating growth factor interaction with its receptor on epidermal keratinocytes to inhibit, reduce or otherwise decrease stimulation of this layer of cells. The present invention contemplates, in a most preferred embodiment, a method for the prophylaxis and/or treatment of psoriasis.

34 Claims, 65 Drawing Sheets

FIGURE 1

```
  1  ATTCGGGGCG AGGGAGGAGG AAGAAGCGGA GGAGGGGGCT CCCGCTCGCA
 51  GGGCCGTGCA CCTGCCCGCC CGCCCGCTCG CTCGCTCGCC CGCCGCGCCG
101  CGCTGCCGAC CGCCAGCATG CTGCCGAGAG TGGGCTGCCC CGCGCTGCCG
151  CTGCCGCCGC CGCCGCTGCT GCCGCTGCTG CCGCTGCTGC TGCTGCTACT
201  GGGCGCGAGT GGCGGGGGCG GCGGGAGGTG CCGGGAGGCA CTGTTCCGCT
251  GCCCGCCCTG CACACCCGAG CGCCTGGCCG CCTGCGGGCC CCCGCCGGTT
301  GCGCCGCCCG CCGCGGGTGG CGCAGTGGCC GGAGGCGCCC GCATGCCATG
351  CGCGGAGCTC GTCCGGGAGC CGGGCTGCGG CTGCTGCTCG GTGTGCCCC
401  GGCTGGAGGG CGAGGCGTGC GGCGTCTACA GGCGTCTACA CCCCGGCTG CGGCCAGGGG
451  CTGCGCTGCT ATCCCCACCC GGGCTCCGAG CTGCCCCTGC AGGCGCTGGT
501  CATGGGCGAG GGCACTTGTG AGAAGCGCCG GGACGCCGAG TATGGCGCCA
551  GCCCGGAGCA GGTTGCAGAC AATGGCGATG ACCACTCAGA AGGAGGCCTG
601  GTGGAGAACC ACGTGGACAG CACCATGAAC ATGTTGGGCG GGGAGGCAG
651  TGCTGGCCGG AAGCCCCTCA AGTCGGGTAT GAAGGAGCTG GCCGTGTTCC
701  GGGAGAAGGT CACTGAGCAG CACCGGCAGA TGGGCAAGGG TGGGCAAGCAT
```

FIGURE 1 (continued...)

```
751  CACCTTGGCC TGGAGGAGCC CAAGAAGCTG CGACCACCCC CTGCCAGGAC
801  TCCTGCCAA  CAGGAACTGG ACCAGGTCCT GGAGCGGATC TCCACCATGC
851  GCCTTCCGGA TGAGCGGGGC CCTCTGGAGC ACCTCTACTC CCTGCACATC
901  CCCAACTGTG ACAAGCATGG CCTGTACAAC CTCAAACAGT GCAAGATGTC
951  TCTGAACGGG CAGCGTGGGG AGTGCTGGTG TGTGAACCCC AACACCGGGA
1001 AGCTGATCCA GGGAGCCCCC ACCATCCGGG GGGACCCCGA GTGTCATCTC
1051 TTCTACAATG AGCAGCAGGA GGCTTGCGGG GTGCACACCC AGCGGATGCA
1101 GTAGACCGCA GCCAGCCGGT GCCTGGCGCC CCTGCCCCCC GCCCCTCTCC
1151 AAACACCGGC AGAAAACGGA GAGTGCTTGG GTGGTGGGTG CTGGAGGATT
1201 TTCCAGTTCT GACACACGTA TTTATATTTG GAAAGAGACC AGCACCGAGC
1251 TCGGCACCTC CCCGGCCTCT CTCTTCCCAG CTGCAGATGC CACACCTGCT
1301 CCTTCTTGCT TTCCCCGGGG GAGGAAGGGG GTTGTGGTCG GGGAGCTGGG
1351 GTACAGGTTT GGGGAGGGGG AAGAGAAATT TTTATTTTG AACCCCTGTG
1401 TCCCTTTTGC ATAAGATTAA AGGAAGGAAA AGT
```

FIGURE 2

```
  1  CTCAGGCCCC AGCCGCTTCC TGCCTGGATT CCACAGCTTC GCGCCGTGTA
 51  CTGTCGCCCC ATCCCTGCGC GCCCAGCCTG CCAAGCAGCG TGCCCCGGTT
101  GCAGGCGTCA TGCAGCGGGC GCGACCCACG CTCTGGGCCG CTGCGCTGAC
151  TCTGCTGGTG CTGCTCCGCG GGCCGCCGGT GGCGCGGGCT GGCGCGGAGCT
201  CGGGGGGCTT GGGTCCCGTG GTGCGCTGCG AGCCGTGCGA CGCGCGTGCA
251  CTGGCCCAGT GCGCGCCCTC GCCCCCGTG TGCGCGGAGC TGGTGCGCGA
301  GCCGGGCTGC GGCTGCTGCC TGACGTGCGC ACTGAGCGAG GGCCAGCCGT
351  GCGGCATCTA CACCGAGCGC TGTGGCTCCG GCCTTCGCTG CCAGCCCGTCG
401  CCCGACGAGG CGCGACCGCT GCAGGCGCTG CTGGACGGCC GCGGGCTCTG
451  CGTCAACGCT AGTGCCGTCA GCCGCCTGCG CGCCTACCTG CTGCCAGCGC
501  CGCCAGCTCC AGGAAATGCT AGTGAGTCGG AGGAAGACCG CAGCGCGGGC
551  AGTGTGGAGA GCCCGTCCGT CTCCAGCACG CACCGGGTGT CTGATCCCAA
601  GTTCCACCCC CTCCATTCAA AGATAATCAT CATCAAGAAA GGGCATGCTA
651  AAGACAGCCA GCGCTACAAA GTTGACTACG AGTCTCAGAG CACAGATACC
701  CAGAACTTCT CCTCCGAGTC CAAGCGGGAG ACAGAATATG GTCCCTGCCG
```

FIGURE 2 (Continued....)

```
 751  TAGAGAAATG GAAGACACAC TGAATCACCT GAAGTTCCTC AATGTGCTGA
 801  GTCCCAGGGG TGTACACATT CCCAACTGTG ACAAGAAGGG ATTTTATAAG
 851  AAAAAGCAGT GTCGCCCTTC CAAAGGCAGG AAGCGGGGCT TCTGCTGGTG
 901  TGTGGATAAG TATGGGCAGC CTCTCCCAGG CTACACCACC AAGGGGAAGG
 951  AGGACGTGCA CTGCTACAGC ATGCAGAGCA AGTAGACGCC TGCCGCAAGT
1001  TAATGTGGAG CTCAAATATG CCTTATTTTG CACAAAAGAC TGCCAAGGAC
1051  ATGACCAGCA GCTGGCTACA GCCTCGATTT ATATTTCTGT TTGTGGTGAA
1101  CTGATTTTTT TTAAACCAAA GTTTAGAAAG AGTTTTTGA AATGCCTATG
1151  GTTTCTTTGA ATGGTAAACT TGAGCATCTT TTCACTTTCC AGTAGTCAGC
1201  AAAGAGCAGT TTGAATTTTC TTGTCGCTTC CTATCAAAAT ATTCAGAGAC
1251  TCGAGCACAG CACCCAGACT GTGGAATGCT CACCACATGT
1301  TGGTCGAAGC GGCCGACCAC TGACTTTGTG ACTTAGGCGG CTGTGTTGCC
1351  TATGTAGAGA ACACGCTTCA CCCCCACTCC CCGTACAGTG CGCACAGGCT
1401  TTATCGAGAA TAGGAAAACC TTTAAACCCC GGTCATCCGG ACATCCCAAC
1451  GCATGCTCCT GGAGCTCACA GCCTTCTGTG GTGTCATTTC TGAAACAAGG
```

FIGURE 2 (continued....)

```
1501 GCGTGGATCC CTCAACCAAG AAGAATGTTT ATGTCTTCAA GTGACCTGTA
1551 CTGCTTGGGG ACTATTGGAG AAAATAAGGT GGAGTCCTAC TTGTTTAAAA
1601 AATATGTATC TAAGAATGTT CTAGGCACT  CTGGAACCT  ATAAAGGCAG
1651 GTATTTCGGG CCCTCCTCTT CAGGAATCTT CCTGAAGACA TGGCCCAGTC
1701 GAAGGCCCAG GATGGCTTTT GCTGCGGCCC CGTGGGGTAG GAGGGACAGA
1751 GAGACGGGAG AGTCAGCCTC CACATTCAGA GGCATCACAA GTAATGGCAC
1801 AATTCTTCGG ATGACTGCAG AAAATAGTGT TTTGTAGTTC AACAACTCAA
1851 GACGAAGCTT ATTTCTGAGG ATAAGCTCTT TAAAGCAAA  GCTTTATTTT
1901 CATCTCTCAT CTTTTGTCCT CCTTAGCACA ATGTAAAAAA GAATAGTAAT
1951 ATCAGAAACAG GAAGGAGGAA TGGCTTGCTG GGGAGCCCAT CCAGGACACT
2001 GGGAGCACAT AGAGATTCAC CCATGTTTGT TGAACTTAGA GTCATTCTCA
2051 TGCTTTTCTT TATAATTCAC ACATATATGC AGAGAAGATA TGTTCTTGTT
2101 AACATTGTAT ACAACATAGC CCCAAATATA GTAAGATCTA TACTAGATAA
2151 TCCTAGATGA AATGTTAGAG ATGCTATATG ATACAACTGT GGCCATGACT
2201 GAGGAAAGGA GCTCACGCCC AGAGACTGGG CTGCTCTCCC GGAGGCCAAA
```

FIGURE 2 (Continued...)

```
2251 CCCAAGAAGG TCTGGCAAAG TCAGGCTCAG GGAGACTCTG CCCTGCTGCA
2301 GACCTCGGTG TGGACACACG CTGCATAGAG CTCTCCTTGA AAACAGAGGG
2351 GTCTCAAGAC ATTCTGCCTA CCTATTAGCT TTTCTTTATT TTTTTAACTT
2401 TTTGGGGGGA AAAGTATTTT TGAGAAGTTT GTCTTGCAAT GTATTTATAA
2451 ATAGTAAATA AAGTTTTTAC CATT
```

FIGURE 3

```
  1  TTTTTTTTT TTTTGAGAAA GGGAATTTCA TCCCAAATAA AAGGAATGAA
 51  GTCTGGCTCC GGAGGAGGGT CCCGACCCTC GCTGTGGGGG CTCCTGTTTC
101  TCTCCGCCGC GCTCTCGCTC TGGCCGACGA GTGGAGAAAT CTGCGGGCCA
151  GGCATCGACA TCCGCAACGA CTATCAGCAG CTGAAGCGCC TGGAGAACTG
201  CACGGTGATC GAGGGCTACC TCCACATCCT GCTCATCTCC AAGGCCGAGG
251  ACTACCGCAG CTACCGCTTC CCCAAGCTCA CGGTCATTAC CGAGTACTTG
301  CTGCTGTTCC GAGTGGCTGG CCTCGAGAGC CTCGGAGACC TCTTCCCCAA
351  CCTCACGGTC ATCCGGGGCT GGAAACTCTT CTACAACTAC GCCCTGGTCA
401  TCTTCGAGAT GACCAATCTC AAGGATATTG GGCTTTACAA CCTGAGGAAC
451  ATTACTCGGG GGGCCATCAG GATTGAGAAA AATGCTGACC TCTGTTACCT
501  CTCCACTGTG GACTGGTCCC TGATCCCTGA TGCGGTGTCC AATAACTACA
551  TTGTGGGGAA TAAGCCCCCA AAGGAATGTG GGACCCGTGT GCCAGGGACC
601  ATGGAGGAGA AGCCGATGTG TGAGAAGACC ACCATCAACA ATGAGTACAA
651  CTACCGCTGC TGGACCACAA ACCGCTGCCA GAAAATGTGC CCAAGCACGT
701  GTGGGAAGCG GGCGTGCACC GAGAACAATG AGTGCTGCCA CCCCGAGTGC
```

FIGURE 3 (Continued....)

```
751  CTGGGCAGCT GCAGCGGCGCC TGACAACGAC ACGGCCTGTG TAGCTTGCCG
801  CCACTACTAC TATGCCGGTG TCTGTGTGCC TGCCTGCCCG CCCAACACCT
851  ACAGGTTTGA GGGCTGGCGC TGTGTGGACC GTGACTTCTG CGCCAACATC
901  CTCAGCGCCG AGAGCAGCGA CTCCGAGGGG TTTGTGATCC ACGACGGCGA
951  GTGCATGCAG GAGTGCCCCT CGGCTTCAT CCGCAACGGC AGCCAGAGCA
1001 TGTACTGCAT CCCTTGTGAA GGTCCTTGCC CGAAGGTCTG TGAGGAAGAA
1051 AAGAAAACAA AGACCATTGA TTCTGTTACT TCTGCTCAGA TGCTCCAAGG
1101 ATGCACCATC TTCAAGGGCA ATTTGCTCAT TAACATCCGA CGGGGAATA
1151 ACATTGCTTC AGAGCTGGAG AACTTCATGG GGCTCATCGA GGTGGTGACG
1201 GGCTACGTGA AGATCCGCCA TTCTCATGCC TTGGTCTCCT TGTCCTTCCT
1251 AAAAAACCTT CGCCTCATCC TAGGAGAGGA GCAGCTAGAA GGGAATTACT
1301 CCTTCTACGT CCTCGACAAC CAGAACTTGC AGCAACTGTG GGACTGGGAC
1351 CACCGCAACC TGACCATCAA AGCAGGGAAA ATGTACTTTG CTTTCAATCC
1401 CAAATTATGT GTTTCCGAAA TTTACCGCAT GGAGGAAGTG ACGGGGACTA
1451 AAGGGCGCCA AAGCAAAGGG GACATAAACA CCAGGAACAA CGGGGAGAGA
```

FIGURE 3 (Continued...)

```
1501 GCCTCCTGTG AAAGTGACGT CCTGCATTTC ACCTCCACCA CCACGTCGAA
1551 GAATCGCATC ATCATAACCT GGCACCGGTA CCGGCCCCCT GACTACAGGG
1601 ATCTCATCAG CTTCACCGTT TACTACAAGG AAGCACCCTT TAAGAATGTC
1651 ACAGAGTATG ATGGGCAGGA TGCCTGCGGC TCCAACAGCT GGAACATGGT
1701 GGACGTGGAC CTCCCGCCCA ACAAGGACGT GGAGCCCGGC ATCTTACTAC
1751 ATGGGCTGAA GCCCTGGACT CAGTACGCCG TTTACGTCAA GGCTGTGACC
1801 CTCACCATGG TGGAGAACGA CCATATCCGT GGGGCCAAGA GTGAGATCTT
1851 GTACATCGC ACCAATGCTT CAGTTCCTTC CATTCCCTTG GACGTTCTTT
1901 CAGCATCGAA CTCCCTCTCT CAGTTAATCG TGAAGTGGAA CCCTCCCTCT
1951 CTGCCCAACG GCAACCTGAG TTACTACATT GTGCGGCTGGC AGCGGGCAGCC
2001 TCAGGACGGC TACCTTTACC GGCACAATTA CTGCTCCAAA GACAAAATCC
2051 CCATCAGGAA GTATGCCGAC GGCACCATCG ACATTGAGGA GGTCACAGAG
2101 AACCCCAAGA CTGAGGTGTG TGGTGGGGAG AAAGGGCCTT GCTGCGCCTG
2151 CCCCAAAACT GAAGCCGAGA AGCAGGCCGA GAAGGAGGAG GCTGAATACC
2201 GCAAAGTCTT TGAGAATTTC CTGCACAACT CCATCTTCGT GCCCAGACCT
```

FIGURE 3 (Continued...)

| | | | | |
|---|---|---|---|---|
| 2251 | GAAAGGAAGC | GGAGAGATGT | CATGCAAGTG | GCCAACACCA | CCATGTCCAG |
| 2301 | CCGAAGCAGG | AACACCACGG | CCGCAGACAC | CTACAACATC | ACCGACCCGG |
| 2351 | AAGAGCTGGA | GACAGAGTAC | CCTTCTTTTG | AGAGCAGAGT | GGATAACAAG |
| 2401 | GAGAGAACTG | TCATTTCTAA | CCTTCGGCCT | TTCACATTGT | ACCGCATCGA |
| 2451 | TATCCACAGC | TGCAACCACG | AGGCTGAGAA | GCTGGGCTGC | AGCCCTCCA |
| 2501 | ACTTCGTCTT | TGCAAGGACT | ATGCCCGCAG | AAGGAGCAGA | TGACATTCCT |
| 2551 | GGGCCAGTGA | CCTGGGAGCC | AAGGCCTGAA | AACTCCATCT | TTTAAAGTG |
| 2601 | GCCGGAACCT | GAGAATCCCA | ATGGATTGAT | TCTAATGTAT | GAAATAAAAT |
| 2651 | ACGGATCACA | AGTTGAGGAT | CAGCGAGAAT | GTGTGTCCAG | ACAGGAATAC |
| 2701 | AGGAAGTATG | GAGGGGCCAA | GCTAAACCCG | CTAAACCCGG | GGAACTACAC |
| 2751 | AGCCCGGATT | CAGGCCACAT | CTCTCTCTGG | GAATGGGTCG | TGGACAGATC |
| 2801 | CTGTGTTCTT | CTATGTCCAG | GCCAAAACAG | GATATGAAAA | CTTCATCCAT |
| 2851 | CTGATCATCG | CTCTGCCCGT | CGCTGTCCTG | TTGATCGTGG | GAGGGTTGGT |
| 2901 | GATTATGCTG | TACGTCTTCC | ATAGAAAGAG | AAATAACAGC | AGGCTGGGGA |
| 2951 | ATGGAGTGCT | GTATGCCCTCT | GTGAACCCGG | AGTACTTCAG | CGCTGCTGAT |

FIGURE 3 (Continued...)

```
3001 GTGTACGTTC CTGATGAGTG GGAGGTGGCT CGGGAGAAGA TCACCATGAG
3051 CCGGGAACTT GGGCAGGGGT CGTTTGGGAT GGTCTATGAA GGAGTTGCCA
3101 AGGGTGTGGT GAAAGATGAA CCTGAAACCA GAGTGGCCAT TAAAACAGTG
3151 AACGAGGCCG CAAGCATGCG TGAGAGGATT GAGTTTCTCA ACGAAGCTTC
3201 TGTGATGAAG GAGTTCAATT GTCACCATGT GGTGCGATTG CTGGGTGTGG
3251 TGTCCCAAGG CCAGCCAACA CTGGTCATCA TGGAACTGAT GACACGGGGC
3301 GATCTCAAAA GTTATCTCCG GTCTCTGAGG CCAGAAATGG AGAATAATCC
3351 AGTCCTAGCA CCTCCAAGCC TGAGCAAGAT GATTCAGATG GCCGGAGAGA
3401 TTGCAGACGG CATGGCATAC CTCAACGCCA ATAAGTTCGT CCACAGAGAC
3451 CTTGCTGCCC GGAATTGCAT GGTAGCCGAA GATTTCACAG TCAAAATCGG
3501 AGATTTGGT ATGACGCGAG ATATCTATGA GACAGACTAT TACCGGAAAG
3551 GAGGCAAAGG GCTGCTGCCC GTGCGCTGGA TGTCTCCCGA GTCCCTCAAG
3601 GATGGAGTCT TCACCACTTA CTCGGACGTC TGGTCCTTCG GGGTCGTCCT
3651 CTGGGAGATC GCCACACTGG CCGAGCAGCC CTACCAGGGC TTGTCCAACG
3701 AGCAAGTCCT TCGCTTCGTC ATGGAGGGCG GCCTTCTGGA CAAGCCAGAC
```

FIGURE 3 (Continued....)

```
3751  AACTGTCCTG ACATGCTGTT TGAACTGATG CGCATGTGCT GGCAGTATAA
3801  CCCCAAGATG AGGCCCTTCCT TCCCTGGAGAT CATCAGCAGC ATCAAAGAGG
3851  AGATGGAGCC TGGCTTCCGG GAGGTCTCCT TCTACTACAG CGAGGAGAAC
3901  AAGCTGCCCG AGCCGGAGGA GCTGGACCTG GAGCCAGAGA ACATGGAGAG
3951  CGTCCCCCTG GACCCCCTCGG CCTCCCTCGTC CTCCCTGCCA CTGCCCGACA
4001  GACACTCAGG ACACAAGGCC GAGAACGGCC CCGGCCCTGG GGTGCTGGTC
4051  CTCCGCGCCA GCTTCGACGA GAGACAGCCT TACGCCCACA TGAACGGGGG
4101  CCGCAAGAAC GAGCGGGCCT TGCCGCTGCC CCAGTCTTCG ACCTGCTGAT
4151  CCTTGGATCC TGAATCTGTG CAAACAGTAA CGTGTGCCA CGCGCAGCGG
4201  GGTGGGGGGG GAGAGAGAGT CATTCACAAG CCTCCTGTAC
4251  CTCAGTGGAT CTTCAGTTCT GCCCTTGCTG CCCGCGGGAG ACAGCTTCTC
4301  TGCAGTAAAA CACATTTGGG ATGTTCCTTT TTTCAATATG CAAGCAGCTT
4351  TTTATTCCCT GCCCAAACCC TTAACTGACA TGGGCCTTTA AGAACCTTAA
4401  TGACAACACT TAATAGCAAC AGAGCACTTG AGAGCCAGTC TCCTCACTCT
4451  GTCCCTGTCC TTCCCTGTCC TCCCTTTCTC TCTCCCTCTCT GCTTCATAAC
```

FIGURE 3 (Continued....)

```
4501 GGAAAATAA TTGCCACAAG TCCAGCTGGG AAGCCCTTTT TATCAGTTTG
4551 AGGAAGTGGC TGTCCCTGTG GCCCCATCCA ACCACTGTAC ACACCCGCCT
4601 GACACCGTGG GTCATTACAA AAAAACACGT GGAGATGGAA ATTTTTACCT
4651 TTATCTTTCA CCTTTCTAGG GACATGAAAT TTACAAAGGG CCATCGTTCA
4701 TCCAAGGCTG TTACCATTTT AACGCTGCCT AATTTTGCCA AAATCCTGAA
4751 CTTTCTCCCT CATCGGCCCG GCGCTGATTC CTCGTGTCCG GAGGCATGGG
4801 TGAGCATGGC AGCTGGTTGC TCCATTTGAG AGACACGCTG GCGACACACT
4851 CCGTCCATCC GACTGCCCCT GCTGTGCTGC TCAAGGCCAC AGGCACACAG
4901 GTCTCATTGC TTCTGACTAG ATTATTATTT GGGGGAACTG GACACAATAG
4951 GTCTTTCTCT CAGTGAAGGT GGGGAGAAGC TGAACCGGC
```

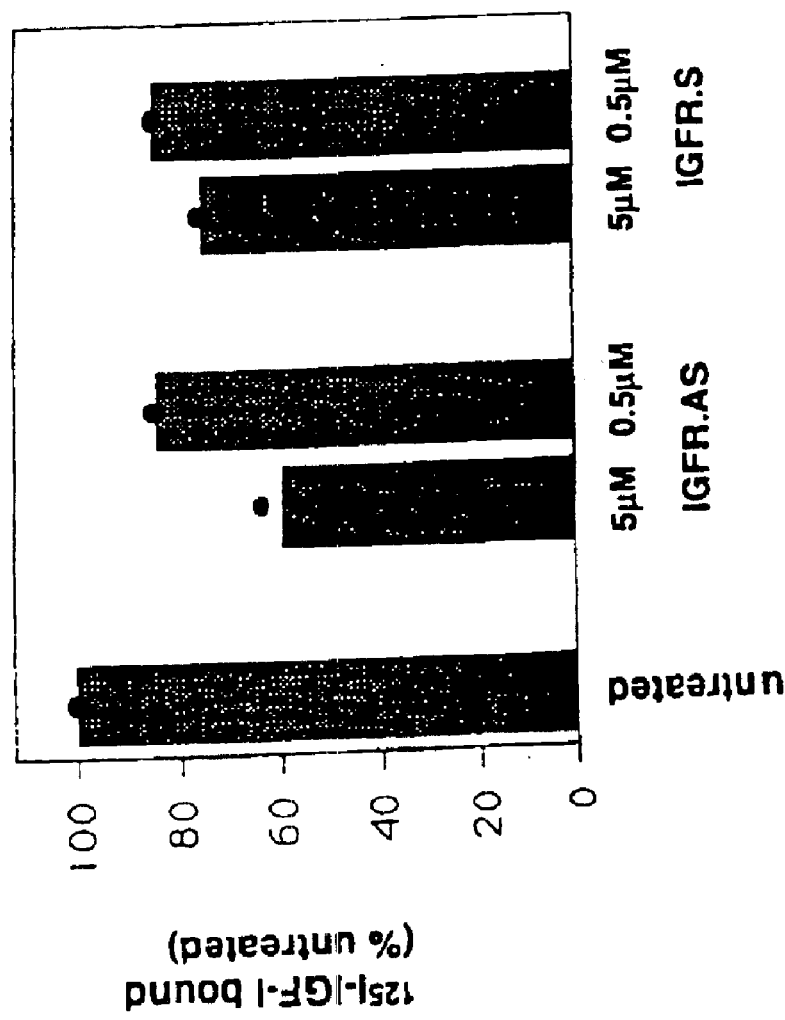
FIGURE 6 Inhibition of IGF-I binding by antisense oligonucleotides to IGF-I receptor

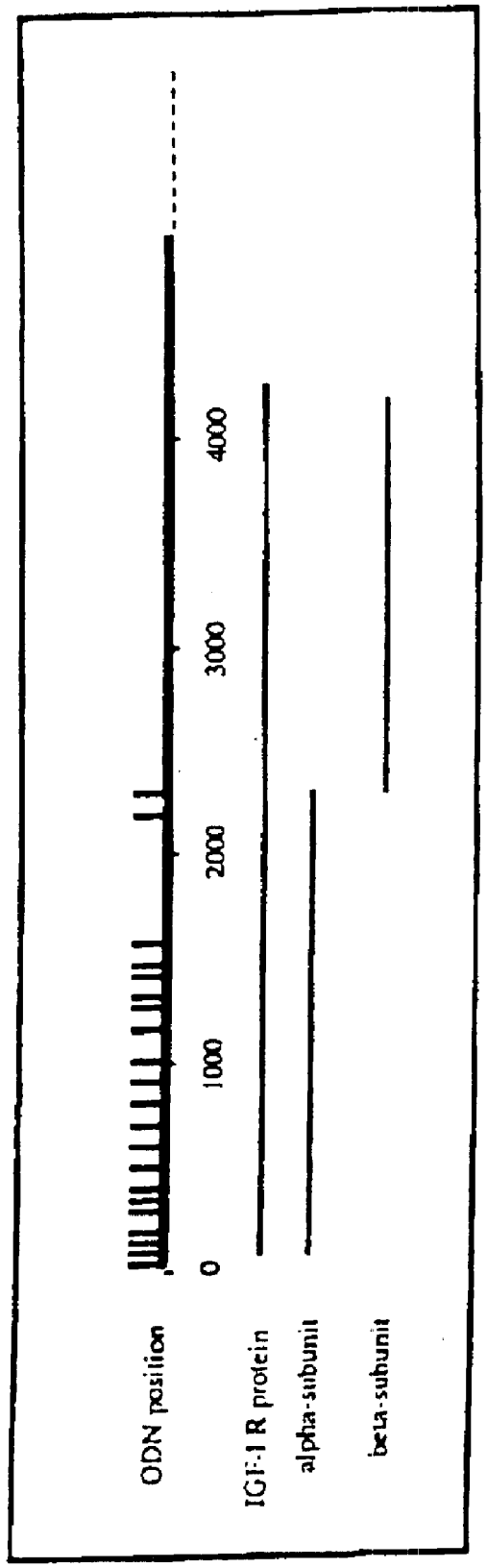
Figure 9 Map of IGF-1 Receptor mRNA and position of target ODNs

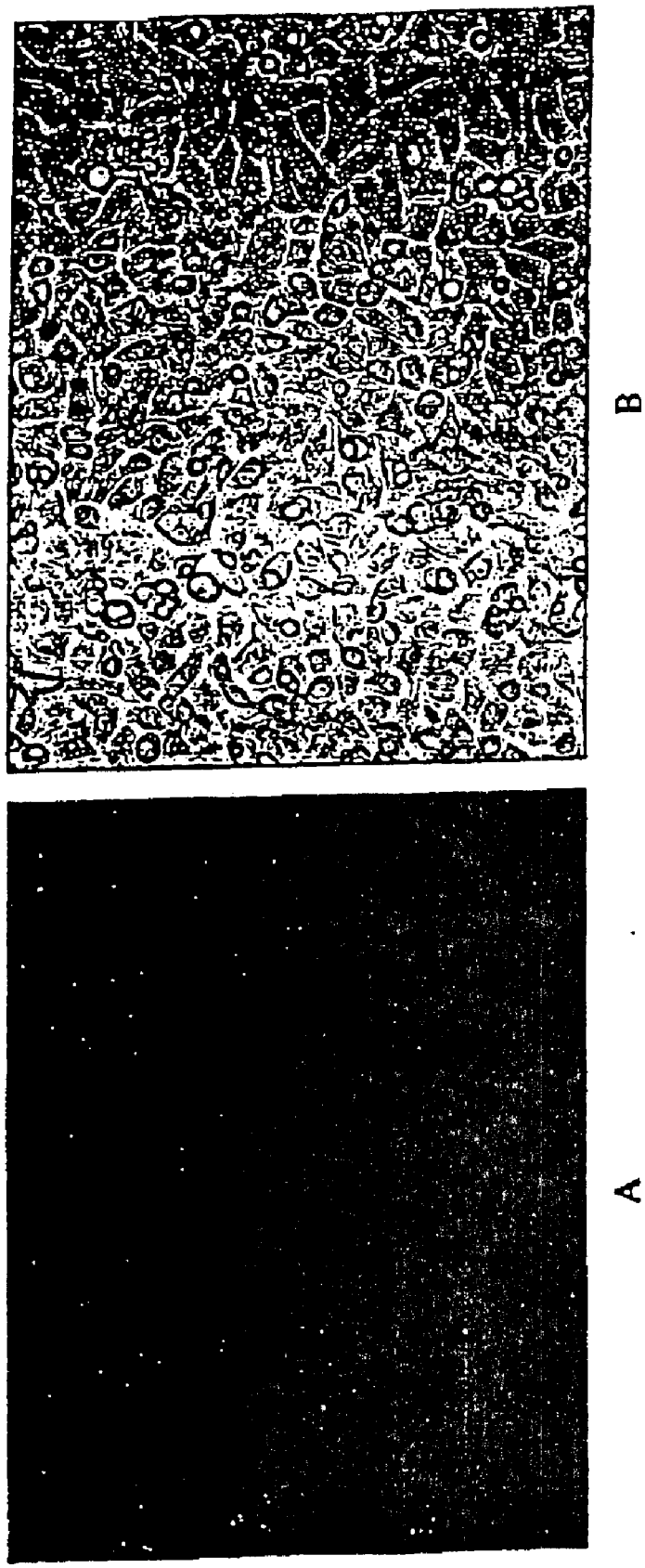
Figure 10  Lipid-mediated uptake of oligonucleotide in keratinocytes

Figure 11 Uptake (A) and toxicity (B) of ODN/ lipid complexes in keratinocytes
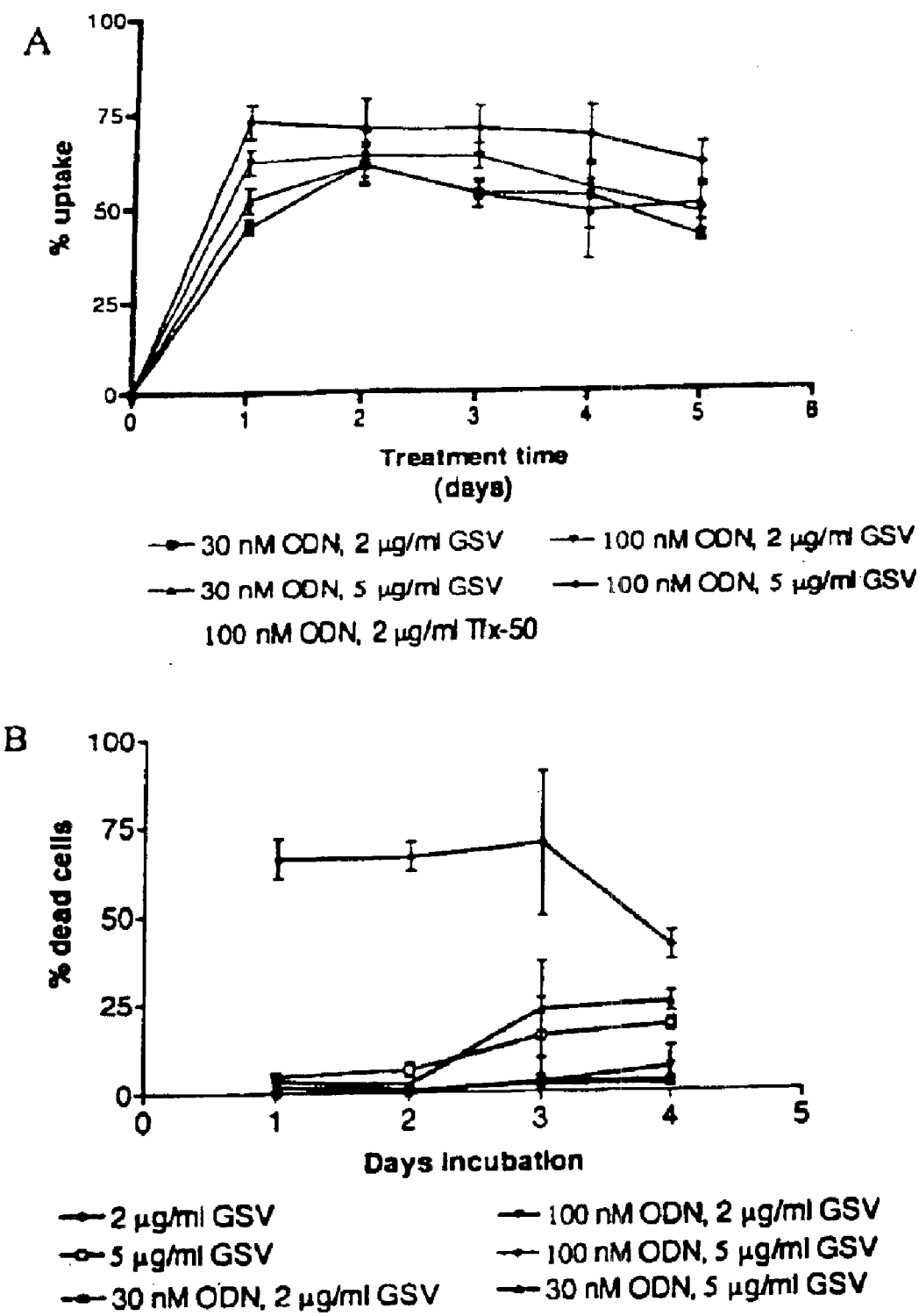

Figure 12  IGF-I Receptor mRNA in ODN treated (30nM) HaCaT cells (2μg/ml GSV)
A
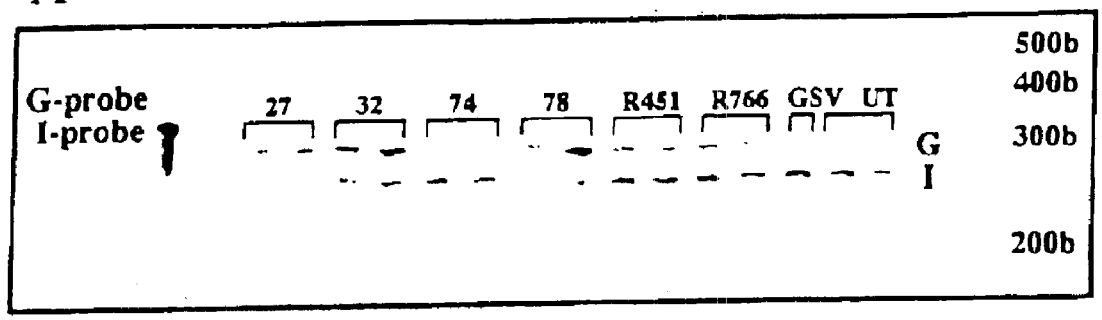
B
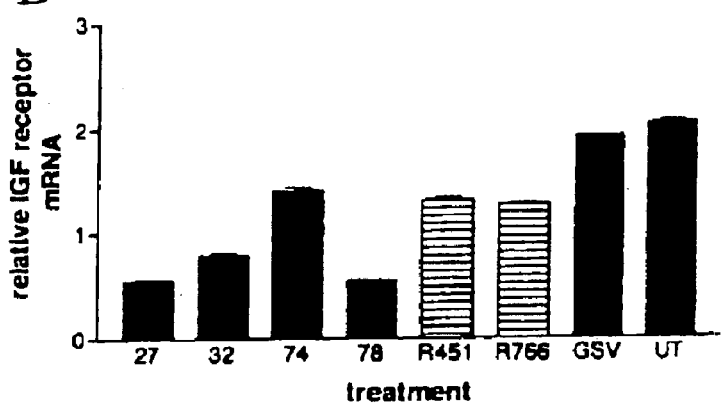

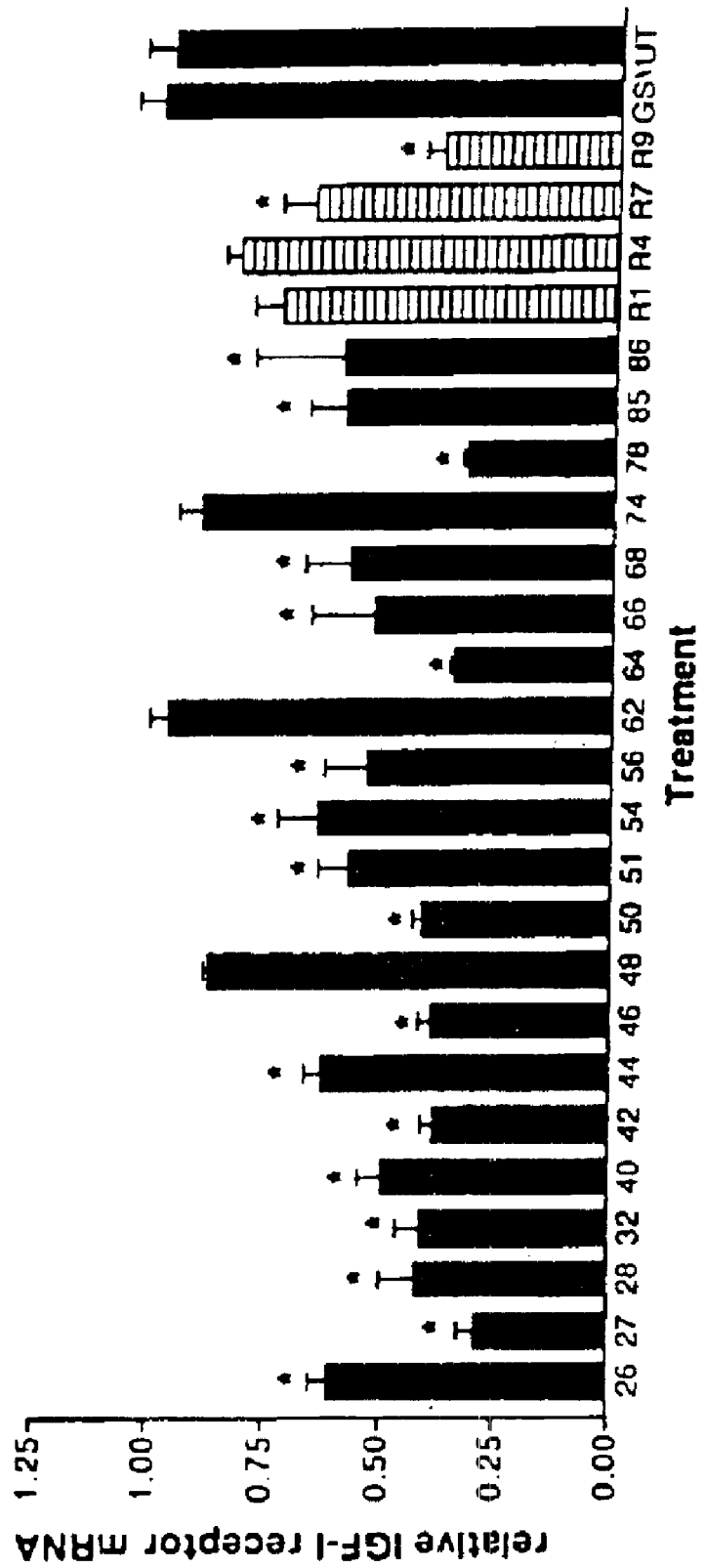
Figure 13 IGF-1 receptor mRNA in ODN treated (30nM) HaCaT cells (2μg/ml GSV)

Effect of antisense oligonucleotides on IGF-1 receptor levels on the surface of keratinocytes:
Competition Assay - $^{125}$I IGF-1 vs Des 1-3 IGF-1

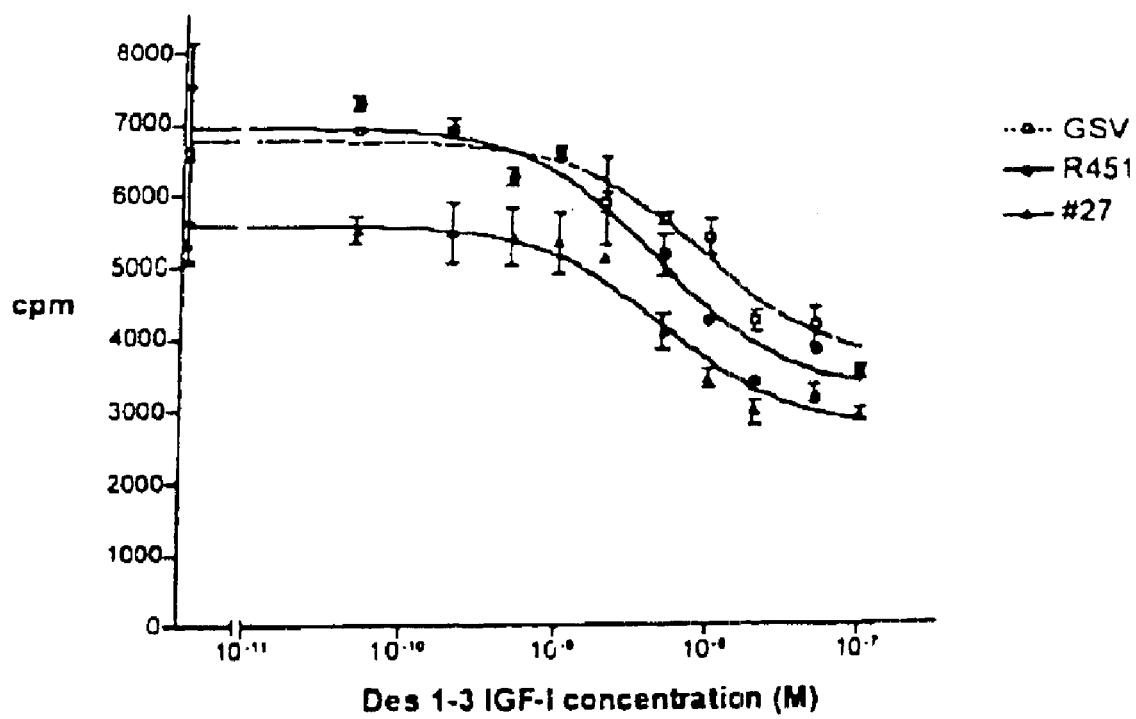

Figure 16  H&E stained sections of (A) psoriatic skin biopsy prior to grafting and (B) 49 day old psoriatic skin graft using skin from the same donor

Figure 17 Uptake of oligonucleotide after intradermal injection into psoriatic skin graft on a nude mouse

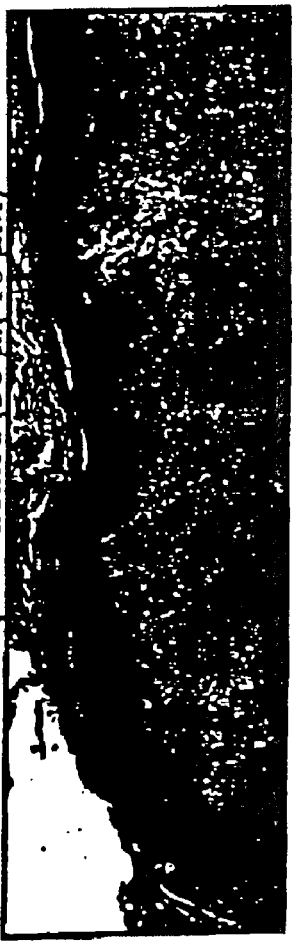
Figure 18c

Figure 19a
Donor JH
Pregraft
Donor JH
PBS treated
50 ul
Donor JH
50 treated
50 ul, 10 uM Figure 19b
Donor LB Pregraft
Donor LB PBS treated 50 ul
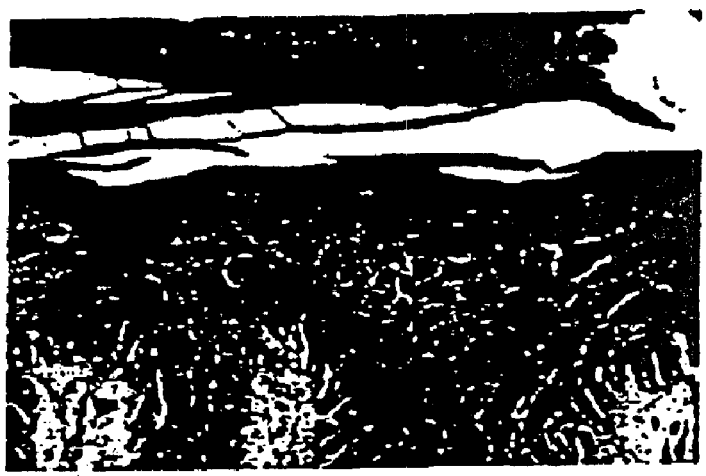
Donor LB # 74 treated 50 ul, 10 uM

Figure 19c
Donor PW
Pregraft
Donor PW
R451 treated
50 ul, 10 uM
Donor PW
74 treated
50 ul, 10 uM Figure 19d
Donor GM
Pregraft
Donor GM
R451 treated
50 ul, 10 uM
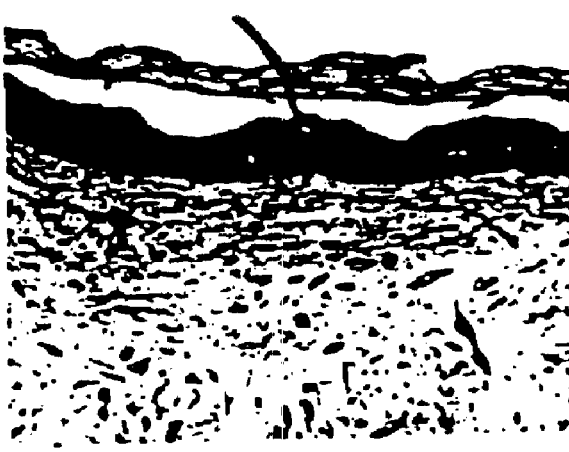
Donor GM
27 treated
50 ul, 10 uM

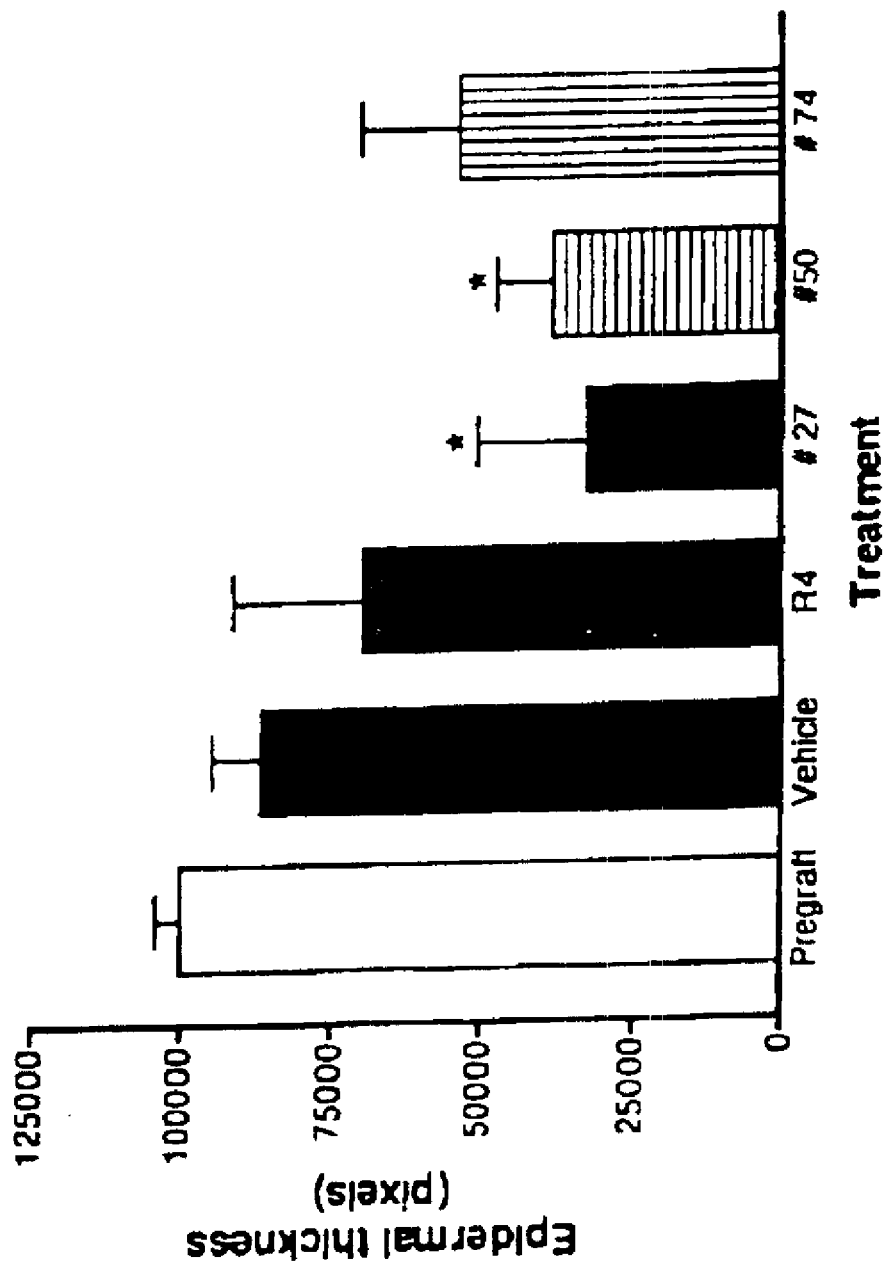
Figure 20 Suppression of psoriasis after treatment with oligonucleotide (quantification)

Figure 22 Penetration of oligonucleotide into human skin after topical treatment

Figure 23 Penetration of oligonucleotide into human skin after application of topical gel formulation

Figure 31c

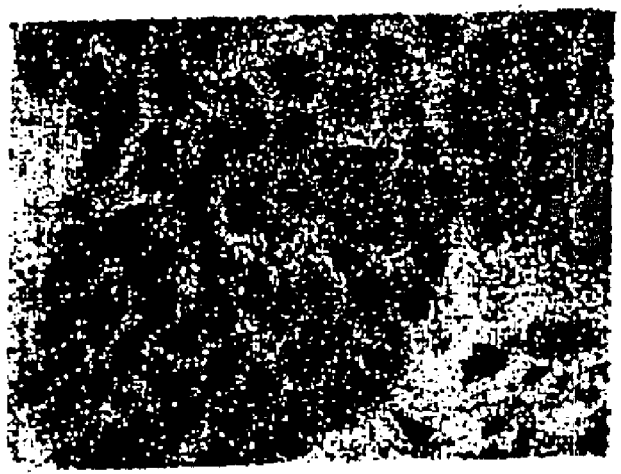
Figure 32b

METHOD FOR THE PROPHYLAXIS AND/OR TREATMENT OF MEDICAL DISORDERS

CROSS REFERENCE TO RELATED APPLICATION

This application claims the benefit of U.S. Application Ser. No. 60/140,345, the disclosure of which is incorporated herein by reference.

FIELD OF THE INVENTION

The present invention relates generally to a method for the prophylaxis and/or treatment of medical disorders, and in particular proliferative and/or inflammatory skin disorders, and to genetic molecules useful for same. The present invention is particularly directed to genetic molecules capable of modulating growth factor interaction with its receptor on cells such as epidermal keratinocytes to inhibit, reduce or otherwise decrease stimulation of this layer of cells. The present invention contemplates, in a particularly preferred embodiment, a method for the prophylaxis and/or treatment of psoriasis or neovascularization conditions such as neovascularization of the retina. The present invention is further directed to the subject genetic molecules in adjunctive therapy for epidermal hyperplasia, such as in combination with UV treatment, and to facilitate apoptosis of cancer cells and in particular cancer cells comprising keratinocytes.

BACKGROUND OF THE INVENTION

Bibliographic details of the publications numerically referred to in this specification are collected at the end of the description.

The reference to any prior art in this specification is not, and should not be taken as, an acknowledgment or any form of suggestion that that prior art forms part of the common general knowledge in Australia or any other country.

Psoriasis and other similar conditions are common and often distressing proliferative and/or inflammatory skin disorders affecting or having the potential to affect a significant proportion of the population. The condition arises from over proliferation of basal keratinocytes in the epidermal layer of the skin associated with inflammation in the underlying dermis. Whilst a range of treatments have been developed, none is completely effective and free of adverse side effects. Although the underlying cause of psoriasis remains elusive, there is some consensus of opinion that the condition arises at least in part from over expression of local growth factors and their interaction with their receptors supporting keratinocyte proliferation via keratinocyte receptors which appear to be more abundant during psoriasis.

One important group of growth factors are the dermally-derived insulin-like growth factors (IGFs) which support keratinocyte proliferation. In particular, IGF-I and IGF-II are ubiquitous peptides each with potent mitogenic effects on a broad range of cells. Molecules of the IGF type are also known as "progression factors" promoting "competent" cells through DNA synthesis. The IGFs act through a common receptor known as the Type I or IGF-I receptor, which is tyrosine kinase linked. They are synthesised in mesenchymal tissues, including the dermis, and act on adjacent cells of mesodermal, endodermal or ectodermal origin. The regulation of their synthesis involves growth hormone (GH) in the liver, but is poorly defined in most tissues [1].

Particular proteins, referred to as IGF binding proteins (IGFBPs), appear to be involved in autocrine/paracrine regulation of tissue IGF availability [2]. Six IGFBPs have so far been identified. The exact effects of the IGFBPs is not clear and observed effects in vitro have been inhibitory or stimulatory depending on the experimental method employed [3]. There is some evidence, however, that certain IGFBPs are involved in targeting IGF-I to its cell surface receptor.

Skin, comprising epidermis and underlying dermis, has GH receptors on dermal fibroblasts [4]. Fibroblasts synthesize IGF-I as well as IGFBPs-3, -4, -5 and -6 [5] which may be involved in targeting IGF-I to adjacent cells as well as to the overlaying epidermis. The major epidermal cell type, the keratinocyte, does not synthesize IGF-I, but possesses IGF-I receptors and is responsive to IGF-I [6].

It is apparent, therefore, that IGF-I and other growth promoting molecules, are responsible for or at least participate in a range of skin cell activities. In accordance with the present invention, the inventors have established that aberrations in the normal functioning of these molecules or aberrations in their interaction with their receptors is an important factor in a variety of medical disorders such as proliferative and/or inflammatory skin disorders. It is proposed, therefore, to target these molecules or other molecules which facilitate their functioning or interaction with their receptors to thereby ameliorate the effects of aberrant activity during or leading to skin disease conditions and other medical conditions such as those involving neovascularization. Furthermore, these molecules may also be used to facilitate apoptosis of target cells and may be useful as adjunctive therapy for epidermal hyperplasia.

SUMMARY OF THE INVENTION

Nucleotide and amino acid sequences are referred to by a sequence identifier, i.e. (SEQ ID NO:1) (SEQ ID NO:2), etc. A sequence listing is provided after the claims.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Accordingly, one aspect of the present invention contemplates a method for ameliorating the effects of a medical disorder such as a proliferative and/or inflammatory skin disorder in a mammal, said method comprising contacting the proliferating and/or inflamed skin or skin capable of proliferation and/or inflammation or a cell otherwise involved in the said medical disorder with an effective amount of a nucleic acid molecule or chemical analogue thereof capable of inhibiting or otherwise reducing a growth factor mediated cell proliferation and/or inflammation and/or other medical disorder.

According to this preferred embodiment, there is provided a method for ameliorating the effects of a medical disorder such as a proliferative and/or inflammatory skin disorder in a mammal, said method comprising contacting the proliferating and/or inflamed skin or skin capable of proliferation and/or inflammation or a cell otherwise involved with said medical disorder with an effective amount of a nucleic acid molecule or chemical analogue thereof capable of inhibiting or otherwise reducing IGF-I mediated cell proliferation and/or inflammation and/or other medical disorder.

According to this embodiment, there is provided a method for ameliorating the effects of a proliferative and/or inflammatory skin disorder such as psoriasis said method comprising contacting the proliferating and/or inflamed skin or skin capable of proliferation and/or inflammation with effective amounts of UV treatment and a nucleic acid molecule or chemical analogue thereof capable of inhibiting or otherwise reducing IGF-I mediated cell proliferation and/or inflammation.

According to this embodiment, there is provided in a particularly preferred aspect a ribozyme comprising a hybridising region and a catalytic region wherein the hybridising region is capable of hybridising to at least part of a target sequence transcribed from a genomic gene corresponding to SEQ ID NO.1 or SEQ ID NO.2 wherein said catalytic domain is capable of cleaving said target mRNA sequence to reduce or inhibit IGF-I mediated cell proliferation and/or inflammation and/or other medical disorders.

Yet another aspect of the present invention contemplates co-suppression to reduce expression or to inhibit translation of an endogenous gene encoding, for example, IGF-I, its receptor, or IGFBPs such as IGFBP-2 and/or -3. In co-suppression, a second copy of an endogenous gene or a substantially similar copy or analogue of an endogenous gene is introduced into a cell following topical administration. As with antisense molecules, nucleic acid molecules defining a ribozyme or nucleic acid molecules useful in co-suppression may first be protected such as by using a nonionic backbone.

Another aspect of the present invention contemplates a pharmaceutical composition for topical administration which comprises a nucleic acid molecule capable of inhibiting or otherwise reducing IGF-I mediated cell proliferation such as psoriasis and one or more pharmaceutically acceptable carriers and/or diluents.

Yet another aspect of the present invention contemplates the use of a nucleic acid molecule in the manufacture of a medicament for the treatment of proliferative and/or inflammatory skin disorders or other medical disorders mediated by a growth factor.

Still a further aspect of the present invention contemplates an agent comprising a nucleic acid molecule as hereinbefore defined useful in the treatment of proliferative and/or inflammatory skin disorders, such as psoriasis or other medical disorder.

The present invention further contemplates the use of the genetic molecules and in particular the antisense molecules to inhibit the anti-apoptotic activity of IGF-I receptor.

BRIEF DESCRIPTION OF THE FIGURES

FIG. 6 is a graphical representation showing inhibition of IGF-I binding by antisense oligonucleotides to IGF-I receptor. IGFR.AS: antisense; IGFR.S: sense.

FIG. 9 is a diagramatic representation of a map of IGF-I Receptor mRNA and position of target ODNs.

FIG. 10 is a photographical representation showing Lipid-mediated uptake of oligonucleotide in keratinocytes. HaCaT keratinocytes were incubated for 24 hours in medium (DMEM plus 10% v/v FCS) containing fluorescently labelled ODN (R451, 30 nM) and cytofectin GSV (2 µg/ml). The cells were then transferred to ODN-free medium and fluorescence microscopy (a) and phase contrast (b) images of the cells were obtained.

FIG. 11 is a graphical representation of uptake (A) and toxicity (B) of ODN/lipid complexes in keratinocytes. Confluence HaCaT keratinocytes were incubated in DMEM containing fluoresently labelled ODN (R451) plus liposome over 120 hours, viewed using fluorescene microscopy and trypan blue stained and counted.

FIG. 12 is a graphical representation of an IGF-I Receptor mRNA in ODN treated (30 µM) HaCaT cells (2 µg/ml GSV). HaCaT keratinocytes were treated for 96 hours with C-5 propynyl, dU, dC ODNs complexed with cytofectin GSV. Cells were treated with ODNs complementary to the human IGF-I receptor mRNA (27, 32, 74 and 78), 2 randomised sequence ODNs (R451) and R766), liposome alone (GSV) or were left untreated (UT). Total RNA was isolated then analysed for IGF-I receptor mRNA and GAPDH TiRNA levels by RNase Protection and PhosphorImager quantitiation.

(A) Electrophoretic analysis of IGF-I receptor and GAPDH mRNA fragments after RNase Protection. Molecular weight markers are shown on the right hand side. Full length probe is shown on the left hand side (G-probe and I-probe). GAPDH protected fragments (G) are seen at 316 bases and IGF-I receptor protected fragments (I) are seen at 276 bases.

(B) Relative level of IGF-I receptor mRNA following each treatment is shown.

FIG. 13 is a graphical representation of an IGF-I receptor mRNA in ODN treated (30 nM) HaCaT cells (2 µg/ml GSV). Summary of IGF-I receptor ODN screening data. HaCaT keratinocytes were treated for 96 hours with C-5 propynyl, dU, dC ODNs complexed with cytofectin GSV. Total RNA was isolated then analysed for IGF-I receptor mRNA and GAPDH mRNA levels by RNase protection and phosphorImager quantitation. Relative level of IGF-I receptor mRNA is shown after treatment with ODNs complementary to the human IGF-I receptor mRNA, 4 randomised sequence ODNs and liposome alone. (26–86=IGF-I receptor ODNs; R1, R4, R7 and R9=randomised ODNs (R1=R121, R4=R451, R7=R766, R9=R961); GSV=liposome alone; UT=untreated). *indicates a significant difference in relative IGF-I receptor mRNA from GSV treated cells (n=4–10, p<0.05).

Figure 14:
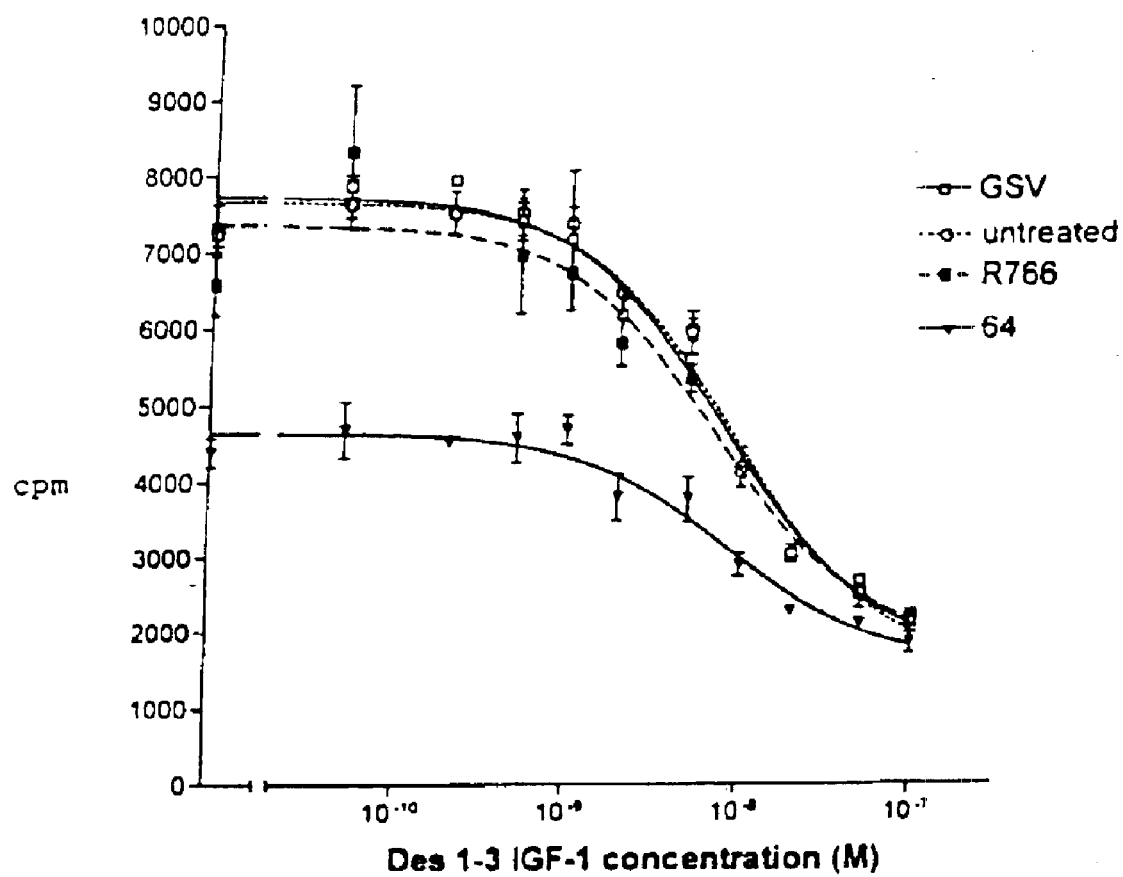

FIG. 14 is a graphical representation of the effect of antisense oligonucleotides on IGF-I receptor levels on the surface of keratinocytes. HaCaT cells were grown to confluence in 24 well plates in DMEM containing 10% v/v FCS. Oligodeoxynucleotide (ODN) and Cytofectin GSV (GSV, Glen Research) were mixed together in serum-free DMEM, incubated at room temperature for 10 minutes before being diluted ten-fold in medium and placed on the cells. Cells were incubated for 72 hours with 30 nM random sequence or antisense ODN and 2 µg/ml GSV or with GSV alone in DMEM containing 10% v/v FCS with solutions replaced every 24 hours. This was followed by incubation with ODN/GSV in serum-free DMEM for 48 hours. All incubations were performed at 37° C. Wells were washed twice with 1 ml cold PBS. Serum-free DMEM containing $10^{-10}$M $^{125}$I-IGF-I was added with or without the IGF-I analogue, des (1–3) IGF-I, at $10^{-10}$M to $10^{-7}$M. Cells were incubated at 4° C. for 17 hours with gentle shaking then washed three times with 1 ml cold PBS and lysed in 250 µl 0.5M NaOH/0.1% v/v Triton X-100 at room temperature for 4 hours. Specific binding of the solubilised cell extract was measured using a γ counter.

FIG. 15 is a graphical representation of the effect of antisense oligonucleotides on IGF-1 receptor levels on the surface of keratinocytes.

FIG. 16 is a photographical representation of H & E stained sections of (A) psoriatic skin biopsy prior to grafting and (B) 49 day old psoriatic skin graft using skin from the same donor.

FIG. 17 is a photographical representation of uptake of oligonucleotide after intradermal injection into psoriatic skin graft on a nude mouse. Psoriatic skin graft was intradermally injected with ODN (R451, 50 µl, 10 µM). The graft was removed and sectioned after 24 hours, then viewed using confocal microscopy.

Figure 18A:
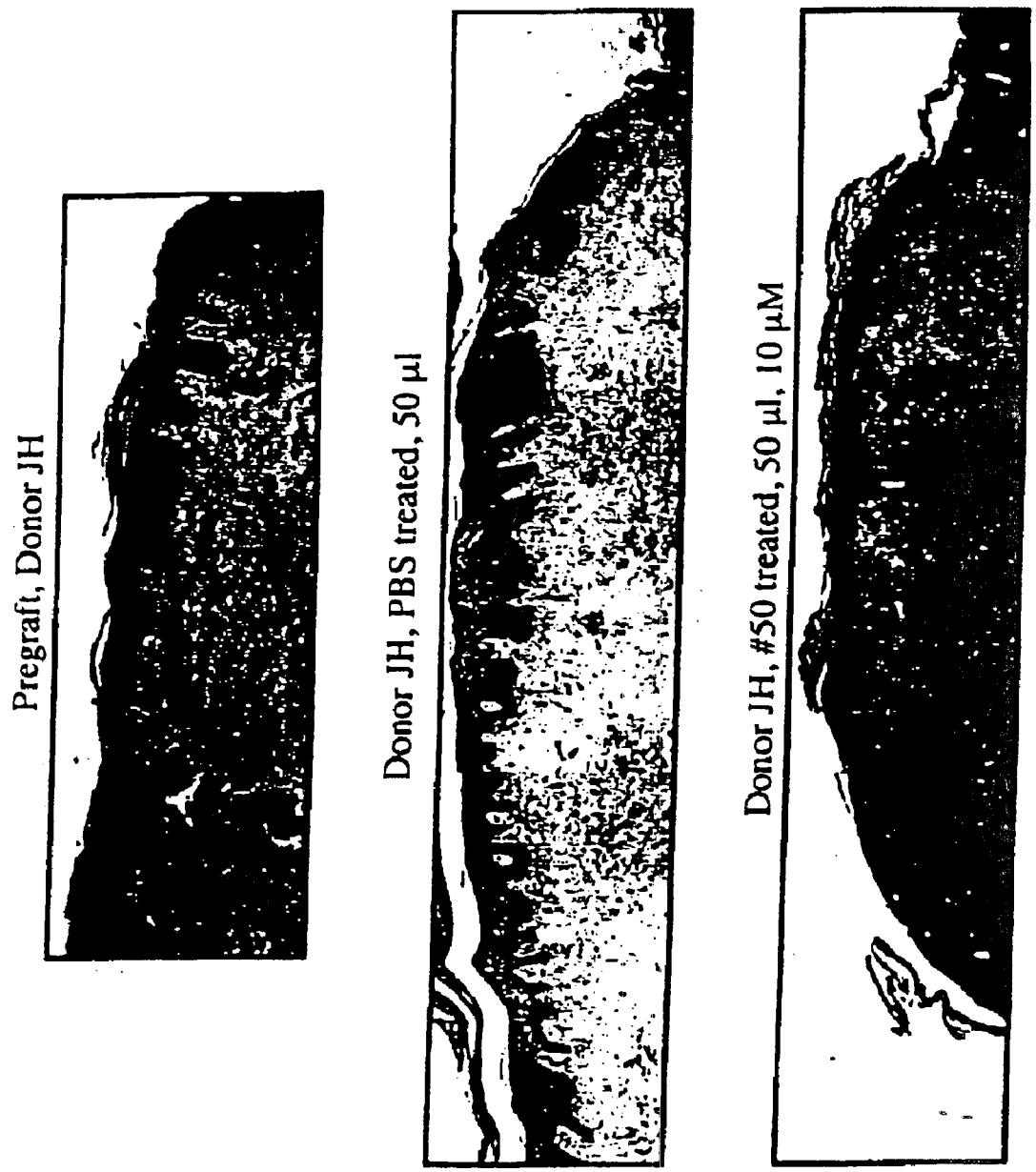

FIG. 18(a) is a photographical representation of Pregraft, Donor JH, Donor JH, PBS treated, 50 µl, Donor JH, #50 treated, 50 µl, 10 µM.

Figure 18B:
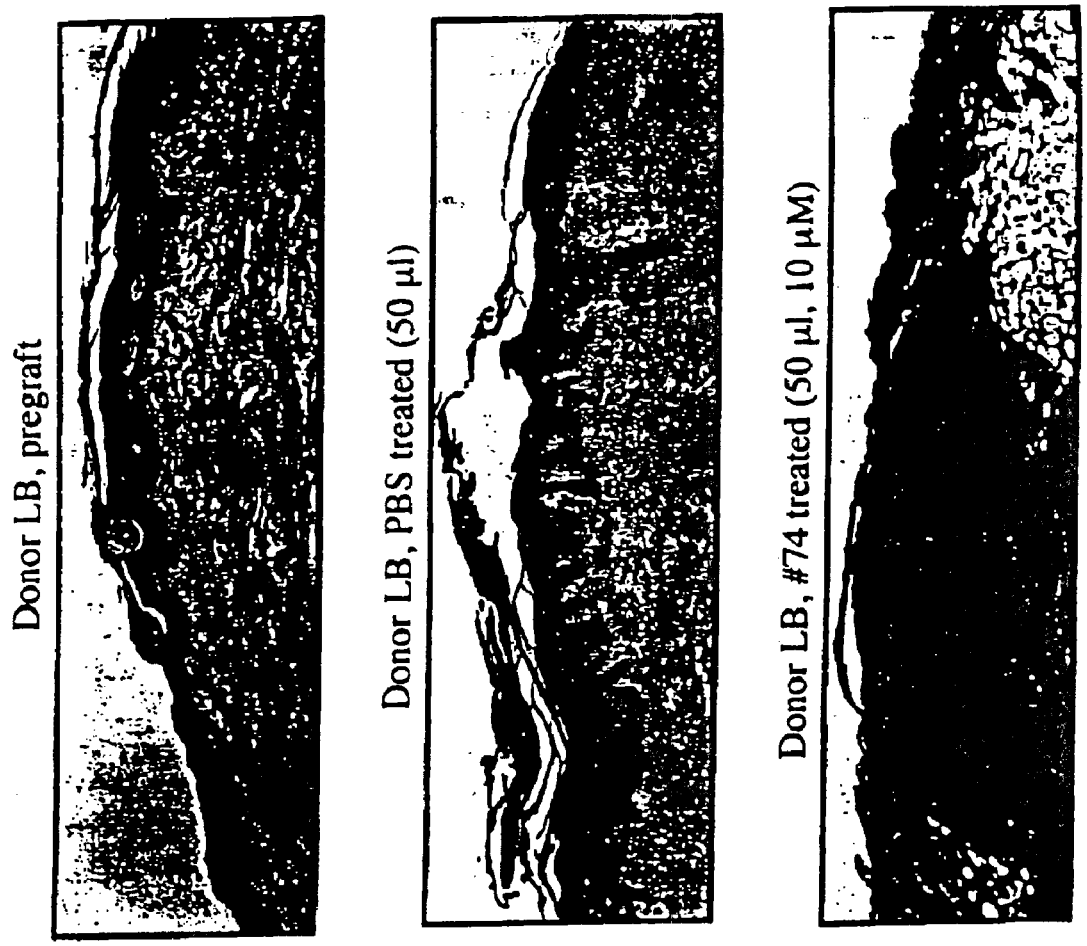

FIG. 18(b) is a photographical representation of Donor LB, pregraft, Donor LB, PBS treated (50 µl), Donor LB, #74 treated (50 µl, 10 µM).

FIG. 18(c) is a photographical representation of Donor PW, pregraft, Donor PW, R451 treated (50 µl, 10 µM), Donor LB, #74 treated (50 µl, 10 µM).

Figure 18D:
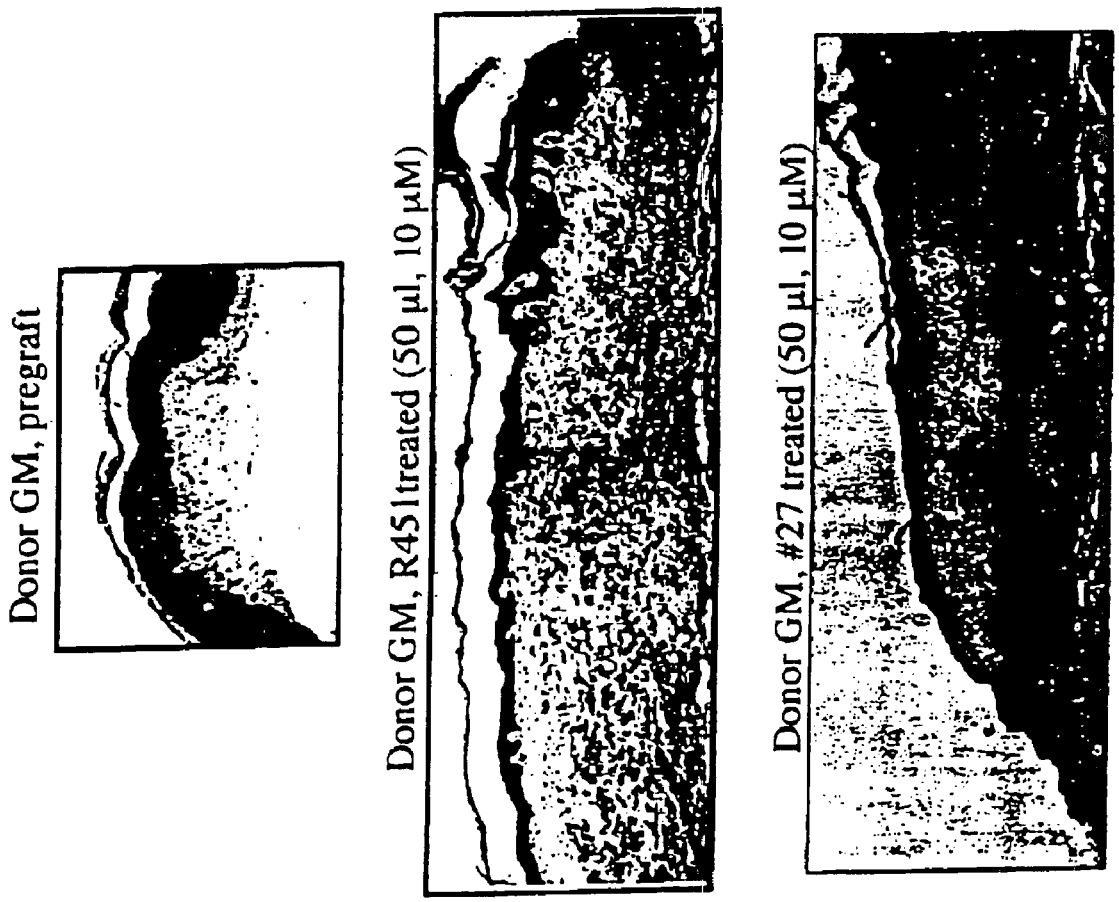

FIG. 18(d) is a photographical representation of Donor GM, pregraft, Donor GB, R451 treated (50 µl, 10 µM), Donor GM, #27 treated (50 µl, 10 µM).

FIG. 19(a) is a photographical representation showing Donor JH pregraft, Donor JH PBS treated 50 µl, Donor JH #50 treated 50 µl, 10 µM.

FIG. 19(b) is a photographical representation Donor LB pregraft, Donor LB PBS treated 50 µl, Donor LB #74 treated 50 µl, 10 µM.

FIG. 19(c) is a photographical representational showing Donor PW pregraft, Donor PW r451 treated 50 µl, 10 µM, Donor PW #74 treated 50 µl, 10 µM.

FIG. 19(d) is a photographical representation showing Donor GM pregraft, Donor GM R451 treated 50 µl, 10 µM, Donor #27 treated 50 µl, 10 µM.

FIG. 20 is a graphical representation showing suppression of psoriasis after treatment with oligonucleotide (quantification). Oligonucleotide (50 µl, 10 µM) was injected every two days for 20 days, as were control treatments. Skin thickness was measured by removing the skin and using computer software (MCID analysis) to measure the exact thickness of each graft. N=3–4 for each treatment. *indicates a significant difference from the pregraft value (ANOVA, P<0.05).

Figure 21:
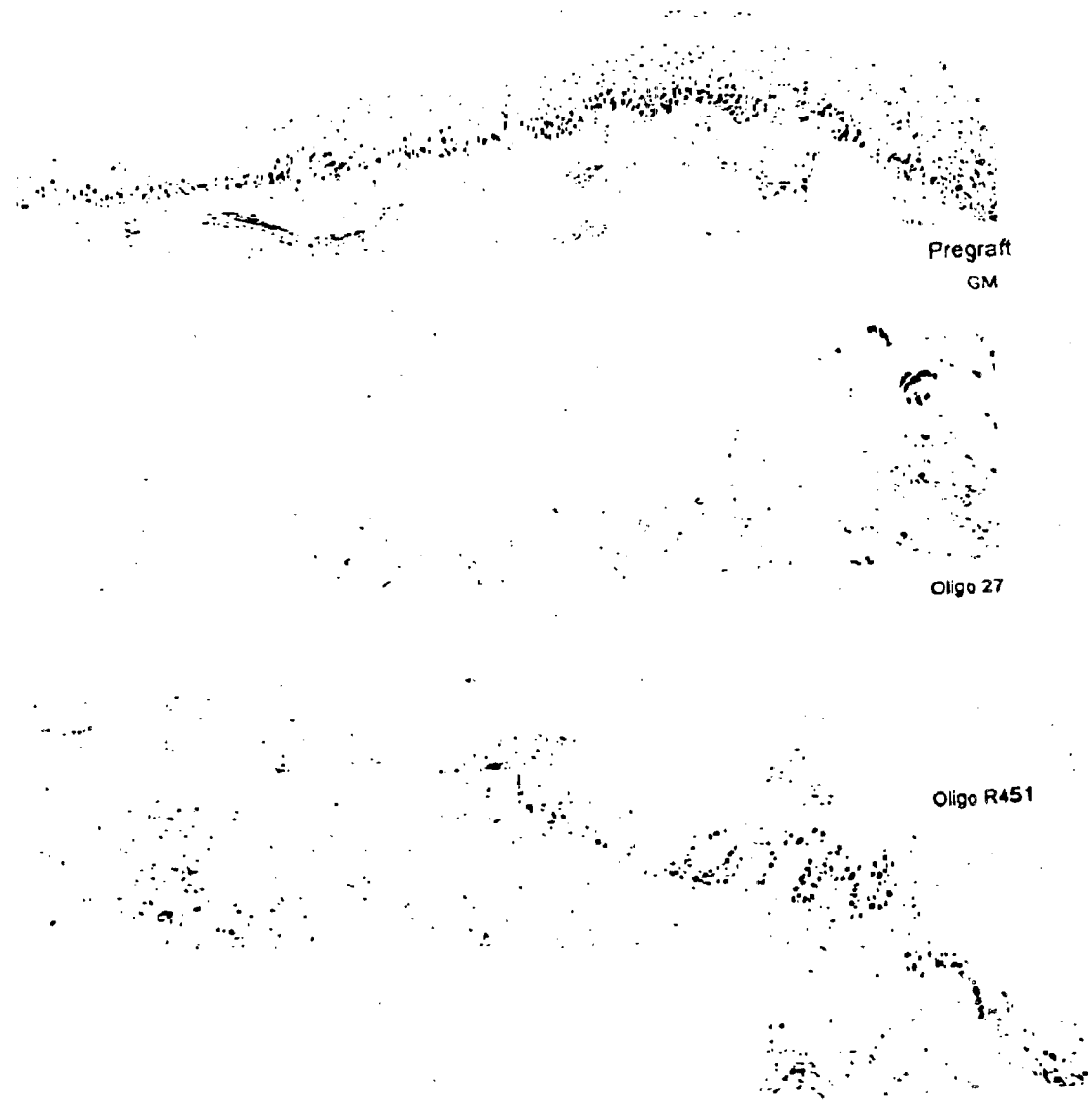

FIG. 21 is a photographic representation of αhKi-67 imunobiological binding.

Figure 22:
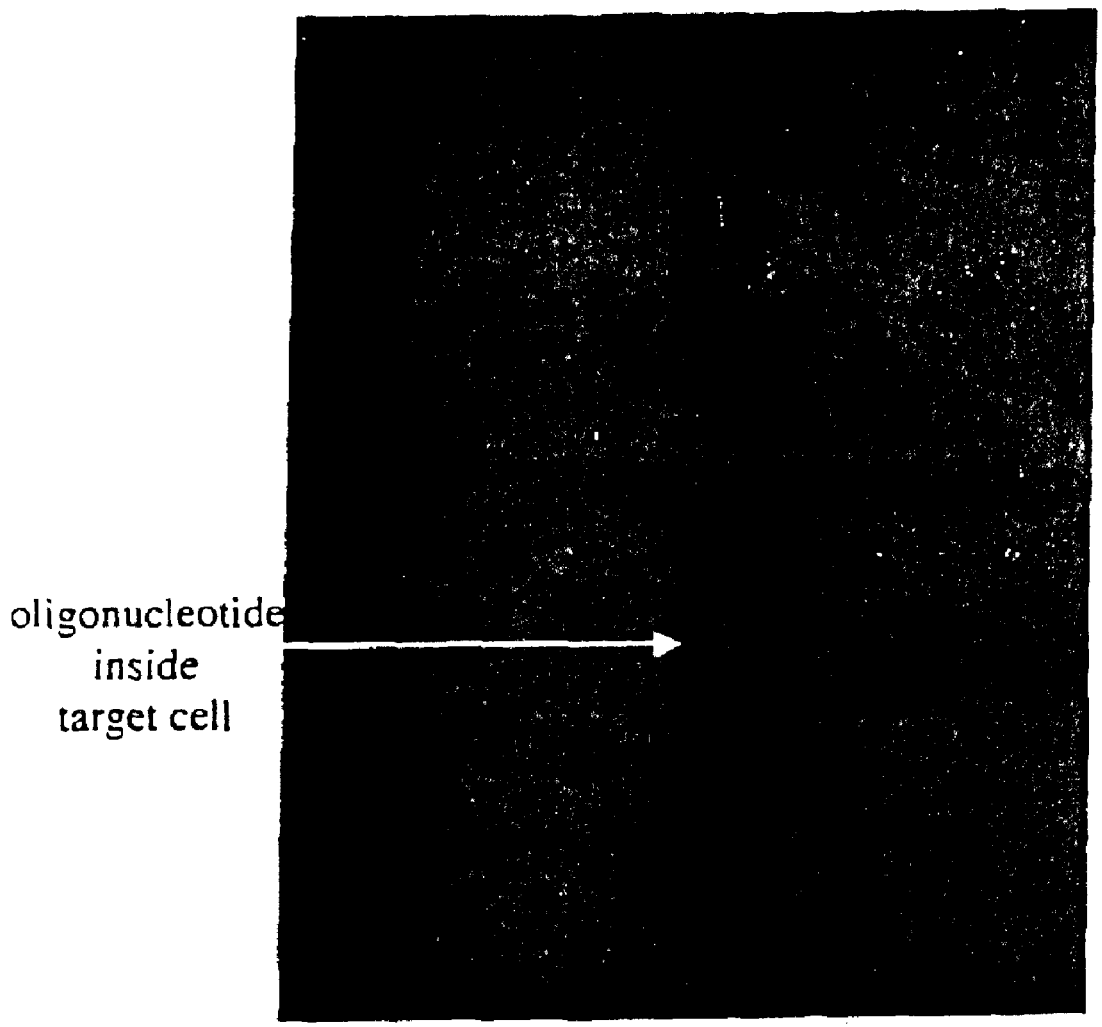

FIG. 22 is a photographical representation showing penetration of oligonucleotide into human skin after topical treatment. Fluorescently labelled oligonucleotide (10 µM R451) was applied topically after formulation with cytofectin GSV (10 µg/ml) and viewed using confocal microscopy.

Figure 23:

FIG. 23 is a photographical representation showing penetration of oligonucleotide into human skin after application of topical gel formation. Fluorescently labelled oligonucleotide (10 µM R451) was applied topically after complexing with cytofectin GSV (10 µg/ml) and formulation into 3% methylcellulose gel. Image was obtained using confocal microscopy.

Figure 24:
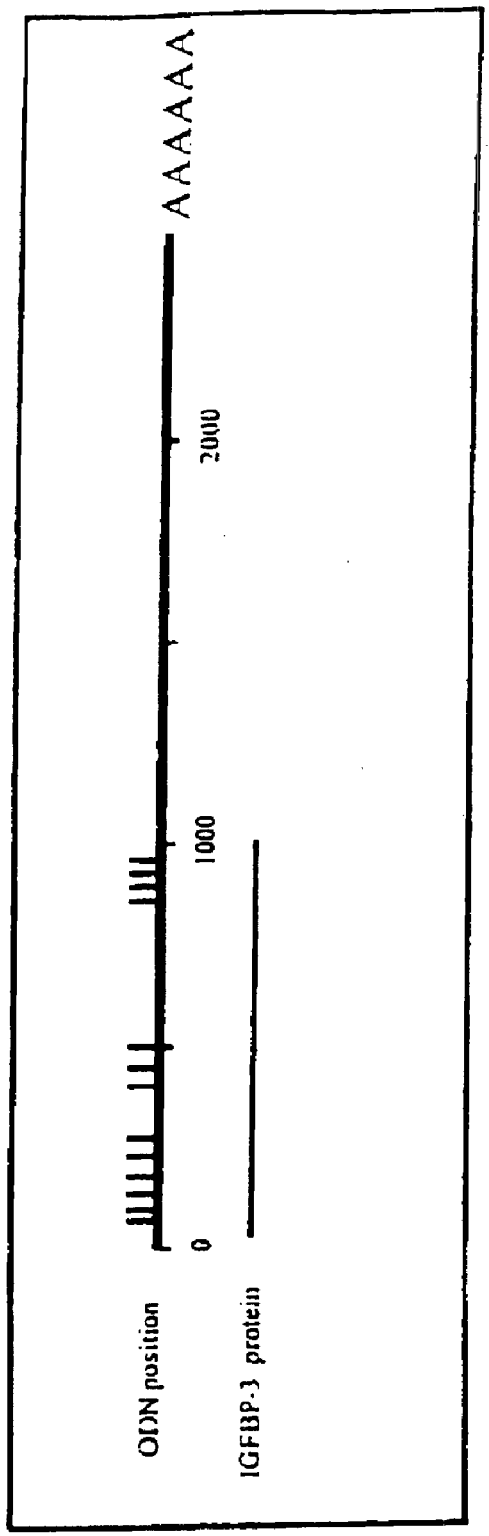

FIG. 24 is a graphical representation showing IGFBP-3 mRNA.

Figure 25A:
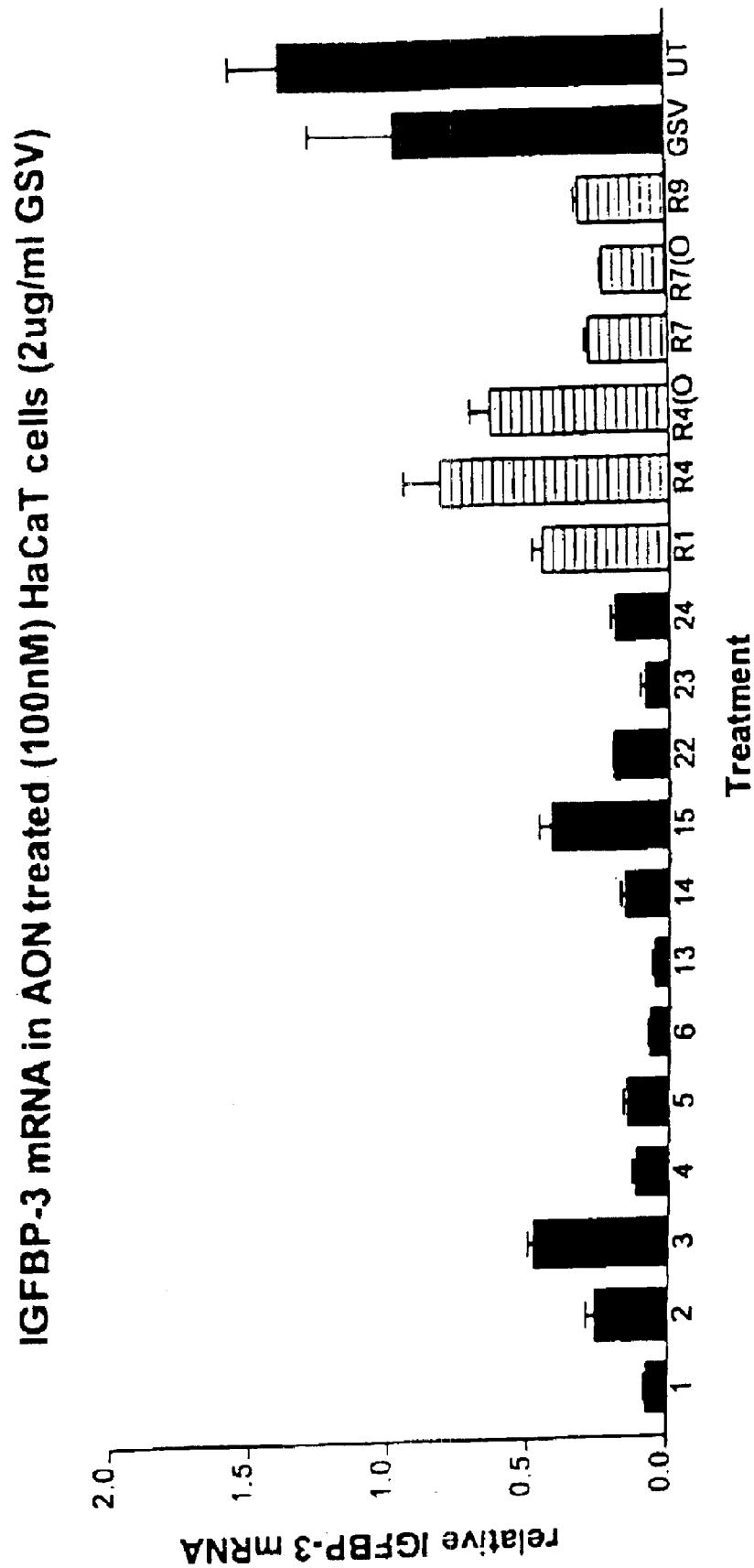

FIG. 25(a) is a graphical representation showing IGFBP-3 mRNA in AON treated (100 nM) HaCaT cells (2 µg/ml GSV).

Figure 25B:
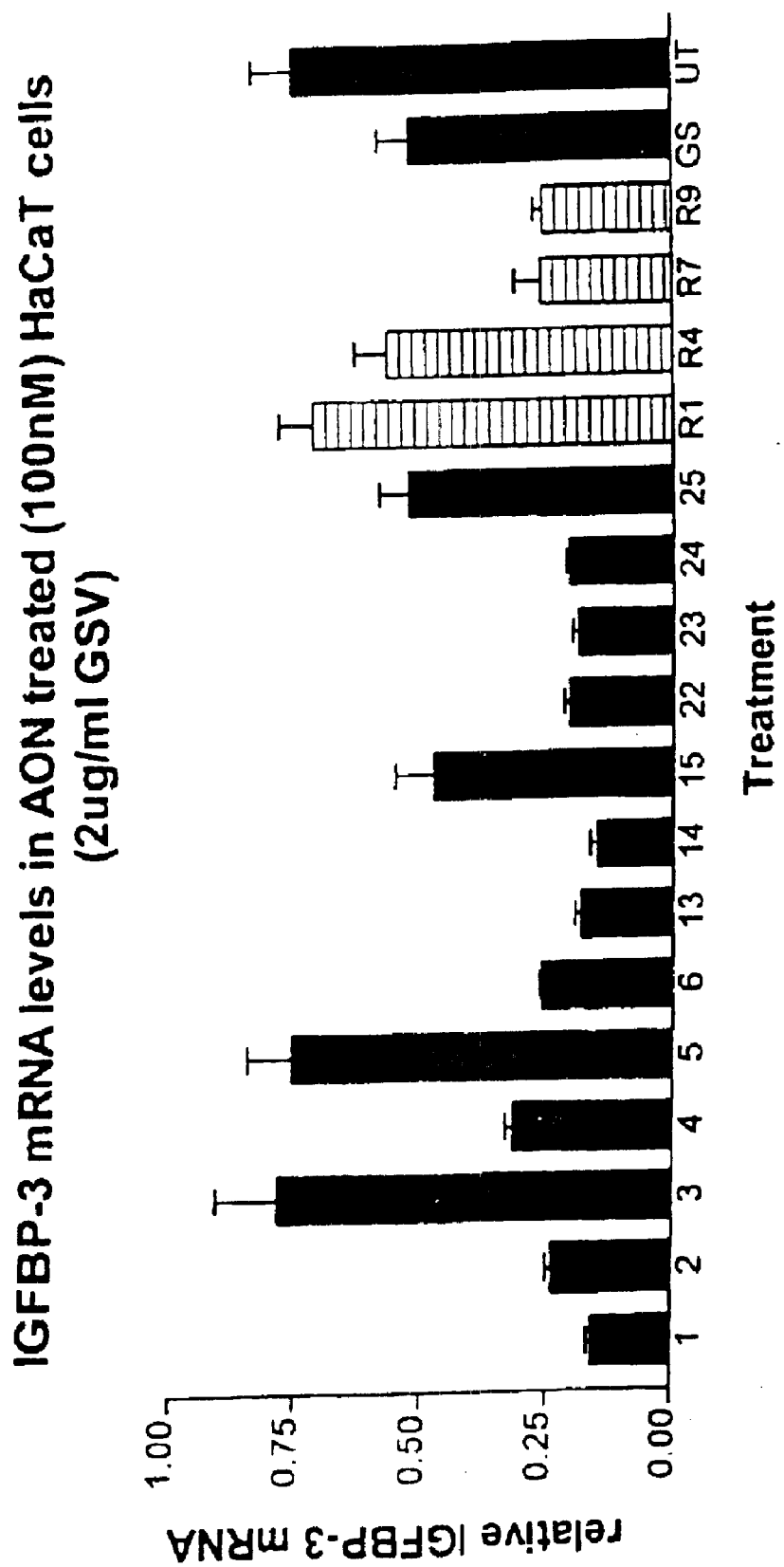

FIG. 25(b) is a graphical representation showing IGFBP-3 mRNA levels of AON treated (100 nm) HaCaT cells (2 µg/ml GSV).

Figure 25C:
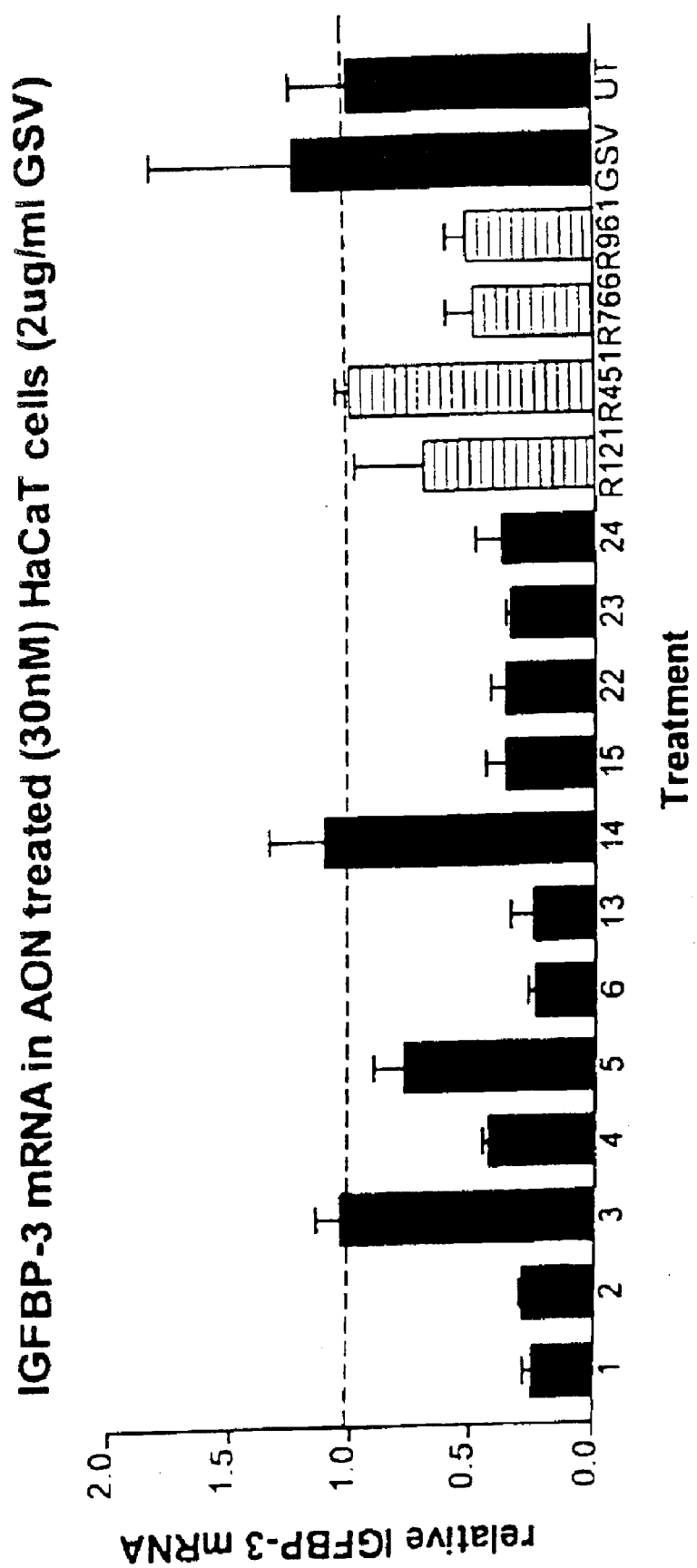

FIG. 25(c) is a graphical representation showing IGFBP-3 mRNA in AON treated (30 nM) HaCaT cells (2 µg/ml GSV).

Figure 25D:
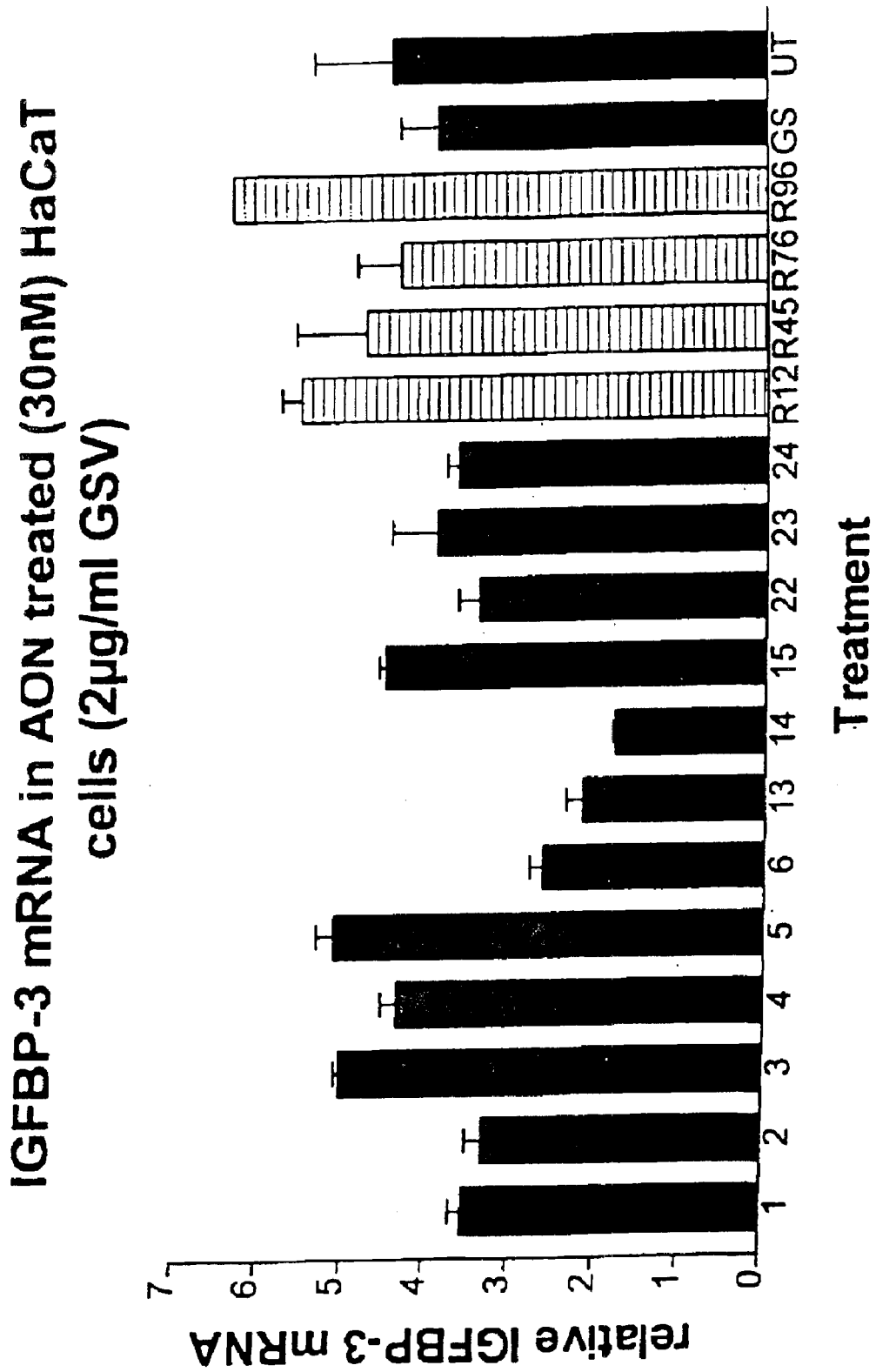

FIG. 25(d) is a graphical representation showing IGFBP-3 mRNA in AON treated (30 nM) HaCaT cells (2 µg/ml GSV).

Figure 26A:
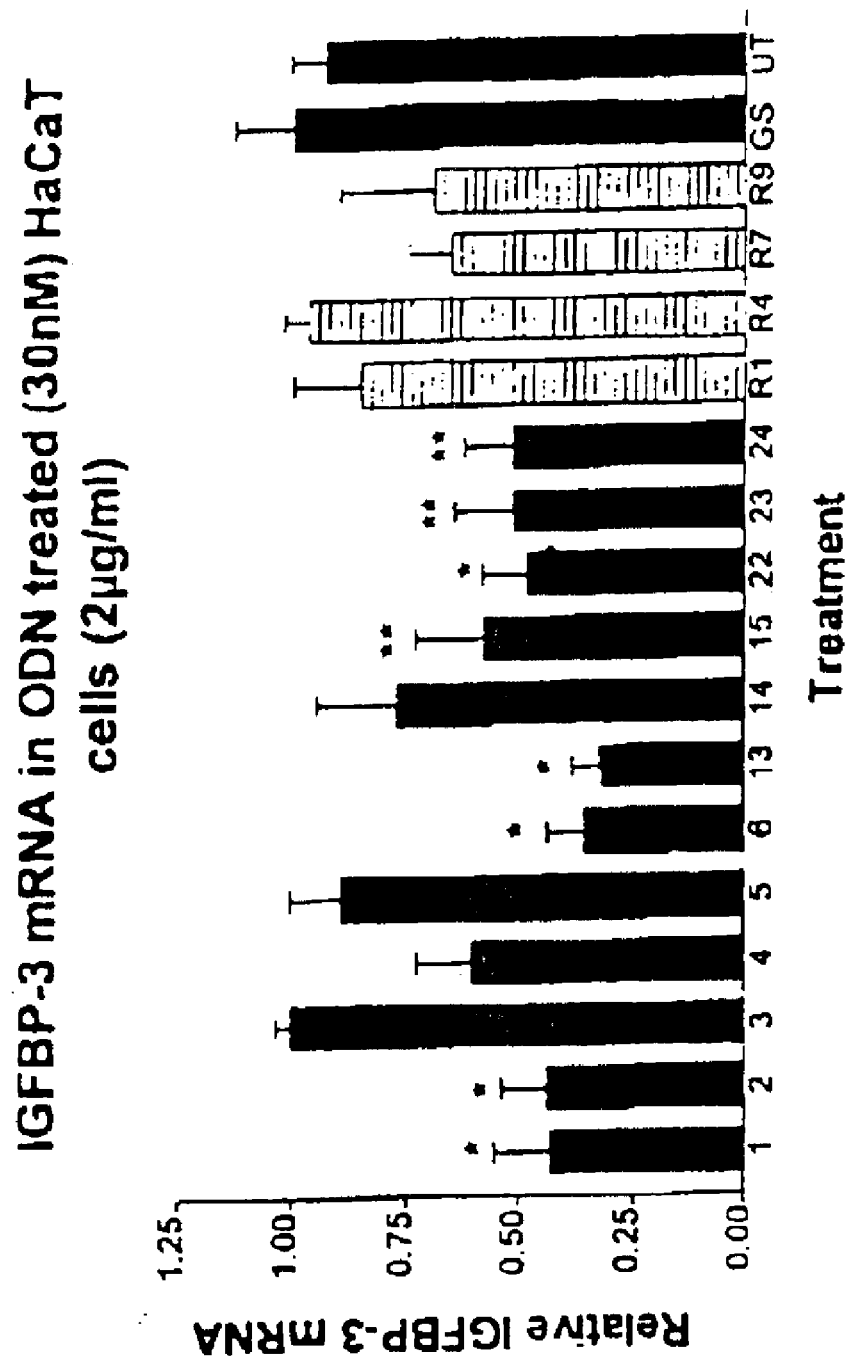

FIG. 26(a) is a graphical representation showing IGFBP-3 rRNA in ODN treated (30 nM) HaCaT cells (2 µg/ml). HaCaT keratinocytes were treated for 51 hours with C-5 propynl, dU, dC ODNs complexed with cytofectin GSV. Total RNA was isolated then analysed for IGFBP-3 mRNA and GAPDH mRNA levels by Northern analysis and phosphorImager quantitation. Relative level of IGFBP-3 mRNA is shown after treatment with ODNs complementary to the human IGFBP-3 mRNA, 4 randomised sequence ODNs and lipsome alone. (1–24=IGFBP-3 ODNs; R1, R4, R7 and R9=randomised ODNs (R1=R121, R4=R451, R7=R766, R9 R961); GS=liposome alone; UT=untreated). *indicates a significant different in relative IGFBP-3 mRNA from GSV treated cells (n=5–8, p<0.01), **indicates a significant difference in relative IGFBP-3 mRNA from GSV treated cells (n=5–8, p<0.05).

Figure 26B:
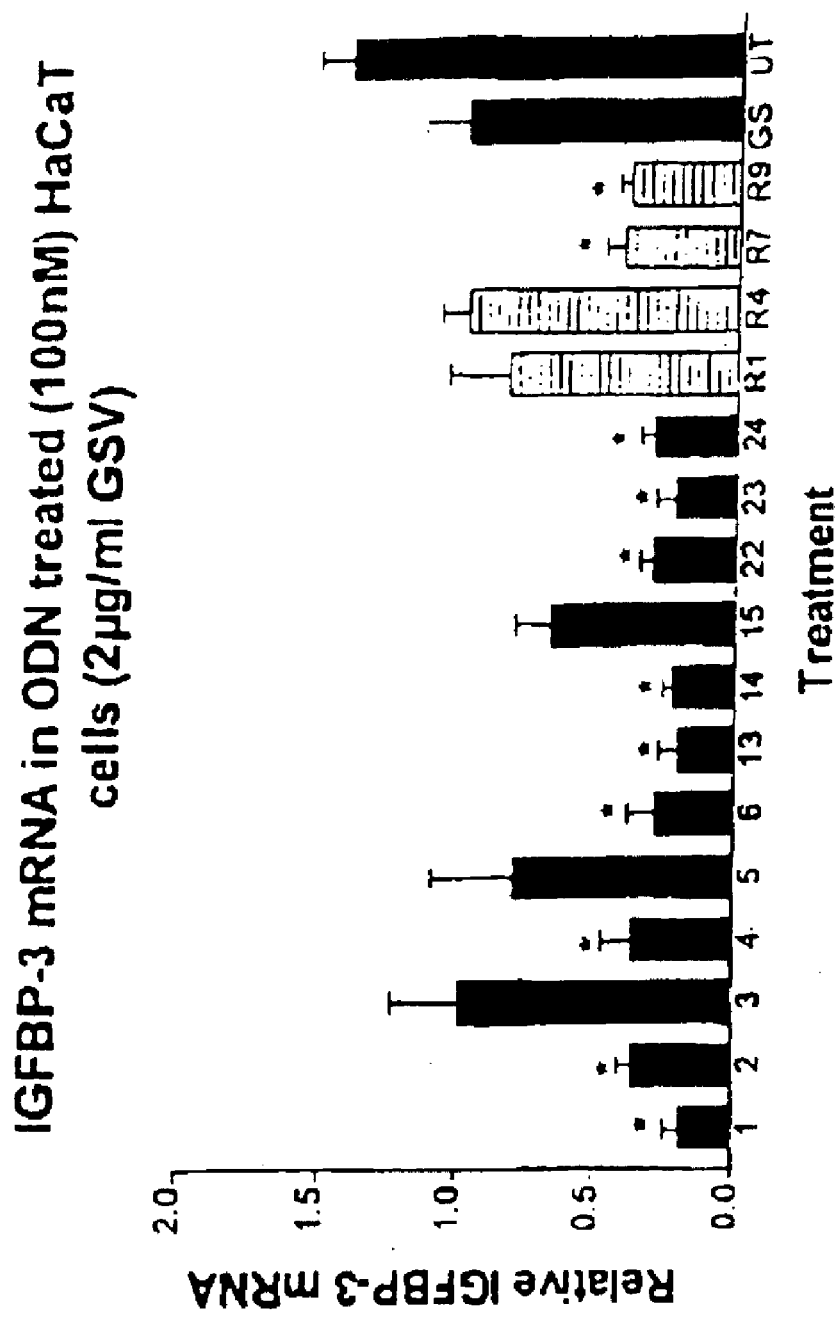

FIG. 26(b) is a graphical representation showing IGFBP-3 mRNA in ODN treated (100 nM) HaCaT cells (2 µg/ml GSV). HaCaT keratinocytes were treated for 51 hours with C-5 propynl, dU, dC ODNs complexed with cytofectin GSV. Total RNA was isolated then analysed for IGFBP-3 mRNA and GAPDH mRNA levels by Northern analysis and phosphorImager quantitation. Relative level of IGFBP-3 mRNA is shown after treatment with ODNs complementary to the human IGFBP-3 mRNA, 4 randomised sequence ODNs and liposome alone. (1–24=IGFBP-3 ODNs; R1, R4, R7 and R9=randomised ODNs (R1–R121, R4=R451, R7=R766, R9–R961), GS=lipsome alone; UT=untreated). *indicates a significant difference in relative IGFBP-3 mRNA from GSV treated cells (n-6–8, p<0.01).

FIG. 27 is a representation showing a reduction in IGF-I receptor mRNA in HaCaT cells following treatment with antisense oligonucleotides. Confluent HaCaT cells were treated every 24 h for 4 days with 2 µg/ml GSV lipid alone (GSV) or complexed with 30 nM IGF-I receptor specific oligonucleotides (#26 to #86) or random sequence oligonucleotides (R121, R451 and R766). Total RNA was isolated and analysed for IGF-I receptor and GAPDH mRNA by RNase protection assay. (a). Representative RNase protection assay gel showing IGF-I receptor (IGFR) and GAPDH mRNA in untreated or treated HaCaT cells. In this example, a reduction in IGFR band intensity relative to GAPDH can be seen with AON #27 and #78, but not with #32, #74 or the controls (R4, R7, random oligonucleotides R451 and R766, respectively; G, GSV lipid; UT, untreated).

(b) Densitometric quantitation of IGF-I receptor mRNA (normalised to GAPDH mRNA) in HaCaT cells following treatment with IGF-I receptor specific oligonucleotides (solid black), random sequence oligonucleotides (horizontal striped bar) or GSV alone (shaded bar) compared to untreated cells (UT, vertical striped bar). Each oligonucleotide was assayed in duplicate in at least two separate experiments.

Results are presented as mean±SEM. A one-way ANOVA followed by Tukey's (▲) test was performed; ▲ indicates a significant difference between cells treated with IGF-I receptor specific AONs and all of the control treatments ($p<0.05$). n=4 except for #27 and #32 (n=6), #28 and #68 (n=3), R766 (n=9), and R451, GSV and untreated (n=10).

FIG. 28 is a representation showing a reduction in total cellular IGF-I receptor protein following antisense oligonucleotide treatment. Confluent HaCaT cells were treated every 24 h for 4 days with 2 µg/ml GSV lipid alone (GSV) or complexed with 30 nM IGF-I receptor specific AONs (#27, #50 and #64) or the random sequence oligonucleotide, R451. Total cellular protein was isolated and analysed for IGF-I receptor by SDS PAGE followed by western blotting with an antibody specific for the human IGF-I receptor. (a) Duplicate treated cellular extracts showing the IGF-I receptor at the predicted size of 110 kD.

(b) Densitometric quantitation of IGF-I receptor protein. Results are presented as mean f SEM of four different experiments each performed in duplicate. A one-way ANOVA followed by a Dunnett's test was performed; * indicates a significant difference from GSV treated cells ($p<0.01$). GSV, GSV lipid alone; UT, untreated; R451, random sequence oligonucleotide; 64, 50, 27, IGF-I receptor-specific AONs.

Figure 29:
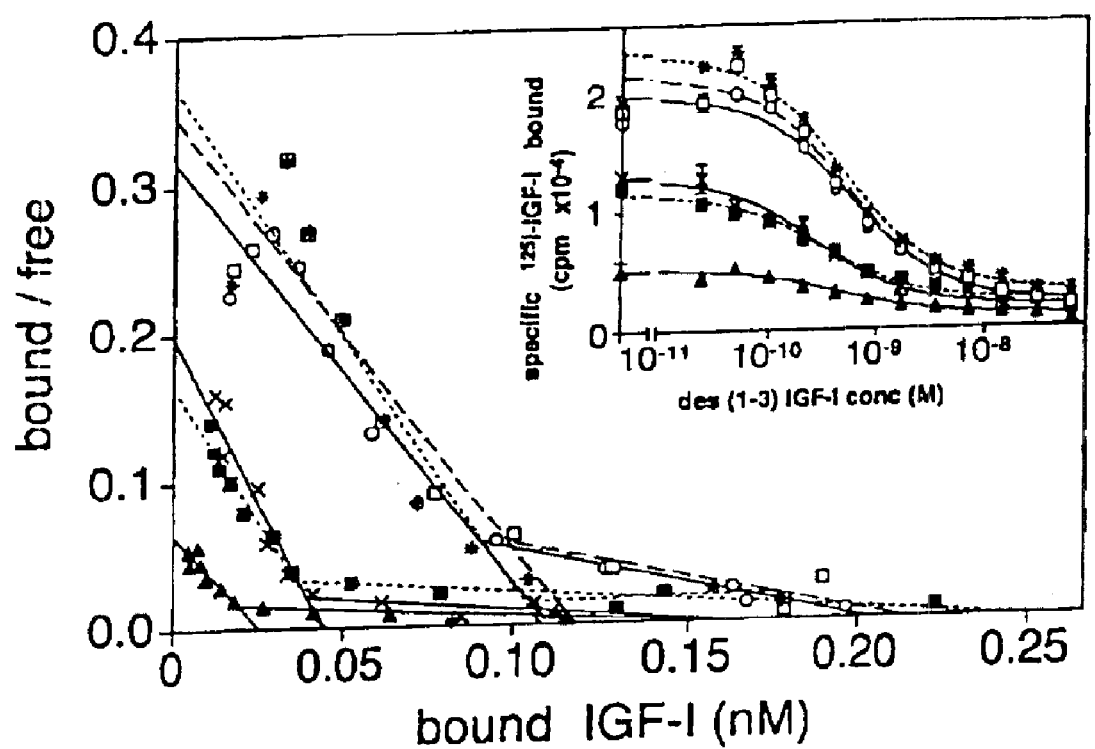

FIG. 29 is a representation showing a reduction in IGF-I receptor numbers on the keratinocyte cell surface after antisense oligonucleotide treatment. HaCaT cells were transfected with IGF-I receptor specific AONs #27 (-▲-), #50 (-x-), #64 (-■-), a random sequence oligonucleotide R451 (-o-), or treated with GSV lipid alone (-□-) every 24 h for four days (untreated cells, -*-). Competition binding assays using $^{125}$I-IGF-I and the receptor-specific analogue, des (1–3) IGF-1, were performed (inset); plotted values are means±standard error. The mean values were then subjected to Scatchard analysis.

Figure 30:
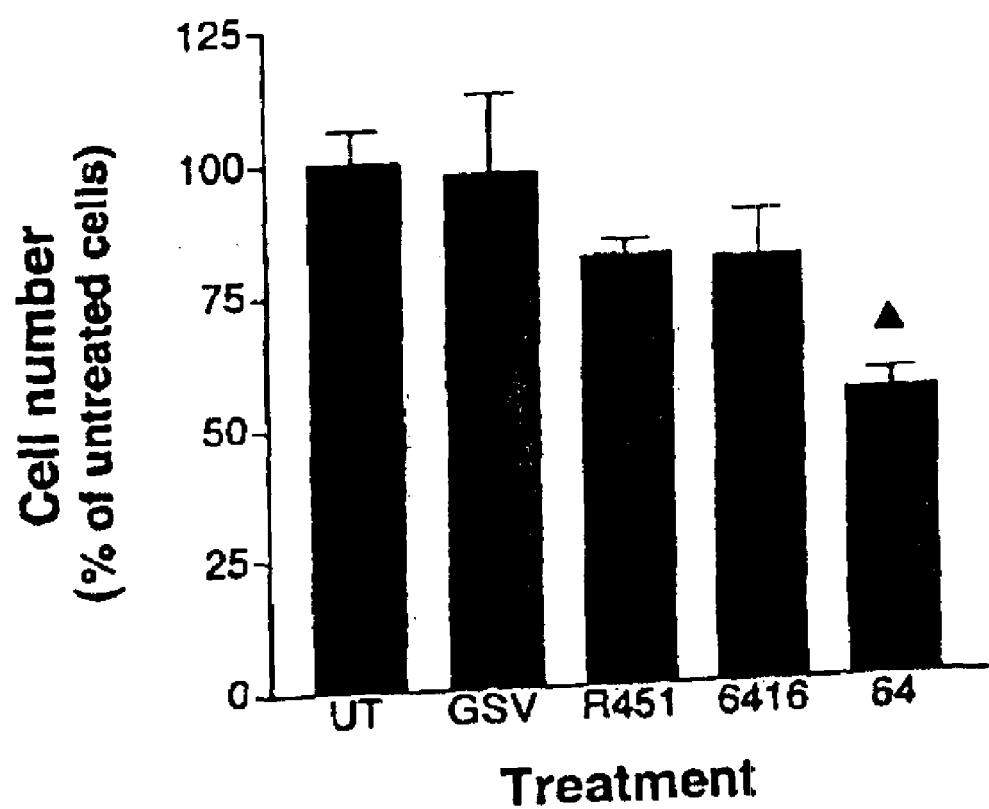

FIG. 30 is a representation showing a reduction in keratinocyte cell number following antisense oligonucleotide treatment. HaCaT cells, initially at 40% confluence, were transfected with the IGF-I receptor specific AON #64, control sequences R451 and 6416, or treated with GSV lipid alone every 24 h for 2 days (UT, untreated cells). Cell number was measured in the culture wells using a dye binding assay (Experimental protocol). Results are presented as mean±SD. A one-way ANOVA was performed, followed by a Tukey's multiple comparison test. ▲ indicates a significant difference between cells treated with AON #64 and all of the control treatments ($p<0.001$).

FIG. 31 is a representation showing a reversal of epidermal hyperplasia in psoriatic human skin grafts on nude mice following intradermal injection with antisense oligonucleotides.

Grafted psoriasis lesions were injected with IGF-I receptor specific AONs, a random sequence oligonucleotide in PBS, or with PBS alone, every 2 days for 20 days, then analysed histologically. (a) Donor A graft treated with AON #50 showing epidermal thinning compared
with pregraft and control (PBS) treated graft, and Donor B graft treated with AON #27 showing epidermal thinning compared with pregraft and control (R451) treated graft. E, epidermis; Scale bar, 400 mm; all pictures are at the same magnification. (b) Mean epidermal cross-sectional area over the full width of grafts was determined by digital image analysis. Results are presented as mean±SEM. Shaded bars, control treatments: R451, random oligonucleotide sequence; solid bars, treatments with oligonucleotides that inhibited IGF-I receptor expression in vitro. * indicates a significant difference from the vehicle treated graft ($p<0.01$, n=5–7), ++ indicates a significant difference from the random sequence (R451) treated graft ($p<0.01$, n=5–7). (c) Parakeratosis (arrow) was absent in grafts treated with IGF-I receptor AONs (AON #50) but persisted in pregraft and control (PBS) treated graft. Scale bar, 100 mm.

FIG. 32 is a representation showing a reversal of epidermal hyperplasia correlates with reduced IGF-I receptor mRNA in grafted psoriasis lesions treated with antisense oligonucleotides (a) A psoriasis lesion prior to grafting, and after grafting and treatment with IGF-I receptor specific oligonucleotide #27 (AON #27) or random sequence (R451) was immunostained with antibodies to Ki67 to identify proliferating cells. Proliferating cells are indicated by a dark brown nucleus (arrows). Scale bar, 250 mm; all pictures are at the same magnification. (b) The same lesion prior to grafting and after oligonucleotide treatment as in (a) was subjected to in situ hybridisation with a $^{35}$S-labeled cRNA probe complementary to the human IGF-I receptor mRNA. The presence of IGF-I receptor mRNA is indicated by silver grains (tiny black speckles), which are almost eliminated in the epidermis of the lesion treated with the IGF-I receptor-specific oligonucleotide #27 (AON #27). Arrows indicate the basal layer of the epidermis with dermis underneath. Scale bar, 50 µm.

Figure 33:
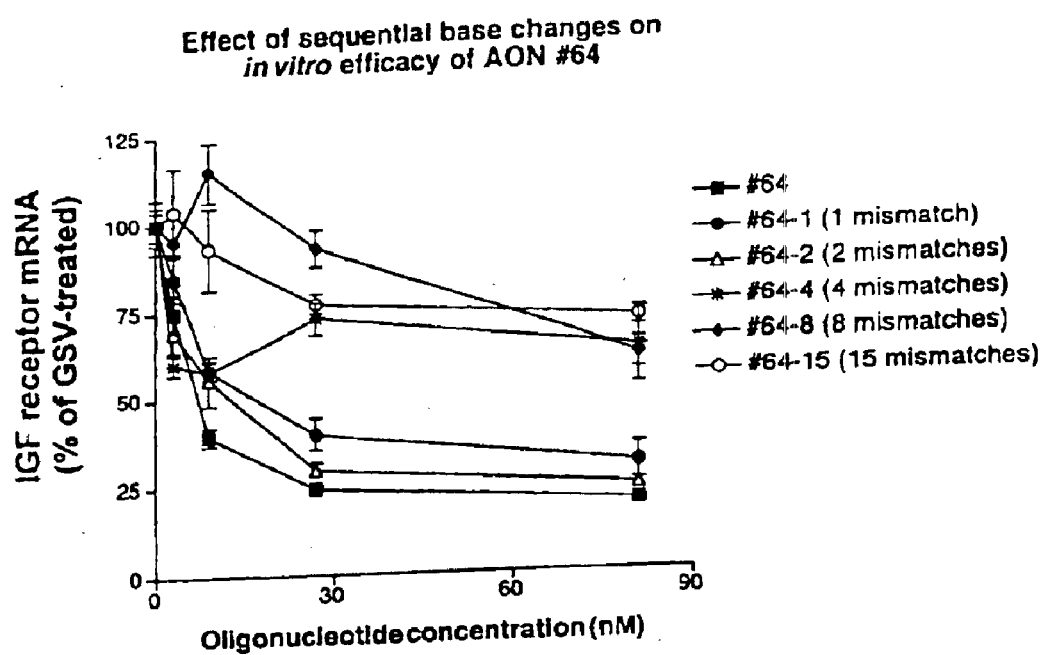

FIG. 33 is a representation showing a reduction in IGF-I receptor mRNA in HaCaT keratinocytes following treatment with oligonucleotides. HaCaT cell monolayers grown to 90% confluence in DMEM contianing 10% v/v fetal calf serum were treated with 24 h for two days with 2µg/ml GSV lipid alone (GSV) or complexed with 30 nM oligonucleotide. Total RNA was isolated and analysed for IGF-I receptor and GAPDH mRNA using a commercially availble ribonuclease protection assay kit (RPAII, Ambicon Inc, Austin, Tex.). Band intensity was quantified using ImageQuant software (Molecular Dynamics, Sunnyvale, Calif.).

Figure 34:
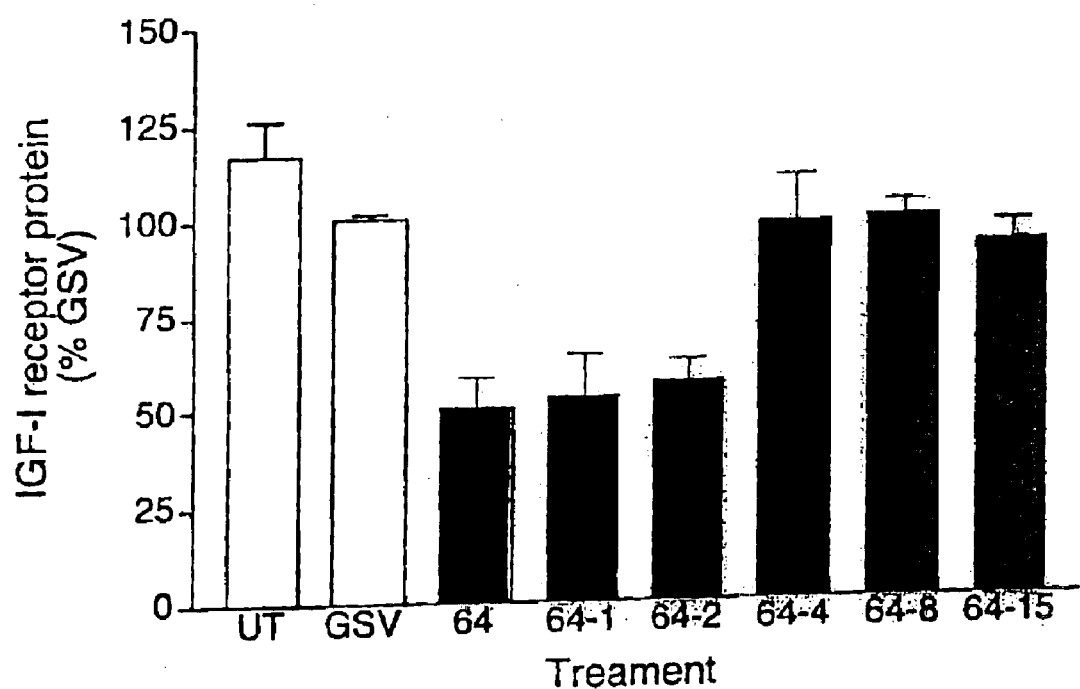

FIG. 34 is a representation showing a reduction in IGF-I receptor protein in HaCaT keratinocytes following treatment with oligonucleotides. HaCaT cell monolayers grown to 90% confluence in DMEM containing 100% v/v fetal calf serum were treated every 24 h for four days with 2 µg/ml GSV lipid alone (GSV) or complexed with 30 nM oligonucleotide. Cells were lyased in a buffer containing 50 mM HEPES, 150 mM NaCl, 10% v/v gycerol, 1% v/v Triton X-100 and 100 µg/ml aprotinin on ice for 30 mins, then 30

μg of lysate was loaded onto a denaturing 7% w/v polyacrylamide gel followed by transfer onto an Immobilon-P membrane (Millipore, Bedford, Mass.). Membranes were incubated with the anti-IGF-I receptor antibody C20 (Sanra Cruz Biotechnology Inc., Santa Cruz, Calif., 25 ng/ml in 150 mM NaCl, 10 mM Tris-HCl, pH 7.4, 0.1% v/v Tween 20) for 1 h at room temperature and developed using the Vistra ECF western blotting kit (Amersham, Buckinghamshire, England). Band intensity was quantified using ImageQuant software (Molecular Dynamics, Sunnyvale, Calif.).

Figure 35:
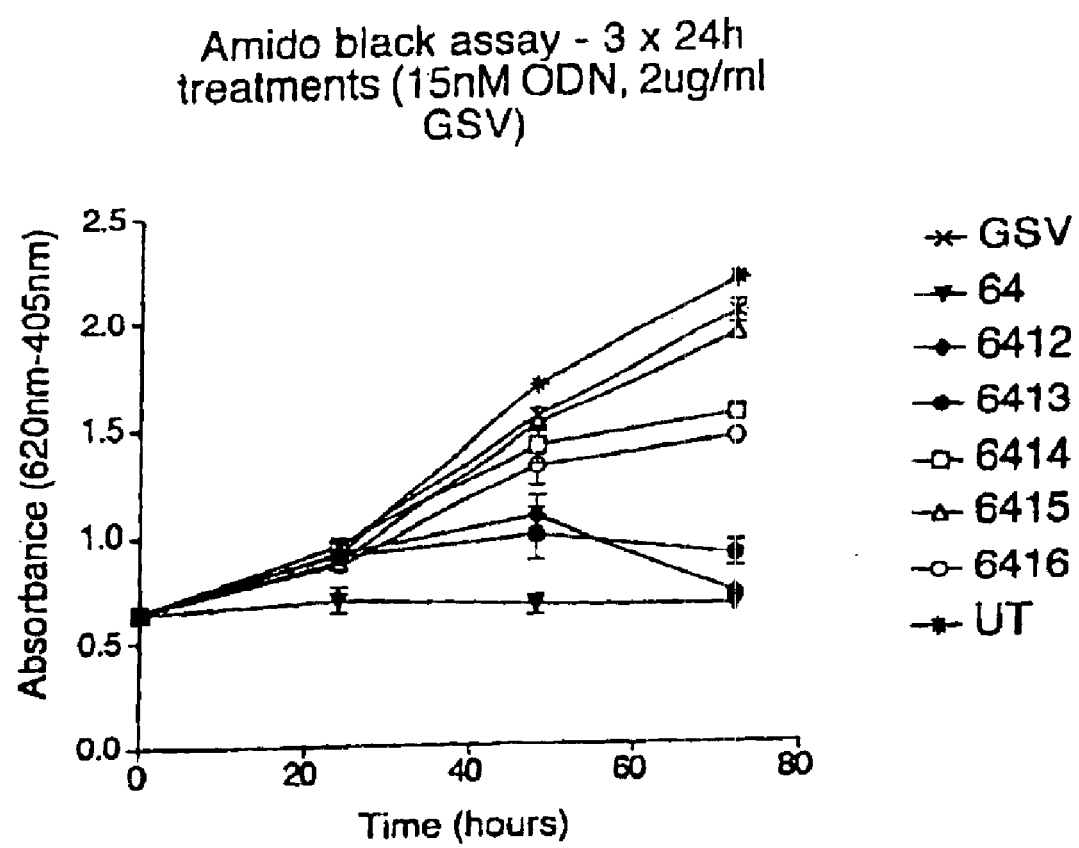

FIG. 35 is a representation showing a reduction in HaCaT keratinocyte cell number following treatment with oligonucleotides. HaCaT cell monolayers grown to 40% confluence in DMEM containing 10% fetal calf serum were treated every 24 h for three days with 2 μg/ml GSV lipid alone (GSV) or complexed with 15 nM oligonucleotide. Cell number was measured every 24 h using the amido black dye binding assay [32].

DETAILED DESCRIPTION OF THE PREFERRED EMBODIMENTS

The present invention is predicated in part on the use of molecules and in particular genetic molecules and more particularly antisense molecules to down-regulate a growth factor, its receptor and/or growth factor expression facilitating sequences.

Accordingly, one aspect of the present invention contemplates a method for ameliorating the effects of a medical disorder such as a proliferative and/or inflammatory skin disorder in a mammal, said method comprising contacting the proliferating and/or inflamed skin or skin capable of proliferation and/or inflammation or a cell otherwise involved in the said medical disorder with an effective amount of a nucleic acid molecule or chemical analogue thereof capable of inhibiting or otherwise reducing a growth factor mediated cell proliferation and/or inflammation and/or other medical disorder.

Growth factor mediated cell proliferation and inflammation are also referred to as epidermal hyperplasias and these and other medical disorders may be mediated by any number of molecules such as but not limited to IGF-I, keratinocyte growth factor (KGF), transforming growth factor-α (TGFα), tumour necrosis factor-α (TNFα), interleukin-1, -4, -6 and 8 (IL-1, IL-4, IL-6 and IL-8, respectively), basic fibroblast growth factor (bFGF) or a combination of one or more of the above. The present invention is particularly described and exemplified with reference to IGF-I and its receptor (IGF-I receptor) and to IGF-I facilitating molecules, IGFBPs, since targeting these molecules according to the methods contemplated herein provides the best results to date. This is done, however, with the understanding that the present invention extends to any growth factor or cytokine-like molecule, a receptor thereof or a facilitating molecule like the IGFBPs involved in skin cell proliferation such as those molecules contemplated above and/or their receptors and/or facilitating molecules therefor.

According to this preferred embodiment, there is provided a method for ameliorating the effects of a medical disorder such as a proliferative and/or inflammatory skin disorder in a mammal, said method comprising contacting the proliferating and/or inflamed skin or skin capable of proliferation and/or inflammation or a cell otherwise involved with said medical disorder with an effective amount of a nucleic acid molecule or chemical analogue thereof capable of inhibiting or otherwise reducing IGF-I mediated cell proliferation and/or inflammation and/or other medical disorder.

The present invention is particularly described by psoriasis as the proliferative skin disorder. However, the subject invention extends to a range of proliferative and/or inflammatory skin disorders or epidermal hyperplasias such as but not limited to psoriasis, ichthyosis, pityriasis rubra pilaris ("PRP"), seborrhoea, keloids, keratoses, neoplasias and scleroderma, warts, benign growths and cancers of the skin. The present invention extends to a range of other disorders such as neovascularization conditions such as but not limited to hyperneovasularization such as neovascularization of the retina, lining of the brain, skin, hyperproliferation of the inside of blood vessels, kidney disease, atherosclerotic disease, hyperplasias of the gut epithelium or growth factor mediated malignancies such as IGFI-mediated malignancies.

Furthermore, down-regulation of IGF-I receptor is useful as adjunctive therapy for epidermal hyperplasia. In accordance with this aspect of the present invention it is known that IGF-I receptor elicits separate intracellular signals which prevent apoptosis [19]. In keratinocytes, IGF-I receptor activation has been shown to protect UV-irradiated cells from apoptosis [20]. In another cell type, a number of IGF-I receptors expressed by the cells correlated with tumorigenicity and apoptotic resistance [21]. Consequently, in accordance with the present invention, by inactivating IGF-I receptor on cells such as epidermal keratinocytes will achieve three important outcomes:

(i) Acute epidermal hyperplasia following UV has been suggested to increase the risk of keratinocyte carcinogenic transformation [22]. By reducing IGF-I receptor expression in the epidermis, the incidence of epidermal hyperplasia following UV exposure is likely to be reduced leading to an overall acceleration in normalization of the lesion and reduced carcinogenic risk.

(ii) Inhibition of anti-apoptotic action of IGF-I receptor will enhance the reversal of epidermal thickening and accelerate normalization of differentiation. Topical or injected IGF-I receptor antisense as adjunctive treatment will increase apoptosis in the epidermal layer thereby enhancing the reduction in acanthosis observed in UV treatments.

(iii) Survival of keratinocytes, ie. those which evade apoptosis is likely to occur when cells have damaged DNA. Such mutations may be in the tumor suppressor region. Consequently, the use of antisense therapy will result in less frequent selection of mutated keratinocytes and therefore reduced incidence of basal cell carcinomas and squamous.

According to this embodiment, there is provided a method for ameliorating the effects of a proliferative and/or inflammatory skin disorder such as psoriasis said method comprising contacting the proliferating and/or inflamed skin or skin capable of proliferation and/or inflammation with effective amounts of UV treatment and a nucleic acid molecule or chemical analogue thereof capable of inhibiting or otherwise reducing IGF-I mediated cell proliferation and/or inflammation.

The UV treatment and nucleic acid molecule or its chemical analogue may be administered in any order or may be done simultaneously. This method is particularly useful in treating psoriasis by combination of UV and antisense therapy. Preferably the antisense therapy is directed to the IGF-I receptor.

In a preferred embodiment, the present invention is directed to a method for ameliorating the effects of psoriasis or other medical disorder, said method comprising contacting proliferating skin or skin capable of proliferation or cells associated with said disorder with an effective amount of a nucleic acid molecule or chemical analogue thereof capable of inhibiting or otherwise reducing IGF-I mediated cell proliferation or ameliorating the medical disorder.

The present invention extends to any mammal such as but not limited to humans, livestock animals (e.g. horses, sheep, cows, goats, pigs, donkeys), laboratory test animals (e.g. rabbits, mice, guinea pigs), companion animals (e.g. cats, dogs) and captive wild animals. However, the instant invention is particularly directed to proliferative and/or inflammatory skin disorders such as psoriasis in humans as well as medical disorders contemplated above.

The aspects of the subject invention instantly contemplated are particularly directed to the topical application of one or more suitable nucleic molecules capable of inhibiting, reducing or otherwise interfering with IGF-mediated cell proliferation and/or inflammation. More particularly, the nucleic acid molecule targets IGF-I interaction with its receptor. Conveniently, therefore, the nucleic acid molecule is an antagonist of IGF-I interaction with its receptor. Most conveniently, the nucleic acid molecule antagonist is an antisense molecule to the IGF-I receptor, to IGF-I itself or to a molecule capable of facilitating IGF-I interaction with its receptor such as but not limited to an IGFBP.

Insofar as the invention relates to IGFBPs, the preferred molecules are IGFBP-2, -3, -4, -5 and -6. The most preferred molecules are IGFBP-2 and IGFBP-3.

Figure 1:
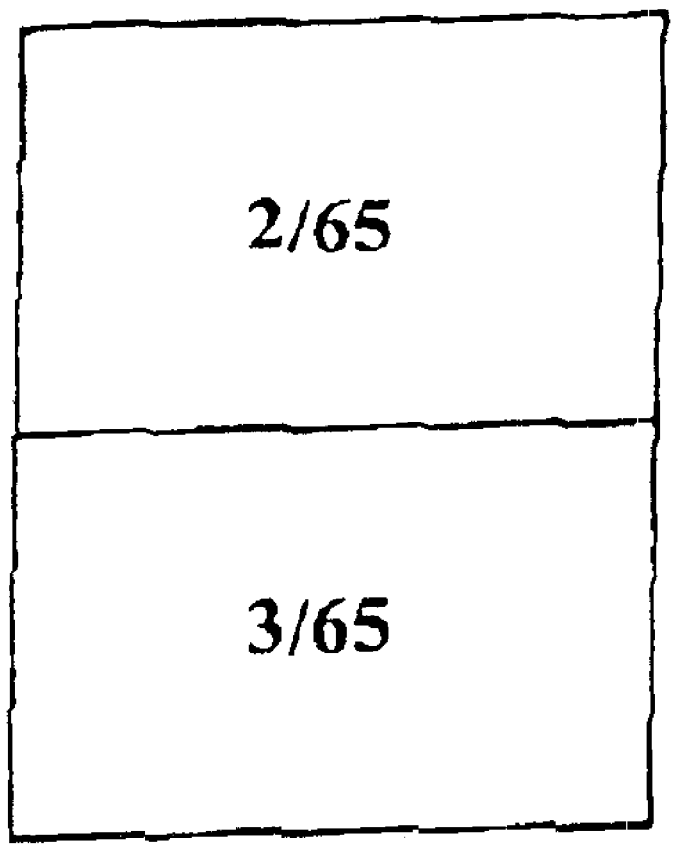
FIG. 1 is a representation of the nucleotide sequence of IGFBP-2 (SEQ ID NO.1).
Figure 2:
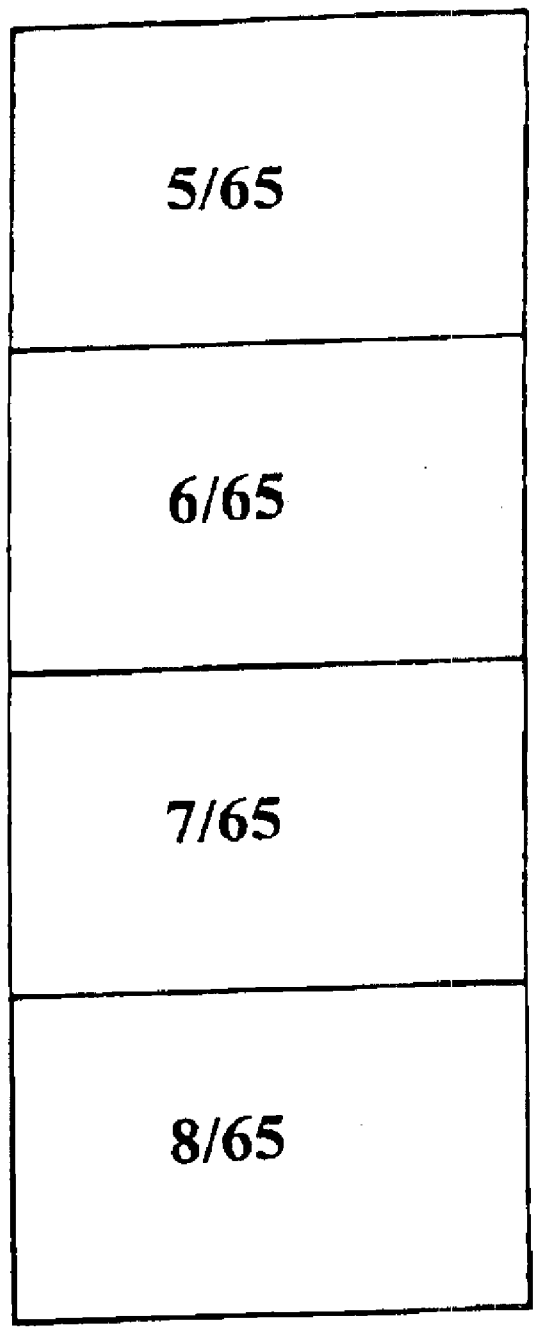
FIG. 2 is a representation of the nucleotide sequence of IGFBP-3 (SEQ ID NO.2).
Figure 3:
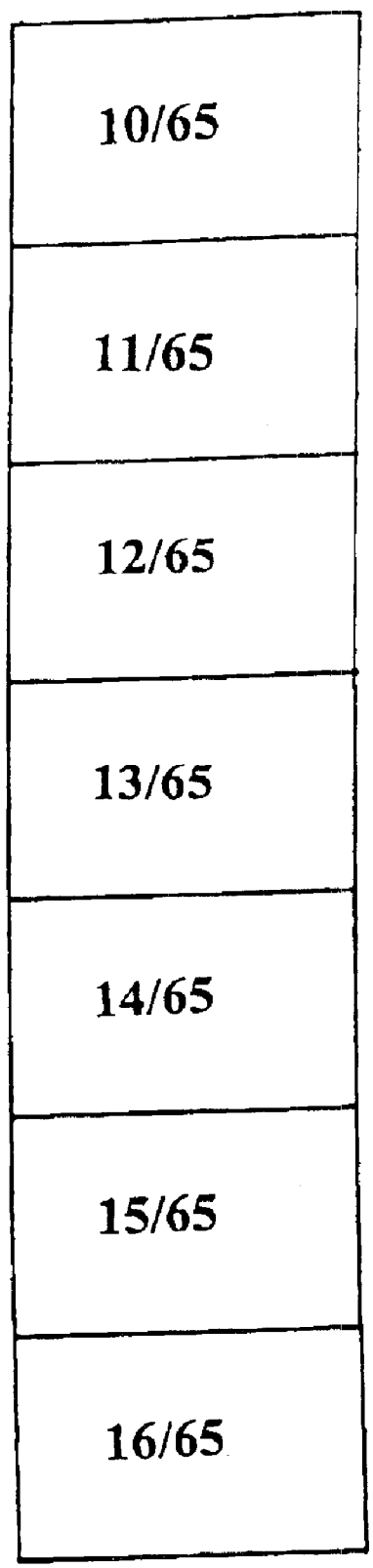
FIG. 3 is a representation of the nucleotide sequence of IGF-1-receptor (SEQ ID NO.3).

The nucleotide sequences of IGFBP-2 and IGFBP-3 are set forth in FIGS. 1 and 2 respectively. According to a particularly preferred aspect of the present invention, there is provided a nucleic acid molecule comprising at least about ten nucleotides capable of hybridising to, forming a heteroduplex or otherwise interacting with an mRNA molecule directed form a gene corresponding to a genomic form of SEQ ID NO.1 and/or SEQ ID NO.2 and which thereby reduces or inhibits translation of said mRNA molecule. Preferably, the nucleic acid molecule is at least about 15 nucleotides in length and more preferably at least about 20–25 nucleotides in length. However, the instant invention extends to any length nucleic acid molecule including a molecule of 100–200 nucleotides in length to correspond to the full length of or near full length of the subject genes.

The nucleotide sequence of the antisense molecules may correspond exactly to a region or portion of SEQ ID NO.1 or SEQ ID NO.2 or may differ by one or more nucleotide substitutions, deletions and/or additions. It is a requirement, however, that the nucleic acid molecule interact with an mRNA molecule to thereby reduce its translation into active protein.

Examples of potential antisense molecules for IGFBP-2 and IGFBP-3 are those capable of interacting with sequences selected from the lists in Examples 6 and 7, respectively.

The nucleic acid molecules in the form of an antisense molecule may be linear or covalently closed circular and single stranded or partially double stranded. A double stranded molecule may form a triplex with target mRNA or a target gene. The molecule may also be protected from, for example, nucleases, by any number of means such as using a nonionic backbone or a phosphorothioate linkage. A convenient nonionic backbone contemplated herein is ethylphosphotriester linkage or a 2'-O-methylribosyl derivative. A particularly useful modification modifies the DNA backbone by introducing phosphorothioate internucleotide linkages. Alternatively or in addition to the pyrimidine bases are modified by inclusion of a C-5 propyne substitution which modification is proposed to enhance duplex stability [23]. The present invention extends to any chemical modification to the bases and/or RNA or DNA backbone. Reference to a "chemical analogue" of a nucleic acid molecule includes reference to a modified base, nucleotide, nucleoside or phosphate backbone.

Examples of suitable oligonucleotide analogues are conveniently described in Ts'O et al [7]. Further suitable examples of oligonucleotide analogues and chemical modifications are described in references 25 to 31.

Alternatively, the antisense molecules of the present invention may target the IGF-I gene itself or its receptor or a multivalent antisense molecule may be constructed or separate molecules administered which target at least two or an IGFBP, IGF-I and/or IGF-I-receptor. Examples of suitable antisense molecules capable of targetting the IGF-I receptor are those capable of interacting with sequences selected from the list in Example 8. One particularly useful antisense molecule is 5'-ATCTCTCCGCTTCCTTTC-3' (SEQ ID NO.10).

Other particularly useful antisense molecules are:
27 UCCGGAGCCAGACUU (SEQ ID NO.12)
64 CACAGUUGCUGCAAG (SEQ ID NO.13)
78 UCUCCGCUUCCUUUC (SEQ ID NO.14)
28 AGCCCCCACAGCGAG (SEQ ID NO.15)
32 GCCUUGGAGAUGAGC (SEQ ID NO.16)
40 UAACAGAGGUCAGCA (SEQ ID NO.17)
42 GGAUCAGGGACCAGU (SEQ ID NO.18)
46 CGGCAAGCUACACAG (SEQ ID NO.19)
50 GGCAGGCAGGCACAC (SEQ ID NO.20).

Particularly useful molecules are selected from #27, #64 and #78. In a p referred embodiment these molecules comprise a C-5 propynyl dU, dC phosphorothioate modification.

A particularly preferred embodiment of the present invention contemplates a method of ameliorating the effects of psoriasis or other medical disorder, said method comprising contacting proliferating skin or skin capable of proliferation or cells associated with said medical disorder with an effective amount of one or more nucleic acid molecules or chemical analogues thereof capable of inhibiting or otherwise reducing IGF-I mediated cell proliferation or ameliorating the medical disorder wherein said one or more molecules comprises a polynucleotide capable of interacting with mRNA directed from an IGF-I gene, an IGF-I receptor gene or a gene encoding an IGFBP such as IGFBP-2 and/or IGFBP-3.

Preferably, the nucleic acid molecule are antisense molecules. Particularly useful antisense molecules may be represented as:
27 UCCGGAGCCAGACUU (SEQ ID NO.12)
64 CACAGUUGCUGCAAG (SEQ ID NO.13)
78 UCUCCGCUUCCUUUC (SEQ ID NO.14)
28 AGCCCCCACAGCGAG (SEQ ID NO.15)
32 GCCUUGGAGAUGAGC (SEQ ID NO.16)
40 UAACAGAGGUCAGCA (SEQ ID NO.17)
42 GGAUCAGGGACCAGU (SEQ ID NO.18)
46 CGGCAAGCUACACAG (SEQ ID NO.19)
50 GGCAGGCAGGCACAC (SEQ ID NO.20).

Even more particularly useful molecules are selected from #27, #64 and #78.

In accordance with one aspect of the present invention the nucleic acid molecule is topically applied in aqueous solution or in conjunction with a cream, ointment, oil or other suitable carrier and/or diluent. A single application may be sufficient depending on the severity or exigencies of the condition although more commonly, multiple applications are required ranging from hourly, multi-hourly, daily, multi-daily, weekly or monthly, or in some other suitable time interval. The treatment might comprise solely the application of the nucleic acid molecule or this may be applied in conjunction with other treatments for the skin proliferation and/or inflammatory disorder being treated or for other associated conditions including microbial infection, bleeding and the formation of a variety of rashes.

As an alternative to or in conjunction with antisense therapy, the subject invention extends to the nucleic acid molecule as, or incorporating, a ribozyme including a minizyme to, for example, IGF-I, its receptor or to molecules such as IGFBPs and in particular IGFBP-2 and -3. Ribozymes are synthetic nucleic acid molecules which possess highly specific endoribonuclease activity. In particular, they comprise a hybridising region which is complementary in nucleotide sequence to at least part of a target RNA. Ribozymes are well described by Haseloff and Gerlach [8] and in International Patent Application No. WO 89/05852. The present invention extends to ribozymes which target mRNA specified by genes encoding IGF-I, its receptor or one or more IGFBPs such as IGFBP-2 and/or IGFBP-3.

According to this embodiment, there is provided in a particularly preferred aspect a ribozyme comprising a hybridising region and a catalytic region wherein the hybridising region is capable of hybridising to at least part of a target mRNA sequence transcribed from a genomic gene corresponding to SEQ ID NO.1 or SEQ ID NO.2 wherein said catalytic domain is capable of cleaving said target mRNA sequence to reduce or inhibit IGF-I mediated cell proliferation and/or inflammation and/or other medical disorders.

Yet another aspect of the present invention contemplates co-suppression to reduce expression or to inhibit translation of an endogenous gene encoding, for example, IGF-I, its receptor, or IGFBPs such as IGFBP-2 and/or -3. In co-suppression, a second copy of an endogenous gene or a substantially similar copy or analogue of an endogenous gene is introduced into a cell following topical administration. As with antisense molecules, nucleic acid molecules defining a ribozyme or nucleic acid molecules useful in co-suppression may first be protected such as by using a nonionic backbone.

The efficacy of the nucleic acid molecules of the present invention can be conveniently tested and screened using an in vitro system comprising a basal keratinocyte cell line. A particularly useful system comprises the HaCaT cell line described by Boukamp et al [9]. In one assay, IGF-I is added to an oligonucleotide treated HaCaT cell line. Alternatively, growth of oligonucleotide treated HaCaT cells is observed on a feeder layer of irradiated 3T3 fibroblasts. Using such in vitro assays, it is observed that antisense oligonucleotides to IGFBP-3, for example, inhibit production of IGFBP-3 by HaCaT cells. Other suitable animal models include the nude mouse/human skin graft model (15; 16) and the "flaky skin" mouse model (17; 18). In the nude mouse model, microdermatome biopsies of psoriasis lesions are taken under local anaesthetic from volunteers then transplanted to congenital athymic (nude) mice. These transplanted human skin grafts maintain the characteristic hyperproliferating epidermis for 6–8 weeks. They are an established model for testing the efficacy of topically applied therapies for psoriasis. In the "flaky skin" mouse model, the fsn/fsn mutation produces mice with skin resembling human psoriasis. This mouse, or another mutant mouse with a similar phenotype is a further in vivo model to test the efficacy of topically applied therapies for psoriasis.

Another aspect of the present invention contemplates a pharmaceutical composition for topical administration which comprises a nucleic acid molecule capable of inhibiting or otherwise reducing IGF-I mediated cell proliferation such as psoriasis and one or more pharmaceutically acceptable carriers and/or diluents. Preferably, the nucleic acid molecule is an antisense molecule to IGF-I, the IGF-I receptor or an IGFBP such as IGFBP-2 and/or IGFBP-3 or comprises a ribozyme to one or more of these targets or is a molecule suitable for co-suppression of one or more of these targets. The composition may comprise a single species of a nucleic acid molecule capable of targeting one of IGF-1, its receptor or an IGFBP, such as IGFBP-2 or IGFBP-3 or may be a multi-valent molecule capable of targeting two or more of IGF-I, its receptor or an IGFBP, such as IGFBP-2 and/or IGFBP-3.

The nucleic acid molecules may be administered in dispersions prepared in creams, ointments, oil or other suitable carrier and/or diluent such as glycerol, liquid polyethylene glycols and/or mixtures thereof. Under ordinary conditions of storage and use, these preparations may contain a preservative to prevent the growth of microorganisms.

The pharmaceutical forms suitable for topical use include sterile aqueous solutions (where water soluble) or dispersions and powders for the extemporaneous preparation of topical solutions or dispersions. In all cases, the form is preferably sterile although this is not an absolute requirement and is stable under the conditions of manufacture and storage. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of superfactants. The prevention of the action of microorganism can be brought about by various antibacterial and antifungal agents, for example, parabens, chlorobutanol, phenol, sorbic acid, thimerosal and the like. In many cases, it will be preferable to include isotonic agents, for example, sugars or sodium chloride.

Topical solutions are prepared by incorporating the nucleic acid molecule compound in the required amount in the appropriate solvent with various of the other ingredients enumerated above, as required, followed by where necessary filter sterilization.

The active agent may alternatively be administered by intravenous, subcutaneous, nasal drip, suppository, implant means amongst other suitable routes of administration including intraperitoneal, intramuscular, absorption through epithelial or mucocutaneous linings for example via nasal, oral, vaginal, rectal or gastrointestinal administration. Reference may conveniently be made to reference 24.

As used herein "pharmaceutically acceptable carriers and/or diluents" include any and all solvents, dispersion media, aqueous solutions, coatings, antibacterial and antifungal agents, isotonic and absorption delaying agents, and the like. The use of such media and agents for pharmaceutical active substances is well known in the art. Except insofar as any conventional media or agent is incompatible with the active ingredient, use thereof in the pharmaceutical compositions is contemplated. Supplementary active ingredients can also be incorporated into the compositions. Conveniently, the nucleic acid molecules of the present invention are stored in freeze-dried form and are reconstituted prior to use.

Yet another aspect of the present invention contemplates the use of a nucleic acid molecule in the manufacture of a medicament for the treatment of proliferative and/or inflammatory skin disorders or other medical disorders mediated by a growth factor. The proliferative and/or inflammatory skin disorder is generally psoriasis or other medical disorders as described above and the nucleic acid molecule targets IGF-I, the IGF-I receptor and/or an IGFBP such as IGFBP-2 and/or IGFBP-3.

Still a further aspect of the present invention contemplates an agent comprising a nucleic acid molecule as hereinbefore defined useful in the treatment of proliferative and/or inflammatory skin disorders, such as psoriasis or other medical disorder.

The present invention further contemplates the use of the genetic molecules and in particular the antisense molecules to inhibit the anti-apoptotic activity of IGF-I receptor. Such a use is appropriate for the treatment of certain cancers and as adjunct therapy for epidermal hyperplasia such as in combination with UV treatment.

The present invention is further described by the following non-limiting Examples.

EXAMPLE 1

The differentiated human keratinocyte cell line, HaCaT [9] was used in the in vitro assay. Cells at passage numbers 33 to 36 were maintained as monolayer cultures in 5% v/v $CO_2$ at 37° C. in Keratinocyte-SFM (Gibco) containing EGF and bovine pituitary extract as supplied. Media containing foetal calf serum were avoided because of the high content of IGF-I binding proteins in serum.

Feeder layer plates of lethally irradiated 3T3 fibroblasts were prepared exactly as described by Rheinwald and Green [10].

EXAMPLE 2

Cells were grown to 4 days post confluence in 2 $cm^2$ wells with daily medium changes of Keratinocyte-SFM, then the medium was changed to DMEM (Cytosystems, Australia), with the following additions: 25 mM Hepes, 0.19% w/v, sodium bicarbonate, 0.03% w/v glutamine (Sigma Chemical Co, USA), 50 IU/ml penicillin and 50 µg/ml streptomycin (Flow Laboratories). After 24 hours, IGF-I or tIGF-I was added to triplicate wells, at the concentrations indicated, in 0.5 ml fresh DMEM containing 0.02% v/v bovine serum albumin (Sigma molecular biology grade) and incubated for a further 21 hours. [3H]-Thymidine (0.1 µCi/well) was then added and the cells incubated for a further 3 hours. The medium was then aspirated and the cells washed once with ice-cold PBS and twice with ice-cold 10% v/v TCA. The TCA-precipitated monolayers were then solubilized with 0.25M NaOH (200 µl/well), transferred to scintillation vials and radioactivity determined by liquid scintillation counting (Pharmacia Wallac 1410 liquid scintillation counter).

EXAMPLE 3

HaCaT conditioned medium (250 µL) was concentrated by adding 75011 cold ethanol, incubating at −20° C. for 2 hours and centrifuging at 16,000 g for 20 min at 4° C. The resulting pellet was air dried, resuspended thoroughly in non-reducing Laemmli sample buffer, heated to 90° C. for 5 minutes and separated on 12% w/v SDS-PAGE according to the method of Laemmli (1970). Separated proteins were electrophoretically transferred to nitrocellulose membrane (0.45 mm, Schleicher and Schuell, Dassel, Germany) in a buffer containing 25 mM Tris, 192 mM glycine and 20% v/v methanol. IGFBPs were then visualised by the procedure of Hossenlopp et al [11], using [$^{125}$I]-IGF-I, followed by autoradiography. Autoradiographs were scanned in a BioRad Model GS-670 Imaging Densitometer and band densities were determined using the Molecular Analyst program.

EXAMPLE 4

Phosphorothioate oligodeoxynucleotides were synthesised by Bresatec, Adelaide, South Australia, Australia. The following antisense sequences were used: BP3AS2, 5'-GCG CCC GCT GCA TGA CGC CTG CAA C-3' (SEQ ID NO.4) a 25 mer complementary to the start codon region of the human IGFBP-3 mRNA; BP3AS3,5'-CGG GCG GCT CAC CTG GAG CTG GCG-3' (SEQ ID NO.5) a 24 mer complementary the exon 1/intron 1 splice site; BP3AS4, 5'-AGG CGG CTG ACG GCA CTA-3' (SEQ ID NO.6) an 18 mer complementary to a region of the coding sequence lacking RNA secondary structure and oligonucleotide-dimer formation (using the computer software "OLIGO for PC"). Since BP3AS4 was found to be ineffective at inhibiting IGFBP-3 synthesis, it was used as a control. The following additional control oligonucleotide sequences were used: BP3S, 5'-CAG GCG TCA TGC AGC GGG C-3' (SEQ ID NO.7) an 18 mer sense control sequence equivalent to the start codon region; BP3AS2NS, 5'-CGG AGA TGC CGC ATG CCA GCG CAG G-3' (SEQ ID NO.8) a 25 mer randomised sequence with the same G (content as BP3AS2; BP3AS4NS, 5'-GAC AGC GTC GGA GCG ATC-3' (SEQ ID NO.9), an 18 mer randomised sequence with the same GC content as BP3AS4NS. Design of the oligonucleotides was based on the human IGFBP-3 cDNA sequence of Spratt et al [12].

Cells were grown to one day post confluence in 2 $cm^2$ wells with daily medium changes of 0.5 ml Keratinocyte-SFM, then subjected to daily medium changes of Keratinocyte-SFM for a further 4 days. Daily additions of 0.5 ml fresh Keratinocyte-SFM were then continued for a further 7 days, except that at the time of medium addition, 5 µl oligonucleotide in PBS was added to give the final concentrations indicated, then the wells were shaken to mix the oligonucleotide. After the final addition, cells were incubated for 24 hours and the medium collected for assay of IGFBPs. Cells were then counted after trypsinisation in a Coulter Industrial D Counter, Coulter Bedfordshire, UK. Cell numbers after oligonucleotide treatment differed by less than 10%.

EXAMPLE 5

Figure 4A:
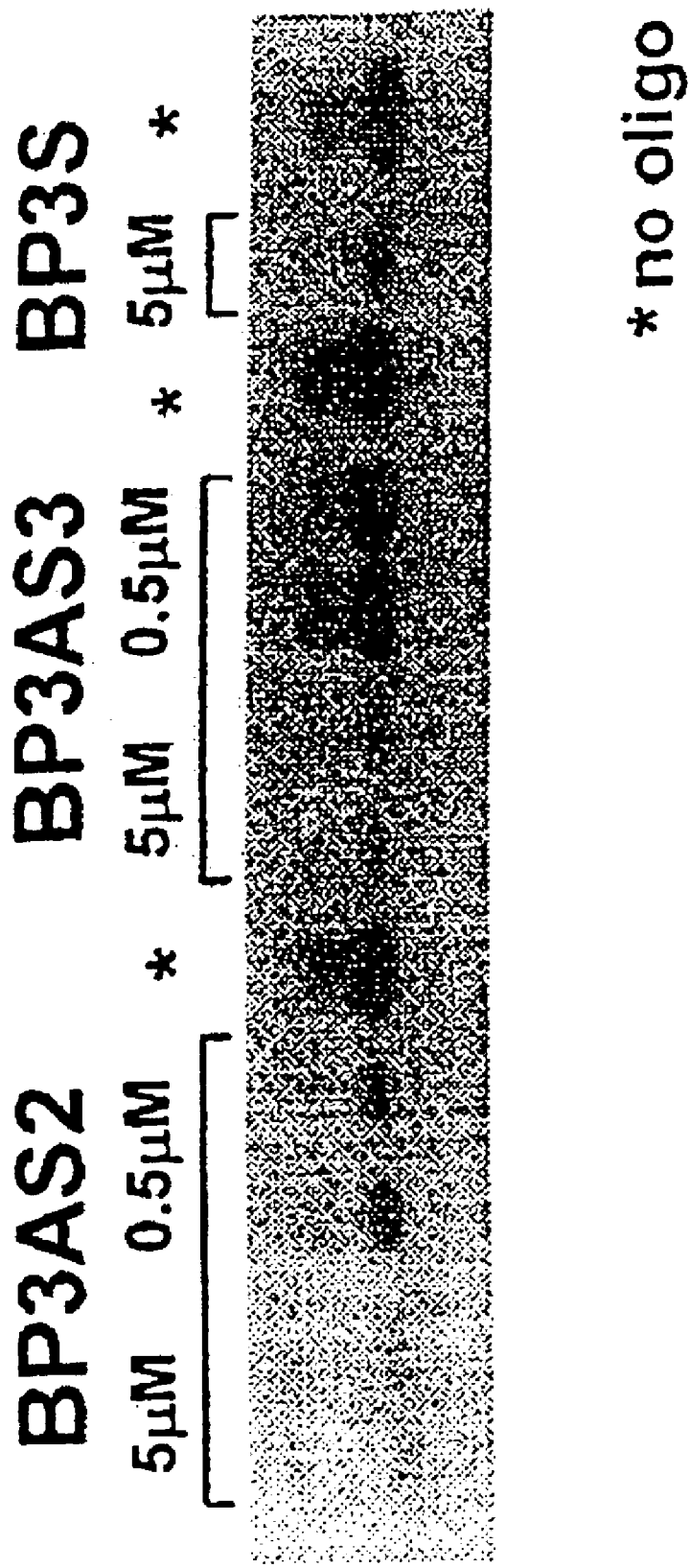
FIG. 4A is a photographic representation of a Western ligand blot of HaCaT conditioned medium showing IGFBP-3 secreted in 24 hours after 7 day treatment with phosphorothioate oligonucleotides (BP3AS2, BP3AS3 and BP3S) at 0.5 µM and 5 µM;
*no oligonucleotide added.
Figure 4B:
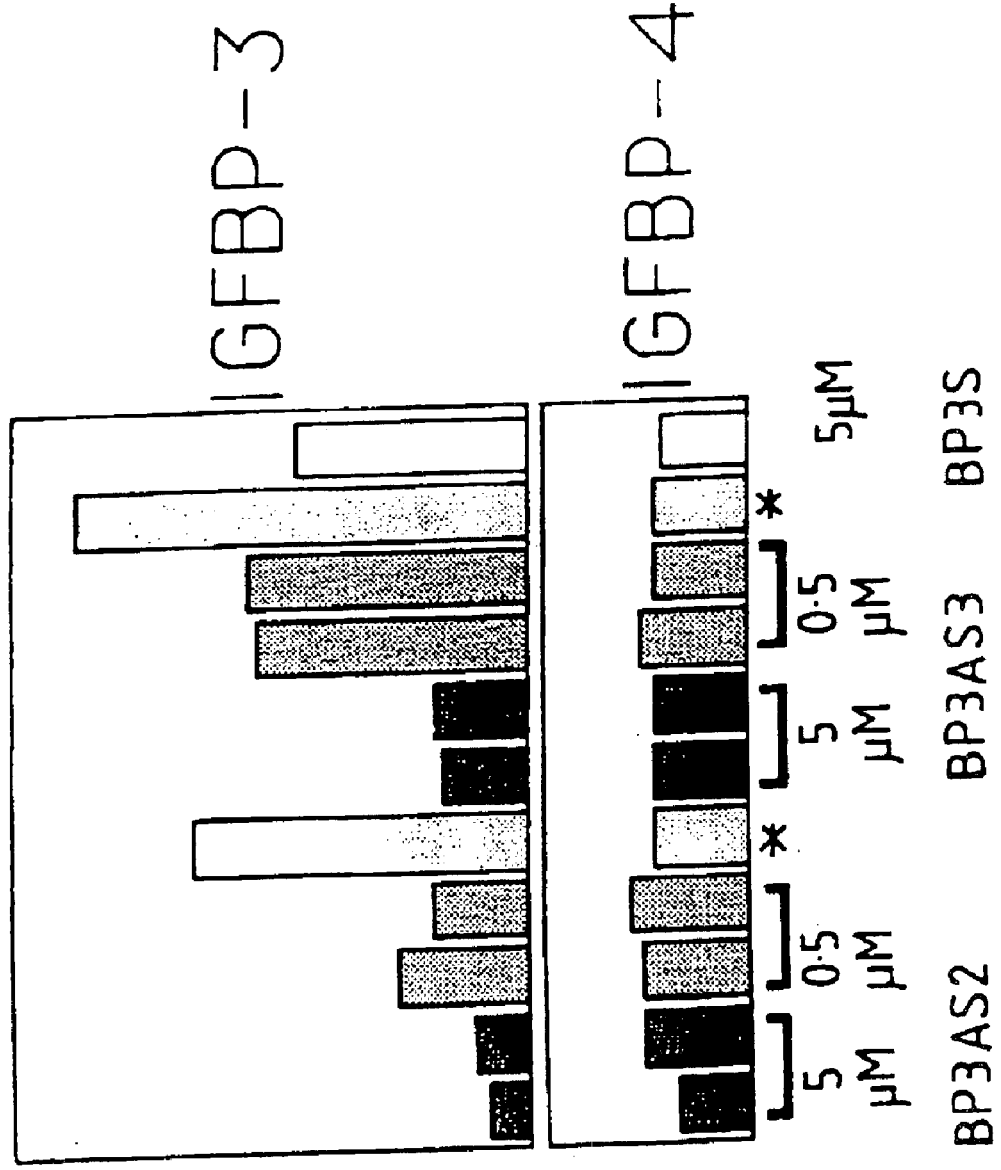
FIG. 4B is a graphical representation of a scanning imaging desitometry of Western ligand blot (FIG. 4A), showing relative band intensities of IGFBP-3 and the 24 kDa IGFBP-4 after treatment with phosphorothioate oligonucleotides;
* no oligonucleotide added.

HaCaT cells secrete mainly IGFBP-3 (>95%), with the only other IGFBP detectable in HaCaT conditioned medium being IGFBP-4 (<5%). The effect on IGFBP-3 and IGFBP-4 synthesis of antisense oligonucleotides at two concentrations, 5 µM and 0.5 µM, was tested. Two oligonucleotides were used, BP3AS2 and BP3AS3, directed against the start site and the intron 1/exon 1 splice site, respectively of the IGFBP-3 mRNA. As a control, a sense oligonucleotide corresponding to the start site was used. As shown in FIGS. 4A and 4B, all oligonucleotides at 5 µM caused a significant reduction of IGFBP-3 synthesis compared with untreated cells, however, the two antisense oligonucleotides inhibited IGFBP-3 synthesis of approximately 50% compared to the sense control (FIG. 4B). The antisense oligonucleotide directed to the start codon appeared to be more effective of the two, the difference being more apparent at the lower concentration of 0.5M. The cells of IGFBP-4 secreted by the HaCaT cells make photographic reproduction of the bands on Western ligand blots difficult, however densitometry measurements provide adequate relative quantitation. This resulted in the significant observation that IGFBP-4 levels were unaffected by oligonucleotide addition to the cells, suggesting that the observed inhibitory effects on IGFBP-3 are specific.

Figure 5A:
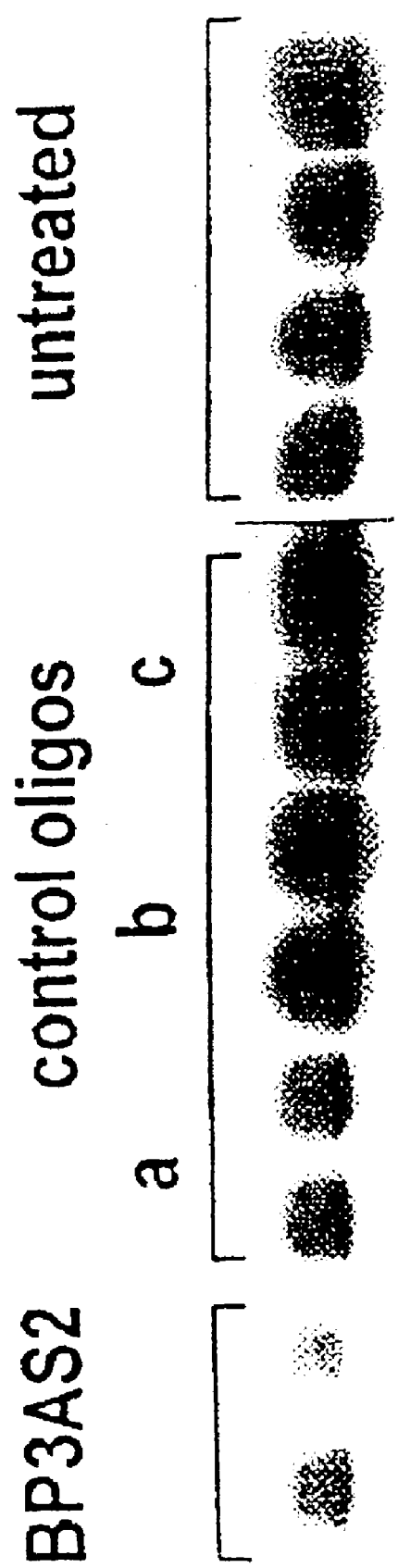
FIG. 5A is a photographic representation of a Western ligand blot of HaCaT conditioned medium showing IGFBP-3 secreted in 24 hours after 7 day treatment with phosophorothioate oligonucleotide BP3AS2 at 0.5 µM compared with several control oligonucleotides at 0.5 µM. (a) oligonucleotide BP3AS2NS; (b) oligonucleotide BP3AS4; (c) oligonucleotide BP3AS4NS; and (untreated), no oligonucleotide added.
Figure 5B:
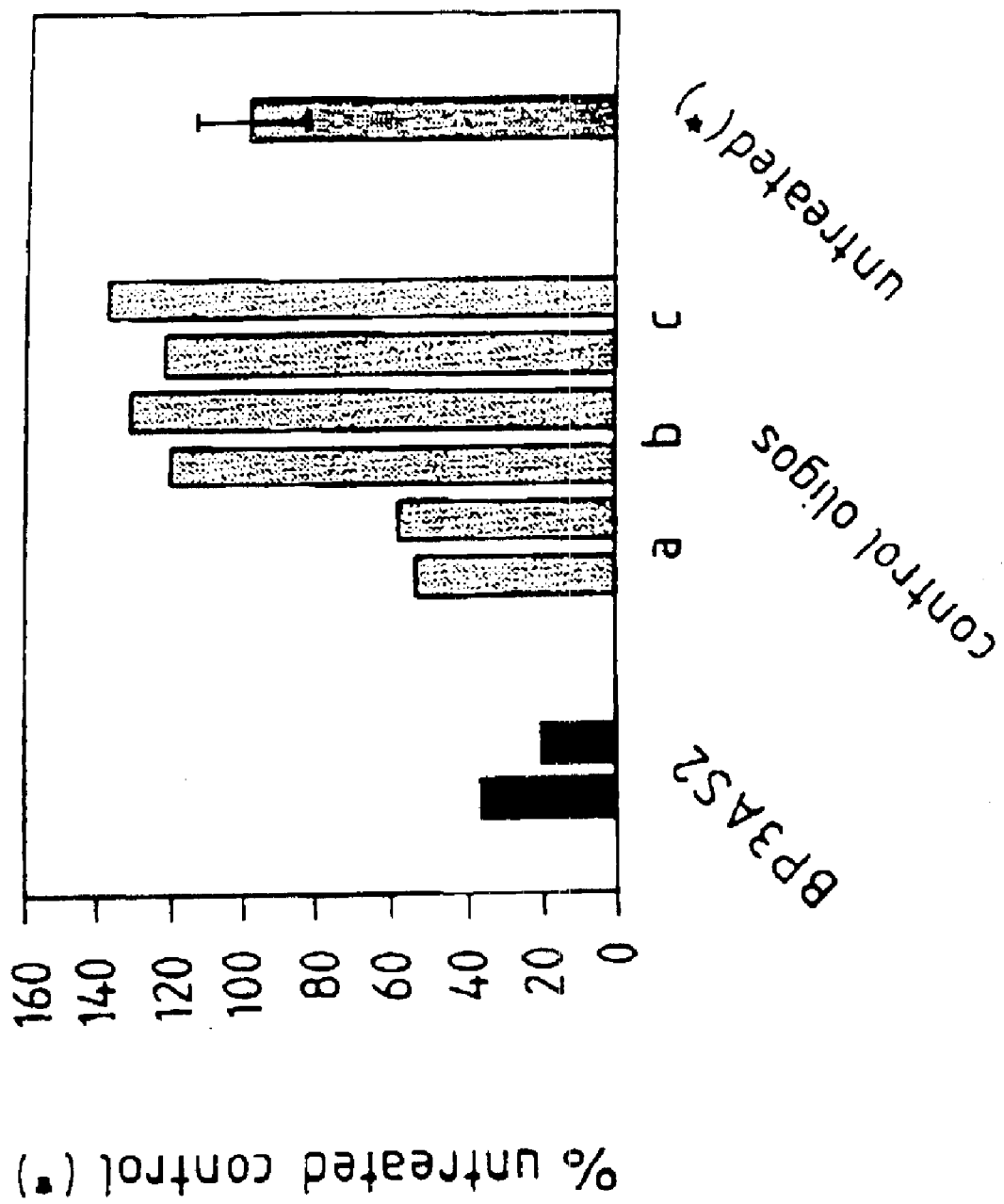
FIG. 5B is a graphical representation of a scanning imaging densitometry of Western ligand blot (FIG. 5A), showing relative band intensities of IGFBP-3 after treatment with phosphorothioate oligonucleotides as in FIG. 5A, showing IGFBP-3 band intensities expressed as a percentage of the average band intensity from conditioned medium of cells not treated with oligonucleotide.

To further investigate the inhibitory effects of the more effective of the two antisense oligonucleotides, BP3AS2, inhibition by this oligonucleotide at 0.5 μM was compared with a number of control oligonucleotides, including one antisense oligonucleotide to IGFBP-3 that had proved to be ineffective at 0.5 μM. As shown in FIGS. 5A and 5B, BP3AS2 was again inhibitory, resulting in levels of IGFBP-3 of approximately 50% of the most non-specifically inhibitory control oligonucleotide, the randomised equivalent of BP3AS2. The other control oligonucleotides caused no reduction in IGFBP-3 levels at 0.5 μM, compared to untreated cells.

Of possible significance is the fact that this control oligonucleotide, BP3AS2NS, like BP3AS2 itself, has the highest potential $T_m$ of the three control oligonucleotides used in this experiment, enhancing the probability of non-specific base pairing with non-target mRNAs. However, the lack of inhibition of IGFBP-4 secretion by BP3AS2 suggests that this oligonucleotide is selective even compared with the most closely related protein likely to be present in this cell line.

EXAMPLE 6

Antisense oligonucleotides to IGFBP2 may be selected from molecules capable of interacting with one or more oligonucleotides selected from oligonucleotides having the sequence of nucleotides 1–15, 2–16, 3–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 29–43, 30–44, 31–45, 32–46, 33–47, 34–48, 35–49, 36–50, 37–51, 38–52, 39–53, 40–54, 41–55, 42–56, 43–57, 44–58, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 84–98, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124, 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166–180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 186–200, 187–201, 188–202, 189–203, 190–204, 191–205, 192–206, 193–207, 194–208, 195–209, 196–210, 197–211, 198–212, 199–213, 200–214, 201–215, 202–216, 203–217, 204–218, 205–219, 206–220, 207–221, 208–222, 209–223, 210–224, 211–225, 212–226, 213–227, 214–228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288; 275–289, 276–290, 277–291, 278–292, 279–293, 280–294, 281–295, 282–296, 283–297, 284–298, 285–299, 286–300, 287–301, 288–302, 289–303, 290–304, 291–305, 292–306, 293–307, 294–308, 295–309, 296–310, 297–311, 298–312, 299–313, 300–314, 301–315, 302–315, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 350–364, 351–365, 352–366, 353–367, 354–368, 355–369, 356–370, 357–371, 358–372, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388402, 389–403, 390404, 391–405, 392–406, 393–407, 394–408, 395–409, 396–410, 397–411, 398–412, 399–413, 400–414, 401–415, 402–416, 403–417, 404–418, 405–419, 406–420, 407–421, 408–422, 409–423, 410–424, 411–425, 412–426, 413–427, 414–428, 415–429, 416–430, 417–431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 461–475, 462–476, 463–477, 464–478, 465–479, 466–480, 467–481, 468–482, 469–483, 470–484, 471485, 472–486, 473–487, 474–488, 475–489, 476–490, 477–491, 478–492, 479–493, 480–494, 481–495, 482–496, 483–497, 484–498, 485–499, 486–500, 487–501, 488–502, 489–503, 490–504, 491–505, 492–506, 493–507, 494–508, 495–509, 496–510, 497–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544–558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 59–604, 591–605, 592–606, 593–607, 594–608, 595–609, 596–610, 597–611, 598–612, 599–613, 600–614, 601–615, 602–616, 603–617, 604–618, 605–619, 606–620, 607–621, 608–622, 609–623, 610–624, 611–625, 612–626, 613–627, 614–628, 615–629, 616–630, 617–631, 618–632, 619–633, 620–634, 621–635, 622–636, 623–637, 624–638, 625–639, 626–640, 627–641, 628–642, 629–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 658–672, 659–673, 660–674, 661–675, 662–676, 663–677, 664–678, 665–679, 666–680, 667–681, 668–682, 669–683, 670–684, 671–685, 672–686, 673–687, 674–688, 675–689, 676–690, 677–691, 678–692, 679–693, 680–694, 681–695, 682–696, 683–697, 684–698, 685–699, 686–700, 687–701,
688–702, 689–703, 690–704, 691–705, 692–706, 693–707,
694–708, 695–709, 696–710, 697–711, 698–712, 699–713,
700–714, 701–715, 702–716, 703–717, 704–718, 705–719,
706–720, 707–721, 708–722, 709–723, 710–724, 711–725,
712–726, 713–727, 714–728, 715–729, 716–730, 717–731,
718–732, 719–733, 720–734, 721–735, 722–736, 723–737,
724–738, 725–739, 726–740, 727–741, 728–742, 729–743,
730–744, 731–745, 732–746, 733–747, 734–748, 735–749,
736–750, 737–751, 738–752, 739–753, 740–754, 741–755,
742–756, 743–757, 744–758, 745–759, 746–760, 747–761,
748–762, 749–763, 750–764, 751–765, 752–766, 753–767,
754–768, 755–769, 756–770, 757–771, 758–772, 759–773,
760–774, 761–775, 762–776, 763–777, 764–778, 765–779,
766–780, 767–781, 768–782, 769–783, 770–784, 771–785,
772–786, 773–787, 774–788, 775–789, 776–790, 777–791,
778–792, 779–793, 780–794, 781–795, 782–796, 783–797,
784–798, 785–799, 786–800, 787–801, 788–802, 789–803,
790–804, 791–805, 792–806, 793–807, 794–808, 795–809,
796–810, 797–811, 798–812, 799–813, 800–814, 801–815,
802–816, 803–817, 804–818, 805–819, 806–820, 807–821,
808–822, 809–823, 810–824, 811–825, 812–826, 813–827,
814–828, 815–829, 816–830, 817–831, 818–832, 819–833,
820–834, 821–835, 822–836, 823–837, 824–838, 825–839,
826–840, 827–841, 828–842, 829–843, 830–844, 831–845,
832–846, 833–847, 834–848, 835–849, 836–850, 837–851,
838–852, 839–853, 840–854, 841–855, 842–856, 843–857,
844–858, 845–859, 846–860, 847–861, 848–862, 849–863,
850–864, 851–865, 852–866, 853–867, 854–868, 855–869,
856–870, 857–871, 858–872, 859–873, 860–874, 861–875,
862–876, 863–877, 864–878, 865–879, 866–880, 867–881,
868–882, 869–883, 870–884, 871–885, 872–886, 873–887,
874–888, 875–889, 876–890, 877–891, 878–892, 879–893,
880–894, 881–895, 882–896, 883–897, 884–898, 885–899,
886–900, 887–901, 888–902, 889–903, 890–904, 891–905,
892–906, 893–907, 894–908, 895–909, 896–910, 897–911,
898–912, 899–913, 900–914, 901–915, 902–916, 903–917,
904–918, 905–919, 906–920, 907–921, 908–922, 909–923,
910–924, 911–925, 912–926, 913–927, 914–928, 915–929,
916–930, 917–931, 918–932, 919–933, 920–934, 921–935,
922–936, 923–937, 924–938, 925–939, 926–940, 927–941,
928–942, 929–943, 930–944, 931–945, 932–946, 933–947,
934–948, 935–949, 936–950, 937–951, 938–952, 939–953,
940–954, 941–955, 942–956, 943–957, 944–958, 945–959,
946–960, 947–961, 948–962, 949–963, 950–964, 951–965,
952–966, 953–967, 954–968, 955–969, 956–970, 957–971,
958–972, 959–973, 960–974, 961–975, 962–976, 963–977,
964–978, 965–979, 966–980, 967–981, 968–982, 969–983,
970–984, 971–985, 972–986, 973–987, 974–988, 975–989,
976–990, 977–991, 978–992, 979–993, 980–994, 981–995,
982–996, 983–997, 984–998, 985–999, 986–1000,
987–1001, 988–1002, 989–1003, 990–1004, 991–1005,
992–1006, 993–1007, 994–1008, 995–1009, 996–1010,
997–1011, 998–1012, 999–1013, 1000–1014, 1001–1015,
1002–1016, 1003–1017, 1004–1018, 1005–1019,
1006–1020, 1007–1021, 1008–1022, 1009–1023,
1010–1024, 1011–1025, 1012–1026, 1013–1027,
1014–1028, 1015–1029, 1016–1030, 1017–1031,
1018–1032, 1019–1033, 1020–1034, 1021–1035,
1022–1036, 1023–1037, 1024–1038, 1025–1039,
1026–1040, 1027–1041, 1028–1042, 1029–1043,
1030–1044, 1031–1045, 1032–1046, 1033–1047,
1034–1048, 1035–1049, 1036–1050, 1037–1051,
1038–1052, 1039–1053, 1040–1054, 1041–1055,
1042–1056, 1043–1057, 1044–1058, 1045–1059,
1046–1060, 1047–1061, 1048–1062, 1049–1063,
1050–1064, 1051–1065, 1052–1066, 1053–1067,
1054–1068, 1055–1069, 1056–1070, 1057–1071,
1058–1072, 1059–1073, 1060–1074, 1061–1075,
1062–1076, 1063–1077, 1064–1078, 1065–1079,
1066–1080, 1067–1081, 1068–1082, 1069–1083,
1070–1084, 1071–1085, 1072–1086, 1073–1087,
1074–1088, 1075–1089, 1076–1090, 1077–1091,
1078–1092, 1079–1093, 1080–1094, 1081–1095,
1082–1096, 1083–1097, 1084–1098, 1085–1099,
1086–1100, 1087–1101, 1088–1102, 1089–1103,
1090–1104, 1091–1105, 1092–1106, 1093–1107,
1094–1108, 1095–1109, 1096–1110, 1097–1111,
1098–1112, 1099–1113, 1100–1114, 1101–1115,
1102–1116, 1103–1117, 1104–1118, 1105–1119,
1106–1120, 1107–1121, 1108–1122, 1109–1123,
1110–1124, 1111–1125, 1112–1126, 1113–1127, 1114–1128,
1115–1129, 1116–1130, 1117–1131, 1118–1132, 1119–1133,
1120–1134, 1121–1135, 1122–1136, 1123–1137,
1124–1138, 1125–1139, 1126–1140, 1127–1141,
1128–1142, 1129–1143, 1130–1144, 1131–1145,
1132–1146, 1133–1147, 1134–1148, 1135–1149,
1136–1150, 1137–1151, 1138–1152, 1139–1153,
1140–1154, 1141–1155, 1142–1156, 1143–1157,
1144–1158, 1145–1159, 1146–1160, 1147–1161,
1148–1162, 1149–1163, 1150–1164, 1151–1165,
1152–1166, 1153–1167, 1154–1168, 1155–1169,
1156–1170, 1157–1171, 1158–1172, 1159–1173,
1160–1174, 1161–1175, 1162–1176, 1163–1177,
1164–1178, 1165–1179, 1166–1180, 1167–1181,
1168–1182, 1169–1183, 1170–1184, 1171–1185,
1172–1186, 1173–1187, 1174–1188, 1175–1189,
1176–1190, 1177–1191, 1178–1192, 1179–1193,
1180–1194, 1181–1195, 1182–1196, 1183–1197,
1184–1198, 1185–1199, 1186–1200, 1187–1201,
1188–1202, 1189–1203, 1190–1204, 1191–1205,
1192–1206, 1193–1207, 1194–1208, 1195–1209,
1196–1210, 1197–1211, 1198–1212, 1199–1213,
1200–1214, 1201–1215, 1202–1216, 1203–1217,
1204–1218, 1205–1219, 1206–1220, 1207–1221,
1208–1222, 1209–1223, 1210–1224, 1211–1225,
1212–1226, 1213–1227, 1214–1228, 1215–1229,
1216–1230, 1217–1231, 1218–1232, 1219–1233,
1220–1234, 1221–1235, 1222–1236, 1223–1237,
1224–1238, 1225–1239, 1226–1240, 1227–1241,
1228–1242, 1229–1243, 1230–1244, 1231–1245,
1232–1246, 1233–1247, 1234–1248, 1235–1249,
1236–1250, 1237–1251, 1238–1252, 1239–1253,
1240–1254, 1241–1255, 1242–1256, 1243–1257,
1244–1258, 1245–1259, 1246–1260, 1247–1261,
1248–1262, 1249–1263, 1250–1264, 1251–1265,
1252–1266, 1253–1267, 1254–1268, 1255–1269,
1256–1270, 1257–1271, 1258–1272, 1259–1273,
1260–1274, 1261–1275, 1262–1276, 1263–1277,
1264–1278, 1265–1279, 1266–1280, 1267–1281,
1268–1282, 1269–1283, 1270–1284, 1271–1285,
1272–1286, 1273–1287, 1274–1288, 1275–1289,
1276–1290, 1277–1291, 1278–1292, 1279–1293,
1280–1294, 1281–1295, 1282–1296, 1283–1297,
1284–1298, 1285–1299, 1286–1300, 1287–1301,
1288–1302, 1289–1303, 1290–1304, 1291–1305,
1292–1306, 1293–1307, 1294–1308, 1295–1309,
1296–1310, 1297–1311, 1298–1312, 1299–1313,
1300–1314, 1301–1315, 1302–1315, 1303–1317,
1304–1318, 1305–1319, 1306–1320, 1307–1321,
1308–1322, 1309–1323, 1310–1324, 1311–1325,
1312–1326, 1313–1327, 1314–1328, 1315–1329,
1316–1330, 1317–1331, 1318–1332, 1319–1333,
1320–1334, 1321–1335, 1322–1336, 1323–1337, 1324–1338, 1325–1339, 1326–1340, 1327–1341, 1328–1342, 1329–1343, 1330–1344, 1331–1345, 1332–1346, 1333–1347, 1334–1348, 1335–1349, 1336–1350, 1337–1351, 1338–1352, 1339–1353, 1340–1354, 1341–1355, 1342–1356, 1343–1357, 1344–1358, 1345–1359, 1346–1360, 1347–1361, 1348–1362, 1349–1363, 1350–1364, 1351–1365, 1352–1366, 1353–1367, 1354–1368, 1355–1369, 1356–1370, 1357–1371, 1358–1372, 1359–1373, 1360–1374, 1361–1375, 1362–1376, 1363–1377, 1364–1378, 1365–1379, 1366–1380, 1367–1381, 1368–1382, 1369–1383, 1370–1384, 1371–1385, 1372–1386, 1373–1387, 1374–1388, 1375–1389, 1376–1390, 1377–1391, 1378–1392, 1379–1393, 1380–1394, 1381–1395, 1382–1396, 1383–1397, 1384–1398, 1385–1399, 1386–1400, 1387–1401, 1388–1402, 1389–1403, 1390–1404, 1391–1405, 1392–1406, 1393–1407, 1394–1408, 1395–1409, 1396–1410, 1397–1411, 1398–1412, 1399–1413, 1400–1414, 1401–1415, 1402–1416, 1403–1417, 1404–1418, 1405–1419, 1406–1420, 1407–1421, 1408–1422, 1409–1423, 1410–1424, 1411–1425, 1412–1426, 1413–1427, 1414–1428, 1415–1429, 1416–1430, 1417–1431, 1418–1432, and 1419–1433 of SEQ ID NO: 1.

EXAMPLE 7

Antisense oligonucleotides to IGFBP3 may be selected from molecules capable of interacting with one or more oligonucleotides selected from oligonucleotides having the sequence of nucleotides 1–15, 2–16, 3–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 2943, 30–44, 31–45, 32–46, 33–47, 34–48, 35–49, 36–50, 37–51, 38–52, 39–53, 40–54, 41–55, 42–56, 43–57, 44–58, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 8498, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124, 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 186–200, 187–201, 188–202, 189–203, 190–204, 191–205, 192–206, 193–207, 194–208, 195–209, 196–210, 197–211, 198–212, 199–213, 200–214, 201–215, 202–216, 203–217, 204–218, 205–219, 206–220, 207–221, 208–222, 209–223, 210–224, 211–225, 212–226, 213–227, 214–228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288, 275–289, 276–290, 277–291, 278–292, 279–293, 280–294, 281–295, 282–296, 283–297, 284–298, 285–299, 286–300, 287–301, 288–302, 289–303, 290–304, 291–305, 292–306, 293–307, 294–308, 295–309, 296–310, 297–311, 298–312, 299–313, 300–314, 301–315, 302–315, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 350–364, 351–365, 352–366, 353–367, 354–368, 355–369, 356–370, 357–371, 358–372, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388–402, 389–403, 390–404, 391–405, 392–406, 393–407, 394408, 395–409, 396–410, 397–411, 398–412, 399413, 400–414, 401–415, 402–416, 403–417, 404–418, 405419, 406–420, 407421, 408–422, 409–423, 410–424, 411–425, 412–426, 413–427, 414–428, 415–429, 416430, 417431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 461–475, 462–476, 463–477, 464–478, 465–479, 466–480, 467–481, 468–482, 469–483, 470–484, 471–485, 472–486, 473–487, 474–488, 475–489, 476–490, 477–491, 478–492, 479–493, 480–494, 481–495, 482–496, 483–497, 484–498, 485–499, 486–500, 487–501, 488–502, 489–503, 490–504, 491–505, 492–506, 493–507, 494–508, 495–509, 496–510, 497–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544–558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 590–604, 591–605, 592–606, 593–607, 594–608, 595–609, 596–610, 597–611, 598–612, 599–613, 600–614, 601–615, 602–616, 603–617, 604–618, 605–619, 606–620, 607–621, 608–622, 609–623, 610–624, 611–625, 612–626, 613–627, 614–628, 615–629, 616–630, 617–631, 618–632, 619–633, 620–634, 621–635, 622–636, 623–637, 624–638, 625–639, 626–640, 627–641, 628–642, 629–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 658–672, 659–673, 660–674, 661–675, 662–676, 663–677, 664–678, 665–679, 666–680, 667–681, 668–682, 669–683, 670–684, 671–685, 672–686, 673–687, 674–688, 675–689, 676–690, 677–691, 678–692, 679–693, 680–694, 681–695, 682–696, 683–697, 684–698, 685–699, 686–700, 687–701, 688–702, 689–703, 690–704, 691–705, 692–706, 693–707, 694–708, 695–709, 696–710, 697–711, 698–712, 699–713, 700–714, 701–715, 702–716, 703–717, 704–718, 705–719, 706–720, 707–721, 708–722, 709–723, 710–724, 711–725, 712–726, 713–727, 714–728, 715–729, 716–730, 717–731, 718–732, 719–733, 720–734, 721–735, 722–736, 723–737, 724–738, 725–739, 726–740, 727–741, 728–742, 729–743, 730–744, 731–745, 732–746, 733–747, 734–748, 735–749, 736–750, 737–751, 738–752, 739–753, 740–754, 741–755, 742–756, 743–757, 744–758, 745–759, 746–760, 747–761, 748–762, 749–763, 750–764, 751–765, 752–766, 753–767, 754–768, 755–769, 756–770, 757–771, 758–772, 759–773, 760–774, 761–775, 762–776, 763–777, 764–778, 765–779, 766–780, 767–781, 768–782, 769–783, 770–784, 771–785, 772–786, 773–787, 774–788, 775–789, 776–790, 777–791, 778–792, 779–793, 780–794, 781–795, 782–796, 783–797, 784–798, 785–799, 786–800, 787–801, 788–802, 789–803, 790–804, 791–805, 792–806, 793–807, 794–808, 795–809, 796–810, 797–811, 798–812, 799–813, 800–814, 801–815, 802–816, 803–817, 804–818, 805–819, 806–820, 807–821, 808–822, 809–823, 810–824, 811–825, 812–826, 813–827, 814–828, 815–829, 816–830, 817–831, 818–832, 819–833, 820–834, 821–835, 822–836, 823–837, 824–838, 825–839, 826–840, 827–841, 828–842, 829–843, 830–844, 831–845, 832–846, 833–847, 834–848, 835–849, 836–850, 837–851, 838–852, 839–853, 840–854, 841–855, 842–856, 843–857, 844–858, 845–859, 846–860, 847–861, 848–862, 849–863, 850–864, 851–865, 852–866, 853–867, 854–868, 855–869, 856–870, 857–871, 858–872, 859–873, 860–874, 861–875, 862–876, 863–877, 864–878, 865–879, 866–880, 867–881, 868–882, 869–883, 870–884, 871–885, 872–886, 873–887, 874–888, 875–889, 876–890, 877–891, 878–892, 879–893, 880–894, 881–895, 882–896, 883–897, 884–898, 885–899, 886–900, 887–901, 888–902, 889–903, 890–904, 891–905, 892–906, 893–907, 894–908, 895–909, 896–910, 897–911, 898–912, 899–913, 900–914, 901–915, 902–916, 903–917, 904–918, 905–919, 906–920, 907–921, 908–922, 909–923, 910–924, 911–925, 912–926, 913–927, 914–928, 915–929, 916–930, 917–931, 918–932, 919–933, 920–934, 921–935, 922–936, 923–937, 924–938, 925–939, 926–940, 927–941, 928–942, 929–943, 930–944, 931–945, 932–946, 933–947, 934–948, 935–949, 936–950, 937–951, 938–952, 939–953, 940–954, 941–955, 942–956, 943–957, 944–958, 945–959, 946–960, 947–961, 948–962, 949–963, 950–964, 951–965, 952–966, 953–967, 954–968, 955–969, 956–970, 957–971, 958–972, 959–973, 960–974, 961–975, 962–976, 963–977, 964–978, 965–979, 966–980, 967–981, 968–982, 969–983, 970–984, 971–985, 972–986, 973–987, 974–988, 975–989, 976–990, 977–991, 978–992, 979–993, 980–994, 981–995, 982–996, 983–997, 984–998, 985–999, 986–1000, 987–1001, 988–1002, 989–1003, 990–1004, 991–1005, 992–1006, 993–1007, 994–1008, 995–1009, 996–1010, 997–1011, 998–1012, 999–1013, 1000–1014, 1001–1015, 1002–1016, 1003–1017, 1004–1018, 1005–1019, 1006–1020, 1007–1021, 1008–1022, 1009–1023, 1010–1024, 1011–1025, 1012–1026, 1013–1027, 1014–1028, 1015–1029, 1016–1030, 1017–1031, 1018–1032, 1019–1033, 1020–1034, 1021–1035, 1022–1036, 1023–1037, 1024–1038, 1025–1039, 1026–1040, 1027–1041, 1028–1042, 1029–1043, 1030–1044, 1031–1045, 1032–1046, 1033–1047, 1034–1048, 1035–1049, 1036–1050, 1037–1051, 1038–1052, 1039–1053, 1040–1054, 1041–1055, 1042–1056, 1043–1057, 1044–1058, 1045–1059, 1046–1060, 1047–1061, 1048–1062, 1049–1063, 1050–1064, 1051–1065, 1052–1066, 1053–1067, 1054–1068, 1055–1069, 1056–1070, 1057–1071, 1058–1072, 1059–1073, 1060–1074, 1061–1075, 1062–1076, 1063–1077, 1064–1078, 1065–1079, 1066–1080, 1067–1081, 1068–1082, 1069–1083, 1070–1084, 1071–1085, 1072–1086, 1073–1087, 1074–1088, 1075–1089, 1076–1090, 1077–1091, 1078–1092, 1079–1093, 1080–1094, 1081–1095, 1082–1096, 1083–1097, 1084–1098, 1085–1099, 1086–1100, 1087–1101, 1088–1102, 1089–1103, 1090–1104, 1091–1105, 1092–1106, 1093–1107, 1094–1108, 1095–1109, 1096–1110, 1097–1111, 1098–1112, 1099–1113, 1100–1114, 1101–1115, 1102–1116, 1103–1117, 1104–1118, 1105–1119, 1106–1120, 1107–1121, 1108–1122, 1109–1123, 1110–1124, 1111–1125, 1112–1126, 1113–1127, 1114–1128, 1115–1129, 1116–1130, 1117–1131, 1118–1132, 1119–1133, 1120–1134, 1121–1135, 1122–1136, 1123–1137, 1124–1138, 1125–1139, 1126–1140, 1127–1141, 1128–1142, 1129–1143, 1130–1144, 1131–1145, 1132–1146, 1133–1147, 1134–1148, 1135–1149, 1136–1150, 1137–1151, 1138–1152, 1139–1153, 1140–1154, 1141–1155, 1142–1156, 1143–1157, 1144–1158, 1145–1159, 1146–1160, 1147–1161, 1148–1162, 1149–1163, 1150–1164, 1151–1165, 1152–1166, 1153–1167, 1154–1168, 1155–1169, 1156–1170, 1157–1171, 1158–1172, 1159–1173, 1160–1174, 1161–1175, 1162–1176, 1163–1177, 1164–1178, 1165–1179, 1166–1180, 1167–1181, 1168–1182, 1169–1183, 1170–1184, 1171–1185, 1172–1186, 1173–1187, 1174–1188, 1175–1189, 1176–1190, 1177–1191, 1178–1192, 1179–1193, 1180–1194, 1181–1195, 1182–1196, 1183–1197, 1184–1198, 1185–1199, 1186–1200, 1187–1201, 1188–1202, 1189–1203, 1190–1204, 1191–1205, 1192–1206, 1193–1207, 1194–1208, 1195–1209, 1196–1210, 1197–1211, 1198–1212, 1199–1213, 1200–1214, 1201–1215, 1202–1216, 1203–1217, 1204–1218, 1205–1219, 1206–1220, 1207–1221, 1208–1222, 1209–1223, 1210–1224, 1211–1225, 1212–1226, 1213–1227, 1214–1228, 1215–1229, 1216–1230, 1217–1231, 1218–1232, 1219–1233, 1220–1234, 1221–1235, 1222–1236, 1223–1237, 1224–1238, 1225–1239, 1226–1240, 1227–1241, 1228–1242, 1229–1243, 1230–1244, 1231–1245, 1232–1246, 1233–1247, 1234–1248, 1235–1249, 1236–1250, 1237–1251, 1238–1252, 1239–1253, 1240–1254, 1241–1255, 1242–1256, 1243–1257, 1244–1258, 1245–1259, 1246–1260, 1247–1261, 1248–1262, 1249–1263, 1250–1264, 1251–1265, 1252–1266, 1253–1267, 1254–1268, 1255–1269, 1256–1270, 1257–1271, 1258–1272, 1259–1273, 1260–1274, 1261–1275, 1262–1276, 1263–1277, 1264–1278, 1265–1279, 1266–1280, 1267–1281, 1268–1282, 1269–1283, 1270–1284, 1271–1285, 1272–1286, 1273–1287, 1274–1288, 1275–1289, 1276–1290, 1277–1291, 1278–1292, 1279–1293, 1280–1294, 1281–1295, 1282–1296, 1283–1297, 1284–1298, 1285–1299, 1286–1300, 1287–1301, 1288–1302, 1289–1303, 1290–1304, 1291–1305, 1292–1306, 1293–1307, 1294–1308, 1295–1309, 1296–1310, 1297–1311, 1298–1312, 1299–1313, 1300–1314, 1301–1315, 1302–1315, 1303–1317,
1304–1318, 1305–1319, 1306–1320, 1307–1321,
1308–1322, 1309–1323, 1310–1324, 1311–1325,
1312–1326, 1313–1327, 1314–1328, 1315–1329,
1316–1330, 1317–1331, 1318–1332, 1319–1333,
1320–1334, 1321–1335, 1322–1336, 1323–1337,
1324–1338, 1325–1339, 1326–1340, 1327–1341,
1328–1342, 1329–1343, 1330–1344, 1331–1345,
1332–1346, 1333–1347, 1334–1348, 1335–1349,
1336–1350, 1337–1351, 1338–1352, 1339–1353,
1340–1354, 1341–1355, 1342–1356, 1343–1357,
1344–1358, 1345–1359, 1346–1360, 1347–1361,
1348–1362, 1349–1363, 1350–1364, 1351–1365,
1352–1366, 1353–1367, 1354–1368, 1355–1369,
1356–1370, 1357–1371, 1358–1372, 1359–1373,
1360–1374, 1361–1375, 1362–1376, 1363–1377,
1364–1378, 1365–1379, 1366–1380, 1367–1381,
1368–1382, 1369–1383, 1370–1384, 1371–1385,
1372–1386, 1373–1387, 1374–1388, 1375–1389,
1376–1390, 1377–1391, 1378–1392, 1379–1393,
1380–1394, 1381–1395, 1382–1396, 1383–1397,
1384–1398, 1385–1399, 1386–1400, 1387–1401,
1388–1402, 1389–1403, 1390–1404, 1391–1405,
1392–1406, 1393–1407, 1394–1408, 1395–1409,
1396–1410, 1397–1411, 1398–1412, 1399–1413,
1400–1414, 1401–1415, 1402–1416, 1403–1417,
1404–1418, 1405–1419, 1406–1420, 1407–1421,
1408–1422, 1409–1423, 1410–1424, 1411–1425,
1412–1426, 1413–1427, 1414–1428, 1415–1429,
1416–1430, 1417–1431, 1418–1432, 1419–1433,
1420–1434, 1421–1435, 1422–1436, 1423–1437,
1424–1438, 1425–1439, 1426–1440, 1427–1441,
1428–1442, 1429–1443, 1430–1444, 1431–1445,
1432–1446, 1433–1447, 1434–1448, 1435–1449,
1436–1450, 1437–1451, 1438–1452, 1439–1453,
1440–1454, 1441–1455, 1442–1456, 1443–1457,
1444–1458, 1445–1459, 1446–1460, 1447–1461,
1448–1462, 1449–1463, 1450–1464, 1451–1465,
1452–1466, 1453–1467, 1454–1468, 1455–1469,
1456–1470, 1457–1471, 1458–1472, 1459–1473,
1460–1474, 1461–1475, 1462–1476, 1463–1477,
1464–1478, 1465–1479, 1466–1480, 1467–1481,
1468–1482, 1469–1483, 1470–1484, 1471–1485,
1472–1486, 1473–1487, 1474–1488, 1475–1489,
1476–1490, 1477–1491, 1478–1492, 1479–1493,
1480–1494, 1481–1495, 1482–1496, 1483–1497,
1484–1498, 1485–1499, 1486–1500, 1487–1501,
1488–1502, 1489–1503, 1490–1504, 1491–1505,
1492–1506, 1493–1507, 1494–1508, 1495–1509,
1496–1510, 1497–1511, 1498–1513, 1499–1514,
1500–1515, 1501–1515, 1502–1516, 1503–1517,
1504–1518, 1505–1519, 1506–1520, 1507–1521,
1508–1522, 1509–1523, 1510–1524, 1511–1525,
1512–1526, 1513–1527, 1514–1528, 1515–1529,
1516–1530, 1517–1531, 1518–1532, 1519–1533,
1520–1534, 1521–1535, 1522–1536, 1523–1537,
1524–1538, 1525–1539, 1526–1540, 1527–1541,
1528–1542, 1529–1543, 1530–1544, 1531–1545,
1532–1546, 1533–1547, 1534–1548, 1535–1549,
1536–1550, 1537–1551, 1538–1552, 1539–1553,
1540–1554, 1541–1555, 1542–1556, 1543–1557,
1544–1558, 1545–1559, 1546–1560, 1547–1561,
1548–1562, 1549–1563, 1550–1564, 1551–1565,
1552–1566, 1553–1567, 1554–1568, 1555–1569,
1556–1570, 1557–1571, 1558–1572, 1559–1573,
1560–1574, 1561–1575, 1562–1576, 1563–1577,
1564–1578, 1565–1579, 1566–1580, 1567–1581,
1568–1582, 1569–1583, 1570–1584, 1571–1585,
1572–1586, 1573–1587, 1574–1588, 1575–1589,
1576–1590, 1577–1591, 1578–1592, 1579–1593,
1580–1594, 1581–1595, 1582–1596, 1583–1597,
1584–1598, 1585–1599, 1586–1600, 1587–1601,
1588–1602, 1589–1603, 1590–1604, 1591–1605,
1592–1606, 1593–1607, 1594–1608, 1595–1609,
1596–1610, 1597–1611, 1598–1612, 1599–1613,
1600–1614, 1601–1615, 1602–1616, 1603–1617,
1604–1618, 1605–1619, 1606–1620, 1607–1621,
1608–1622, 1609–1623, 1610–1624, 1611–1625,
1612–1626, 1613–1627, 1614–1628, 1615–1629,
1616–1630, 1617–1631, 1618–1632, 1619–1633,
1620–1634, 1621–1635, 1622–1636, 1623–1637,
1624–1638, 1625–1639, 1626–1640, 1627–1641,
1628–1642, 1629–1643, 1630–1644, 1631–1645,
1632–1646, 1633–1647, 1634–1648, 1635–1649,
1636–1650, 1637–1651, 1638–1652, 1639–1653,
1640–1654, 1641–1655, 1642–1656, 1643–1657,
1644–1658, 1645–1659, 1646–1660, 1647–1661,
1648–1662, 1649–1663, 1650–1664, 1651–1665,
1652–1666, 1653–1667, 1654–1668, 1655–1669,
1656–1670, 1657–1671, 1658–1672, 1659–1673,
1660–1674, 1661–1675, 1662–1676, 1663–1677,
1664–1678, 1665–1679, 1666–1680, 1667–1681,
1668–1682, 1669–1683, 1670–1684, 1671–1685,
1672–1686, 1673–1687, 1674–1688, 1675–1689,
1676–1690, 1677–1691, 1678–1692, 1679–1693,
1680–1694, 1681–1695, 1682–1696, 1683–1697,
1684–1698, 1685–1699, 1686–1700, 1687–1701,
1688–1702, 1689–1703, 1690–1704, 1691–1705,
1692–1706, 1693–1707, 1694–1708, 1695–1709,
1696–1710, 1697–1711, 1698–1712, 1699–1713,
1700–1714, 1701–1715, 1702–1716, 1703–1717,
1704–1718, 1705–1719, 1706–1720, 1707–1721,
1708–1722, 1709–1723, 1710–1724, 1711–1725,
1712–1726, 1713–1727, 1714–1728, 1715–1729,
1716–1730, 1717–1731, 1718–1732, 1719–1733,
1720–1734, 1721–1735, 1722–1736, 1723–1737,
1724–1738, 1725–1739, 1726–1740, 1727–1741,
1728–1742, 1729–1743, 1730–1744, 1731–1745,
1732–1746, 1733–1747, 1734–1748, 1735–1749,
1736–1750, 1737–1751, 1738–1752, 1739–1753,
1740–1754, 1741–1755, 1742–1756, 1743–1757,
1744–1758, 1745–1759, 1746–1760, 1747–1761,
1748–1762, 1749–1763, 1750–1764, 1751–1765,
1752–1766, 1753–1767, 1754–1768, 1755–1769,
1756–1770, 1757–1771, 1758–1772, 1759–1773,
1760–1774, 1761–1775, 1762–1776, 1763–1777,
1764–1778, 1765–1779, 1766–1780, 1767–1781,
1768–1782, 1769–1783, 1770–1784, 1771–1785,
1772–1786, 1773–1787, 1774–1788, 1775–1789,
1776–1790, 1777–1791, 1778–1792, 1779–1793,
1780–1794, 1781–1795, 1782–1796, 1783–1797,
1784–1798, 1785–1799, 1786–1800, 1787–1801,
1788–1802, 1789–1803, 1790–1804, 1791–1805,
1792–1806, 1793–1807, 1794–1808, 1795–1809,
1796–1810, 1797–1811, 1798–1812, 1799–1813,
1800–1814, 1801–1815, 1802–1816, 1803–1817,
1804–1818, 1805–1819, 1806–1820, 1807–1821,
1808–1822, 1809–1823, 1810–1824, 1811–1825,
1812–1826, 1813–1827, 1814–1828, 1815–1829,
1816–1830, 1817–1831, 1818–1832, 1819–1833,
1820–1834, 1821–1835, 1822–1836, 1823–1837,
1824–1838, 1825–1839, 1826–1840, 1827–1841,
1828–1842, 1829–1843, 1830–1844, 1831–1845,
1832–1846, 1833–1847, 1834–1848, 1835–1849, 1836–1850, 1837–1851, 1838–1852, 1839–1853,
1840–1854, 1841–1855, 1842–1856, 1843–1857,
1844–1858, 1845–1859, 1846–1860, 1847–1861,
1848–1862, 1849–1863, 1850–1864, 1851–1865,
1852–1866, 1853–1867, 1854–1868, 1855–1869,
1856–1870, 1857–1871, 1858–1872, 1859–1873,
1860–1874, 1861–1875, 1862–1876, 1863–1877,
1864–1878, 1865–1879, 1866–1880, 1867–1881,
1868–1882, 1869–1883, 1870–1884, 1871–1885,
1872–1886, 1873–1887, 1874–1888, 1875–1889,
1876–1890, 1877–1891, 1878–1892, 1879–1893,
1880–1894, 1881–1895, 1882–1896, 1883–1897,
1884–1898, 1885–1899, 1886–1900, 1887–1901,
1888–1902, 1889–1903, 1890–1904, 1891–1905,
1892–1906, 1893–1907, 1894–1908, 1895–1909,
1896–1910, 1897–1911, 1898–1912, 1899–1913,
1900–1914, 1901–1915, 1902–1916, 1903–1917,
1904–1918, 1905–1919, 1906–1920, 1907–1921,
1908–1922, 1909–1923, 1910–1924, 1911–1925,
1912–1926, 1913–1927, 1914–1928, 1915–1929,
1916–1930, 1917–1931, 1918–1932, 1919–1933,
1920–1934, 1921–1935, 1922–1936, 1923–1937,
1924–1938, 1925–1939, 1926–1940, 1927–1941,
1928–1942, 1929–1943, 1930–1944, 1931–1945,
1932–1946, 1933–1947, 1934–1948, 1935–1949,
1936–1950, 1937–1951, 1938–1952, 1939–1953,
1940–1954, 1941–1955, 1942–1956, 1943–1957,
1944–1958, 1945–1959, 1946–1960, 1947–1961,
1948–1962, 1949–1963, 1950–1964, 1951–1965,
1952–1966, 1953–1967, 1954–1968, 1955–1969,
1956–1970, 1957–1971, 1958–1972, 1959–1973,
1960–1974, 1961–1975, 1962–1976, 1963–1977,
1964–1978, 1965–1979, 1966–1980, 1967–1981,
1968–1982, 1969–1983, 1970–1984, 1971–1985,
1972–1986, 1973–1987, 1974–1988, 1975–1989,
1976–1990, 1977–1991, 1978–1992, 1979–1993,
1980–1994, 1981–1995, 1982–1996, 1983–1997,
1984–1998, 1985–1999, 1986–2000, 1987–2001,
1988–2002, 1989–2003, 1990–2004, 1991–2005,
1992–2006, 1993–2007, 1994–2008, 1995–2009,
1996–2010, 1997–2011, 1998–2012, 1999–2013,
2000–2014, 2001–2015, 2002–2016, 2003–2017,
2004–2018, 2005–2019, 2006–2020, 2007–2021,
2008–2022, 2009–2023, 2010–2024, 2011–2025,
2012–2026, 2013–2027, 2014–2028, 2015–2029,
2016–2030, 2017–2031, 2018–2032, 2019–2033,
2020–2034, 2021–2035, 2022–2036, 2023–2037,
2024–2038, 2025–2039, 2026–2040, 2027–2041,
2028–2042, 2029–2043, 2030–2044, 2031–2045,
2032–2046, 2033–2047, 2034–2048, 2035–2049,
2036–2050, 2037–2051, 2038–2052, 2039–2053,
2040–2054, 2041–2055, 2042–2056, 2043–2057,
2044–2058, 2045–2059, 2046–2060, 2047–2061,
2048–2062, 2049–2063, 2050–2064, 2051–2065,
2052–2066, 2053–2067, 2054–2068, 2055–2069,
2056–2070, 2057–2071, 2058–2072, 2059–2073,
2060–2074, 2061–2075, 2062–2076, 2063–2077,
2064–2078, 2065–2079, 2066–2080, 2067–2081,
2068–2082, 2069–2083, 2070–2084, 2071–2085,
2072–2086, 2073–2087, 2074–2088, 2075–2089,
2076–2090, 2077–2091, 2078–2092, 2079–2093,
2080–2094, 2081–2095, 2082–2096, 2083–2097,
2084–2098, 2085–2099, 2086–2100, 2087–2101,
2088–2102, 2089–2103, 2090–2104, 2091–2105,
2092–2106, 2093–2107, 2094–2108, 2095–2109,
2096–2110, 2097–2111, 2098–2112, 2099–2113,
2100–2114, 2101–2115, 2102–2116, 2103–2117,
2104–2118, 2105–2119, 2106–2120, 2107–2121,
2108–2122, 2109–2123, 2110–2124, 2111–2125,
2112–2126, 2113–2127, 2114–2128, 2115–2129,
2116–2130, 2117–2131, 2118–2132, 2119–2133,
2120–2134, 2121–2135, 2122–2136, 2123–2137,
2124–2138, 2125–2139, 2126–2140, 2127–2141,
2128–2142, 2129–2143, 2130–2144, 2131–2145,
2132–2146, 2133–2147, 2134–2148, 2135–2149,
2136–2150, 2137–2151, 2138–2152, 2139–2153,
2140–2154, 2141–2155, 2142–2156, 2143–2157,
2144–2158, 2145–2159, 2146–2160, 2147–2161,
2148–2162, 2149–2163, 2150–2164, 2151–2165,
2152–2166, 2153–2167, 2154–2168, 2155–2169,
2156–2170, 2157–2171, 2158–2172, 2159–2173,
2160–2174, 2161–2175, 2162–2176, 2163–2177,
2164–2178, 2165–2179, 2166–2180, 2167–2181,
2168–2182, 2169–2183, 2170–2184, 2171–2185,
2172–2186, 2173–2187, 2174–2188, 2175–2189,
2176–2190, 2177–2191, 2178–2192, 2179–2193,
2180–2194, 2181–2195, 2182–2196, 2183–2197,
2184–2198, 2185–2199, 2186–2200, 2187–2201,
2188–2202, 2189–2203, 2190–2204, 2191–2205,
2192–2206, 2193–2207, 2194–2208, 2195–2209,
2196–2210, 2197–2211, 2198–2212, 2199–2213,
2200–2214, 2201–2215, 2202–2216, 2203–2217,
2204–2218, 2205–2219, 2206–2220, 2207–2221,
2208–2222, 2209–2223, 2210–2224, 2211–2225,
2212–2226, 2213–2227, 2214–2228, 2215–2229,
2216–2230, 2217–2231, 2218–2232, 2219–2233,
2220–2234, 2221–2235, 2222–2236, 2223–2237,
2224–2238, 2225–2239, 2226–2240, 2227–2241,
2228–2242, 2229–2243, 2230–2244, 2231–2245,
2232–2246, 2233–2247, 2234–2248, 2235–2249,
2236–2250, 2237–2251, 2238–2252, 2239–2253,
2240–2254, 2241–2255, 2242–2256, 2243–2257,
2244–2258, 2245–2259, 2246–2260, 2247–2261,
2248–2262, 2249–2263, 2250–2264, 2251–2265,
2252–2266, 2253–2267, 2254–2268, 2255–2269,
2256–2270, 2257–2271, 2258–2272, 2259–2273,
2260–2274, 2261–2275, 2262–2276, 2263–2277,
2264–2278, 2265–2279, 2266–2280, 2267–2281,
2268–2282, 2269–2283, 2270–2284, 2271–2285,
2272–2286, 2273–2287, 2274–2288, 2275–2289,
2276–2290, 2277–2291, 2278–2292, 2279–2293,
2280–2294, 2281–2295, 2282–2296, 2283–2297,
2284–2298, 2285–2299, 2286–2300, 2287–2301,
2288–2302, 2289–2303, 2290–2304, 2291–2305,
2292–2306, 2293–2307, 2294–2308, 2295–2309,
2296–2310, 2297–2311, 2298–2312, 2299–2313,
2300–2314, 2301–2315, 2302–2315, 2303–2317,
2304–2318, 2305–2319, 2306–2320, 2307–2321,
2308–2322, 2309–2323, 2310–2324, 2311–2325,
2312–2326, 2313–2327, 2314–2328, 2315–2329,
2316–2330, 2317–2331, 2318–2332, 2319–2333,
2320–2334, 2321–2335, 2322–2336, 2323–2337,
2324–2338, 2325–2339, 2326–2340, 2327–2341,
2328–2342, 2329–2343, 2330–2344, 2331–2345,
2332–2346, 2333–2347, 2334–2348, 2335–2349,
2336–2350, 2337–2351, 2338–2352, 2339–2353,
2340–2354, 2341–2355, 2342–2356, 2343–2357,
2344–2358, 2345–2359, 2346–2360, 2347–2361,
2348–2362, 2349–2363, 2350–2364, 2351–2365,
2352–2366, 2353–2367, 2354–2368, 2355–2369,
2356–2370, 2357–2371, 2358–2372, 2359–2373,
2360–2374, 2361–2375, 2362–2376, 2363–2377,
2364–2378, 2365–2379, 2366–2380, 2367–2381,
2368–2382, 2369–2383, 2370–2384, 2371–2385, 2372–2386, 2373–2387, 2374–2388, 2375–2389, 2376–2390, 2377–2391, 2378–2392, 2379–2393, 2380–2394, 2381–2395, 2382–2396, 2383–2397, 2384–2398, 2385–2399, 2386–2400, 2387–2401, 2388–2402, 2389–2403, 2390–2404, 2391–2405, 2392–2406, 2393–2407, 2394–2408, 2395–2409, 2396–2410, 2397–2411, 2398–2412, 2399–2413, 2400–1412, 2401–2415, 2402–2416, 2403–2417, 2404–2418, 2405–2419, 2406–2420, 2407–2421, 2408–2422, 2409–2423, 2410–2424, 2411–2425, 2412–2426, 2413–2427, 2414–2428, 2415–2429, 2416–2430, 2417–2431, 2418–2432, 2419–2433, 2420–2434, 2421–2435, 2422–2436, 2423–2437, 2424–2438, 2425–2439, 2426–2440, 2427–2441, 2428–2442, 2429–2443, 2430–2444, 2431–2445, 2432–2446, 2433–2447, 2434–2448, 2435–2449, 2436–2450, 2437–2451, 2438–2452, 2439–2453, 2440–2454, 2441–2455, 2442–2456, 2443–2457, 2444–2458, 2445–2459, 2446–2460, 2447–2461, 2448–2462, 2449–2463, 2450–2464, 2451–2465, 2452–2466, 2453–2467, 2454–2468, 2455–2469, 2456–2470, 2457–2471, 2458–2472, 2459–2473, and 2460–2474 of SEQ ID NO:2.

EXAMPLE 8

Antisense oligonucleotides to IGF-I may be selected from molecules capable of interacting with one or more oligonucleotides selected from oligonucleotides having the sequence of nucleotides 1–15, 2–16, 3–17, 4–18, 5–19, 6–20, 7–21, 8–22, 9–23, 10–24, 11–25, 12–26, 13–27, 14–28, 15–29, 16–30, 17–31, 18–32, 19–33, 20–34, 21–35, 22–36, 23–37, 24–38, 25–39, 26–40, 27–41, 28–42, 29–43, 30–44, 31–45, 32–46, 33–47, 34–48, 3549, 36–50, 37–51, 38–52, 39–53, 40–54, 41–55, 42–56, 43–57, 4458, 45–59, 46–60, 47–61, 48–62, 49–63, 50–64, 51–65, 52–66, 53–67, 54–68, 55–69, 56–70, 57–71, 58–72, 59–73, 60–74, 61–75, 62–76, 63–77, 64–78, 65–79, 66–80, 67–81, 68–82, 69–83, 70–84, 71–85, 72–86, 73–87, 74–88, 75–89, 76–90, 77–91, 78–92, 79–93, 80–94, 81–95, 82–96, 83–97, 84–98, 85–99, 86–100, 87–101, 88–102, 89–103, 90–104, 91–105, 92–106, 93–107, 94–108, 95–109, 96–110, 97–111, 98–112, 99–113, 100–114, 101–115, 102–116, 103–117, 104–118, 105–119, 106–120, 107–121, 108–122, 109–123, 110–124, 111–125, 112–126, 113–127, 114–128, 115–129, 116–130, 117–131, 118–132, 119–133, 120–134, 121–135, 122–136, 123–137, 124–138, 125–139, 126–140, 127–141, 128–142, 129–143, 130–144, 131–145, 132–146, 133–147, 134–148, 135–149, 136–150, 137–151, 138–152, 139–153, 140–154, 141–155, 142–156, 143–157, 144–158, 145–159, 146–160, 147–161, 148–162, 149–163, 150–164, 151–165, 152–166, 153–167, 154–168, 155–169, 156–170, 157–171, 158–172, 159–173, 160–174, 161–175, 162–176, 163–177, 164–178, 165–179, 166–180, 167–181, 168–182, 169–183, 170–184, 171–185, 172–186, 173–187, 174–188, 175–189, 176–190, 177–191, 178–192, 179–193, 180–194, 181–195, 182–196, 183–197, 184–198, 185–199, 186–200, 187–201, 188–202, 189–203, 190–204, 191–205, 192–206, 193–207, 194–208, 195–209, 196210, 197–211, 198–212, 199–213, 200–214, 201–215, 202–216, 203–217, 204–218, 205–219, 206–220, 207–221, 208–222, 209–223, 210–224, 211–225, 212–226, 213–227, 214228, 215–229, 216–230, 217–231, 218–232, 219–233, 220–234, 221–235, 222–236, 223–237, 224–238, 225–239, 226–240, 227–241, 228–242, 229–243, 230–244, 231–245, 232–246, 233–247, 234–248, 235–249, 236–250, 237–251, 238–252, 239–253, 240–254, 241–255, 242–256, 243–257, 244–258, 245–259, 246–260, 247–261, 248–262, 249–263, 250–264, 251–265, 252–266, 253–267, 254–268, 255–269, 256–270, 257–271, 258–272, 259–273, 260–274, 261–275, 262–276, 263–277, 264–278, 265–279, 266–280, 267–281, 268–282, 269–283, 270–284, 271–285, 272–286, 273–287, 274–288, 275–289, 276–290, 277–291, 278–292, 279–293, 280–294, 281–295, 282–296, 283–297, 284–298, 285–299, 286–300, 287–301, 288–302, 289–303, 290–304, 291–305, 292–306, 293–307, 294–308, 295–309, 296–310, 297–311, 298–312, 299–313, 300–314, 301–315, 302–315, 303–317, 304–318, 305–319, 306–320, 307–321, 308–322, 309–323, 310–324, 311–325, 312–326, 313–327, 314–328, 315–329, 316–330, 317–331, 318–332, 319–333, 320–334, 321–335, 322–336, 323–337, 324–338, 325–339, 326–340, 327–341, 328–342, 329–343, 330–344, 331–345, 332–346, 333–347, 334–348, 335–349, 336–350, 337–351, 338–352, 339–353, 340–354, 341–355, 342–356, 343–357, 344–358, 345–359, 346–360, 347–361, 348–362, 349–363, 350–364, 351–365, 352–366, 353–367, 354–368, 355–369, 356–370, 357–371, 358–372, 359–373, 360–374, 361–375, 362–376, 363–377, 364–378, 365–379, 366–380, 367–381, 368–382, 369–383, 370–384, 371–385, 372–386, 373–387, 374–388, 375–389, 376–390, 377–391, 378–392, 379–393, 380–394, 381–395, 382–396, 383–397, 384–398, 385–399, 386–400, 387–401, 388–402, 389–403, 390–404, 391–405, 392–406, 393–407, 394–408, 395–409, 396–410, 397–411, 398–412, 399–413, 400–414, 401–415, 402–416, 403–417, 404–418, 405–419, 406–420, 407–421, 408–422, 409–423, 410–424, 411–425, 412–426, 413–427, 414–428, 415–429, 416–430, 417–431, 418–432, 419–433, 420–434, 421–435, 422–436, 423–437, 424–438, 425–439, 426–440, 427–441, 428–442, 429–443, 430–444, 431–445, 432–446, 433–447, 434–448, 435–449, 436–450, 437–451, 438–452, 439–453, 440–454, 441–455, 442–456, 443–457, 444–458, 445–459, 446–460, 447–461, 448–462, 449–463, 450–464, 451–465, 452–466, 453–467, 454–468, 455–469, 456–470, 457–471, 458–472, 459–473, 460–474, 461–475, 462–476, 463–477, 464–478, 465–479, 466–480, 467–481, 468–482, 469–483, 470–484, 471–485, 472–486, 473–487, 474–488, 475–489, 476–490, 477–491, 478–492, 479–493, 480–494, 481–495, 482–496, 483–497, 484–498, 485499, 486–500, 487–501, 488–502, 489–503, 490–504, 491–505, 492–506, 493–507, 494–508, 495–509, 496–510, 497–511, 498–513, 499–514, 500–515, 501–515, 502–516, 503–517, 504–518, 505–519, 506–520, 507–521, 508–522, 509–523, 510–524, 511–525, 512–526, 513–527, 514–528, 515–529, 516–530, 517–531, 518–532, 519–533, 520–534, 521–535, 522–536, 523–537, 524–538, 525–539, 526–540, 527–541, 528–542, 529–543, 530–544, 531–545, 532–546, 533–547, 534–548, 535–549, 536–550, 537–551, 538–552, 539–553, 540–554, 541–555, 542–556, 543–557, 544558, 545–559, 546–560, 547–561, 548–562, 549–563, 550–564, 551–565, 552–566, 553–567, 554–568, 555–569, 556–570, 557–571, 558–572, 559–573, 560–574, 561–575, 562–576, 563–577, 564–578, 565–579, 566–580, 567–581, 568–582, 569–583, 570–584, 571–585, 572–586, 573–587, 574–588, 575–589, 576–590, 577–591, 578–592, 579–593, 580–594, 581–595, 582–596, 583–597, 584–598, 585–599, 586–600, 587–601, 588–602, 589–603, 590–604, 591–605, 592–606, 593–607, 594–608, 595–609, 596–610, 597–611, 598–612, 599–613, 600–614, 601–615, 602–616, 603–617, 604618, 605–619, 606–620, 607–621, 608–622, 609–623, 610–624, 611–625, 612–626, 613–627, 614–628, 615–629, 616–630, 617–631, 618–632, 619–633, 620–634, 621–635, 622–636, 623–637, 624–638, 625–639, 626–640, 627–641, 628–642, 629–643, 630–644, 631–645, 632–646, 633–647, 634–648, 635–649, 636–650, 637–651, 638–652, 639–653, 640–654, 641–655, 642–656, 643–657, 644–658, 645–659, 646–660, 647–661, 648–662, 649–663, 650–664, 651–665, 652–666, 653–667, 654–668, 655–669, 656–670, 657–671, 658–672, 659–673, 660–674, 661–675, 662–676, 663–677,
664–678, 665–679, 666–680, 667–681, 668–682, 669–683,
670–684, 671–685, 672–686, 673–687, 674–688, 675–689,
676–690, 677–691, 678–692, 679–693, 680–694, 681–695,
682–696, 683–697, 684–698, 685–699, 686–700, 687–701,
688–702, 689–703, 690–704, 691–705, 692–706, 693–707,
694–708, 695–709, 696–710, 697–711, 698–712, 699–713,
700–714, 701–715, 702–716, 703–717, 704–718, 705–719,
706–720, 707–721, 708–722, 709–723, 710–724, 711–725,
712–726, 713–727, 714–728, 715–729, 716–730, 717–731,
718–732, 719–733, 720–734, 721–735, 722–736, 723–737,
724–738, 725–739, 726–740, 727–741, 728–742, 729–743,
730–744, 731–745, 732–746, 733–747, 734–748, 735–749,
736–750, 737–751, 738–752, 739–753, 740–754, 741–755,
742–756, 743–757, 744–758, 745–759, 746–760, 747–761,
748–762, 749–763, 750–764, 751–765, 752–766, 753–767,
754–768, 755–769, 756–770, 757–771, 758–772, 759–773,
760–774, 761–775, 762–776, 763–777, 764–778, 765–779,
766–780, 767–781, 768–782, 769–783, 770–784, 771–785,
772–786, 773–787, 774–788, 775–789, 776–790, 777–791,
778–792, 779–793, 780–794, 781–795, 782–796, 783–797,
784–798, 785–799, 786–800, 787–801, 788–802, 789–803,
790–804, 791–805, 792–806, 793–807, 794–808, 795–809,
796–810, 797–811, 798–812, 799–813, 800–814, 801–815,
802–816, 803–817, 804–818, 805–819, 806–820, 807–821,
808–822, 809–823, 810–824, 811–825, 812–826, 813–827,
814–828, 815–829, 816–830, 817–831, 818–832, 819–833,
820–834, 821–835, 822–836, 823–837, 824–838, 825–839,
826–840, 827–841, 828–842, 829–843, 830–844, 831–845,
832–846, 833–847, 834–848, 835–849, 836–850, 837–851,
838–852, 839–853, 840–854, 841–855, 842–856, 843–857,
844–858, 845–859, 846–860, 847–861, 848–862, 849–863,
850–864, 851–865, 852–866, 853–867, 854–868, 855–869,
856–870, 857–871, 858–872, 859–873, 860–874, 861–875,
862–876, 863–877, 864–878, 865–879, 866–880, 867–881,
868–882, 869–883, 870–884, 871–885, 872–886, 873–887,
874–888, 875–889, 876–890, 877–891, 878–892, 879–893,
880–894, 881–895, 882–896, 883–897, 884–898, 885–899,
886–900, 887–901, 888–902, 889–903, 890–904, 891–905,
892–906, 893–907, 894–908, 895–909, 896–910, 897–911,
898–912, 899–913, 900–914, 901–915, 902–916, 903–917,
904–918, 905–919, 906–920, 907–921, 908–922, 909–923,
910–924, 911–925, 912–926, 913–927, 914–928, 915–929,
916–930, 917–931, 918–932, 919–933, 920–934, 921–935,
922–936, 923–937, 924–938, 925–939, 926–940, 927–941,
928–942, 929–943, 930–944, 931–945, 932–946, 933–947,
934–948, 935–949, 936–950, 937–951, 938–952, 939–953,
940–954, 941–955, 942–956, 943–957, 944–958, 945–959,
946–960, 947–961, 948–962, 949–963, 950–964, 951–965,
952–966, 953–967, 954968, 955–969, 956–970, 957–971,
958–972, 959–973, 960–974, 961–975, 962–976, 963–977,
964–978, 965–979, 966–980, 967–981, 968–982, 969–983,
970–984, 971–985, 972–986, 973–987, 974–988, 975–989,
976–990, 977–991, 978–992, 979–993, 980–994, 981–995,
982–996, 983–997, 984–998, 985–999, 986–1000,
987–1001, 988–1002, 989–1003, 990–1004, 991–1005,
992–1006, 993–1007, 994–1008, 995–1009, 996–1010,
997–1011, 998–1012, 999–1013, 1000–1014, 1001–1015,
1002–1016, 1003–1017, 1004–1018, 1005–1019,
1006–1020, 1007–1021, 1008–1022, 1009–1023,
1010–1024, 1011–1025, 1012–1026, 1013–1027,
1014–1028, 1015–1029, 1016–1030, 1017–1031,
1018–1032, 1019–1033, 1020–1034, 1021–1035,
1022–1036, 1023–1037, 1024–1038, 1025–1039,
1026–1040, 1027–1041, 1028–1042, 1029–1043,
1030–1044, 1031–1045, 1032–1046, 1033–1047,
1034–1048, 1035–1049, 1036–1050, 1037–1051,
1038–1052, 1039–1053, 1040–1054, 1041–1055,
1042–1056, 1043–1057, 1044–1058, 1045–1059,
1046–1060, 1047–1061, 1048–1062, 1049–1063,
1050–1064, 1051–1065, 1052–1066, 1053–1067,
1054–1068, 1055–1069, 1056–1070, 1057–1071,
1058–1072, 1059–1073, 1060–1074, 1061–1075,
1062–1076, 1063–1077, 1064–1078, 1065–1079,
1066–1080, 1067–1081, 1068–1082, 1069–1083,
1070–1084, 1071–1085, 1072–1086, 1073–1087,
1074–1088, 1075–1089, 1076–1090, 1077–1091,
1078–1092, 1079–1093, 1080–1094, 1081–1095,
1082–1096, 1083–1097, 1084–1098, 1085–1099,
1086–1100, 1087–1101, 1088–1102, 1089–1103,
1090–1104, 1091–1105, 1092–1106, 1093–1107,
1094–1108, 1095–1109, 1096–1110, 1097–1111,
1098–1112, 1099–1113, 1100–1114, 1101–1115,
1102–1116, 1103–1117, 1104–1118, 1105–1119,
1106–1120, 1107–1121, 1108–1122, 1109–1123,
1110–1124, 1111–1125, 1112–1126, 1113–1127, 1114–1128,
1115–1129, 1116–1130, 1117–1131, 1118–1132, 1119–1133,
1120–1134, 1121–1135, 1122–1136, 1123–1137,
1124–1138, 1125–1139, 1126–1140, 1127–1141,
1128–1142, 1129–1143, 1130–1144, 1131–1145,
1132–1146, 1133–1147, 1134–1148, 1135–1149,
1136–1150, 1137–1151, 1138–1152, 1139–1153,
1140–1154, 1141–1155, 1142–1156, 1143–1157,
1144–1158, 1145–1159, 1146–1160, 1147–1161,
1148–1162, 1149–1163, 1150–1164, 1151–1165,
1152–1166, 1153–1167, 1154–1168, 1155–1169,
1156–1170, 1157–1171, 1158–1172, 1159–1173,
1160–1174, 1161–1175, 1162–1176, 1163–1177,
1164–1178, 1165–1179, 1166–1180, 1167–1181,
1168–1182, 1169–1183, 1170–1184, 1171–1185,
1172–1186, 1173–1187, 1174–1188, 1175–1189,
1176–1190, 1177–1191, 1178–1192, 1179–1193,
1180–1194, 1181–1195, 1182–1196, 1183–1197,
1184–1198, 1185–1199, 1186–1200, 1187–1201,
1188–1202, 1189–1203, 1190–1204, 1191–1205,
1192–1206, 1193–1207, 1194–1208, 1195–1209,
1196–1210, 1197–1211, 1198–1212, 1199–1213,
1200–1214, 1201–1215, 1202–1216, 1203–1217,
1204–1218, 1205–1219, 1206–1220, 1207–1221,
1208–1222, 1209–1223, 1210–1224, 1211–1225,
1212–1226, 1213–1227, 1214–1228, 1215–1229,
1216–1230, 1217–1231, 1218–1232, 1219–1233,
1220–1234, 1221–1235, 1222–1236, 1223–1237,
1224–1238, 1225–1239, 1226–1240, 1227–1241,
1228–1242, 1229–1243, 1230–1244, 1231–1245,
1232–1246, 1233–1247, 1234–1248, 1235–1249,
1236–1250, 1237–1251, 1238–1252, 1239–1253,
1240–1254, 1241–1255, 1242–1256, 1243–1257,
1244–1258, 1245–1259, 1246–1260, 1247–1261,
1248–1262, 1249–1263, 1250–1264, 1251–1265,
1252–1266, 1253–1267, 1254–1268, 1255–1269,
1256–1270, 1257–1271, 1258–1272, 1259–1273,
1260–1274, 1261–1275, 1262–1276, 1263–1277,
1264–1278, 1265–1279, 1266–1280, 1267–1281,
1268–1282, 1269–1283, 1270–1284, 1271–1285,
1272–1286, 1273–1287, 1274–1288, 1275–1289,
1276–1290, 1277–1291, 1278–1292, 1279–1293,
1280–1294, 1281–1295, 1282–1296, 1283–1297,
1284–1298, 1285–1299, 1286–1300, 1287–1301,
1288–1302, 1289–1303, 1290–1304, 1291–1305,
1292–1306, 1293–1307, 1294–1308, 1295–1309,
1296–1310, 1297–1311, 1298–1312, 1299–1313,
1300–1314, 1301–1315, 1302–1315, 1303–1317,
1304–1318, 1305–1319, 1306–1320, 1307–1321, 1308–1322, 1309–1323, 1310–1324, 1311–1325,
1312–1326, 1313–1327, 1314–1328, 1315–1329,
1316–1330, 1317–1331, 1318–1332, 1319–1333,
1320–1334, 1321–1335, 1322–1336, 1323–1337,
1324–1338, 1325–1339, 1326–1340, 1327–1341,
1328–1342, 1329–1343, 1330–1344, 1331–1345,
1332–1346, 1333–1347, 1334–1348, 1335–1349,
1336–1350, 1337–1351, 1338–1352, 1339–1353,
1340–1354, 1341–1355, 1342–1356, 1343–1357,
1344–1358, 1345–1359, 1346–1360, 1347–1361,
1348–1362, 1349–1363, 1350–1364, 1351–1365,
1352–1366, 1353–1367, 1354–1368, 1355–1369,
1356–1370, 1357–1371, 1358–1372, 1359–1373,
1360–1374, 1361–1375, 1362–1376, 1363–1377,
1364–1378, 1365–1379, 1366–1380, 1367–1381,
1368–1382, 1369–1383, 1370–1384, 1371–1385,
1372–1386, 1373–1387, 1374–1388, 1375–1389,
1376–1390, 1377–1391, 1378–1392, 1379–1393,
1380–1394, 1381–1395, 1382–1396, 1383–1397,
1384–1398, 1385–1399, 1386–1400, 1387–1401,
1388–1402, 1389–1403, 1390–1404, 1391–1405,
1392–1406, 1393–1407, 1394–1408, 1395–1409,
1396–1410, 1397–1411, 1398–1412, 1399–1413,
1400–1414, 1401–1415, 1402–1416, 1403–1417,
1404–1418, 1405–1419, 1406–1420, 1407–1421,
1408–1422, 1409–1423, 1410–1424, 1411–1425,
1412–1426, 1413–1427, 1414–1428, 1415–1429,
1416–1430, 1417–1431, 1418–1432, 1419–1433,
1420–1434, 1421–1435, 1422–1436, 1423–1437,
1424–1438, 1425–1439, 1426–1440, 1427–1441,
1428–1442, 1429–1443, 1430–1444, 1431–1445,
1432–1446, 1433–1447, 1434–1448, 1435–1449,
1436–1450, 1437–1451, 1438–1452, 1439–1453,
1440–1454, 1441–1455, 1442–1456, 1443–1457,
1444–1458, 1445–1459, 1446–1460, 1447–1461,
1448–1462, 1449–1463, 1450–1464, 1451–1465,
1452–1466, 1453–1467, 1454–1468, 1455–1469,
1456–1470, 1457–1471, 1458–1472, 1459–1473,
1460–1474, 1461–1475, 1462–1476, 1463–1477,
1464–1478, 1465–1479, 1466–1480, 1467–1481,
1468–1482, 1469–1483, 1470–1484, 1471–1485,
1472–1486, 1473–1487, 1474–1488, 1475–1489,
1476–1490, 1477–1491, 1478–1492, 1479–1493,
1480–1494, 1481–1495, 1482–1496, 1483–1497,
1484–1498, 1485–1499, 1486–1500, 1487–1501,
1488–1502, 1489–1503, 1490–1504, 1491–1505,
1492–1506, 1493–1507, 1494–1508, 1495–1509,
1496–1510, 1497–1511, 1498–1513, 1499–1514,
1500–1515, 1501–1515, 1502–1516, 1503–1517,
1504–1518, 1505–1519, 1506–1520, 1507–1521,
1508–1522, 1509–1523, 1510–1524, 1511–1525,
1512–1526, 1513–1527, 1514–1528, 1515–1529,
1516–1530, 1517–1531, 1518–1532, 1519–1533,
1520–1534, 1521–1535, 1522–1536, 1523–1537,
1524–1538, 1525–1539, 1526–1540, 1527–1541,
1528–1542, 1529–1543, 1530–1544, 1531–1545,
1532–1546, 1533–1547, 1534–1548, 1535–1549,
1536–1550, 1537–1551, 1538–1552, 1539–1553,
1540–1554, 1541–1555, 1542–1556, 1543–1557,
1544–1558, 1545–1559, 1546–1560, 1547–1561,
1548–1562, 1549–1563, 1550–1564, 1551–1565,
1552–1566, 1553–1567, 1554–1568, 1555–1569,
1556–1570, 1557–1571, 1558–1572, 1559–1573,
1560–1574, 1561–1575, 1562–1576, 1563–1577,
1564–1578, 1565–1579, 1566–1580, 1567–1581,
1568–1582, 1569–1583, 1570–1584, 1571–1585,
1572–1586, 1573–1587, 1574–1588, 1575–1589,
1576–1590, 1577–1591, 1578–1592, 1579–1593,
1580–1594, 1581–1595, 1582–1596, 1583–1597,
1584–1598, 1585–1599, 1586–1600, 1587–1601,
1588–1602, 1589–1603, 1590–1604, 1591–1605,
1592–1606, 1593–1607, 1594–1608, 1595–1609,
1596–1610, 1597–1611, 1598–1612, 1599–1613,
1600–1614, 1601–1615, 1602–1616, 1603–1617,
1604–1618, 1605–1619, 1606–1620, 1607–1621,
1608–1622, 1609–1623, 1610–1624, 1611–1625,
1612–1626, 1613–1627, 1614–1628, 1615–1629,
1616–1630, 1617–1631, 1618–1632, 1619–1633,
1620–1634, 1621–1635, 1622–1636, 1623–1637,
1624–1638, 1625–1639, 1626–1640, 1627–1641,
1628–1642, 1629–1643, 1630–1644, 1631–1645,
1632–1646, 1633–1647, 1634–1648, 1635–1649,
1636–1650, 1637–1651, 1638–1652, 1639–1653,
1640–1654, 1641–1655, 1642–1656, 1643–1657,
1644–1658, 1645–1659, 1646–1660, 1647–1661,
1648–1662, 1649–1663, 1650–1664, 1651–1665,
1652–1666, 1653–1667, 1654–1668, 1655–1669,
1656–1670, 1657–1671, 1658–1672, 1659–1673,
1660–1674, 1661–1675, 1662–1676, 1663–1677,
1664–1678, 1665–1679, 1666–1680, 1667–1681,
1668–1682, 1669–1683, 1670–1684, 1671–1685,
1672–1686, 1673–1687, 1674–1688, 1675–1689,
1676–1690, 1677–1691, 1678–1692, 1679–1693,
1680–1694, 1681–1695, 1682–1696, 1683–1697,
1684–1698, 1685–1699, 1686–1700, 1687–1701,
1688–1702, 1689–1703, 1690–1704, 1691–1705,
1692–1706, 1693–1707, 1694–1708, 1695–1709,
1696–1710, 1697–1711, 1698–1712, 1699–1713,
1700–1714, 1701–1715, 1702–1716, 1703–1717,
1704–1718, 1705–1719, 1706–1720, 1707–1721,
1708–1722, 1709–1723, 1710–1724, 1711–1725,
1712–1726, 1713–1727, 1714–1728, 1715–1729,
1716–1730, 1717–1731, 1718–1732, 1719–1733,
1720–1734, 1721–1735, 1722–1736, 1723–1737,
1724–1738, 1725–1739, 1726–1740, 1727–1741,
1728–1742, 1729–1743, 1730–1744, 1731–1745,
1732–1746, 1733–1747, 1734–1748, 1735–1749,
1736–1750, 1737–1751, 1738–1752, 1739–1753,
1740–1754, 1741–1755, 1742–1756, 1743–1757,
1744–1758, 1745–1759, 1746–1760, 1747–1761,
1748–1762, 1749–1763, 1750–1764, 1751–1765,
1752–1766, 1753–1767, 1754–1768, 1755–1769,
1756–1770, 1757–1771, 1758–1772, 1759–1773,
1760–1774, 1761–1775, 1762–1776, 1763–1777,
1764–1778, 1765–1779, 1766–1780, 1767–1781,
1768–1782, 1769–1783, 1770–1784, 1771–1785,
1772–1786, 1773–1787, 1774–1788, 1775–1789,
1776–1790, 1777–1791, 1778–1792, 1779–1793,
1780–1794, 1781–1795, 1782–1796, 1783–1797,
1784–1798, 1785–1799, 1786–1800, 1787–1801,
1788–1802, 1789–1803, 1790–1804, 1791–1805,
1792–1806, 1793–1807, 1794–1808, 1795–1809,
1796–1810, 1797–1811, 1798–1812, 1799–1813,
1800–1814, 1801–1815, 1802–1816, 1803–1817,
1804–1818, 1805–1819, 1806–1820, 1807–1821,
1808–1822, 1809–1823, 1810–1824, 1811–1825,
1812–1826, 1813–1827, 1814–1828, 1815–1829,
1816–1830, 1817–1831, 1818–1832, 1819–1833,
1820–1834, 1821–1835, 1822–1836, 1823–1837,
1824–1838, 1825–1839, 1826–1840, 1827–1841,
1828–1842, 1829–1843, 1830–1844, 1831–1845,
1832–1846, 1833–1847, 1834–1848, 1835–1849,
1836–1850, 1837–1851, 1838–1852, 1839–1853,
1840–1854, 1841–1855, 1842–1856, 1843–1857, 1844–1858, 1845–1859, 1846–1860, 1847–1861,
1848–1862, 1849–1863, 1850–1864, 1851–1865,
1852–1866, 1853–1867, 1854–1868, 1855–1869,
1856–1870, 1857–1871, 1858–1872, 1859–1873,
1860–1874, 1861–1875, 1862–1876, 1863–1877,
1864–1878, 1865–1879, 1866–1880, 1867–1881,
1868–1882, 1869–1883, 1870–1884, 1871–1885,
1872–1886, 1873–1887, 1874–1888, 1875–1889,
1876–1890, 1877–1891, 1878–1892, 1879–1893,
1880–1894, 1881–1895, 1882–1896, 1883–1897,
1884–1898, 1885–1899, 1886–1900, 1887–1901,
1888–1902, 1889–1903, 1890–1904, 1891–1905,
1892–1906, 1893–1907, 1894–1908, 1895–1909,
1896–1910, 1897–1911, 1898–1912, 1899–1913,
1900–1914, 1901–1915, 1902–1916, 1903–1917,
1904–1918, 1905–1919, 1906–1920, 1907–1921,
1908–1922, 1909–1923, 1910–1924, 1911–1925,
1912–1926, 1913–1927, 1914–1928, 1915–1929,
1916–1930, 1917–1931, 1918–1932, 1919–1933,
1920–1934, 1921–1935, 1922–1936, 1923–1937,
1924–1938, 1925–1939, 1926–1940, 1927–1941,
1928–1942, 1929–1943, 1930–1944, 1931–1945,
1932–1946, 1933–1947, 1934–1948, 1935–1949,
1936–1950, 1937–1951, 1938–1952, 1939–1953,
1940–1954, 1941–1955, 1942–1956, 1943–1957,
1944–1958, 1945–1959, 1946–1960, 1947–1961,
1948–1962, 1949–1963, 1950–1964, 1951–1965,
1952–1966, 1953–1967, 1954–1968, 1955–1969,
1956–1970, 1957–1971, 1958–1972, 1959–1973,
1960–1974, 1961–1975, 1962–1976, 1963–1977,
1964–1978, 1965–1979, 1966–1980, 1967–1981,
1968–1982, 1969–1983, 1970–1984, 1971–1985,
1972–1986, 1973–1987, 1974–1988, 1975–1989,
1976–1990, 1977–1991, 1978–1992, 1979–1993,
1980–1994, 1981–1995, 1982–1996, 1983–1997,
1984–1998, 1985–1999, 1986–2000, 1987–2001,
1988–2002, 1989–2003, 1990–2004, 1991–2005,
1992–2006, 1993–2007, 1994–2008, 1995–2009,
1996–2010, 1997–2011, 1998–2012, 1999–2013,
2000–2014, 2001–2015, 2002–2016, 2003–2017,
2004–2018, 2005–2019, 2006–2020, 2007–2021,
2008–2022, 2009–2023, 2010–2024, 2011–2025,
2012–2026, 2013–2027, 2014–2028, 2015–2029,
2016–2030, 2017–2031, 2018–2032, 2019–2033,
2020–2034, 2021–2035, 2022–2036, 2023–2037,
2024–2038, 2025–2039, 2026–2040, 2027–2041,
2028–2042, 2029–2043, 2030–2044, 2031–2045,
2032–2046, 2033–2047, 2034–2048, 2035–2049,
2036–2050, 2037–2051, 2038–2052, 2039–2053,
2040–2054, 2041–2055, 2042–2056, 2043–2057,
2044–2058, 2045–2059, 2046–2060, 2047–2061,
2048–2062, 2049–2063, 2050–2064, 2051–2065,
2052–2066, 2053–2067, 2054–2068, 2055–2069,
2056–2070, 2057–2071, 2058–2072, 2059–2073,
2060–2074, 2061–2075, 2062–2076, 2063–2077,
2064–2078, 2065–2079, 2066–2080, 2067–2081,
2068–2082, 2069–2083, 2070–2084, 2071–2085,
2072–2086, 2073–2087, 2074–2088, 2075–2089,
2076–2090, 2077–2091, 2078–2092, 2079–2093,
2080–2094, 2081–2095, 2082–2096, 2083–2097,
2084–2098, 2085–2099, 2086–2100, 2087–2101,
2088–2102, 2089–2103, 2090–2104, 2091–2105,
2092–2106, 2093–2107, 2094–2108, 2095–2109,
2096–2110, 2097–2111, 2098–2112, 2099–2113,
2100–2114, 2101–2115, 2102–2116, 2103–2117,
2104–2118, 2105–2119, 2106–2120, 2107–2121,
2108–2122, 2109–2123, 2110–2124, 2111–2125,
2112–2126, 2113–2127, 2114–2128, 2115–2129,
2116–2130, 2117–2131, 2118–2132, 2119–2133,
2120–2134, 2121–2135, 2122–2136, 2123–2137,
2124–2138, 2125–2139, 2126–2140, 2127–2141,
2128–2142, 2129–2143, 2130–2144, 2131–2145,
2132–2146, 2133–2147, 2134–2148, 2135–2149,
2136–2150, 2137–2151, 2138–2152, 2139–2153,
2140–2154, 2141–2155, 2142–2156, 2143–2157,
2144–2158, 2145–2159, 2146–2160, 2147–2161,
2148–2162, 2149–2163, 2150–2164, 2151–2165,
2152–2166, 2153–2167, 2154–2168, 2155–2169,
2156–2170, 2157–2171, 2158–2172, 2159–2173,
2160–2174, 2161–2175, 2162–2176, 2163–2177,
2164–2178, 2165–2179, 2166–2180, 2167–2181,
2168–2182, 2169–2183, 2170–2184, 2171–2185,
2172–2186, 2173–2187, 2174–2188, 2175–2189,
2176–2190, 2177–2191, 2178–2192, 2179–2193,
2180–2194, 2181–2195, 2182–2196, 2183–2197,
2184–2198, 2185–2199, 2186–2200, 2187–2201,
2188–2202, 2189–2203, 2190–2204, 2191–2205,
2192–2206, 2193–2207, 2194–2208, 2195–2209,
2196–2210, 2197–2211, 2198–2212, 2199–2213,
2200–2214, 2201–2215, 2202–2216, 2203–2217,
2204–2218, 2205–2219, 2206–2220, 2207–2221,
2208–2222, 2209–2223, 2210–2224, 2211–2225,
2212–2226, 2213–2227, 2214–2228, 2215–2229,
2216–2230, 2217–2231, 2218–2232, 2219–2233,
2220–2234, 2221–2235, 2222–2236, 2223–2237,
2224–2238, 2225–2239, 2226–2240, 2227–2241,
2228–2242, 2229–2243, 2230–2244, 2231–2245,
2232–2246, 2233–2247, 2234–2248, 2235–2249,
2236–2250, 2237–2251, 2238–2252, 2239–2253,
2240–2254, 2241–2255, 2242–2256, 2243–2257,
2244–2258, 2245–2259, 2246–2260, 2247–2261,
2248–2262, 2249–2263, 2250–2264, 2251–2265,
2252–2266, 2253–2267, 2254–2268, 2255–2269,
2256–2270, 2257–2271, 2258–2272, 2259–2273,
2260–2274, 2261–2275, 2262–2276, 2263–2277,
2264–2278, 2265–2279, 2266–2280, 2267–2281,
2268–2282, 2269–2283, 2270–2284, 2271–2285,
2272–2286, 2273–2287, 2274–2288, 2275–2289,
2276–2290, 2277–2291, 2278–2292, 2279–2293,
2280–2294, 2281–2295, 2282–2296, 2283–2297,
2284–2298, 2285–2299, 2286–2300, 2287–2301,
2288–2302, 2289–2303, 2290–2304, 2291–2305,
2292–2306, 2293–2307, 2294–2308, 2295–2309,
2296–2310, 2297–2311, 2298–2312, 2299–2313,
2300–2314, 2301–2315, 2302–2315, 2303–2317,
2304–2318, 2305–2319, 2306–2320, 2307–2321,
2308–2322, 2309–2323, 2310–2324, 2311–2325,
2312–2326, 2313–2327, 2314–2328, 2315–2329,
2316–2330, 2317–2331, 2318–2332, 2319–2333,
2320–2334, 2321–2335, 2322–2336, 2323–2337,
2324–2338, 2325–2339, 2326–2340, 2327–2341,
2328–2342, 2329–2343, 2330–2344, 2331–2345,
2332–2346, 2333–2347, 2334–2348, 2335–2349,
2336–2350, 2337–2351, 2338–2352, 2339–2353,
2340–2354, 2341–2355, 2342–2356, 2343–2357,
2344–2358, 2345–2359, 2346–2360, 2347–2361,
2348–2362, 2349–2363, 2350–2364, 2351–2365,
2352–2366, 2353–2367, 2354–2368, 2355–2369,
2356–2370, 2357–2371, 2358–2372, 2359–2373,
2360–2374, 2361–2375, 2362–2376, 2363–2377,
2364–2378, 2365–2379, 2366–2380, 2367–2381,
2368–2382, 2369–2383, 2370–2384, 2371–2385,
2372–2386, 2373–2387, 2374–2388, 2375–2389,
2376–2390, 2377–2391, 2378–2392, 2379–2393, 2380–2394, 2381–2395, 2382–2396, 2383–2397,
2384–2398, 2385–2399, 2386–2400, 2387–2401,
2388–2402, 2389–2403, 2390–2404, 2391–2405,
2392–2406, 2393–2407, 2394–2408, 2395–2409,
2396–2410, 2397–2411, 2398–2412, 2399–2413,
2400–1412, 2401–2415, 2402–2416, 2403–2417,
2404–2418, 2405–2419, 2406–2420, 2407–2421,
2408–2422, 2409–2423, 2410–2424, 2411–2425,
2412–2426, 2413–2427, 2414–2428, 2415–2429,
2416–2430, 2417–2431, 2418–2432, 2419–2433,
2420–2434, 2421–2435, 2422–2436, 2423–2437,
2424–2438, 2425–2439, 2426–2440, 2427–2441,
2428–2442, 2429–2443, 2430–2444, 2431–2445,
2432–2446, 2433–2447, 2434–2448, 2435–2449,
2436–2450, 2437–2451, 2438–2452, 2439–2453,
2440–2454, 2441–2455, 2442–2456, 2443–2457,
2444–2458, 2445–2459, 2446–2460, 2447–2461,
2448–2462, 2449–2463, 2450–2464, 2451–2465,
2452–2466, 2453–2467, 2454–2468, 2455–2469,
2456–2470, 2457–2471, 2458–2472, 2459–2473,
2460–2474, 2461–2475, 2462–2476, 2463–2477,
2464–2478, 2465–2479, 2466–2480, 2467–2481,
2468–2482, 2469–2483, 2470–2484, 2471–2485,
2472–2486, 2473–2487, 2474–2488, 2475–2489,
2476–2490, 2477–2491, 2478–2492, 2479–2493,
2480–2494, 2481–2495, 2482–2496, 2483–2497,
2484–2498, 2485–2499, 2486–2500, 2487–2501,
2488–2502, 2489–2503, 2490–2504, 2491–2505,
2492–2506, 2493–2507, 2494–2508, 2495–2509,
2496–2510, 2497–2511, 2498–2513, 2499–2514,
2500–2515, 2501–2515, 2502–2516, 2503–2517,
2504–2518, 2505–2519, 2506–2520, 2507–2521,
2508–2522, 2509–2523, 2510–2524, 2511–2525,
2512–2526, 2513–2527, 2514–2528, 2515–2529,
2516–2530, 2517–2531, 2518–2532, 2519–2533,
2520–2534, 2521–2535, 2522–2536, 2523–2537,
2524–2538, 2525–2539, 2526–2540, 2527–2541,
2528–2542, 2529–2543, 2530–2544, 2531–2545,
2532–2546, 2533–2547, 2534–2548, 2535–2549,
2536–2550, 2537–2551, 2538–2552, 2539–2553,
2540–2554, 2541–2555, 2542–2556, 2543–2557,
2544–2558, 2545–2559, 2546–2560, 2547–2561,
2548–2562, 2549–2563, 2550–2564, 2551–2565,
2552–2566, 2553–2567, 2554–2568, 2555–2569,
2556–2570, 2557–2571, 2558–2572, 2559–2573,
2560–2574, 2561–2575, 2562–2576, 2563–2577,
2564–2578, 2565–2579, 2566–2580, 2567–2581,
2568–2582, 2569–2583, 2570–2584, 2571–2585,
2572–2586, 2573–2587, 2574–2588, 2575–2589,
2576–2590, 2577–2591, 2578–2592, 2579–2593,
2580–2594, 2581–2595, 2582–2596, 2583–2597,
2584–2598, 2585–2599, 2586–2600, 2587–2601,
2588–2602, 2589–2603, 2590–2604, 2591–2605,
2592–2606, 2593–2607, 2594–2608, 2595–2609,
2596–2610, 2597–2611, 2598–2612, 2599–2613,
2600–2614, 2601–2615, 2602–2616, 2603–2617,
2604–2618, 2605–2619, 2606–2620, 2607–2621,
2608–2622, 2609–2623, 2610–2624, 2611–2625,
2612–2626, 2613–2627, 2614–2628, 2615–2629,
2616–2630, 2617–2631, 2618–2632, 2619–2633,
2620–2634, 2621–2635, 2622–2636, 2623–2637,
2624–2638, 2625–2639, 2626–2640, 2627–2641,
2628–2642, 2629–2643, 2630–2644, 2631–2645,
2632–2646, 2633–2647, 2634–2648, 2635–2649,
2636–2650, 2637–2651, 2638–2652, 2639–2653,
2640–2654, 2641–2655, 2642–2656, 2643–2657,
2644–2658, 2645–2659, 2646–2660, 2647–2661,
2648–2662, 2649–2663, 2650–2664, 2651–2665,
2652–2666, 2653–2667, 2654–2668, 2655–2669,
2656–2670, 2657–2671, 2658–2672, 2659–2673,
2660–2674, 2661–2675, 2662–2676, 2663–2677,
2664–2678, 2665–2679, 2666–2680, 2667–2681,
2668–2682, 2669–2683, 2670–2684, 2671–2685,
2672–2686, 2673–2687, 2674–2688, 2675–2689,
2676–2690, 2677–2691, 2678–2692, 2679–2693,
2680–2694, 2681–2695, 2682–2696, 2683–2697,
2684–2698, 2685–2699, 2686–2700, 2687–2701,
2688–2702, 2689–2703, 2690–2704, 2691–2705,
2692–2706, 2693–2707, 2694–2708, 2695–2709,
2696–2710, 2697–2711, 2698–2712, 2699–2713,
2700–2714, 2701–2715, 2702–2716, 2703–2717,
2704–2718, 2705–2719, 2706–2720, 2707–2721,
2708–2722, 2709–2723, 2710–2724, 2711–2725,
2712–2726, 2713–2727, 2714–2728, 2715–2729,
2716–2730, 2717–2731, 2718–2732, 2719–2733,
2720–2734, 2721–2735, 2722–2736, 2723–2737,
2724–2738, 2725–2739, 2726–2740, 2727–2741,
2728–2742, 2729–2743, 2730–2744, 2731–2745,
2732–2746, 2733–2747, 2734–2748, 2735–2749,
2736–2750, 2737–2751, 2738–2752, 2739–2753,
2740–2754, 2741–2755, 2742–2756, 2743–2757,
2744–2758, 2745–2759, 2746–2760, 2747–2761,
2748–2762, 2749–2763, 2750–2764, 2751–2765,
2752–2766, 2753–2767, 2754–2768, 2755–2769,
2756–2770, 2757–2771, 2758–2772, 2759–2773,
2760–2774, 2761–2775, 2762–2776, 2763–2777,
2764–2778, 2765–2779, 2766–2780, 2767–2781,
2768–2782, 2769–2783, 2770–2784, 2771–2785,
2772–2786, 2773–2787, 2774–2788, 2775–2789,
2776–2790, 2777–2791, 2778–2792, 2779–2793,
2780–2794, 2781–2795, 2782–2796, 2783–2797,
2784–2798, 2785–2799, 2786–2800, 2787–2801,
2788–2802, 2789–2803, 2790–2804, 2791–2805,
2792–2806, 2793–2807, 2794–2808, 2795–2809,
2796–2810, 2797–2811, 2798–2812, 2799–2813,
2800–2814, 2801–2815, 2802–2816, 2803–2817,
2804–2818, 2805–2819, 2806–2820, 2807–2821,
2808–2822, 2809–2823, 2810–2824, 2811–2825,
2812–2826, 2813–2827, 2814–2828, 2815–2829,
2816–2830, 2817–2831, 2818–2832, 2819–2833,
2820–2834, 2821–2835, 2822–2836, 2823–2837,
2824–2838, 2825–2839, 2826–2840, 2827–2841,
2828–2842, 2829–2843, 2830–2844, 2831–2845,
2832–2846, 2833–2847, 2834–2848, 2835–2849,
2836–2850, 2837–2851, 2838–2852, 2839–2853,
2840–2854, 2841–2855, 2842–2856, 2843–2857,
2844–2858, 2845–2859, 2846–2860, 2847–2861,
2848–2862, 2849–2863, 2850–2864, 2851–2865,
2852–2866, 2853–2867, 2854–2868, 2855–2869,
2856–2870, 2857–2871, 2858–2872, 2859–2873,
2860–2874, 2861–2875, 2862–2876, 2863–2877,
2864–2878, 2865–2879, 2866–2880, 2867–2881,
2868–2882, 2869–2883, 2870–2884, 2871–2885,
2872–2886, 2873–2887, 2874–2888, 2875–2889,
2876–2890, 2877–2891, 2878–2892, 2879–2893,
2880–2894, 2881–2895, 2882–2896, 2883–2897,
2884–2898, 2885–2899, 2886–2900, 2887–2901,
2888–2902, 2889–2903, 2890–2904, 2891–2905,
2892–2906, 2893–2907, 2894–2908, 2895–2909,
2896–2910, 2897–2911, 2898–2912, 2899–2913,
2900–2914, 2901–2915, 2902–2916, 2903–2917,
2904–2918, 2905–2919, 2906–2920, 2907–2921,
2908–2922, 2909–2923, 2910–2924, 2911–2925,
2912–2926, 2913–2927, 2914–2928, 2915–2929, 2916–2930, 2917–2931, 2918–2932, 2919–2933, 2920–2934, 2921–2935, 2922–2936, 2923–2937, 2924–2938, 2925–2939, 2926–2940, 2927–2941, 2928–2942, 2929–2943, 2930–2944, 2931–2945, 2932–2946, 2933–2947, 2934–2948, 2935–2949, 2936–2950, 2937–2951, 2938–2952, 2939–2953, 2940–2954, 2941–2955, 2942–2956, 2943–2957, 2944–2958, 2945–2959, 2946–2960, 2947–2961, 2948–2962, 2949–2963, 2950–2964, 2951–2965, 2952–2966, 2953–2967, 2954–2968, 2955–2969, 2956–2970, 2957–2971, 2958–2972, 2959–2973, 2960–2974, 2961–2975, 2962–2976, 2963–2977, 2964–2978, 2965–2979, 2966–2980, 2967–2981, 2968–2982, 2969–2983, 2970–2984, 2971–2985, 2972–2986, 2973–2987, 2974–2988, 2975–2989, 2976–2990, 2977–2991, 2978–2992, 2979–2993, 2980–2994, 2981–2995, 2982–2996, 2983–2997, 2984–2998, 2985–2999, 2986–3000, 2987–3001, 2988–3002, 2989–3003, 2990–3004, 2991–3005, 2992–3006, 2993–3007, 2994–3008, 2995–3009, 2996–3010, 2997–3011, 2998–3012, 2999–3013, 3000–3014, 3001–3015, 3002–3016, 3003–3017, 3004–3018, 3005–3019, 3006–3020, 3007–3021, 3008–3022, 3009–3023, 3010–3024, 3011–3025, 3012–3026, 3013–3027, 3014–3028, 3015–3029, 3016–3030, 3017–3031, 3018–3032, 3019–3033, 3020–3034, 3021–3035, 3022–3036, 3023–3037, 3024–3038, 3025–3039, 3026–3040, 3027–3041, 3028–3042, 3029–3043, 3030–3044, 3031–3045, 3032–3046, 3033–3047, 3034–3048, 3035–3049, 3036–3050, 3037–3051, 3038–3052, 3039–3053, 3040–3054, 3041–3055, 3042–3056, 3043–3057, 3044–3058, 3045–3059, 3046–3060, 3047–3061, 3048–3062, 3049–3063, 3050–3064, 3051–3065, 3052–3066, 3053–3067, 3054–3068, 3055–3069, 3056–3070, 3057–3071, 3058–3072, 3059–3073, 3060–3074, 3061–3075, 3062–3076, 3063–3077, 3064–3078, 3065–3079, 3066–3080, 3067–3081, 3068–3082, 3069–3083, 3070–3084, 3071–3085, 3072–3086, 3073–3087, 3074–3088, 3075–3089, 3076–3090, 3077–3091, 3078–3092, 3079–3093, 3080–3094, 3081–3095, 3082–3096, 3083–3097, 3084–3098, 3085–3099, 3086–3100, 3087–3101, 3088–3102, 3089–3103, 3090–3104, 3091–3105, 3092–3106, 3093–3107, 3094–3108, 3095–3109, 3096–3110, 3097–3111, 3098–3112, 3099–3113, 3100–3114, 3101–3115, 3102–3116, 3103–3117, 3104–3118, 3105–3119, 3106–3120, 3107–3121, 3108–3122, 3109–3123, 3110–3124, 3111–3125, 3112–3126, 3113–3127, 3114–3128, 3115–3129, 3116–3130, 3117–3131, 3118–3132, 3119–3133, 3120–3134, 3121–3135, 3122–3136, 3123–3137, 3124–3138, 3125–3139, 3126–3140, 3127–3141, 3128–3142, 3129–3143, 3130–3144, 3131–3145, 3132–3146, 3133–3147, 3134–3148, 3135–3149, 3136–3150, 3137–3151, 3138–3152, 3139–3153, 3140–3154, 3141–3155, 3142–3156, 3143–3157, 3144–3158, 3145–3159, 3146–3160, 3147–3161, 3148–3162, 3149–3163, 3150–3164, 3151–3165, 3152–3166, 3153–3167, 3154–3168, 3155–3169, 3156–3170, 3157–3171, 3158–3172, 3159–3173, 3160–3174, 3161–3175, 3162–3176, 3163–3177, 3164–3178, 3165–3179, 3166–3180, 3167–3181, 3168–3182, 3169–3183, 3170–3184, 3171–3185, 3172–3186, 3173–3187, 3174–3188, 3175–3189, 3176–3190, 3177–3191, 3178–3192, 3179–3193, 3180–3194, 3181–3195, 3182–3196, 3183–3197, 3184–3198, 3185–3199, 3186–3200, 3187–3201, 3188–3202, 3189–3203, 3190–3204, 3191–3205, 3192–3206, 3193–3207, 3194–3208, 3195–3209, 3196–3210, 3197–3211, 3198–3212, 3199–3213, 3200–3214, 3201–3215, 3202–3216, 3203–3217, 3204–3218, 3205–3219, 3206–3220, 3207–3221, 3208–3222, 3209–3223, 3210–3224, 3211–3225, 3212–3226, 3213–3227, 3214–3228, 3215–3229, 3216–3230, 3217–3231, 3218–3232, 3219–3233, 3220–3234, 3221–3235, 3222–3236, 3223–3237, 3224–3238, 3225–3239, 3226–3240, 3227–3241, 3228–3242, 3229–3243, 3230–3244, 3231–3245, 3232–3246, 3233–3247, 3234–3248, 3235–3249, 3236–3250, 3237–3251, 3238–3252, 3239–3253, 3240–3254, 3241–3255, 3242–3256, 3243–3257, 3244–3258, 3245–3259, 3246–3260, 3247–3261, 3248–3262, 3249–3263, 3250–3264, 3251–3265, 3252–3266, 3253–3267, 3254–3268, 3255–3269, 3256–3270, 3257–3271, 3258–3272, 3259–3273, 3260–3274, 3261–3275, 3262–3276, 3263–3277, 3264–3278, 3265–3279, 3266–3280, 3267–3281, 3268–3282, 3269–3283, 3270–3284, 3271–3285, 3272–3286, 3273–3287, 3274–3288, 3275–3289, 3276–3290, 3277–3291, 3278–3292, 3279–3293, 3280–3294, 3281–3295, 3282–3296, 3283–3297, 3284–3298, 3285–3299, 3286–3300, 3287–3301, 3288–3302, 3289–3303, 3290–3304, 3291–3305, 3292–3306, 3293–3307, 3294–3308, 3295–3309, 3296–3310, 3297–3311, 3298–3312, 3299–3313, 3300–3314, 3301–3315, 3302–3315, 3303–3317, 3304–3318, 3305–3319, 3306–3320, 3307–3321, 3308–3322, 3309–3323, 3310–3324, 3311–3325, 3312–3326, 3313–3327, 3314–3328, 3315–3329, 3316–3330, 3317–3331, 3318–3332, 3319–3333, 3320–3334, 3321–3335, 3322–3336, 3323–3337, 3324–3338, 3325–3339, 3326–3340, 3327–3341, 3328–3342, 3329–3343, 3330–3344, 3331–3345, 3332–3346, 3333–3347, 3334–3348, 3335–3349, 3336–3350, 3337–3351, 3338–3352, 3339–3353, 3340–3354, 3341–3355, 3342–3356, 3343–3357, 3344–3358, 3345–3359, 3346–3360, 3347–3361, 3348–3362, 3349–3363, 3350–3364, 3351–3365, 3352–3366, 3353–3367, 3354–3368, 3355–3369, 3356–3370, 3357–3371, 3358–3372, 3359–3373, 3360–3374, 3361–3375, 3362–3376, 3363–3377, 3364–3378, 3365–3379, 3366–3380, 3367–3381, 3368–3382, 3369–3383, 3370–3384, 3371–3385, 3372–3386, 3373–3387, 3374–3388, 3375–3389, 3376–3390, 3377–3391, 3378–3392, 3379–3393, 3380–3394, 3381–3395, 3382–3396, 3383–3397, 3384–3398, 3385–3399, 3386–3400, 3387–3401, 3388–3402, 3389–3403, 3390–3404, 3391–3405, 3392–3406, 3393–3407, 3394–3408, 3395–3409, 3396–3410, 3397–3411, 3398–3412, 3399–3413, 3400–3414, 3401–3415, 3402–3416, 3403–3417, 3404–3418, 3405–3419, 3406–3420, 3407–3421, 3408–3422, 3409–3423, 3410–3424, 3411–3425, 3412–3426, 3413–3427, 3414–3428, 3415–3429, 3416–3430, 3417–3431, 3418–3432, 3419–3433, 3420–3434, 3421–3435, 3422–3436, 3423–3437, 3424–3438, 3425–3439, 3426–3440, 3427–3441, 3428–3442, 3429–3443, 3430–3444, 3431–3445, 3432–3446, 3433–3447, 3434–3448, 3435–3449, 3436–3450, 3437–3451, 3438–3452, 3439–3453, 3440–3454, 3441–3455, 3442–3456, 3443–3457, 3444–3458, 3445–3459, 3446–3460, 3447–3461, 3448–3462, 3449–3463, 3450–3464, 3451–3465, 3452–3466, 3453–3467, 3454–3468, 3455–3469,
3456–3470, 3457–3471, 3458–3472, 3459–3473,
3460–3474, 3461–3475, 3462–3476, 3463–3477,
3464–3478, 3465–3479, 3466–3480, 3467–3481,
3468–3482, 3469–3483, 3470–3484, 3471–3485,
3472–3486, 3473–3487, 3474–3488, 3475–3489,
3476–3490, 3477–3491, 3478–3492, 3479–3493,
3480–3494, 3481–3495, 3482–3496, 3483–3497,
3484–3498, 3485–3499, 3486–3500, 3487–3501,
3488–3502, 3489–3503, 3490–3504, 3491–3505,
3492–3506, 3493–3507, 3494–3508, 3495–3509,
3496–3510, 3497–3511, 3498–3513, 3499–3514,
3500–3515, 3501–3515, 3502–3516, 3503–3517,
3504–3518, 3505–3519, 3506–3520, 3507–3521,
3508–3522, 3509–3523, 3510–3524, 3511–3525,
3512–3526, 3513–3527, 3514–3528, 3515–3529,
3516–3530, 3517–3531, 3518–3532, 3519–3533,
3520–3534, 3521–3535, 3522–3536, 3523–3537,
3524–3538, 3525–3539, 3526–3540, 3527–3541,
3528–3542, 3529–3543, 3530–3544, 3531–3545,
3532–3546, 3533–3547, 3534–3548, 3535–3549,
3536–3550, 3537–3551, 3538–3552, 3539–3553,
3540–3554, 3541–3555, 3542–3556, 3543–3557,
3544–3558, 3545–3559, 3546–3560, 3547–3561,
3548–3562, 3549–3563, 3550–3564, 3551–3565,
3552–3566, 3553–3567, 3554–3568, 3555–3569,
3556–3570, 3557–3571, 3558–3572, 3559–3573,
3560–3574, 3561–3575, 3562–3576, 3563–3577,
3564–3578, 3565–3579, 3566–3580, 3567–3581,
3568–3582, 3569–3583, 3570–3584, 3571–3585,
3572–3586, 3573–3587, 3574–3588, 3575–3589,
3576–3590, 3577–3591, 3578–3592, 3579–3593,
3580–3594, 3581–3595, 3582–3596, 3583–3597,
3584–3598, 3585–3599, 3586–3600, 3587–3601,
3588–3602, 3589–3603, 3590–3604, 3591–3605,
3592–3606, 3593–3607, 3594–3608, 3595–3609,
3596–3610, 3597–3611, 3598–3612, 3599–3613,
3600–3614, 3601–3615, 3602–3616, 3603–3617,
3604–3618, 3605–3619, 3606–3620, 3607–3621,
3608–3622, 3609–3623, 3610–3624, 3611–3625,
3612–3626, 3613–3627, 3614–3628, 3615–3629,
3616–3630, 3617–3631, 3618–3632, 3619–3633,
3620–3634, 3621–3635, 3622–3636, 3623–3637,
3624–3638, 3625–3639, 3626–3640, 3627–3641,
3628–3642, 3629–3643, 3630–3644, 3631–3645,
3632–3646, 3633–3647, 3634–3648, 3635–3649,
3636–3650, 3637–3651, 3638–3652, 3639–3653,
3640–3654, 3641–3655, 3642–3656, 3643–3657,
3644–3658, 3645–3659, 3646–3660, 3647–3661,
3648–3662, 3649–3663, 3650–3664, 3651–3665,
3652–3666, 3653–3667, 3654–3668, 3655–3669,
3656–3670, 3657–3671, 3658–3672, 3659–3673,
3660–3674, 3661–3675, 3662–3676, 3663–3677,
3664–3678, 3665–3679, 3666–3680, 3667–3681,
3668–3682, 3669–3683, 3670–3684, 3671–3685,
3672–3686, 3673–3687, 3674–3688, 3675–3689,
3676–3690, 3677–3691, 3678–3692, 3679–3693,
3680–3694, 3681–3695, 3682–3696, 3683–3697,
3684–3698, 3685–3699, 3686–3700, 3687–3701,
3688–3702, 3689–3703, 3690–3704, 3691–3705,
3692–3706, 3693–3707, 3694–3708, 3695–3709,
3696–3710, 3697–3711, 3698–3712, 3699–3713,
3700–3714, 3701–3715, 3702–3716, 3703–3717,
3704–3718, 3705–3719, 3706–3720, 3707–3721,
3708–3722, 3709–3723, 3710–3724, 3711–3725,
3712–3726, 3713–3727, 3714–3728, 3715–3729,
3716–3730, 3717–3731, 3718–3732, 3719–3733,
3720–3734, 3721–3735, 3722–3736, 3723–3737,
3724–3738, 3725–3739, 3726–3740, 3727–3741,
3728–3742, 3729–3743, 3730–3744, 3731–3745,
3732–3746, 3733–3747, 3734–3748, 3735–3749,
3736–3750, 3737–3751, 3738–3752, 3739–3753,
3740–3754, 3741–3755, 3742–3756, 3743–3757,
3744–3758, 3745–3759, 3746–3760, 3747–3761,
3748–3762, 3749–3763, 3750–3764, 3751–3765,
3752–3766, 3753–3767, 3754–3768, 3755–3769,
3756–3770, 3757–3771, 3758–3772, 3759–3773,
3760–3774, 3761–3775, 3762–3776, 3763–3777,
3764–3778, 3765–3779, 3766–3780, 3767–3781,
3768–3782, 3769–3783, 3770–3784, 3771–3785,
3772–3786, 3773–3787, 3774–3788, 3775–3789,
3776–3790, 3777–3791, 3778–3792, 3779–3793,
3780–3794, 3781–3795, 3782–3796, 3783–3797,
3784–3798, 3785–3799, 3786–3800, 3787–3801,
3788–3802, 3789–3803, 3790–3804, 3791–3805,
3792–3806, 3793–3807, 3794–3808, 3795–3809,
3796–3810, 3797–3811, 3798–3812, 3799–3813,
3800–3814, 3801–3815, 3802–3816, 3803–3817,
3804–3818, 3805–3819, 3806–3820, 3807–3821,
3808–3822, 3809–3823, 3810–3824, 3811–3825,
3812–3826, 3813–3827, 3814–3828, 3815–3829,
3816–3830, 3817–3831, 3818–3832, 3819–3833,
3820–3834, 3821–3835, 3822–3836, 3823–3837,
3824–3838, 3825–3839, 3826–3840, 3827–3841,
3828–3842, 3829–3843, 3830–3844, 3831–3845,
3832–3846, 3833–3847, 3834–3848, 3835–3849,
3836–3850, 3837–3851, 3838–3852, 3839–3853,
3840–3854, 3841–3855, 3842–3856, 3843–3857,
3844–3858, 3845–3859, 3846–3860, 3847–3861,
3848–3862, 3849–3863, 3850–3864, 3851–3865,
3852–3866, 3853–3867, 3854–3868, 3855–3869,
3856–3870, 3857–3871, 3858–3872, 3859–3873,
3860–3874, 3861–3875, 3862–3876, 3863–3877,
3864–3878, 3865–3879, 3866–3880, 3867–3881,
3868–3882, 3869–3883, 3870–3884, 3871–3885,
3872–3886, 3873–3887, 3874–3888, 3875–3889,
3876–3890, 3877–3891, 3878–3892, 3879–3893,
3880–3894, 3881–3895, 3882–3896, 3883–3897,
3884–3898, 3885–3899, 3886–3900, 3887–3901,
3888–3902, 3889–3903, 3890–3904, 3891–3905,
3892–3906, 3893–3907, 3894–3908, 3895–3909,
3896–3910, 3897–3911, 3898–3912, 3899–3913,
3900–3914, 3901–3915, 3902–3916, 3903–3917,
3904–3918, 3905–3919, 3906–3920, 3907–3921,
3908–3922, 3909–3923, 3910–3924, 3911–3925,
3912–3926, 3913–3927, 3914–3928, 3915–3929,
3916–3930, 3917–3931, 3918–3932, 3919–3933,
3920–3934, 3921–3935, 3922–3936, 3923–3937,
3924–3938, 3925–3939, 3926–3940, 3927–3941,
3928–3942, 3929–3943, 3930–3944, 3931–3945,
3932–3946, 3933–3947, 3934–3948, 3935–3949,
3936–3950, 3937–3951, 3938–3952, 3939–3953,
3940–3954, 3941–3955, 3942–3956, 3943–3957,
3944–3958, 3945–3959, 3946–3960, 3947–3961,
3948–3962, 3949–3963, 3950–3964, 3951–3965,
3952–3966, 3953–3967, 3954–3968, 3955–3969,
3956–3970, 3957–3971, 3958–3972, 3959–3973,
3960–3974, 3961–3975, 3962–3976, 3963–3977,
3964–3978, 3965–3979, 3966–3980, 3967–3981,
3968–3982, 3969–3983, 3970–3984, 3971–3985,
3972–3986, 3973–3987, 3974–3988, 3975–3989,
3976–3990, 3977–3991, 3978–3992, 3979–3993,
3980–3994, 3981–3995, 3982–3996, 3983–3997,
3984–3998, 3985–3999, 3986–4000, 39874001, 3988–4002, 3989–4003, 3990–4004, 3991–4005,
3992–4006, 3993–4007, 3994–4008, 3995–4009,
3996–4010, 3997–4011, 3998–4012, 3999–4013,
4000–4014, 4001–4015, 4002–4016, 4003–4017,
4004–4018, 4005–4019, 4006–4020, 4007–4021,
4008–4022, 4009–4023, 4010–4024, 4011–4025,
4012–4026, 4013–4027, 4014–4028, 4015–4029,
4016–4030, 4017–4031, 4018–4032, 4019–4033,
4020–4034, 4021–4035, 4022–4036, 4023–4037,
4024–4038, 4025–4039, 4026–4040, 4027–4041,
4028–4042, 4029–4043, 4030–4044, 4031–4045,
4032–4046, 4033–4047, 4034–4048, 4035–4049,
4036–4050, 4037–4051, 4038–4052, 4039–4053,
4040–4054, 4041–4055, 4042–4056, 4043–4057,
4044–4058, 4045–4059, 4046–4060, 4047–4061,
4048–4062, 4049–4063, 4050–4064, 4051–4065,
4052–4066, 4053–4067, 4054–4068, 4055–4069,
4056–4070, 4057–4071, 4058–4072, 4059–4073,
4060–4074, 4061–4075, 4062–4076, 4063–4077,
4064–4078, 4065–4079, 4066–4080, 4067–4081,
4068–4082, 4069–4083, 4070–4084, 4071–4085,
4072–4086, 4073–4087, 4074–4088, 4075–4089,
4076–4090, 4077–4091, 4078–4092, 4079–4093,
4080–4094, 4081–4095, 4082–4096, 4083–4097,
4084–4098, 4085–4099, 4086–4100, 4087–4101,
4088–4102, 4089–4103, 4090–4104, 4091–4105,
4092–4106, 4093–4107, 4094–4108, 4095–4109,
4096–4110, 4097–4111, 4098–4112, 4099–4113,
4100–4114, 4101–4115, 4102–4116, 4103–4117,
4104–4118, 4105–4119, 4106–4120, 4107–4121,
4108–4122, 4109–4123, 4110–4124, 4111–4125,
4112–4126, 4113–4127, 4114–4128, 41154129, 4116–4130,
4117–4131, 4118–4132, 4119–4133, 4120–4134,
4121–4135, 4122–4136, 4123–4137, 4124–4138,
4125–4139, 4126–4140, 4127–4141, 4128–4142,
4129–4143, 4130–4144, 4131–4145, 4132–4146,
4133–4147, 4134–4148, 4135–4149, 4136–4150,
4137–4151, 4138–4152, 4139–4153, 4140–4154,
4141–4155, 4142–4156, 4143–4157, 4144–4158,
4145–4159, 4146–4160, 4147–4161, 4148–4162,
4149–4163, 4150–4164, 4151–4165, 4152–4166,
4153–4167, 4154–4168, 4155–4169, 4156–4170,
4157–4171, 4158–4172, 4159–4173, 4160–4174,
4161–4175, 4162–4176, 4163–4177, 4164–4178,
4165–4179, 4166–4180, 4167–4181, 4168–4182,
4169–4183, 4170–4184, 4171–4185, 4172–4186,
4173–4187, 4174–4188, 4175–4189, 4176–4190,
4177–4191, 4178–4192, 4179–4193, 4180–4194,
4181–4195, 4182–4196, 4183–4197, 4184–4198,
4185–4199, 4186–4200, 4187–4201, 4188–4202,
4189–4203, 4190–4204, 4191–4205, 4192–4206,
4193–4207, 4194–4208, 4195–4209, 4196–4210,
4197–4211, 4198–4212, 4199–4213, 4200–4214,
4201–4215, 4202–4216, 4203–4217, 4204–4218,
4205–4219, 4206–4220, 4207–4221, 4208–4222,
4209–4223, 4210–4224, 4211–4225, 42124226,
4213–4227, 4214–4228, 4215–4229, 4216–4230,
4217–4231, 4218–4232, 4219–4233, 4220–4234,
42214235, 4222–4236, 4223–4237, 4224–4238,
4225–4239, 4226–4240, 4227–4241, 4228–4242,
4229–4243, 4230–4244, 4231–4245, 4232–4246,
4233–4247, 4234–4248, 4235–4249, 4236–4250,
4237–4251, 4238–4252, 4239–4253, 4240–4254,
4241–4255, 4242–4256, 4243–4257, 4244–4258,
4245–4259, 4246–4260, 4247–4261, 4248–4262,
4249–4263, 4250–4264, 4251–4265, 4252–4266,
4253–4267, 4254–4268, 4255–4269, 4256–4270,
4257–4271, 4258–4272, 4259–4273, 4260–4274,
4261–4275, 4262–4276, 4263–4277, 4264–4278,
4265–4279, 4266–4280, 4267–4281, 4268–4282,
4269–4283, 4270–4284, 4271–4285, 42724286,
4273–4287, 4274–4288, 4275–4289, 4276–4290,
4277–4291, 4278–4292, 4279–4293, 4280–4294,
4281–4295, 4282–4296, 4283–4297, 4284–4298,
4285–4299, 42864300, 4287–4301, 4288–4302,
4289–4303, 4290–4304, 4291–4305, 4292–4306,
4293–4307, 4294–4308, 4295–4309, 4296–4310,
4297–4311, 4298–4312, 4299–4313, 4300–4314,
4301–4315, 4302–4315, 4303–4317, 4304–4318,
4305–4319, 4306–4320, 4307–4321, 4308–4322,
4309–4323, 4310–4324, 4311–4325, 4312–4326,
4313–4327, 4314–4328, 4315–4329, 4316–4330,
4317–4331, 4318–4332, 4319–4333, 4320–4334,
4321–4335, 4322–4336, 4323–4337, 4324–4338,
4325–4339, 4326–4340, 4327–4341, 4328–4342,
4329–4343, 4330–4344, 4331–4345, 4332–4346,
4333–4347, 4334–4348, 4335–4349, 43364350,
4337–4351, 4338–4352, 4339–4353, 4340–4354,
4341–4355, 4342–4356, 4343–4357, 4344–4358,
4345–4359, 4346–4360, 4347–4361, 4348–4362,
4349–4363, 4350–4364, 4351–4365, 4352–4366,
4353–4367, 4354–4368, 4355–4369, 4356–4370,
4357–4371, 4358–4372, 4359–4373, 4360–4374,
4361–4375, 4362–4376, 43634377, 4364–4378,
4365–4379, 4366–4380, 4367–4381, 4368–4382,
4369–4383, 43704384, 4371–4385, 4372–4386,
4373–4387, 4374–4388, 4375–4389, 4376–4390,
4377–4391, 4378–4392, 4379–4393, 4380–4394,
4381–4395, 4382–4396, 4383–4397, 4384–4398,
4385–4399, 4386–4400, 4387–4401, 4388–4402,
4389–4403, 4390–4404, 4391–4405, 4392–4406,
4393–4407, 4394–4408, 4395–4409, 4396–4410,
4397–4411, 4398–4412, 4399–4413, 4400–4414,
4401–4415, 4402–4416, 4403–4417, 4404–4418,
4405–4419, 4406–4420, 4407–4421, 4408–4422,
4409–4423, 4410–4424, 4411–4425, 4412–4426,
4413–4427, 4414–4428, 4415–4429, 4416–4430,
4417–4431, 4418–4432, 4419–4433, 4420–4434,
4421–4435, 4422–4436, 4423–4437, 4424–4438,
4425–4439, 44264440, 4427–4441, 4428–4442,
4429–4443, 4430–4444, 4431–4445, 4432–4446,
4433–4447, 4434–4448, 4435–4449, 4436–4450,
4437–4451, 4438–4452, 4439–4453, 4440–4454,
4441–4455, 4442–4456, 4443–4457, 4444–4458,
4445–4459, 4446–4460, 4447–4461, 4448–4462,
4449–4463, 4450–4464, 4451–4465, 4452–4466,
4453–4467, 4454–4468, 4455–4469, 4456–4470,
4457–4471, 4458–4472, 4459–4473, 4460–4474,
44614475, 4462–4476, 4463–4477, 4464–4478,
4465–4479, 4466–4480, 4467–4481, 4468–4482,
4469–4483, 4470–4484, 4471–4485, 4472–4486,
4473–4487, 4474–4488, 4475–4489, 4476–4490,
4477–4491, 4478–4492, 4479–4493, 4480–4494,
4481–4495, 4482–4496, 4483–4497, 4484–4498,
4485–4499, 4486–4500, 4487–4501, 4488–4502,
4489–4503, 4490–4504, 4491–4505, 44924506,
4493–4507, 4494–4508, 4495–4509, 4496–4510,
4497–4511, 4498–4513, 4499–4514, 4500–4515,
4501–4515, 4502–4516, 4503–4517, 4504–4518,
4505–4519, 4506–4520, 4507–4521, 4508–4522,
4509–4523, 4510–4524, 4511–4525, 4512–4526,
4513–4527, 4514–4528, 4515–4529, 4516–4530,
4517–4531, 4518–4532, 4519–4533, 4520–4534,
4521–4535, 4522–4536, 4523–4537, 4524–4538, 4525–4539, 4526–4540, 4527–4541, 4528–4542, 4529–4543, 4530–4544, 4531–4545, 4532–4546, 4533–4547, 4534–4548, 4535–4549, 4536–4550, 4537–4551, 4538–4552, 4539–4553, 4540–4554, 4541–4555, 4542–4556, 4543–4557, 4544–4558, 4545–4559, 4546–4560, 4547–4561, 4548–4562, 4549–4563, 4550–4564, 4551–4565, 4552–4566, 4553–4567, 4554–4568, 4555–4569, 4556–4570, 4557–4571, 4558–4572, 4559–4573, 4560–4574, 4561–4575, 4562–4576, 4563–4577, 4564–4578, 4565–4579, 4566–4580, 4567–4581, 4568–4582, 4569–4583, 4570–4584, 4571–4585, 4572–4586, 4573–4587, 4574–4588, 4575–4589, 4576–4590, 4577–4591, 4578–4592, 4579–4593, 4580–4594, 4581–4595, 4582–4596, 4583–4597, 4584–4598, 4585–4599, 4586–4600, 4587–4601, 4588–4602, 4589–4603, 4590–4604, 4591–4605, 4592–4606, 4593–4607, 4594–4608, 4595–4609, 4596–4610, 4597–4611, 4598–4612, 4599–4613, 4600–4614, 4601–4615, 4602–4616, 4603–4617, 4604–4618, 4605–4619, 4606–4620, 4607–4621, 4608–4622, 4609–4623, 4610–4624, 4611–4625, 4612–4626, 4613–4627, 4614–4628, 4615–4629, 4616–4630, 4617–4631, 4618–4632, 4619–4633, 4620–4634, 4621–4635, 4622–4636, 4623–4637, 46244638, 4625–4639, 4626–4640, 4627–4641, 4628–4642, 4629–4643, 4630–4644, 4631–4645, 4632–4646, 4633–4647, 4634–4648, 4635–4649, 4636–4650, 4637–4651, 4638–4652, 4639–4653, 4640–4654, 4641–4655, 4642–4656, 4643–4657, 4644–4658, 4645–4659, 4646–4660, 4647–4661, 4648–4662, 4649–4663, 4650–4664, 4651–4665, 4652–4666, 4653–4667, 4654–4668, 4655–4669, 4656–4670, 4657–4671, 4658–4672, 4659–4673, 4660–4674, 4661–4675, 4662–4676, 4663–4677, 4664–4678, 4665–4679, 4666–4680, 4667–4681, 4668–4682, 4669–4683, 4670–4684, 4671–4685, 4672–4686, 4673–4687, 4674–4688, 4675–4689, 4676–4690, 4677–4691, 4678–4692, 4679–4693, 4680–4694, 4681–4695, 4682–4696, 4683–4697, 4684–4698, 4685–4699, 4686–4700, 4687–4701, 4688–4702, 4689–4703, 4690–4704, 4691–4705, 4692–4706, 4693–4707, 4694–4708, 4695–4709, 4696–4710, 4697–4711, 4698–4712, 4699–4713, 4700–4714, 4701–4715, 4702–4716, 4703–4717, 4704–4718, 4705–4719, 4706–4720, 4707–4721, 4708–4722, 4709–4723, 4710–4724, 4711–4725, 4712–4726, 4713–4727, 4714–4728, 4715–4729, 4716–4730, 4717–4731, 4718–4732, 4719–4733, 4720–4734, 4721–4735, 4722–4736, 4723–4737, 4724–4738, 4725–4739, 4726–4740, 4727–4741, 4728–4742, 4729–4743, 4730–4744, 4731–4745, 4732–4746, 4733–4747, 4734–4748, 4735–4749, 4736–4750, 4737–4751, 4738–4752, 4739–4753, 4740–4754, 4741–4755, 4742–4756, 4743–4757, 4744–4758, 4745–4759, 4746–4760, 4747–4761, 4748–4762, 4749–4763, 4750–4764, 4751–4765, 4752–4766, 4753–4767, 4754–4768, 4755–4769, 4756–4770, 4757–4771, 4758–4772, 4759–4773, 4760–4774, 4761–4775, 4762–4776, 4763–4777, 4764–4778, 4765–4779, 4766–4780, 4767–4781, 4768–4782, 4769–4783, 4770–4784, 4771–4785, 4772–4786, 4773–4787, 4774–4788, 4775–4789, 4776–4790, 4777–4791, 4778–4792, 4779–4793, 4780–4794, 4781–4795, 4782–4796, 4783–4797, 4784–4798, 4785–4799, 4786–4800, 4787–4801, 4788–4802, 4789–4803, 4790–4804, 4791–4805, 4792–4806, 4793–4807, 4794–4808, 4795–4809, 4796–4810, 4797–4811, 4798–4812, 4799–4813, 4800–4814, 4801–4815, 4802–4816, 4803–4817, 4804–4818, 4805–4819, 4806–4820, 4807–4821, 4808–4822, 4809–4823, 4810–4824, 4811–4825, 4812–4826, 4813–4827, 4814–4828, 4815–4829, 4816–4830, 4817–4831, 4818–4832, 4819–4833, 4820–4834, 4821–4835, 4822–4836, 4823–4837, 4824–4838, 4825–4839, 4826–4840, 4827–4841, 4828–4842, 4829–4843, 4830–4844, 4831–4845, 4832–4846, 4833–4847, 4834–4848, 4835–4849, 4836–4850, 4837–4851, 4838–4852, 4839–4853, 4840–4854, 4841–4855, 4842–4856, 4843–4857, 4844–4858, 4845–4859, 4846–4860, 4847–4861, 4848–4862, 4849–4863, 4850–4864, 4851–4865, 4852–4866, 4853–4867, 4854–4868, 4855–4869, 4856–4870, 4857–4871, 4858–4872, 4859–4873, 4860–4874, 486–4875, 4862–4876, 4863–4877, 4864–4878, 4865–4879, 4866–4880, 4867–4881, 4868–4882, 4869–4883, 4870–4884, 4871–4885, 4872–4886, 4873–4887, 4874–4888, 4875–4889, 4876–4890, 4877–4891, 4878–4892, 4879–4893, 4880–4894, 4881–4895, 4882–4896, 4883–4897, 4884–4898, 4885–4899, 4886–4900, 4887–4901, 4888–4902, 4889–4903, 4890–4904, 4891–4905, 4892–4906, 4893–4907, 4894–4908, 4895–4909, 4896–4910, 4897–4911, 4898–4912, 4899–4913, 4900–4914, 4901–4915, 4902–4916, 4903–4917, 4904–4918, 4905–4919, 4906–4920, 4907–4921, 4908–4922, 4909–4923, 4910–4924, 4911–4925, 4912–4926, 4913–4927, 4914–4928, 4915–4929, 4916–4930, 4917–4931, 4918–4932, 4919–4933, 4920–4934, 4921–4935, 4922–4936, 4923–4937, 4924–4938, 4925–4939, 4926–4940, 4927–4941, 4928–4942, 4929–4943, 4930–4944, 4931–4945, 4932–4946, 4933–4947, 4934–4948, 4935–4949, 4936–4950, 4937–4951, 4938–4952, 4939–4953, 4940–4954, 4941–4955, 4942–4956, 4943–4957, 4944–4958, 4945–4959, 4946–4960, 4947–4961, 4948–4962, 4949–4963, 4950–4964, 4951–4965, 4952–4966, 4953–4967, 4954–4968, 4955–4969, 4956–4970, 4957–4971, 4958–4972, 4959–4973, 4960–4974, 4961–4975, 4962–4976, 4963–4977, 4964–4978, 4965–4979, 4966–4980, 4967–4981, 4968–4982, 4969–4983, 4970–4984, 4971–4985, 4972–4986, 4973–4987, 4974–4988 and 4975–4989 of SEQ ID NO:3.

EXAMPLE 9

Sub-confluent HaCaT cells were treated as described above with phosphorothioate oligonucleotides IGFR.AS (antisense: 5'-ATCTCTCCGCTTCCTTTC-3' (SEQ ID NO.10) ref 13) and IGFR.S (sense control: 5-GAAAGGAAGCGGAGAGAT-3' (SEQ ID NO.11) ref 13) IGF-I binding to the cell monolayers was then measured as $^{125}$I-IGF-I.

EXAMPLE 10

Figure 7:
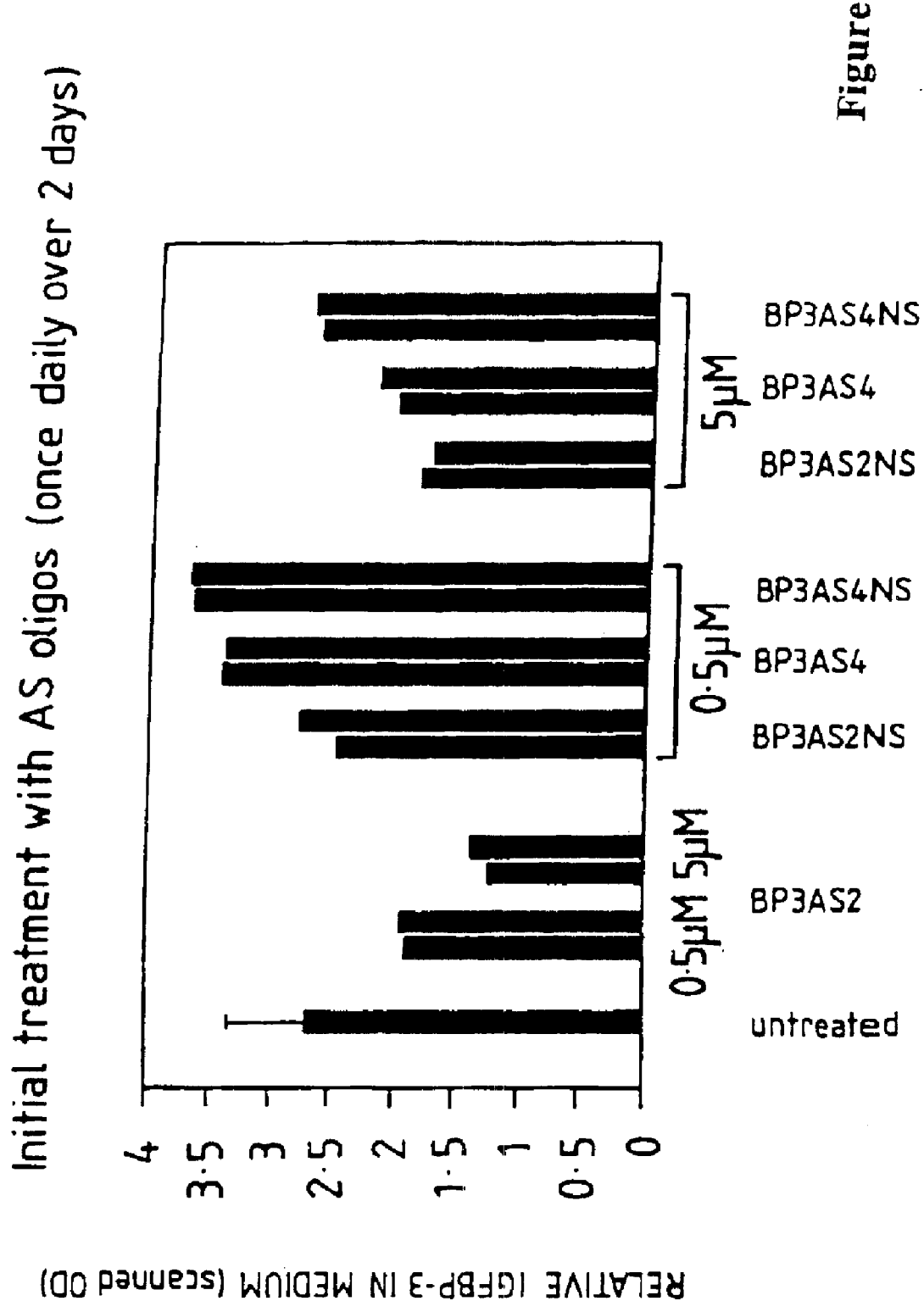
FIG. 7 is a graphical representation showing inhibition of IGFBP-3 production in culture medium following initial treatment with antisense oligonucleotides once daily over a 2 day period.
Figure 8:
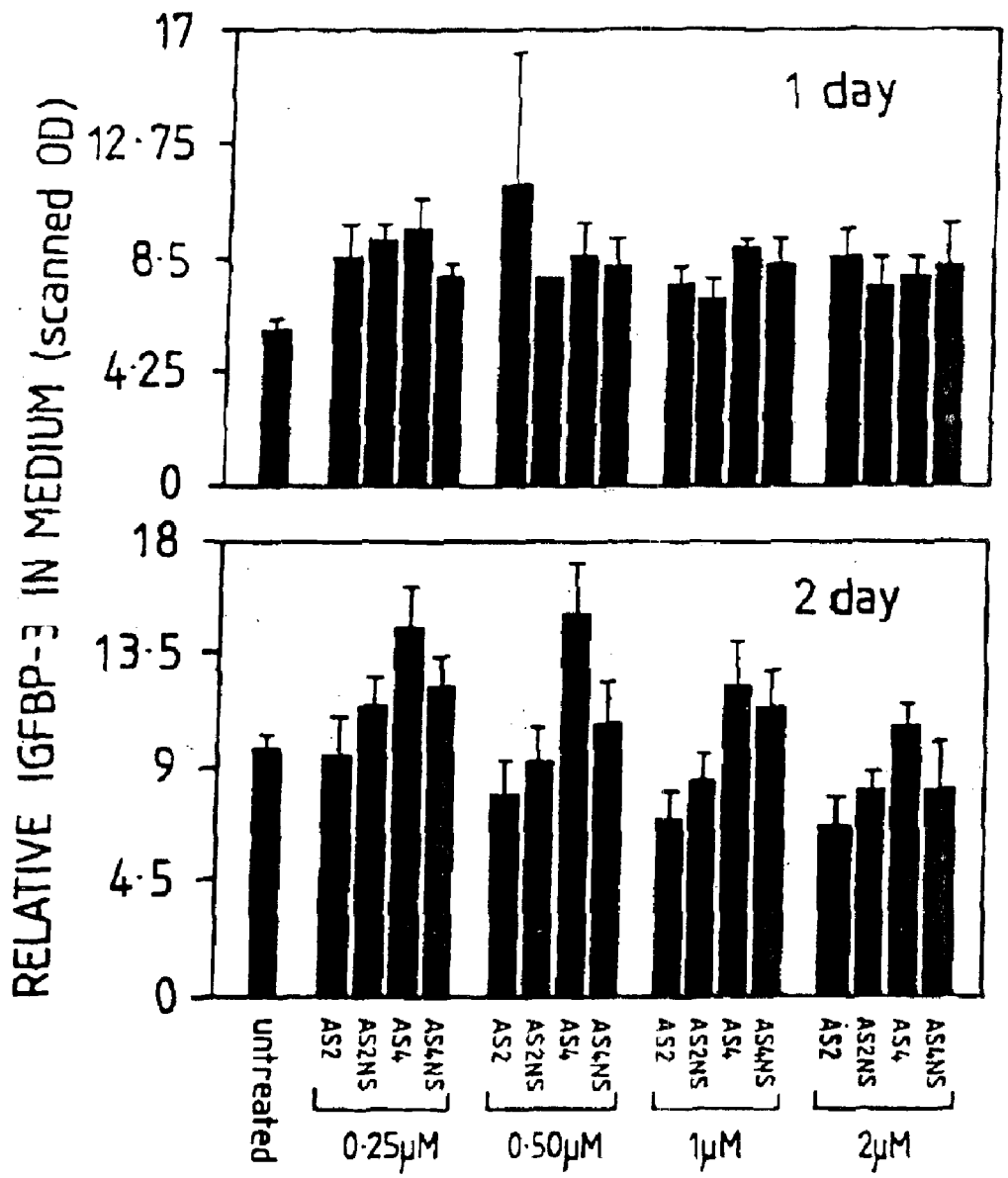
FIG. 8 is a graphical representation showing optimization of IGFBP-3 antisense oligonucleotide concentration as determined by relative IGFBP-3 concentration in culture medium.

The results of this experiment are shown in FIGS. 7 and 8.

HaCaT cells were initially plated in DMEM with 10% v/v serum, then AS oligo experiments were performed in complete "Keratinocyte-SFM" (Gibco) to exclude the influence of exogenous IGFBPs. Oiigos were synthesised as phosphorothioate (nuclease-resistant) derivatives (Bresatec, South Australia) and were as follows: antisense: AS2, 5'-GCGCCCGCTGCATGACGCCTGCAAC-3' (SEQ ID NO.4) (IGFBP-3 start codon); controls: AS2NS, 5'-CGGAG ATGCCGCATGCCAGCGCAGG-3' (SEQ ID NO.5) AS4, 5'-AGGCGGCTGACGGCACTA-3' (SEQ ID NO.6) AS4NS, 5'-GACAGCGTCGGAGCGATC-3' (SEQ ID NO.9), IGFRAS, 5'-ATCTCTCCGCTTCCTTTC-3' (SEQ ID NO.10) IGFRS, 5'-GAAAGGAAGCGGAGAGAT-3' (SEQ ID NO.11). Oligos to IGFBP-3 were based on the published sequence of Spratt et al [12]. AS oligos were added to HaCaT monolayers in 0.5 ml medium in 24-well plates at the concentrations and addition frequencies indicated. IGFBP-3 measured in cell-conditioned medium using a dot-blot assay, adapted from the Western ligand blot method of Hossenlopp et al [11], in which 100 µl of conditioned medium was applied to nitrocellulose filters with a vacuum dot-blot apparatus. After drying the membranes at 37° C., relative amounts of IGFBP are determined by $^{125}$I-IGF-1-binding, autoradiography and computerised imaging densitometry. Triplicate wells (except in FIG. 7, where duplicate wells were measured as shown) were analysed and corrected for changes in cell number per well. Relative cell number per well was determined using an amido black dye method, developed specifically for cultured monolayers of HaCaT cells [14]. Cell numbers differed by less than 10% after treatment. For oligos to the IGF receptor, receptor quantitation in intact HaCaT monolayers was by overnight incubation with $^{125}$I-IGF-I (30,000 cpm/well) at 4° C.

EXAMPLE 11

Experiments involving ribozymes are generally conducted as described in International Patent Application No. WO 89/05852 and in Haselhoff and Gerlach [8]. Ribozymes are constructed with a hybridising region which is complementary in nucleotide sequence to at least part of a target RNA which, in this case, encodes IGFBP-2. Activity of ribozymes is measurable on, for example, Northern blots or using animal models such as in the nude mouse model (15; 16) or the "flaky skin" mouse model (17; 18).

EXAMPLE 12

The methods described in Example 11 are used for the screening of ribozymes which inhibit IGFBP-3 production. The activity of the ribozymes is determined as in Example 1.

EXAMPLE 13

The methods described in Example 11 are used for the screening of ribozymes which inhibit IGF-1 production. The activity of the ribozymes is determined as in Example 11.

EXAMPLE 14

The methods described in Example 11 are used for the screening of ribozymes which inhibit IGF-I production. The activity of the ribozymes is determined as in Example 11.

EXAMPLE 15

Twenty-one antisense oligonucleotides targeted to mRNA sequences enducing the IGF-I receptor, and four random oligonucleotides were synthesized. The antisense oligonucleotides are C5-propynyl-dU, dC 15 mer phosphorothioate oligodeoxyribonucleotides. In these oligonucleotides, a phosphorothioate backbone replaces the phosphodiester backbone of naturally occurring DNA. The positions of the 21 sequence specific antisense oligonucleotides relative to the IGF-I receptor mRNA structure are shown in FIG. 9.

EXAMPLE 16

Experiments were performed to determine the uptake of the antisense oligonucleotides of Example 15 into keratinocytes. Cells of the differentiated human keratinocyte cell line, HaCaT, were incubated for 24 hours in Dulbecco's Modified Eagle Medium (DMEM) supplemented with 10% (w/v) fetal calf serum (FCS) containing fluorescently labelled oligonucleotide (R451, a randomized sequence oligonucleotide, 30 nM) and cytofectin GSV (2 µg/ml, Glen Research, 44901 Falcon Place, Sterling, Va. 20166, Cat. No. 70–3815–78). Cells were then transferred to oligonucleotide-free medium and fluorescence microcopy and phase contrast images of the cells were obtained. FIG. 10 shows fluorescence microscopy (Panel A) and phase contrast (Panel B) images of uptake of fluorescently labelled oligonucleotide in the majority of cells in a HaCaT monolayer. The degree of uptake obtained with the cationic lipid cytofectin was far greater than the uptake obtained with the next best lipid tried, Tfx-50.

A further experiment was performed to assess the uptake and toxicity associated with the use of cytofectin GSV over five days. Confluent HaCaT keratinocytes were incubated in DMEM containing fluorescently labelled oligonucleotide R451 (30 nM or 100 nM) plus cytofectin GSV (2 µg/ml or 5 µg/ml) over 120 hours, viewed by fluorescence microscopy, tryptan blue stained, and counted. The graphs in FIG. 11 depict uptake (Panel A) and toxicity (Panel B). The proportion of cells containing oligonucleotide remained high over the 120 hour period. The combination of 30 nM oligonucleotide and 2 µg/ml GSV provided optimal uptake and minimal toxicity.

EXAMPLE 17

The twenty-one oligonucleotides of Example 15 were then screened for their ability to inhibit IGF-I receptor mRNA levels in HaCaT cells, in accordance with the teachings herein. HaCaT cells were grown to 90% confluence in DMEM supplemented with 10% (v/v) FCS. Antisense oligonucleotides (30 nM) were completed with cytofectin GSV (2 µg/ml) and added to the cells in the presence of serum. HaCaT keratinocytes were treated with the oligonucleotide/ GSV complexes or randomized sequence oligonucleotides (R451, R766), liposome alone (GSV), or were left untreated (UT). Duplicate treatments were performed. Repeat additions of the oligonucleotides/GSV complex were performed at 24, 48 and 76 hours following the first addition. Total RNA was isolated as per the RNAzolB protocol (Biotecx Laboratories, Inc. 6023 South Loop East, Houston, Tex. 77033) 96 hours following the first addition.

IGF-I receptor mRNA and glyceraldehyde-3-phosphate dehydrogenase (GAPDH) mRNA levels were simultaneously determined by a ribonuclease (RNase) protection assay. The RNase Protection Assay kit, in vitro transcription kit, and IGF-I receptor and GAPDH DNA templates were obtained from Ambion, Inc. (2130 Woodward St., Houston, Tex. 78744). The amount of IGF-I receptor mRNA in any given sample was expressed as the amount of IGF-I receptor mRNA relative to the amount of GAPDH mRNA. Each oligonucleotide was tested in at least two separate experiments.

FIG. 12 depicts representative results of the screening process. Panel A shows an electrophoretic analysis of IGF-I receptor and GAPDH mRNA fragments after RNase protection. Molecular weight markers are shown on the right hand side. The full-length probe is shown on the left hand side; G-probe indicates the IGF-I receptor probe. GAPDH protected fragments (G) are seen at 316 bases and IGF-I protected fragments (I) are seen at 276 bases. Exhibit E, Panel B provides a graph indicating the relative level of IGF-I receptor mRNA following each treatment.

The results obtaining from the above screening assays are summarized in FIG. 13. The graph depicts the relative level of IGF-I receptor mRNA after treatment with oligonucleotides complementary to the human IGF-I receptor mRNA (26–86), four randomized sequence oligonucleotides (R1, R4, R7, R9), liposome alone (GSV), or no treatment (UT). Asterisks indicate a significant different in relative IGF-I receptor mRNA as compared to GSV treated cells (n=4–10, p<0.05).

As demonstrated in FIG. 13, treatment with eighteen of the twenty-one oligonucleotides resulted in a significant different in levels of IGF-I receptor mRNA relative to GSV treated cells. Three of the antisense oligonucleotides tested in the screening assay reduce IGF-I receptor mRNA to less than 35% of GSV-treated cells. These antisense oligonucleotides have the following sequences, presented in the 5' to 3' direction:
27 UCCGGAGCCAGACUU (SEQ ID NO.12)
64 CACAGUUGCUGCAAG (SEQ ID NO.13)
78 UCUCCGCUUCCUUUC (SEQ ID NO.14).

As further demonstrated in FIG. 13, six of the antisense oligonucleotides tested in the screening assay reduce IGF-I receptor mRNA to between 35 and 50% of GSV-treated cells. These antisense oligonucleotides have the following sequences, presented in the 5' to 3' direction:
28 AGCCCCCACAGCGAG (SEQ ID NO.15)
32 GCCUUGGAGAUGAGC (SEQ ID NO.16)
40 UAACAGAGGUCAGCA (SEQ ID NO.17)
42 GGAUCAGGGACCAGU (SEQ ID NO.18)
46 CGGCAAGCUACACAG (SEQ ID NO.19)
50 GGCAGGCAGGCACAC (SEQ ID NO.20).

EXAMPLE 19

Another experiment was performed demonstrating that antisense oligonucleotides targeted to genetic sequences encoding the IGF0I receptor and that reduce IGF-I receptor mRNA levels also inhibit the IGF-I receptor level on the surface of the treated cultured keratinocytes. HaCaT cells were grown to confluence in 24-well plates in DMEM containing 10% (v/v) FCS. Oligodeoxynucleotide and cytofectin GSV were mixed together in serum-free DMEM, and incubated at room temperature for 10 minutes before being diluted ten-fold in medium and placed on the cells. Cells were incubated for 72 hours with 30 µM random sequence or antisense oligonucleotide and 2 µm/ml GSV, or with GSV alone in DMEM containing 10% FCS with solutions replaced every 24 hours. This was followed by incubation with oligonucleotide/GSV in serum-free DMEM for 48 hours. All incubations were performed at 37° C. Cells were washed twice with 1 ml cold PBS. Serum-free DMEM containing $10^{-10}M^{125}$I-IGF-I was added with or without the IGF-I analogue, des (1–3) IGF-I, at $10^{-11}M$ to $10^{-7}M$. Cells were incubated at 4° C. for 17 hours with gentle shaking, then washed three times with 1 ml cold PBS and lysed in 250 µl 0.5M NaOH/0.1% (v/v) Triton X-100 at room temperature for 4 hours. Specific binding of the solubilised cell extract was measured using a gamma counter. As shown in FIG. 14, treatment of HaCaT keratinocytes with oligonucleotide reduced cell surface IGF-I receptor levels to 30% of levels in untreated keratinocytes or in keratinocytes treated with liposome alone or a random oligonucleotide, R766. As shown in FIG. 15, treatment with oligonucleotide #27 also significantly reduced cell surface IGF-I receptor levels relative to untreated keratinocytes or treatment with liposome alone or random nucleotide R451. As demonstrated in Example 17, oligonucleotides #64 and #27 reduce IGF-I receptor mRNA levels in cultured keratinocytes to less than 35% of GSV-treated cells. Accordingly, the ability of an oligonucleotide to reduce IGF-I receptor mRNA levels in correlated with its ability to reduce cell surface IGF-I receptor levels.

The forgoing Examples demonstrate that antisense oligonucleotides targeted to the IGF-I receptor can be delivered to human keratinocytes in vitro, can inhibit IGF-I receptor mRNA levels in human keratinocytes in vitro, and that inhibition of mRNA levels is correlated with reduction of cell surface IGF-I receptor levels.

EXAMPLE 19

Further experiments demonstrated the efficacy of antisense oligonucleotides targeted tot he IGF-I receptor in an in vivo model of psoriasis. An animal model of psoriasis is the human psoriatic skin xenograft model. The skin used in this model contains the true disease state. In this model, reduction in epidermal thickness of psoriatic grafts in response to treatment is positively correlated with efficacy of treatment. Both normal and psoriatic human skin were grafted into a thymic (nude) mice in accordance with the methods of Baker et al (1992) *Brit. J. Dermatol.* 126:105 and Nanney et al (1992) *J. Invest. Dermatol,* 92:296. Successful grafting was achieved, as demonstrated in FIG. 16, which shows hemotoxylin and eosin (H&E) stained sections of a 49-day old psoriatic human skin graft (Panel B) compared to the histology of the skin graft prior to grafting (Panel A). The histological features of psoriasis present in the pregraft section (e.g., parakeratosis, acanthosis and pronounced rete ridges) are present in the grafts more than seven weeks post grafting.

Using the model, oligonucleotide uptake was measured in epidermal keratinocytes in vivo after intradermally injection. Fluorescently labelled oligonucleotide (R451, 50 µl, 10 µM injection) was intradermally injected into psoriatic and normal skin grafts on a thymic mice. Live confocal microscopy and fluorescence microscopy of fixed sections was then employed.

Using both techniques, oligonucleotide was found to localize in the nucleus of over 90% of basal keratinocytes. FIG. 17 shows the nuclear localization of oligonucleotide in psoriatic skin cells using conventional fluorescence microscopy of a graft that was removed and sectioned after 24 hours.

After establishing oligonucleotide uptake in the in vivo model, a small number of pilots experiments were performed to determine a schedule for treatment of grafted mice with antisense oligonucleotides targeted to genetic sequences encoding the IGF-I receptor. The treatment schedule was finalized as follows:

| Graft Number | Treatment | Volume of Injection | ODN Concentration | Duration of Treatment |
|---|---|---|---|---|
| 1–3 | Vehicle (PBS) | 50 µl | — | 20 days |
| 4–6 | RandomODN#R451 | 50 µl | 10 µM | 20 days |
| 7–9 | ODN#27 | 50 µl | 10 µM | 20 days |
| 10–12 | ODN#74 | 50 µl | 10 µM | 20 days |
| 13–15 | ODN#50 | 50 µl | 10 µM | 20 days |

As determined above, oligonucleotide #27 (ODN #27) reduced IGF-I receptor mRNA in vitro to less than 35% of GSV-treated cells. Oligonucleotide #50 (ODN#50) reduced IGF-I receptor mRNA in vitro to between 35 and 50% of GSV-treated cells. Oligonucleotide #74 (ODN #74) was not inhibitory to IGF-I receptor mRNA in vitro. In the in vivo model, each mouse received two grafts. Random oligonucleotide or vehicle was injected intradermally in one graft and acted as a control. The second graft was injected with the targeted oligonucleotide. Each graft received an injection every second day for the duration of the treatment.

Histology of representative grafts from each treatment type are shown in FIGS. 18(a)–(d) and 19(a)–(d). Each sheet shows three images of H&E stained sections: the pregraft histology, the control treated graft, and the targeted oligonucleotide treated graft. FIGS. 18(a)–(d) are shown at 100× magnification; FIGS. 19(a)–(d) are shown at 400× magnification. The total cross sectional area of epidermis of each graft was assessed using MCID analysis software. The pooled results from all of the treated grafts are shown in FIG. 20.

As shown in FIGS. 18(a)–(d) and 19(a)–(d), the vehicle-treated (control) grafts were marginally thinner than the pregraft sections. The degree of regression in these experiments (ie., less than 10%) is not significant. A similar amount of marginal thinning of epidermis compared to pregraft also occurred in pilot experiments in which psoriatic grafts were not injected, and thus it is unlikely that the vehicle itself has any effect. Histological features of psoriasis present in skin samples prior to grafting (clubbing of rete ridges, parakeratosis, acanthosis) were present in these grafts.

The random oliognucleotide treated grafts varied in epidermal thickness after 20 days of treatment. Grafts were either a similar thickness to the pregraft histology, or marginally thinner. Random oligonucleotide treated grafts were in each case significantly thicker than their targeted oligonucleotide treated pairs.

As shown in FIG. 20, the targeted oligonucleotide treated grafts were significantly thinner than the pregraft sections and showed less parakeratosis and clubbing of rete ridges. Antisense oligonucleotides which were effective at reducing IGF-I receptor mRNA levels in vitro (#27 and #50) produced greater epidermal thinning than an oligonucleotide which was not inhibitory to IGF-I receptor mRNA in vitro (#74). Accordingly, there is a direct correlation between the ability of an oligonucleotide targeted to the IGF-I receptor to inhibit IGF-I receptor mRNA levels in vitro and the efficacy of the oligonucleotide as an anti-psoriasis agent in an in vivo model.

EXAMPLE 20

Another experiment demonstrated that treatment of psoriatic grafts with an oligonucleotide targeted to a genetic sequence encoding the IGF-I receptor results in inhibition of proliferation. Pregrafts from psoriatic patients, control grafts treated with R4541, and grafts treated with oligonucleotide #27 were obtained as described in Example 19. An antibody to the cell cycle-specific nuclear antigen Ki67 was used to immunohistochemically detect actively dividing cells and thereby assess proliferation. The αKi67 antibody (DAKO, Glostrup, Denmark) recognizes the Ki67 antigen transiently expressed in nuclei of proliferating cells during late $G_1$, S, M and $G_2$ phase of the cycle and thus provides a marker for proliferation. Pregraft and graft sections were immunohistochemically processed by standard methods using αKi67 (according to the manufacturer's instructions), peroxidase-conjugated anti-rabbit second stage antibody, and a chromogenic peroxidase substrate.

The results of this experiment are presented in FIG. 21 as immunohistochemical sections at 100× magnification. The top panel of FIG. 21 depicts a pregraft section obtained from a psoriatic patient. The epidermis is thicker than normal and nucleic are evident in the stratum corneum. Ki67 positive cells, appearing as brown dots, are evidence in the basal and suprabasal layers, and indicate actively proliferating cells. The control (R450-treated) graft in the bottom panel of FIG. 21 also exhibits evidence of proliferation, including parakeratosis and Ki67-positive cells appearing as brown-staining nuclei. The center panel of FIG. 21 exhibits the oligonucleotide #27-treated graft. This graft exhibits significantly reduced proliferation as evidenced by normal (thin) epidermis, lack of invaginations, and substantial loss of Ki67-positive cells.

These results indicate that treatment of human psoriatic grafts with an oligonucleotide targeted to mRNA encoding the IGF-I receptor results in inhibition of epidermal proliferation.

EXAMPLE 21

Topical formulations of complexes of oligonucleotides with cytofectin GSV in aqueous or methylcellulose gel formulations were prepared and assessed foruptake of the oligonucleotide by keratinocytes in viva. The topical formulations contained oligonucleotides complexed with cytofectin GSV in an aqueous solution or methylcellulose carrier, as taught herein. With both aqueous and methylcellulose gel formulations, locatlization of oligonucleotide R451 to nuclei and cytoplasm of keratinocytes in normal human skin grafts on nuce nice was observed. FIG. 22 shows an image from confocal microscopy demonstrating oligonucleotide locatlization in the nuclei and cytoplasm of keratinocytes in normal human skin grafts after topical application of fluroescently labeled oligonucleotide (10 μM R451) complexed with cytofectin GSV (10 μg/ml). FIG. 23 shows an image from confocal microscopy demonstrating that topical application of the same oligonucleotide/GSV concentrations in a 3% (w/v) methylcellulose gel produced similar uptake in the target keratinocyte population. Using an aqueous formulation of oligonucleotide/GSV complexes, penetration of oligonucleotide into the viable epidermis was observed, whereas application of formulations of oligonucleotide complexed with other cationic lipids resulted in localization of oligonucleotide in the stratum corneum.

EXAMPLE 22

Thirteen antisense oligonucleotides targeted to IGFBP-3 were synthesized. The antisense oligonucleotides are C5-propynyl-dU, Dc15 mer phosphorothioate oligodeoxyribonucleotides. FIG. 24 attached hereto is a schematic diagram indicating the position of the thirteen oligonucleotides relative to the IGFBP-3 mRNA structure.

These oligonucleotides were screened for their ability to inhibit IGFBP-3 mRNA levels of HaCaT cells in accordance with the teachings herein. HaCaT cells were grown to 90% confluence in DMEM supplemented with 10% (v/v) FCS, then placed in complete keratinocyte serum free medium (KSFM, Gibco), which has a defined amount of EGF, for 24 hours. Oligonucleotides (30 nM or 100 nM) were complexed with GSV cytofectin (2 μg/ml) and added to cells in complete KSFM to allow oligonucleotides to enter the nucleus before removal of EGF. Repeat additions were performed at three hours (in serum free DMEM, which releases the EGF inhibition of IGFBP-3 mRNA) and again after another 24 hours. HaCaT cells were also treated with randomized sequence oligonucleotides (R121, R451, R766 and R961), liposome alone (GSV) or were left untreated (UT). Total RNA was isolated as described in Example 17, 24 hours after the last treatment. Total RNA (15 µg) was analyzed by Northern analysis and phosphoroimager quantitation for IGFBP-3 and GADPH mRNA. IGFBP-3 mRNA is expressed as the amount of IGFBP-3 mRNA relative to the amount of GAPDH mRNA.

FIGS. 25(a)–(d) provide graphs which depict results in this screening process. In these graphs, R1 and R12 refer to R121; R4, R4(O) and R45 rfer to R451; R7, R7(O) and R76 refer to R766; and R9 and R96 refer to R961. The values were standardized to GSV-treated cells, and data was pooled and statistically analyzed by ANOVA followed by Domet's test to compare each treatment to GSV-treated cells. The pooled data are presented as a bar graph in FIG. 26. As demonstrated, at a concentration of 30 nM, treatment of HaCaT cells with 8 of the 12 targeted oligonucleotides tested resulted in a statistically significant reduction in levels of IGFBP-3 mRNA relative to GSV-treated cells. At a concentration of 100 nM, treatment with 9 fo the 13 targeted oligonucleotides tested resulted in a statistically significant reduction in levels of IGFBP-3 mRNA relative to GSV-treated cells.

These experiments demonstrate that antisense oligonucleotides targeted to genetic sequences encoding IGFBP-3 can inhibit IGFBP-3 mRNA levels in human keratinocytes in vitro.

EXAMPLE 23

IGF-I receptor is a potent mitotic signalling molecule for keratinocytes and the human receptor elicits separate intracellular signals that prevent apoptosis (19). It is proposed in accordance with the present invention that inactivation of IGF-I receptors in epidermal keratinocytes will achieve three important outcomes in subsequent UV treatment of lesions:

(i) Acute epidermal hyperplasia following UV has been suggested to increase the risk of keratinocyte carcinogenic transformation (22). By reducing IGF-I receptor expression in the epidermis, the incidence of epidermal hyperplasia following UV exposure is likely to be reduced leading to an overall acceleration in normalization of the lesion and reduced carcinogenic risk.

(ii) Inhibition of anti-apoptotic action of IGF-I receptor will enhance the reversal of epidermal thickening and accelerate normalization of differentiation. Topical or injected IGF-I receptor antisense as adjunctive treatment will increase apoptosis in the epidermal layer thereby enhancing the reduction in acanthosis observed in UV treatments.

(iii) Survival of keratinocytes, ie. those which evade apoptosis is likely to occur when cells have damaged DNA. Such mutations may be in the tumor suppressor region. Consequently, the use of antisense therapy will result in less frequent selection of mutated keratinocytes and therefore reduced incidence of basal cell carcinomas and squamous.

Accordingly, antisense therapy, especially against IGF-I-receptor is useful in combination with UV therapy in the treatment of epidermal hyperplasia.

EXAMPLE 24

Figure 27A:
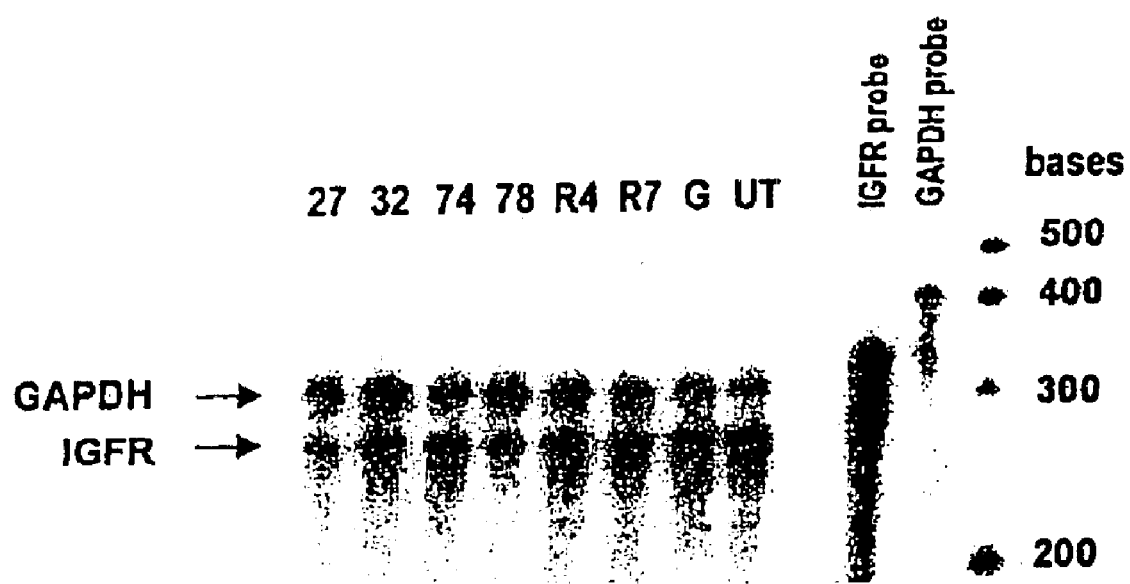
Figure 27B:
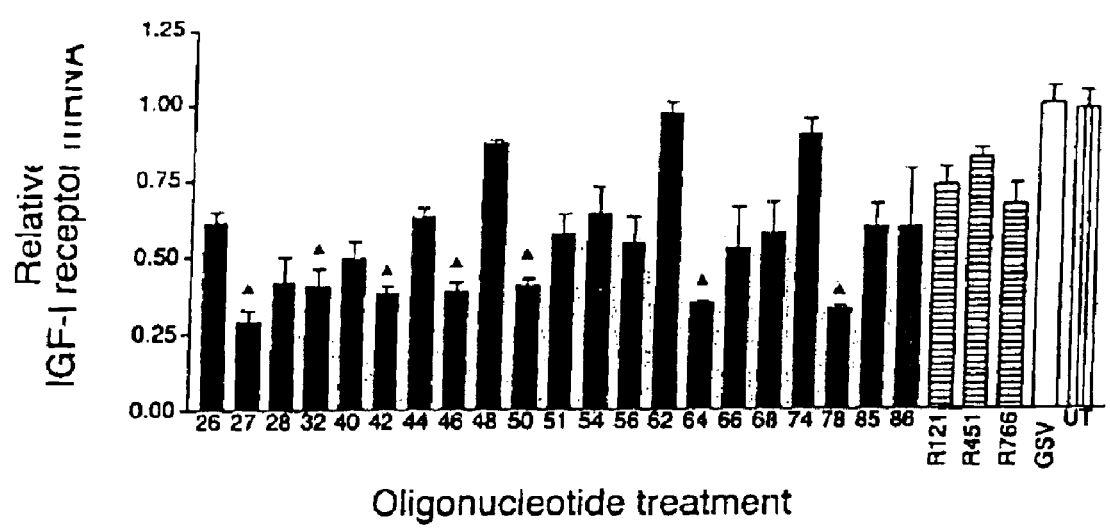

HaCaT cells were treated with antisense oligonucleotides directed to IGF-I receptor mRNA. Levels of IGF-I receptor mRNA were then monitored. In essence, confluent HaCaT cells were treated every 24 hours for four days with 2 µg/ml GSV lipid alone (GSV) or complexed with 30 nM IGF-I receptor specific oligonucleotides (#26 to #86) or random sequence oligonucleotides (R121, R451 and R766). FIG. 27(a) is a photographic representation showing representative RNase protection assay gel showing IGF-I receptor (IGFR) and GAPDH mRNA in untreated or treated HaCaT cells. FIG. 27(b) is a densitometric quantification of IGF-I receptor mRNA in a HaCaT cells following treatment with IGF-I receptor specific oligonucleotides (solid black) random sequence oligonucleotides (horizontal striped bar) or GSV alone (shaded bar) compared to untreated cells (UT, vertical striped bar).

EXAMPLE 25

Figure 28A:
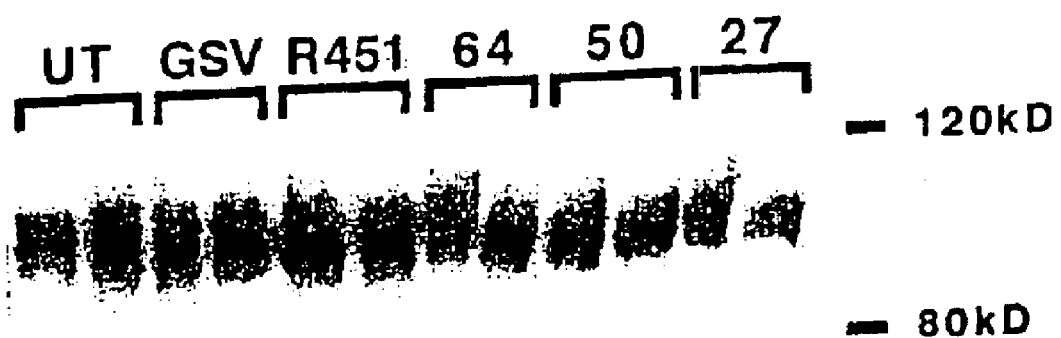
Figure 28B:
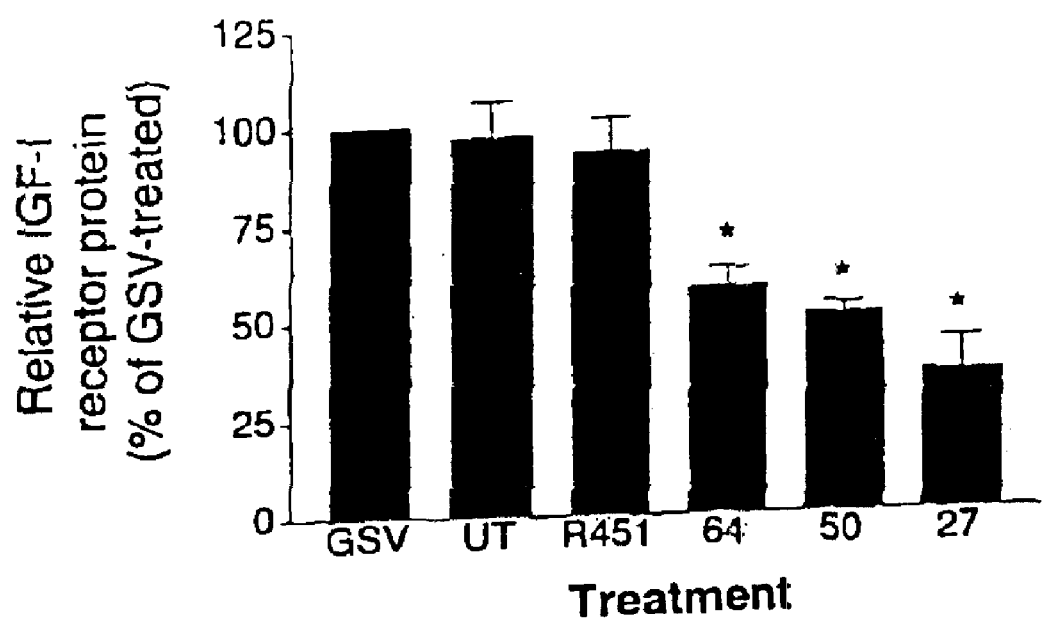

In this example, reduction in total cellular IGF-I receptor protein was monitored following antisense oligonucleotide treatment. Confluence HaCaT cells were treated with 24 hours for 4 days with 2 µg/ml GSV lipid alone (GSV) or complexed with 30 nM IGF-I receptor specific AONS (#27, #50 and #64) or the random sequence oligonucleotide, R451. Total cellular protein was isolated and analysed for IGF-I receptor by SDS PAGE followed by western blotting with antibody specific for the human IGF-I receptor. FIG. 28(a) shows duplicate treated cellular extracts following the IGF-I receptor at the predicted size of 110 kD. FIG. 28(b) is a densitometric quantification of IGF-I receptor protein.

EXAMPLE 26

The reduction in IGF-I receptor numbers was determined on the keratinocyte cell surface after antisense oligonucleotide treatment. HaCaT cells were tranfected with IGF-I receptor specific AONs #27, #50, #64, a random sequence oligonucleotides (R451) or following treatment with GSV a lipid alone every 24 hours for 4 days. Competition binding assays using $^{125}$I-IGF-I and the receptor-specific analogue, des(1–3) IGF-I were performed. Results are shown in FIG. 29.

EXAMPLE 27

In this example, the apoptotic protecting effects of IGF-I receptor on keratinocyte cells was tested by following the reduction in keratino cell numbers following antisense oligonucleotide treatment. HaCaT cells, initially at 40% confluence, were transfected with the IGF-I receptor specific AON #64, control sequences R451 and 6414 or treated with GSV a lipid alone every 24 hours for 2 days. The cell number was measured in culture wells using a dye binding assay. The results are presented in FIG. 30. The results clearly confirm that the IGF-I receptor exhibits an anti-apoptotic effect. By reducing IGF-I receptor levels using antisense oligonucleotide treatment, the anti-apoptotic effect is interrupted and apoptosis results in the reduction in keratinocyte cell number. Results are shown in FIG. 30.

EXAMPLE 28

Figure 31A:
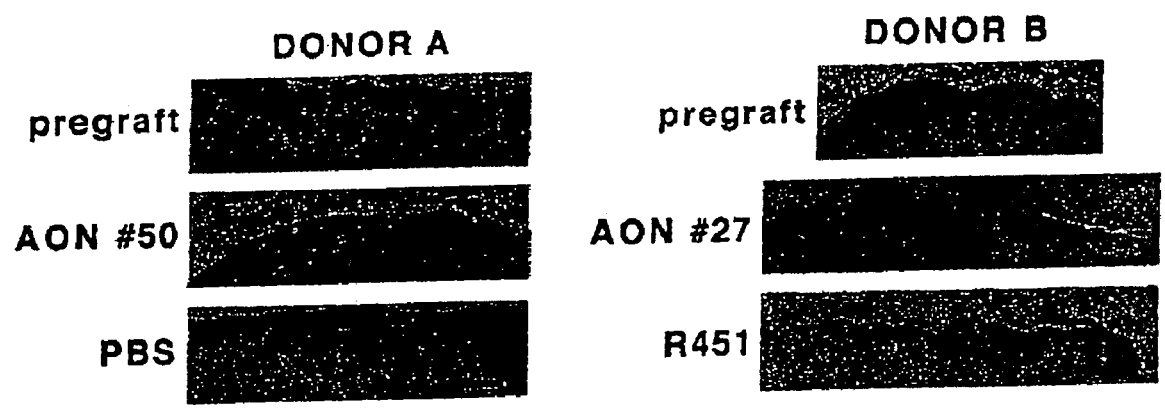
Figure 31B:
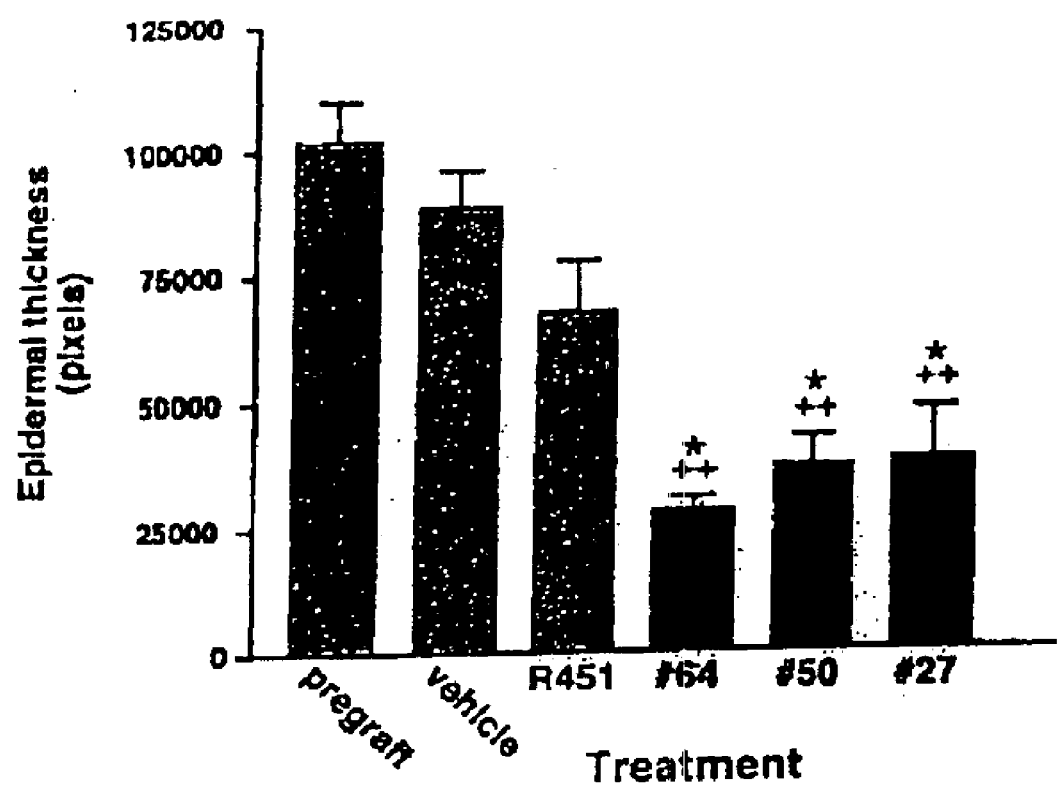

This example shows a reversal of epidermal hyperplasia in psoriatic human skin grafts on nude mice following intradermal injection with antisense oligonucleotides. Grafted psoriasis lesions were injected with IGF-I receptor specific AONs, a random sequence oligonucleotide in PBS, or with PBS alone, every 2 days for 20 days, then analysed histologically. The results are shown in FIG. 31. In FIG. 31(a), donor A graft treated with AON #50 showing epidermal thinning compared with the pregraft and control (PBS)

treated graft and donor graft treated with AON #27 showing epidermal thinning compared with pregraft and control (R451) treated graft. In FIG. 31(b), the mean epidermal cross-sectional area over the full width of grafts is shown as determined by digital image analysis. The results show that epidermal hyperplasia is reversed following the intradermal injection of antisense oligonucleotides.

EXAMPLE 29

Figure 32A:
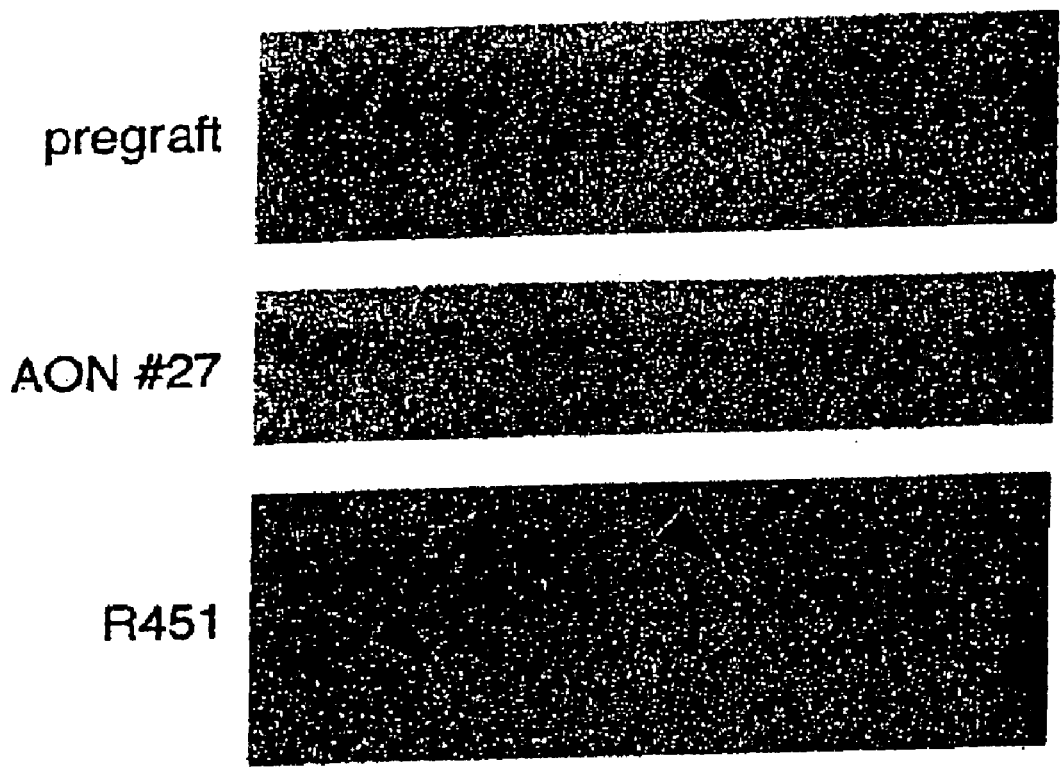

FIG. 32 shows the reversal of epidermal hyperplasia correlating with reduced IGF-I receptor mRNA in grafted psoriasis lesions treated with antisense oligonucleotides. FIG. 32(a) shows a psoriasis lesion prior to grafting and after grafting and treatment with IGF-I receptor specific oligonucleotide #27 (AON #27) or random sequence (R451) immunostained with antibodies to Ki67 to identify proliferating cells. Proliferating cells are indicated by a dark brown nucleus (arrows). FIG. 32(b) shows the same lesion prior to grafting and after oligonucleotide treatment as in FIG. 32(a) but subjected to in situ hybridization with $^{31}$S-labelled cRNA probe complementary to the human IGF-I receptor mRNA. The presence of IGF-I receptor mRNA is indicated by silver grains which are almost eliminated in the epidermis of the lesion treated with IGF-I receptor specific oligonucleotide # 27 (AON #27). This experiment shows that reversal of epidermal hyperplasia correlates with reduced IGF-I receptor mRNA in grafted psoriasis lesions treated with antisense oligonucleotides.

EXAMPLE 30

FIG. 33 treatment with oligonucleotides. HaCaT cell monolayers were grown to 90% confluence in DMEM containing 10% fetal calf serum treated every 24 hours for two days with 2 µg/ml GSV lipid alone (GSV) or complexed with 30 nM oligonucleotide. Total RNA was isolated and analysed for IGF-I receptor and GAPDH mRNA using a commercially available ribonuclease protection assay kit. The results show a reduction in IGF-I receptor mRNA in the HaCaT keratinocyte cells.

EXAMPLE 31

FIG. 34 treatment with oligonucleotides. HaCaT cell monolayers were grown to 90% confluence in DMEM containing 10% fetal calf serum treated every 24 hours for 4 days with 2 µg/ml GSV lipid alone (GSV) or complexed with 30 nM oligonucleotide. Cells were lysed in a buffer containing 50 mM HEPES, 150 mM NaCl, 10% v/v glycerol, 1 v/v Trison X-100 and 100 µg/ml aprotinin on ice for 30 minutes, then 30 µg of lysate was loaded onto a denaturing 7% w/v polyacrylamide gel followed by transfer onto an Immobilon-P membrane. Membranes were then incubated with anti-IGF-I receptor antibodies C20 (available from Santa Cruz Biotechnology Inc., Santa Cruz, Calif.) for 1 hour at room temperature and developed using the Vistra ECF western blotting kit (Amersham). The results shown in FIG. 34 confirm that IGF-I receptor protein is reduced in HaCaT keratinocytes following treatment with oligonucleotides.

EXAMPLE 32

This example shows a reduction in HaCaT keratinocyte cell number following treatment with oligonucleotides. The results are shown in FIG. 35. HaCaT cell monolayers were grown at 40% confluence in DMEM containing 10% fetal calf serum treated every 24 hours for 3 days with 2 µg/li GSV lipid alone (GSV) or complexed with 15 nM oligonucleotide. Cell numbers were then measured every 24 hours using the amido black dye binding assay [32]. Results show that HaCaT keratino cells decrease in number following treatment with oligonucleotides due to a reduction in the anti-apoptotic effect of the IGF-I receptor.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Sara V *Physiological Reviews* 70:591–614, 1990.
2. Rechler M M and Brown A L *Growth Regulation* 2:55–68, 1992.
3. Clemmons D R Growth Regn 2:80, 1992.
4. Oakes S R, K M Haynes, M J Waters, A C Herington and G A Werther *J Clin Endocrinol Metab* 73:1368–1373, 1992.
5. Camacho-Hubner C et al. *J. Biol Chem* 267:11949–11956, 1992.
6. Neely K E et al. *J Inv Derm* 96:104, 1991.
7. Ts'O P O P, Aurelian L, Chang E and Miller P S. Nonionic oligonucleotide analogs (Matagen T M) as anticodic agents in duplex and triplex formation. in "Antisense Strategies", Annals of the New York Academy of Sciences 660:159–177 (Baserga R and Denhardt D T, eds.), 1993.
8. Haseloff J and Gerlach L *Nature* 334:586–591, 1988.
9. Boukamp P, Petrussevska R T, Breitkreuz D, Hornung J, Markham A, Fusenig N E. *J Cell Biol* 106:761–771, 1988.
10. Rheinwald and Green *Cell* 6:331–344, 1975.
11. Hossenlopp P, Seurin D, Segovia-Quinson B, Hardouin S, Binoux M. *Anal Biochem* 154:138–143, 1986.
12. Spratt S K, Tatsuno G P, Yamanaka M K, Ark B C, Detmer J, Mascarenhas D, Flynn J, Talkington-Verser C, Spencer E M. *Growth Factors* 3:63–72, 1990.
13. Pietrzkowski, Z, Sell C, Lammers R, Ullrich A and Baserga R. *Mol. Cell. Biol.* 12: 3883–3889, 1992.
14. Schulz J, Dettlaff S, Fritzsche U, Harms U, Schiebel H, Derer W, Fusenig N E, Hulsen A and Bohm M. *J. Immunol. Meth.* 167:1–13, 1994.
15. Baker B S, Brent L, Valdimarsson H, Powles A V, Al-Imara L, Walker M and Fry L. *Brit. J. Bermatol* 126:105–110, 1992.
16. Nanney L B et al *J. Invest. Bermatol* 98:296–301, 1992.
17. Sundberg J P et al *Immunol. Investigations* 22:389–401, 1993.
18. Sundberg J P et al *J. Invest. Dermatol* 102:781–788, 1994.
19. O'Connor et al *Mol Cell Biol* 17:427–435, 1997.
20. Kuhn et at *Int J Cancer* 80:431–438, 1999.
21. Resnicoff et al *Cancer Res* 55:3739–3741, 1995.
22. Ouhtit et al *Am J Pathol* 156:201–207, 2000.
23. Froehler et al *Tetrahedrin Lett* 34:1003–1006, 1992.
24. Gennaro (Ed) *Remington 's Pharmaceutical Sciences* 18th Edition Mack Publishing Co., Easton Pa. USA, 1990.
25. Flanagan et al *Nat Biotechnol* 14:1139–1145, 1996.
26. Flanagan et al *Nucleic Acids Res* 24:2936–2941, 1996.
27. Flanagan et al *Mol Cell Biochem* 172:213–225, 1997.
28. Gutierrez et al *Biochemistry* 36:743–748, 1997.
29. Moulds et al *Biochemistry* 34:5044–5053, 1995.
30. Wagner et al *Science* 260:1510–1513, 1993.
31. Wagner et al *Nature* 372:333–335, 1994.
32. Schultz et al *J Immunol Meth* 167:1–13, 1994.

What is claimed is:

1. A method for ameliorating the effects of a proliferative and/or inflammatory skin disorder in a mammal, said method comprising contacting the proliferating and/or inflamed skin with an effective amount of a nucleic acid molecule selected from the group consisting of 5'-UCCGGAGCCAGACUU-3' (SEQ ID NO:12); 5'-CACAGUUGCUGCAAG-3' (SEQ ID NO:13); 5'-UCUCCGCUUCCUUUC-3' (SEQ ID NO:14); 5'-AGCCCCCACAGCGAG-3' (SEQ ID NO:15); 5'-GCCULGGAGAUGAGC-3' (SEQ ID NO:16); 5'-UAACAGAGGUCAGCA-3' (SEQ ID NO:17); 5'-GGAUCAGGGACCAGU-3' (SEQ ID NO:18); 5'-CGGCAAGCUACACAG-5' (SEQ ID NO:19); 5'-GGCAGGCAGGCACAC-3' (SEQ ID NO:20) or chemical modification of any one of said nucleic acid molecules, wherein said modification produces a modified nucleic acid molecule having a length and nucleotide sequence which is the same as the nucleic acid molecule prior to modification, and wherein the nucleic acid molecule or modified nucleic acid molecule is capable of reducing the level of IGF-I receptor in said mammal.

2. The method according to claim 1 wherein the mammal is a human.

3. The method according to claim 1 wherein the proliferative or inflammatory skin disorder is psoriasis, eczema, ichthyosis, pityriasis, rubra, pilaris, serborrhoea, keloids, keratosis, neoplasias, scleroderma, warts, benign growths or cancers of the skin.

4. The method according to claim 3 wherein the disorder is psoriasis.

5. The method according to claim 1 wherein the nucleic acid molecule is 5'-UCCGGAGCCAGACUU-3' (SEQ ID NO:12).

6. The method according to claim 1 wherein the nucleic acid molecule is 5'-CACAGUUGCUGCAAG-3' (SEQ ID NO:13).

7. The method according to claim 1 wherein the nucleic acid molecule is 5'-UCUCCGCUUCCUUUC-3' (SEQ ID NO:14).

8. The method according to claim 1 wherein the nucleic acid molecule is 5'-AGCCCCCACAOCGAG-3' (SEQ ID NO:15).

9. The method according to claim 1 herein the nucleic acid molecule is 5'-GCCUUGGAGAUGAGC-3' (SEQ ID NO:16).

10. The method according to claim 1 wherein the nucleic acid molecule is 5'-UAACAGAGGUCAGCA-3' (SEQ ID NO:17).

11. The method according to claim 1 wherein the nucleic acid molecule is 5'-GGAUCAGGGACCAGU-3' (SEQ ID NO:18).

12. The method according to claim 1 wherein the nucleic acid molecule is 5'-CGGCAAGCUACACAG-5' (SEQ ID NO:19).

13. The method according to claim 1 wherein the nucleic acid molecule is 5'-GGCAGGCAGGCACAC-3' (SEQ ID NO:20).

14. A method of ameliorating the effects of psoriasis in a mammal, said method comprising contacting proliferating skin with an effective amount of one or more nucleic acid molecules selected from the group consisting of 5'-UCCGGAGCCAGACUU-3' (SEQ ID NO:12); 5'-CACAGUUGCUGCAAG-3' (SEQ ID NO:13); 5'-UCUCCGCULCCUUUC-3' (SEQ ID NO:14); 5'-AGCCCCCACAGCGAG-3' (SEQ ID NO:15); 5'-GCCUUGGAGAUGAGC-3' (SEQ ID NO:16); 5'-UAACAGAGGUCAGCA-3' (SEQ ID NO:17); 5'-GGAUCAGGGACCAGU-3' (SEQ ID NO:18); 5'-CGGCAAGCUACACAG-5' (SEQ ID NO:19); 5'-GGCAGGCAGGCACAC-3' (SEQ ID NO:20) or chemical modification of any one of said nucleic acid molecules, wherein said modification produces a modified nucleic acid molecule having a length and nucleotide sequence which is the same as the nucleic acid molecule prior to modification and wherein said nucleic acid molecule or modified nucleic acid molecule is capable of interacting with mRNA transcribed from an IGF-I gene, an IGF-I receptor gene or a gene encoding an IGF binding protein.

15. The method according to claim 14 wherein the mammal is a human.

16. The method according to claim 14 wherein the nucleic acid molecule is 5'-UCCGGAGCCAGACUU-3' (SEQ ID NO:12).

17. The method according to claim 14 wherein the nucleic acid molecule is 5'-CACAGUUGCUGCAAG-3' (SEQ ID NO:13).

18. The method according to claim 14 wherein the nucleic acid molecule is 5'-UCUCCGCUUCCUUUC-3' (SEQ ID NO:14).

19. The method according to claim 14 wherein the nucleic acid molecule is 5'-AGCCCCCACAGCGAG-3' (SEQ ID NO:15).

20. The method according to claim 14 wherein the nucleic acid molecule is 5'-GCCUUGGAGAUGAGC-3' (SEQ ID NO:16).

21. The method according to claim 14 wherein the nucleic acid molecule is 5'-UAACAGAGGUCAGCA-3' (SEQ ID NO:17).

22. The method according to claim 14 wherein the nucleic acid molecule is 5'-GGAUCAGGGACCAGU-3' (SEQ ID NO:18).

23. The method according to claim 14 wherein the nucleic acid molecule is 5'-CGGCAAGCUACACAG-5' (SEQ ID NO:19).

24. The method according to claim 14 wherein the nucleic acid molecule is 5'-GGCAGGCAGGCACAC-3' (SEQ ID NO:20).

25. A composition comprising a nucleic acid molecule selected from the group consisting of 5'-CACAGUUGCUGCAAG-3' (SEQ ID NO:13); 5'-AGCCCCCACAGCGAG-3' (SEQ ID NO:15); 5'-GCCUUGGAGAUGAGC-3' (SEQ ID NO:16); 5'-UAACAGAGGUCAGCA-3' (SEQ ID NO:17); 5'-GGAUCAGGGACCAGU-3' (SEQ ID NO:18); 5'-CGGCAAGCUACACAG-5' (SEQ ID NO:19); 5'-GGCAGGCAGGCACAC-3' (SEQ ID NO:20) or chemical modification of any one of said nucleic acid molecules, wherein said modification produces a modified nucleic acid molecule having a length and nucleotide sequence which is the same as the nucleic acid molecule prior to modification, and wherein said nucleic acid molecule or modified nucleic acid molecule is capable of reducing the level of IGF-I receptor in a mammal said composition further comprising one or more pharmaceutically acceptable carriers and/or diluents.

26. The composition according to claim 25 wherein the mammal is a human.

27. A composition comprising a nucleic acid molecule consisting essentially of 5'-UCCGGAGCCAGACUU-3' (SEQ ID NO:12) or a modification thereof or chemical modification of said nucleic acid molecule, wherein said modification produces a modified nucleic acid molecule having a length and nucleotide sequence which is the same as the nucleic acid molecule prior to modification, and wherein said nucleic acid molecule or modified nucleic acid molecule is capable of reducing the level of IGF-I receptor in a mammal said composition further comprising one or more pharmaceutically acceptable carriers and/or diluents.

28. The composition according to claim 25 wherein the nucleic acid molecule is 5'-CACAGLTUGCUGCAAG-3' (SEQ ID NO:13).

29. The composition according to claim 25 wherein the nucleic acid molecule is 5'-AGCCCCCACAGCGAG-3' (SEQ ID NO:15).

30. The composition according to claim 25 wherein the nucleic acid molecule is 5'-GCCUUGGAGAUGAGC-3' (SEQ ID NO:16).

31. A composition according to claim 25 wherein the nucleic acid molecule is 5'-UAACAGAGGUCAGCA-3' (SEQ ID NO:17).

32. The composition according to claim 25 wherein the nucleic acid molecule is 5'-CGGCAAGCUACACAG-5' (SEQ ID NO:19).

33. The composition according to claim 25 wherein the nucleic acid molecule is 5'-GGCAGGCAGGCACAC-3' (SEQ ID NO:20).

34. The composition according to claim 25 wherein the nucleic acid molecule is 5'-GGAUCAGGGACCAGU-3' (SEQ ID NO:18).

* * * * *

SEQUENCE LISTING

<160> NUMBER OF SEQ ID NOS: 20

<210> SEQ ID NO 1
<211> LENGTH: 1433
<212> TYPE: DNA
<213> ORGANISM: Human
<220> FEATURE:
<221> NAME/KEY: polyA_signal
<222> LOCATION: (1416)...(1420)
<221> NAME/KEY: polyA_site
<222> LOCATION: (1433)...(1433)
<221> NAME/KEY: CDS
<222> LOCATION: (118)...(1104)
<223> OTHER INFORMATION: Insulin-like growth factor binding protein (IGFBP-2)
<221> NAME/KEY: sig_peptide
<222> LOCATION: (118)...(234)
<221> NAME/KEY: mat_peptide
<222> LOCATION: (235)...(1101)
<223> OTHER INFORMATION: mature IGFBP-2

<400> SEQUENCE: 1

```
attcggggcg agggaggagg aagaagcgga ggaggcggct cccgctcgca gggccgtgca      60
cctgcccgcc cgcccgctcg ctcgctcgcc cgccgcgccg cgctgccgac cgccagc atg    120
                                                                Met ctg ccg aga gtg ggc tgc ccc gcg ctg ccg ctg ccg ccg ccg ctg              168
Leu Pro Arg Val Gly Cys Pro Ala Leu Pro Leu Pro Pro Pro Leu
        -35                 -30                 -25 ctg ccg ctg ctg ccg ctg ctg ctg ctg cta ctg ggc gcg agt ggc ggc          216
Leu Pro Leu Leu Pro Leu Leu Leu Leu Leu Gly Ala Ser Gly Gly
    -20                 -15                 -10 ggc ggc ggg gcg cgc gcg gag gtg ctg ttc cgc tgc ccg ccc tgc aca          264
Gly Gly Gly Ala Arg Ala Glu Val Leu Phe Arg Cys Pro Pro Cys Thr
     -5                   1                  5                  10 ccc gag cgc ctg gcc gcc tgc ggg ccc ccg ccg gtt gcg ccg ccc gcc          312
Pro Glu Arg Leu Ala Ala Cys Gly Pro Pro Pro Val Ala Pro Pro Ala
                15                  20                  25 gcg gtg gcc gca gtg gcc gga ggc gcc cgc atg cca tgc gcg gag ctc          360
Ala Val Ala Ala Val Ala Gly Gly Ala Arg Met Pro Cys Ala Glu Leu
                30                  35                  40 gtc cgg gag ccg ggc tgc ggc tgc tgc tcg gtg tgc gcc cgg ctg gag          408
Val Arg Glu Pro Gly Cys Gly Cys Cys Ser Val Cys Ala Arg Leu Glu
                45                  50                  55 ggc gag gcg tgc ggc gtc tac acc ccg cgc tgc ggc cag ggg ctg cgc          456
Gly Glu Ala Cys Gly Val Tyr Thr Pro Arg Cys Gly Gln Gly Leu Arg
            60                  65                  70 tgc tat ccc cac ccg ggc tcc gag ctg ccc ctg cag gcg ctg gtc atg          504
Cys Tyr Pro His Pro Gly Ser Glu Leu Pro Leu Gln Ala Leu Val Met
75                  80                  85                  90 ggc gag ggc act tgt gag aag cgc cgg gac gcc gag tat ggc gcc agc          552
Gly Glu Gly Thr Cys Glu Lys Arg Arg Asp Ala Glu Tyr Gly Ala Ser
                    95                 100                 105 ccg gag cag gtt gca gac aat ggc gat gac cac tca gaa gga ggc ctg          600
Pro Glu Gln Val Ala Asp Asn Gly Asp Asp His Ser Glu Gly Gly Leu
                110                 115                 120 gtg gag aac cac gtg gac agc acc atg aac atg ttg ggc ggg gga ggc          648
Val Glu Asn His Val Asp Ser Thr Met Asn Met Leu Gly Gly Gly Gly
            125                 130                 135 agt gct ggc cgg aag ccc ctc aag tcg ggt atg aag gag ctg gcc gtg          696
Ser Ala Gly Arg Lys Pro Leu Lys Ser Gly Met Lys Glu Leu Ala Val
        140                 145                 150
```

-continued

| | | |
|---|---|---|
| ttc cgg gag aag gtc act gag cag cac cgg cag atg ggc aag ggt ggc<br>Phe Arg Glu Lys Val Thr Glu Gln His Arg Gln Met Gly Lys Gly Gly<br>155                           160                       165                     170 | 744 |
| aag cat cac ctt ggc ctg gag gag ccc aag aag ctg cga cca ccc cct<br>Lys His His Leu Gly Leu Glu Glu Pro Lys Lys Leu Arg Pro Pro Pro<br>                       175                      180                       185 | 792 |
| gcc agg act ccc tgc caa cag gaa ctg gac cag gtc ctg gag cgg atc<br>Ala Arg Thr Pro Cys Gln Gln Glu Leu Asp Gln Val Leu Glu Arg Ile<br>                 190                     195                     200 | 840 |
| tcc acc atg cgc ctt ccg gat gag cgg ggc cct ctg gag cac ctc tac<br>Ser Thr Met Arg Leu Pro Asp Glu Arg Gly Pro Leu Glu His Leu Tyr<br>         205                     210                     215 | 888 |
| tcc ctg cac atc ccc aac tgt gac aag cat ggc ctg tac aac ctc aaa<br>Ser Leu His Ile Pro Asn Cys Asp Lys His Gly Leu Tyr Asn Leu Lys<br>         220                     225                     230 | 936 |
| cag tgc aag atg tct ctg aac ggg cag cgt ggg gag tgc tgg tgt gtg<br>Gln Cys Lys Met Ser Leu Asn Gly Gln Arg Gly Glu Cys Trp Cys Val<br>235                           240                       245                     250 | 984 |
| aac ccc aac acc ggg aag ctg atc cag gga gcc ccc acc atc cgg ggg<br>Asn Pro Asn Thr Gly Lys Leu Ile Gln Gly Ala Pro Thr Ile Arg Gly<br>                       255                      260                   265 | 1032 |
| gac ccc gag tgt cat ctc ttc tac aat gag cag cag gag gct tgc ggg<br>Asp Pro Glu Cys His Leu Phe Tyr Asn Glu Gln Gln Glu Ala Cys Gly<br>         270                     275                     280 | 1080 |
| gtg cac acc cag cgg atg cag tag accgcagcca gccggtgcct ggcgcccctg<br>Val His Thr Gln Arg Met Gln *<br>         285 | 1134 |
| cccccgccc ctctccaaac accggcagaa acggagagt gcttgggtgg tgggtgctgg | 1194 |
| aggattttcc agttctgaca cacgtattta tatttggaaa gagaccagca ccgagctcgg | 1254 |
| cacctccccg gcctctctct tcccagctgc agatgccaca cctgctcctt cttgctttcc | 1314 |
| ccggggagg aagggggttg tggtcgggga gctggggtac aggtttgggg aggggaaga | 1374 |
| gaaattttta tttttgaacc cctgtgtccc ttttgcataa gattaaagga aggaaaagt | 1433 |

<210> SEQ ID NO 2
<211> LENGTH: 2474
<212> TYPE: DNA
<213> ORGANISM: Human
<220> FEATURE:
<221> NAME/KEY: CDS
<222> LOCATION: (110)...(985)
<223> OTHER INFORMATION: Insulin-like growth factor-binding protein
     (IGFBP-3)

<400> SEQUENCE: 2

| | |
|---|---|
| ctcagcgccc agccgcttcc tgcctggatt ccacagcttc gcgccgtgta ctgtcgcccc | 60 |
| atccctgcgc gcccagcctg ccaagcagcg tgccccggtt gcaggcgtc atg cag cgg<br>                                                                                              Met Gln Arg<br>                                                                                             1 | 118 |
| gcg cga ccc acg ctc tgg gcc gct gcg ctg act ctg ctg gtg ctg ctc<br>Ala Arg Pro Thr Leu Trp Ala Ala Ala Leu Thr Leu Leu Val Leu Leu<br>     5                      10                      15 | 166 |
| cgc ggg ccg ccg gtg gcg cgg gct ggc gcg agc tcg ggg ggc ttg ggt<br>Arg Gly Pro Pro Val Ala Arg Ala Gly Ala Ser Ser Gly Gly Leu Gly<br>20                           25                       30                       35 | 214 |
| ccc gtg gtg cgc tgc gag ccg tgc gac gcg cgt gca ctg gcc cag tgc<br>Pro Val Val Arg Cys Glu Pro Cys Asp Ala Arg Ala Leu Ala Gln Cys<br>                       40                      45                       50 | 262 |
| gcg cct ccg ccc gcc gtg tgc gcg gag ctg gtg cgc gag ccg ggc tgc<br>Ala Pro Pro Pro Ala Val Cys Ala Glu Leu Val Arg Glu Pro Gly Cys | 310 |

-continued

| | | | | | | | | | | | | | | | |
|---|---|---|---|---|---|---|---|---|---|---|---|---|---|---|---|
| | | 55 | | | | | 60 | | | | | 65 | | | |
| ggc | tgc | tgc | ctg | acg | tgc | gca | ctg | agc | gag | ggc | cag | ccg | tgc | ggc | atc | 358 |
| Gly | Cys | Cys | Leu | Thr | Cys | Ala | Leu | Ser | Glu | Gly | Gln | Pro | Cys | Gly | Ile |
| | | 70 | | | | | 75 | | | | | 80 | | | |

| tac | acc | gag | cgt | tgt | ggc | tcc | ggc | ctt | cgc | tgc | cag | ccg | tcg | ccc | gac | 406 |
|---|---|---|---|---|---|---|---|---|---|---|---|---|---|---|---|---|
| Tyr | Thr | Glu | Arg | Cys | Gly | Ser | Gly | Leu | Arg | Cys | Gln | Pro | Ser | Pro | Asp |
| | 85 | | | | | 90 | | | | | 95 | | | | |

| gag | gcg | cga | ccg | ctg | cag | gcg | ctg | ctg | gac | ggc | cgc | ggg | ctc | tgc | gtc | 454 |
|---|---|---|---|---|---|---|---|---|---|---|---|---|---|---|---|---|
| Glu | Ala | Arg | Pro | Leu | Gln | Ala | Leu | Leu | Asp | Gly | Arg | Gly | Leu | Cys | Val |
| 100 | | | | | 105 | | | | | 110 | | | | | 115 |

| aac | gct | agt | gcc | gtc | agc | cgc | ctg | cgc | gcc | tac | ctg | ctg | cca | gcg | ccg | 502 |
|---|---|---|---|---|---|---|---|---|---|---|---|---|---|---|---|---|
| Asn | Ala | Ser | Ala | Val | Ser | Arg | Leu | Arg | Ala | Tyr | Leu | Leu | Pro | Ala | Pro |
| | | | 120 | | | | | 125 | | | | | 130 | | |

| cca | gct | cca | gga | aat | gct | agt | gag | tcg | gag | gaa | gac | cgc | agc | gcc | ggc | 550 |
|---|---|---|---|---|---|---|---|---|---|---|---|---|---|---|---|---|
| Pro | Ala | Pro | Gly | Asn | Ala | Ser | Glu | Ser | Glu | Glu | Asp | Arg | Ser | Ala | Gly |
| | | | | 135 | | | | | 140 | | | | | 145 | |

| agt | gtg | gag | agc | ccg | tcc | gtc | tcc | agc | acg | cac | cgg | gtg | tct | gat | ccc | 598 |
|---|---|---|---|---|---|---|---|---|---|---|---|---|---|---|---|---|
| Ser | Val | Glu | Ser | Pro | Ser | Val | Ser | Ser | Thr | His | Arg | Val | Ser | Asp | Pro |
| | 150 | | | | | 155 | | | | | 160 | | | | |

| aag | ttc | cac | ccc | ctc | cat | tca | aag | ata | atc | atc | atc | aag | aaa | ggg | cat | 646 |
|---|---|---|---|---|---|---|---|---|---|---|---|---|---|---|---|---|
| Lys | Phe | His | Pro | Leu | His | Ser | Lys | Ile | Ile | Ile | Ile | Lys | Lys | Gly | His |
| | 165 | | | | | 170 | | | | | 175 | | | | |

| gct | aaa | gac | agc | cag | cgc | tac | aaa | gtt | gac | tac | gag | tct | cag | agc | aca | 694 |
|---|---|---|---|---|---|---|---|---|---|---|---|---|---|---|---|---|
| Ala | Lys | Asp | Ser | Gln | Arg | Tyr | Lys | Val | Asp | Tyr | Glu | Ser | Gln | Ser | Thr |
| 180 | | | | | 185 | | | | | 190 | | | | | 195 |

| gat | acc | cag | aac | ttc | tcc | tcc | gag | tcc | aag | cgg | gag | aca | gaa | tat | ggt | 742 |
|---|---|---|---|---|---|---|---|---|---|---|---|---|---|---|---|---|
| Asp | Thr | Gln | Asn | Phe | Ser | Ser | Glu | Ser | Lys | Arg | Glu | Thr | Glu | Tyr | Gly |
| | | | | 200 | | | | | 205 | | | | | 210 | |

| ccc | tgc | cgt | aga | gaa | atg | gaa | gac | aca | ctg | aat | cac | ctg | aag | ttc | ctc | 790 |
|---|---|---|---|---|---|---|---|---|---|---|---|---|---|---|---|---|
| Pro | Cys | Arg | Arg | Glu | Met | Glu | Asp | Thr | Leu | Asn | His | Leu | Lys | Phe | Leu |
| | | | 215 | | | | | 220 | | | | | 225 | | |

| aat | gtg | ctg | agt | ccc | agg | ggt | gta | cac | att | ccc | aac | tgt | gac | aag | aag | 838 |
|---|---|---|---|---|---|---|---|---|---|---|---|---|---|---|---|---|
| Asn | Val | Leu | Ser | Pro | Arg | Gly | Val | His | Ile | Pro | Asn | Cys | Asp | Lys | Lys |
| | | | 230 | | | | | 235 | | | | | 240 | | |

| gga | ttt | tat | aag | aaa | aag | cag | tgt | cgc | cct | tcc | aaa | ggc | agg | aag | cgg | 886 |
|---|---|---|---|---|---|---|---|---|---|---|---|---|---|---|---|---|
| Gly | Phe | Tyr | Lys | Lys | Lys | Gln | Cys | Arg | Pro | Ser | Lys | Gly | Arg | Lys | Arg |
| | 245 | | | | | 250 | | | | | 255 | | | | |

| ggc | ttc | tgc | tgg | tgt | gtg | gat | aag | tat | ggg | cag | cct | ctc | cca | ggc | tac | 934 |
|---|---|---|---|---|---|---|---|---|---|---|---|---|---|---|---|---|
| Gly | Phe | Cys | Trp | Cys | Val | Asp | Lys | Tyr | Gly | Gln | Pro | Leu | Pro | Gly | Tyr |
| 260 | | | | | 265 | | | | | 270 | | | | | 275 |

| acc | acc | aag | ggg | aag | gag | gac | gtg | cac | tgc | tac | agc | atg | cag | agc | aag | 982 |
|---|---|---|---|---|---|---|---|---|---|---|---|---|---|---|---|---|
| Thr | Thr | Lys | Gly | Lys | Glu | Asp | Val | His | Cys | Tyr | Ser | Met | Gln | Ser | Lys |
| | | | | 280 | | | | | 285 | | | | | 290 | |

| tag | acgcctgccg | caagttaatg | tggagctcaa | atatgcctta | ttttgcacaa | 1035 |
|---|---|---|---|---|---|---|
| * | | | | | | | aagactgcca aggacatgac cagcagctgg ctacagcctc gatttatatt tctgtttgtg  1095 gtgaactgat ttttttttaaa ccaaagttta gaaagaggtt tttgaaatgc ctatggtttc  1155 tttgaatggt aaacttgagc atcttttcac tttccagtag tcagcaaaga gcagtttgaa  1215 ttttcttgtc gcttcctatc aaaatattca gagactcgag cacagcaccc agacttcatg  1275 cgcccgtgga atgctcacca catgttggtc gaagcggccg accactgact ttgtgactta  1335 ggcggctgtg ttgcctatgt agagaacacg cttcaccccc actccccgta cagtgcgcac  1395 aggctttatc gagaatagga aaacctttaa accccggtca tccggacatc ccaacgcatg  1455 ctcctggagc tcacagcctt ctgtggtgtc atttctgaaa caagggcgtg gatccctcaa  1515 ccaagaagaa tgtttatgtc ttcaagtgac ctgtactgct tggggactat tggagaaaat  1575

-continued

```
aaggtggagt cctacttgtt taaaaaatat gtatctaaga atgttctagg gcactctggg    1635
aacctataaa ggcaggtatt tcgggccctc ctcttcagga atcttcctga agacatggcc    1695
cagtcgaagg cccaggatgg cttttgctgc ggccccgtgg ggtaggaggg acagagagac    1755
gggagagtca gcctccacat tcagaggcat cacaagtaat ggcacaattc ttcggatgac    1815
tgcagaaaat agtgttttgt agttcaacaa ctcaagacga agcttatttc tgaggataag    1875
ctctttaaag gcaaagcttt attttcatct ctcatctttt gtcctcctta gcacaatgta    1935
aaaaagaata gtaatatcag aacaggaagg aggaatggct tgctggggag cccatccagg    1995
acactgggag cacatagaga ttcacccatg tttgttgaac ttagagtcat tctcatgctt    2055
ttctttataa ttcacacata tatgcagaga agatatgttc ttgttaacat tgtatacaac    2115
atagccccaa atatagtaag atctatacta gataatccta gatgaaatgt tagagatgct    2175
atatgataca actgtggcca tgactgagga aaggagctca cgcccagaga ctgggctgct    2235
ctcccggagg ccaaacccaa gaaggtctgg caaagtcagg ctcagggaga ctctgccctg    2295
ctgcagacct cggtgtggac acacgctgca tagagctctc cttgaaaaca gagggtctc     2355 aagacattct gcctacctat tagcttttct ttattttttt aacttttgg gggaaaagt      2415 attttgaga agtttgtctt gcaatgtatt tataaatagt aaataaagtt tttaccatt      2474
```

```
<210> SEQ ID NO 3
<211> LENGTH: 4989
<212> TYPE: DNA
<213> ORGANISM: Human
<220> FEATURE:
<221> NAME/KEY: sig_peptide
<222> LOCATION: (32)...(121)
<221> NAME/KEY: mat_peptide
<222> LOCATION: (122)...(4132)
<221> NAME/KEY: misc_feature
<222> LOCATION: (122)...(2251)
<223> OTHER INFORMATION: Alpha subunit
<221> NAME/KEY: misc_feature
<222> LOCATION: (182)...(190)
<223> OTHER INFORMATION: Potential N-linked glycosylation site
<221> NAME/KEY: misc_feature
<222> LOCATION: (335)...(343)
<223> OTHER INFORMATION: Potential N-linked glycosylation site
<221> NAME/KEY: misc_feature
<222> LOCATION: (434)...(442)
<223> OTHER INFORMATION: Potential N-linked glycosylation site
<221> NAME/KEY: misc_feature
<222> LOCATION: (761)...(769)
<223> OTHER INFORMATION: Potential N-linked glycosylation site
<221> NAME/KEY: misc_feature
<222> LOCATION: (971)...(979)
<223> OTHER INFORMATION: Potential N-linked glycosylation site
<221> NAME/KEY: misc_feature
<222> LOCATION: (1280)...(1288)
<223> OTHER INFORMATION: Potential N-linked glycosylation site
<221> NAME/KEY: misc_feature
<222> LOCATION: (1343)...(1351)
<223> OTHER INFORMATION: Potential N-linked glycosylation site
<221> NAME/KEY: misc_feature
<222> LOCATION: (1631)...(1639)
<223> OTHER INFORMATION: Potential N-linked glycosylation site
<221> NAME/KEY: misc_feature
<222> LOCATION: (1850)...(1858)
<223> OTHER INFORMATION: Potential N-linked glycosylation site
<221> NAME/KEY: misc_feature
<222> LOCATION: (1895)...(1903)
<223> OTHER INFORMATION: Potential N-linked glycosylation site
<221> NAME/KEY: misc_feature
<222> LOCATION: (1949)...(1957)
<223> OTHER INFORMATION: Potential N-linked glycosylation site
<221> NAME/KEY: misc_feature
<222> LOCATION: (2240)...(2251)
<223> OTHER INFORMATION: Putative proreceptor processing site
```

```
<221> NAME/KEY: misc_feature
<222> LOCATION: (2252)...(4132)
<223> OTHER INFORMATION: Beta subunit
<221> NAME/KEY: misc_feature
<222> LOCATION: (2270)...(2278)
<223> OTHER INFORMATION: Potential N-linked glycosylation site
<221> NAME/KEY: misc_feature
<222> LOCATION: (2297)...(2305)
<223> OTHER INFORMATION: Potential N-linked glycosylation site
<221> NAME/KEY: misc_feature
<222> LOCATION: (2321)...(2329)
<223> OTHER INFORMATION: Potential N-linked glycosylation site
<221> NAME/KEY: misc_feature
<222> LOCATION: (2729)...(2737)
<223> OTHER INFORMATION: Potential N-linked glycosylation site
<221> NAME/KEY: misc_feature
<222> LOCATION: (2768)...(2776)
<223> OTHER INFORMATION: Potential N-linked glycosylation site
<221> NAME/KEY: misc_feature
<222> LOCATION: (2837)...(2908)
<223> OTHER INFORMATION: Transmembrane region
<221> NAME/KEY: misc_feature
<222> LOCATION: (2918)...(2926)
<223> OTHER INFORMATION: Potential N-linked glycosylation site
<221> NAME/KEY: misc_binding
<222> LOCATION: (3047)...(3049)
<223> OTHER INFORMATION: Potential ATP binding site
<221> NAME/KEY: misc_binding
<222> LOCATION: (3053)...(3055)
<223> OTHER INFORMATION: Potential ATP binding site
<221> NAME/KEY: misc_binding
<222> LOCATION: (3062)...(3064)
<223> OTHER INFORMATION: Potential ATP binding site
<221> NAME/KEY: misc_binding
<222> LOCATION: (3128)...(3130)
<223> OTHER INFORMATION: Potential ATP binding site
<221> NAME/KEY: CDS
<222> LOCATION: (32)...(4132)
<223> OTHER INFORMATION: Insulin-like growth factor I receptor (IGF-I
      receptor)

<400> SEQUENCE: 3
tttttttttt ttttgagaaa gggaatttca t ccc aaa taa aag gaa tga agt        52
                                   Pro Lys  *  Lys Glu  *  Ser
                                         -30 ctg gct ccg gag gag ggt ccc cga cct cgc tgt ggg ggc tcc tgt ttc      100
Leu Ala Pro Glu Glu Gly Pro Arg Pro Arg Cys Gly Gly Ser Cys Phe
-25             -20             -15             -10 tct ccg ccg cgc tct cgc tct ggc cga cga gtg gag aaa tct gcg ggc      148
Ser Pro Pro Arg Ser Arg Ser Gly Arg Arg Val Glu Lys Ser Ala Gly
            -5                   1               5 cag gca tcg aca tcc gca acg act atc agc agc tga agc gcc tgg aga      196
Gln Ala Ser Thr Ser Ala Thr Thr Ile Ser Ser  *  Ser Ala Trp Arg
        10                  15                  20 act gca cgg tga tcg agg gct acc tcc aca tcc tgc tca tct cca agg      244
Thr Ala Arg  *  Ser Arg Ala Thr Ser Thr Ser Cys Ser Ser Pro Arg
        25                  30                  35 ccg agg act acc gca gct acc gct tcc cca agc tca cgg tca tta ccg      292
Pro Arg Thr Thr Ala Ala Thr Ala Ser Pro Ser Ser Arg Ser Leu Pro
        40                  45                  50 agt act tgc tgc tgt tcc gag tgg ctg gcc tcg aga gcc tcg gag acc      340
Ser Thr Cys Cys Cys Ser Glu Trp Leu Ala Ser Arg Ala Ser Glu Thr
        55                  60                  65 tct tcc cca acc tca cgg tca tcc gcg gct gga aac tct tct aca act      388
Ser Ser Pro Thr Ser Arg Ser Ser Ala Ala Gly Asn Ser Ser Thr Thr
70                  75                  80                  85 acg ccc tgg tca tct tcg aga tga cca atc tca agg ata ttg ggc ttt     436
Thr Pro Trp Ser Ser Ser Arg  *  Pro Ile Ser Arg Ile Leu Gly Phe
                    90                  95                  100
```

-continued

| | |
|---|---|
| aca acc tga gga aca tta ctc ggg ggg cca tca gga ttg aga aaa atg<br>Thr Thr \* Gly Thr Leu Leu Gly Gly Pro Ser Gly Leu Arg Lys Met<br>                            105                        110                        115 | 484 |
| ctg acc tct gtt acc tct cca ctg tgg act ggt ccc tga tcc tgg atg<br>Leu Thr Ser Val Thr Ser Pro Leu Trp Thr Gly Pro \* Ser Trp Met<br>                120                        125                        130 | 532 |
| cgg tgt cca ata act aca ttg tgg gga ata agc ccc caa agg aat gtg<br>Arg Cys Pro Ile Thr Thr Leu Trp Gly Ile Ser Pro Gln Arg Asn Val<br>                            135                        140                        145 | 580 |
| ggg acc tgt gtc cag gga cca tgg agg aga agc cga tgt gtg aga aga<br>Gly Thr Cys Val Gln Gly Pro Trp Arg Arg Ser Arg Cys Val Arg Arg<br>                      150                        155                        160 | 628 |
| cca cca tca aca atg agt aca act acc gct gct gga cca caa acc gct<br>Pro Pro Ser Thr Met Ser Thr Thr Thr Ala Ala Gly Pro Gln Thr Ala<br>        165                        170                        175 | 676 |
| gcc aga aaa tgt gcc caa gca cgt gtg gga agc ggg cgt gca ccg aga<br>Ala Arg Lys Cys Ala Gln Ala Arg Val Gly Ser Gly Arg Ala Pro Arg<br>180                          185                        190 | 724 |
| aca atg agt gct gcc acc ccg agt gcc tgg gca gct gca gcg cgc ctg<br>Thr Met Ser Ala Ala Thr Pro Ser Ala Trp Ala Ala Ala Ala Arg Leu<br>195                          200                        205                        210 | 772 |
| aca acg aca cgg cct gtg tag ctt gcc gcc act act act atg ccg gtg<br>Thr Thr Thr Arg Pro Val \* Leu Ala Ala Thr Thr Thr Met Pro Val<br>                            215                                  220                        225 | 820 |
| tct gtg tgc ctg cct gcc cgc cca aca cct aca ggt ttg agg gct ggc<br>Ser Val Cys Leu Pro Ala Arg Pro Thr Pro Thr Gly Leu Arg Ala Gly<br>                      230                        235                        240 | 868 |
| gct gtg tgg acc gtg act tct gcg cca aca tcc tca gcg ccg aga gca<br>Ala Val Trp Thr Val Thr Ser Ala Pro Thr Ser Ser Ala Pro Arg Ala<br>                      245                        250                        255 | 916 |
| gcg act ccg agg ggt ttg tga tcc acg acg gcg agt gca tgc agg agt<br>Ala Thr Pro Arg Gly Leu \* Ser Thr Thr Ala Ser Ala Cys Arg Ser<br>        260                        265                        270 | 964 |
| gcc cct cgg gct tca tcc gca acg gca gcc aga gca tgt act gca tcc<br>Ala Pro Arg Ala Ser Ser Ala Thr Ala Ala Arg Ala Cys Thr Ala Ser<br>                      275                        280                        285 | 1012 |
| ctt gtg aag gtc ctt gcc cga agg tct gtg agg aag aaa aga aaa caa<br>Leu Val Lys Val Leu Ala Arg Arg Ser Val Arg Lys Arg Lys Gln<br>        290                        295                        300 | 1060 |
| aga cca ttg att ctg tta ctt ctg ctc aga tgc tcc aag gat gca cca<br>Arg Pro Leu Ile Leu Leu Leu Leu Arg Cys Ser Lys Asp Ala Pro<br>305                          310                        315                        320 | 1108 |
| tct tca agg gca att tgc tca tta aca tcc gac ggg gga ata aca ttg<br>Ser Ser Arg Ala Ile Cys Ser Leu Thr Ser Asp Gly Gly Ile Thr Leu<br>                            325                        330                        335 | 1156 |
| ctt cag agc tgg aga act tca tgg ggc tca tcg agg tgg tga cgg gct<br>Leu Gln Ser Trp Arg Thr Ser Trp Gly Ser Ser Arg Trp \* Arg Ala<br>                      340                        345                        350 | 1204 |
| acg tga aga tcc gcc att ctc atg cct tgg tct cct tgt cct tcc taa<br>Thr \* Arg Ser Ala Ile Leu Met Pro Trp Ser Pro Cys Pro Ser \*<br>                      355                        360                        365 | 1252 |
| aaa acc ttc gcc tca tcc tag gag agg agc agc tag aag gga att act<br>Lys Thr Phe Ala Ser Ser \* Glu Arg Ser Ser \* Lys Gly Ile Thr<br>                        370                                  375 | 1300 |
| cct tct acg tcc tcg aca acc aga act tgc agc aac tgt ggg act ggg<br>Pro Ser Thr Ser Ser Thr Thr Arg Thr Cys Ser Asn Cys Gly Thr Gly<br>380                          385                        390                        395 | 1348 |
| acc acc gca acc tga cca tca aag cag gga aaa tgt act ttg ctt tca<br>Thr Thr Ala Thr \* Pro Ser Lys Gln Gly Lys Cys Thr Leu Leu Ser<br>                                400                        405                        410 | 1396 |

```
atc cca aat tat gtg ttt ccg aaa ttt acc gca tgg agg aag tga cgg      1444
Ile Pro Asn Tyr Val Phe Pro Lys Phe Thr Ala Trp Arg Lys  *  Arg
            415                 420                 425 gga cta aag ggc gcc aaa gca aag ggg aca taa aca cca gga aca acg      1492
Gly Leu Lys Gly Ala Lys Ala Lys Gly Thr  *  Thr Pro Gly Thr Thr
                430                 435                 440 ggg aga gag cct cct gtg aaa gtg acg tcc tgc att tca cct cca cca      1540
Gly Arg Glu Pro Pro Val Lys Val Thr Ser Cys Ile Ser Pro Pro Pro
                    445                 450                 455 cca cgt cga aga atc gca tca tca taa cct ggc acc ggt acc ggc ccc      1588
Pro Arg Arg Arg Ile Ala Ser Ser  *  Pro Gly Thr Gly Thr Gly Pro
                460                 465                 470 ctg act aca ggg atc tca tca gct tca ccg ttt act aca agg aag cac      1636
Leu Thr Thr Gly Ile Ser Ser Ala Ser Pro Phe Thr Thr Arg Lys His
                475                 480                 485 cct tta aga atg tca cag agt atg atg ggc agg atg cct gcg gct cca      1684
Pro Leu Arg Met Ser Gln Ser Met Met Gly Arg Met Pro Ala Ala Pro
            490                 495                 500 aca gct gga aca tgg tgg acg tgg acc tcc cgc cca aca agg acg tgg      1732
Thr Ala Gly Thr Trp Trp Thr Trp Thr Ser Arg Pro Thr Arg Thr Trp
            505                 510                 515 agc ccg gca tct tac tac atg ggc tga agc cct gga ctc agt acg ccg      1780
Ser Pro Ala Ser Tyr Tyr Met Gly  *  Ser Pro Gly Leu Ser Thr Pro
520                 525                 530 ttt acg tca agg ctg tga ccc tca cca tgg tgg aga acg acc ata tcc      1828
Phe Thr Ser Arg Leu  *  Pro Ser Pro Trp Trp Arg Thr Thr Ile Ser
535                 540                 545 gtg ggg cca aga gtg aga tct tgt aca ttc gca cca atg ctt cag ttc      1876
Val Gly Pro Arg Val Arg Ser Cys Thr Phe Ala Pro Met Leu Gln Phe
550                 555                 560                 565 ctt cca ttc cct tgg acg ttc ttt cag cat cga act cct ctt ctc agt      1924
Leu Pro Phe Pro Trp Thr Phe Phe Gln His Arg Thr Pro Leu Leu Ser
                570                 575                 580 taa tcg tga agt gga acc ctc cct ctc tgc cca acg gca acc tga gtt      1972
 *  Ser  *  Ser Gly Thr Leu Pro Leu Cys Pro Thr Ala Thr  *  Val
                585                 590 act aca ttg tgc gct ggc agc ggc agc ctc agg acg gct acc ttt acc      2020
Thr Thr Leu Cys Ala Gly Ser Gly Ser Leu Arg Thr Ala Thr Phe Thr
595                 600                 605                 610 ggc aca att act gct cca aag aca aaa tcc cca tca gga agt atg ccg      2068
Gly Thr Ile Thr Ala Pro Lys Thr Lys Ser Pro Ser Gly Ser Met Pro
            615                 620                 625 acg gca cca tcg aca ttg agg agg tca cag aga acc cca aga ctg agg      2116
Thr Ala Pro Ser Thr Leu Arg Arg Ser Gln Arg Thr Pro Arg Leu Arg
            630                 635                 640 tgt gtg gtg ggg aga aag ggc ctt gct gcg cct gcc cca aaa ctg aag      2164
Cys Val Val Gly Arg Lys Gly Leu Ala Ala Pro Ala Pro Lys Leu Lys
            645                 650                 655 ccg aga agc agg ccg aga agg agg agg ctg aat acc gca aag tct ttg      2212
Pro Arg Ser Arg Pro Arg Arg Arg Leu Asn Thr Ala Lys Ser Leu
            660                 665                 670 aga att tcc tgc aca act cca tct tcg tgc cca gac ctg aaa gga agc      2260
Arg Ile Ser Cys Thr Thr Pro Ser Ser Cys Pro Asp Leu Lys Gly Ser
675                 680                 685                 690 gga gag atg tca tgc aag tgg cca aca cca tgt cca gcc gaa gca          2308
Gly Glu Met Ser Cys Lys Trp Pro Thr Pro Cys Pro Ala Glu Ala
                695                 700                 705 gga aca cca cgg ccg cag aca cct aca aca tca ccg acc cgg aag agc      2356
Gly Thr Pro Arg Pro Gln Thr Pro Thr Thr Ser Pro Thr Arg Lys Ser
```

-continued

|  |  |  |  |  |  |  |  |  |  |  |  |  |  |  |  |
|---|---|---|---|---|---|---|---|---|---|---|---|---|---|---|---|
|  |  |  | 710 |  |  |  | 715 |  |  |  | 720 |  |  |  |  |
| tgg | aga | cag | agt | acc | ctt | tct | ttg | aga | gca | gag | tgg | ata | aca | agg | aga | 2404 |
| Trp | Arg | Gln | Ser | Thr | Leu | Ser | Leu | Arg | Ala | Glu | Trp | Ile | Thr | Arg | Arg |  |
|  |  | 725 |  |  |  | 730 |  |  |  | 735 |  |  |  |  |  |
| gaa | ctg | tca | ttt | cta | acc | ttc | ggc | ctt | tca | cat | tgt | acc | gca | tcg | ata | 2452 |
| Glu | Leu | Ser | Phe | Leu | Thr | Phe | Gly | Leu | Ser | His | Cys | Thr | Ala | Ser | Ile |  |
| 740 |  |  |  |  | 745 |  |  |  |  | 750 |  |  |  |  |  |  |
| tcc | aca | gct | gca | acc | acg | agg | ctg | aga | agc | tgg | gct | gca | gcg | cct | cca | 2500 |
| Ser | Thr | Ala | Ala | Thr | Thr | Arg | Leu | Arg | Ser | Trp | Ala | Ala | Ala | Pro | Pro |  |
| 755 |  |  |  | 760 |  |  |  |  | 765 |  |  |  |  | 770 |  |  |
| act | tcg | tct | ttg | caa | gga | cta | tgc | ccg | cag | aag | gag | cag | atg | aca | ttc | 2548 |
| Thr | Ser | Ser | Leu | Gln | Gly | Leu | Cys | Pro | Gln | Lys | Glu | Gln | Met | Thr | Phe |  |
|  |  |  |  | 775 |  |  |  |  | 780 |  |  |  |  | 785 |  |  |
| ctg | ggc | cag | tga | cct | ggg | agc | caa | ggc | ctg | aaa | act | cca | tct | ttt | taa | 2596 |
| Leu | Gly | Gln | * | Pro | Gly | Ser | Gln | Gly | Leu | Lys | Thr | Pro | Ser | Phe | * |  |
|  |  |  | 790 |  |  |  |  | 795 |  |  |  |  | 800 |  |  |  |
| agt | ggc | cgg | aac | ctg | aga | atc | cca | atg | gat | tga | ttc | taa | tgt | atg | aaa | 2644 |
| Ser | Gly | Arg | Asn | Leu | Arg | Ile | Pro | Met | Asp | * | Phe | * | Cys | Met | Lys |  |
|  |  |  |  |  | 805 |  |  |  |  | 810 |  |  |  |  |  |  |
| taa | aat | acg | gat | cac | aag | ttg | agg | atc | agc | gag | aat | gtg | tgt | cca | gac | 2692 |
| * | Asn | Thr | Asp | His | Lys | Leu | Arg | Ile | Ser | Glu | Asn | Val | Cys | Pro | Asp |  |
|  | 815 |  |  |  |  | 820 |  |  |  |  | 825 |  |  |  |  |  |
| agg | aat | aca | gga | agt | atg | gag | ggg | cca | agc | taa | acc | ggc | taa | acc | cgg | 2740 |
| Arg | Asn | Thr | Gly | Ser | Met | Glu | Gly | Pro | Ser | * | Thr | Gly | * | Thr | Arg |  |
| 830 |  |  |  |  | 835 |  |  |  |  |  |  | 840 |  |  |  |  |
| gga | act | aca | cag | ccc | gga | ttc | agg | cca | cat | ctc | tct | ctg | gga | atg | ggt | 2788 |
| Gly | Thr | Thr | Gln | Pro | Gly | Phe | Arg | Pro | His | Leu | Ser | Leu | Gly | Met | Gly |  |
|  |  | 845 |  |  |  |  | 850 |  |  |  |  | 855 |  |  |  |  |
| cgt | gga | cag | atc | ctg | tgt | tct | tct | atg | tcc | agg | cca | aaa | cag | gat | atg | 2836 |
| Arg | Gly | Gln | Ile | Leu | Cys | Ser | Ser | Met | Ser | Arg | Pro | Lys | Gln | Asp | Met |  |
| 860 |  |  |  |  | 865 |  |  |  |  | 870 |  |  |  |  | 875 |  |
| aaa | act | tca | tcc | atc | tga | tca | tcg | ctc | tgc | ccg | tcg | ctg | tcc | tgt | tga | 2884 |
| Lys | Thr | Ser | Ser | Ile | * | Ser | Ser | Leu | Cys | Pro | Ser | Leu | Ser | Cys | * |  |
|  |  |  |  | 880 |  |  |  |  | 885 |  |  |  |  |  |  |  |
| tcg | tgg | gag | ggt | tgg | tga | tta | tgc | tgt | acg | tct | tcc | ata | gaa | aga | gaa | 2932 |
| Ser | Trp | Glu | Gly | Trp | * | Leu | Cys | Cys | Thr | Ser | Ser | Ile | Glu | Arg | Glu |  |
| 890 |  |  |  |  | 895 |  |  |  |  | 900 |  |  |  |  |  |  |
| ata | aca | gca | ggc | tgg | gga | atg | gag | tgc | tgt | atg | cct | ctg | tga | acc | cgg | 2980 |
| Ile | Thr | Ala | Gly | Trp | Gly | Met | Glu | Cys | Cys | Met | Pro | Leu | * | Thr | Arg |  |
| 905 |  |  |  |  | 910 |  |  |  |  | 915 |  |  |  |  |  |  |
| agt | act | tca | gcg | ctg | ctg | atg | tgt | acg | ttc | ctg | atg | agt | ggg | agg | tgg | 3028 |
| Ser | Thr | Ser | Ala | Leu | Leu | Met | Cys | Thr | Phe | Leu | Met | Ser | Gly | Arg | Trp |  |
| 920 |  |  |  |  | 925 |  |  |  |  | 930 |  |  |  |  | 935 |  |
| ctc | ggg | aga | aga | tca | cca | tga | gcc | ggg | aac | ttg | gca | ggg | ggt | cgt | ttg | 3076 |
| Leu | Gly | Arg | Arg | Ser | Pro | * | Ala | Gly | Asn | Leu | Gly | Arg | Gly | Arg | Leu |  |
|  |  |  | 940 |  |  |  |  | 945 |  |  |  |  | 950 |  |  |  |
| gga | tgg | tct | atg | aag | gag | ttg | cca | agg | gtg | tgg | tga | aag | atg | aac | ctg | 3124 |
| Gly | Trp | Ser | Met | Lys | Glu | Leu | Pro | Arg | Val | Trp | * | Lys | Met | Asn | Leu |  |
|  |  |  | 955 |  |  |  |  | 960 |  |  |  |  | 965 |  |  |  |
| aaa | cca | gag | tgg | cca | tta | aaa | cag | tga | acg | agg | ccg | caa | gca | tgc | gtg | 3172 |
| Lys | Pro | Glu | Trp | Pro | Leu | Lys | Gln | * | Thr | Arg | Pro | Gln | Ala | Cys | Val |  |
|  |  |  | 970 |  |  |  |  | 975 |  |  |  |  | 980 |  |  |  |
| aga | gga | ttg | agt | ttc | tca | acg | aag | ctt | ctg | tga | tga | agg | agt | tca | att | 3220 |
| Arg | Gly | Leu | Ser | Phe | Ser | Thr | Lys | Leu | Leu | * | * | Arg | Ser | Ser | Ile |  |
|  |  |  |  | 985 |  |  |  |  | 990 |  |  |  |  |  |  |  |
| gtc | acc | atg | tgg | tgc | gat | tgc | tgg | gtg | tgg | tgt | ccc | aag | gcc | agc | caa | 3268 |
| Val | Thr | Met | Trp | Cys | Asp | Cys | Trp | Val | Trp | Cys | Pro | Lys | Ala | Ser | Gln |  |
| 995 |  |  |  | 1000 |  |  |  |  | 1005 |  |  |  |  | 1010 |  |  |
| cac | tgg | tca | tca | tgg | aac | tga | tga | cac | ggg | gcg | atc | tca | aaa | gtt | atc | 3316 |

```
                                        -continued

His Trp Ser Ser Trp Asn  *   *  His Gly Ala Ile Ser Lys Val Ile
            1015                    1020 tcc ggt ctc tga ggc cag aaa tgg aga ata atc cag tcc tag cac ctc    3364
Ser Gly Leu  *  Gly Gln Lys Trp Arg Ile Ile Gln Ser  *  His Leu
1025                1030                1035 caa gcc tga gca aga tga ttc aga tgg ccg gag aga ttg cag acg gca    3412
Gln Ala  *  Ala Arg  *  Phe Arg Trp Pro Glu Arg Leu Gln Thr Ala
        1040                1045                1050 tgg cat acc tca acg cca ata agt tcg tcc aca gag acc ttg ctg ccc    3460
Trp His Thr Ser Thr Pro Ile Ser Ser Ser Thr Glu Thr Leu Leu Pro
            1055                1060                1065 gga att gca tgg tag ccg aag att tca cag tca aaa tcg gag att ttg    3508
Gly Ile Ala Trp  *  Pro Lys Ile Ser Gln Ser Lys Ser Glu Ile Leu
        1070                1075                1080 gta tga cgc gag ata tct atg aga cag act att acc gga aag gag gca    3556
Val  *  Arg Glu Ile Ser Met Arg Gln Thr Ile Thr Gly Lys Glu Ala
            1085                1090                1095 aag ggc tgc tgc ccg tgc gct gga tgt ctc ctg agt ccc tca agg atg    3604
Lys Gly Cys Cys Pro Cys Ala Gly Cys Leu Leu Ser Pro Ser Arg Met
        1100                1105                1110 gag tct tca cca ctt act cgg acg tct ggt cct tcg ggg tcg tcc tct    3652
Glu Ser Ser Pro Leu Thr Arg Thr Ser Gly Pro Ser Gly Ser Ser Ser
1115                1120                1125                1130 ggg aga tcg cca cac tgg ccg agc agc cct acc agg gct tgt cca acg    3700
Gly Arg Ser Pro His Trp Pro Ser Ser Pro Thr Arg Ala Cys Pro Thr
        1135                1140                1145 agc aag tcc ttc gct tcg tca tgg agg gcg gcc ttc tgg aca agc cag    3748
Ser Lys Ser Phe Ala Ser Ser Trp Arg Ala Ala Phe Trp Thr Ser Gln
            1150                1155                1160 aca act gtc ctg aca tgc tgt ttg aac tga tgc gca tgt gct ggc agt    3796
Thr Thr Val Leu Thr Cys Cys Leu Asn  *  Cys Ala Cys Ala Gly Ser
        1165                1170                1175 ata acc cca aga tga ggc ctt cct tcc tgg aga tca tca gca gca tca    3844
Ile Thr Pro Arg  *  Gly Leu Pro Ser Trp Arg Ser Ser Ala Ala Ser
            1180                1185                1190 aag agg aga tgg agc ctg gct tcc ggg agg tct cct tct act aca gcg    3892
Lys Arg Arg Trp Ser Leu Ala Ser Gly Arg Ser Pro Ser Thr Thr Ala
        1195                1200                1205 agg aga aca agc tgc ccg agc cgg agg agc tgg acc tgg agc cag aga    3940
Arg Arg Thr Ser Cys Pro Ser Arg Arg Ser Trp Thr Trp Ser Gln Arg
1210                1215                1220 aca tgg aga gcg tcc ccc tgg acc cct cgg cct cct cgt cct ccc tgc    3988
Thr Trp Arg Ala Ser Pro Trp Thr Pro Arg Pro Pro Arg Pro Pro Cys
1225                1230                1235                1240 cac tgc ccg aca gac act cag gac aca agg ccg aga acg gcc ccg gcc    4036
His Cys Pro Thr Asp Thr Gln Asp Thr Arg Pro Arg Thr Ala Pro Ala
            1245                1250                1255 ctg ggg tgc tgg tcc tcc gcg cca gct tcg acg aga gac agc ctt acg    4084
Leu Gly Cys Trp Ser Ser Ala Pro Ala Ser Thr Arg Asp Ser Leu Thr
        1260                1265                1270 ccc aca tga acg ggg gcc gca aga acg agc ggg cct tgc cgc tgc ccc    4132
Pro Thr  *  Thr Gly Ala Ala Arg Thr Ser Gly Pro Cys Arg Cys Pro
            1275                1280                1285 agtcttcgac ctgctgatcc ttggatcctg aatctgtgca aacagtaacg tgtgcgcacg  4192
cgcagcgggg tggggggggga gagagagttt taacaatcca ttcacaagcc tcctgtacct  4252
cagtggatct tcagttctgc ccttgctgcc cgcgggagac agcttctctg cagtaaaaca  4312
catttgggat gttcctttttt tcaatatgca agcagctttt tattccctgc ccaaacccctt  4372
```

-continued

```
aactgacatg ggcctttaag aaccttaatg acaacactta atagcaacag agcacttgag      4432
aaccagtctc ctcactctgt ccctgtcctt ccctgttctc cctttctctc tcctctctgc      4492
ttcataacgg aaaataatt gccacaagtc cagctgggaa gcccttttta tcagtttgag       4552
gaagtggctg tccctgtggc cccatccaac cactgtacac acccgcctga caccgtgggt     4612
cattacaaaa aaacacgtgg agatggaaat ttttacccttt atctttcacc tttctaggga    4672
catgaaattt acaagggcc atcgttcatc caaggctgtt accattttaa cgctgcctaa      4732
ttttgccaaa atcctgaact ttctccctca tcggcccggc gctgattcct cgtgtccgga    4792
ggcatgggtg agcatggcag ctggttgctc catttgagag acacgctggc gacacactcc    4852
gtccatccga ctgcccctgc tgtgctgctc aaggccacag gcacacaggt ctcattgctt    4912
ctgactagat tattatttgg gggaactgga cacaataggt ctttctctca gtgaaggtgg    4972
ggagaagctg aaccggc                                                    4989
```

```
<210> SEQ ID NO 4
<211> LENGTH: 25
<212> TYPE: DNA
<213> ORGANISM: Human

<400> SEQUENCE: 4
gcgcccgctg catgacgcct gcaac                                           25

<210> SEQ ID NO 5
<211> LENGTH: 24
<212> TYPE: DNA
<213> ORGANISM: Human

<400> SEQUENCE: 5
cgggcggctc acctggagct ggcg                                            24

<210> SEQ ID NO 6
<211> LENGTH: 18
<212> TYPE: DNA
<213> ORGANISM: Human

<400> SEQUENCE: 6
aggcggctga cggcacta                                                   18

<210> SEQ ID NO 7
<211> LENGTH: 19
<212> TYPE: DNA
<213> ORGANISM: Human

<400> SEQUENCE: 7
caggcgtcat gcagcgggc                                                  19

<210> SEQ ID NO 8
<211> LENGTH: 25
<212> TYPE: DNA
<213> ORGANISM: Human

<400> SEQUENCE: 8
cggagatgcc gcatgccagc gcagg                                           25

<210> SEQ ID NO 9
<211> LENGTH: 18
<212> TYPE: DNA
<213> ORGANISM: Human

<400> SEQUENCE: 9
```

-continued

```
gacagcgtcg gagcgatc                                              18

<210> SEQ ID NO 10
<211> LENGTH: 18
<212> TYPE: DNA
<213> ORGANISM: Human

<400> SEQUENCE: 10
atctctccgc ttcctttc                                              18

<210> SEQ ID NO 11
<211> LENGTH: 18
<212> TYPE: DNA
<213> ORGANISM: Human

<400> SEQUENCE: 11
gaaaggaagc ggagagat                                              18

<210> SEQ ID NO 12
<211> LENGTH: 15
<212> TYPE: RNA
<213> ORGANISM: Human

<400> SEQUENCE: 12
uccggagcca gacuu                                                 15

<210> SEQ ID NO 13
<211> LENGTH: 15
<212> TYPE: RNA
<213> ORGANISM: Human

<400> SEQUENCE: 13
cacaguugcu gcaag                                                 15

<210> SEQ ID NO 14
<211> LENGTH: 15
<212> TYPE: RNA
<213> ORGANISM: Human

<400> SEQUENCE: 14
ucuccgcuuc cuuuc                                                 15

<210> SEQ ID NO 15
<211> LENGTH: 15
<212> TYPE: RNA
<213> ORGANISM: Human

<400> SEQUENCE: 15
agcccccaca gcgag                                                 15

<210> SEQ ID NO 16
<211> LENGTH: 15
<212> TYPE: RNA
<213> ORGANISM: Human

<400> SEQUENCE: 16
gccuuggaga ugagc                                                 15

<210> SEQ ID NO 17
<211> LENGTH: 15
<212> TYPE: RNA
<213> ORGANISM: Human
```

```
<400> SEQUENCE: 17
uaacagaggu cagca                                                15

<210> SEQ ID NO 18
<211> LENGTH: 15
<212> TYPE: RNA
<213> ORGANISM: Human

<400> SEQUENCE: 18
ggaucaggga ccagu                                                15

<210> SEQ ID NO 19
<211> LENGTH: 15
<212> TYPE: RNA
<213> ORGANISM: Human

<400> SEQUENCE: 19
cggcaagcua cacag                                                15

<210> SEQ ID NO 20
<211> LENGTH: 15
<212> TYPE: RNA
<213> ORGANISM: Human

<400> SEQUENCE: 20
ggcaggcagg cacac                                                15
```